US006811978B2

(12) United States Patent
Jannes et al.

(10) Patent No.: US 6,811,978 B2
(45) Date of Patent: Nov. 2, 2004

(54) DETECTION AND IDENTIFICATION OF PSEUDOMONAS SPECIES USING THE 16S-23S RRNA SPACER

(75) Inventors: Geert Jannes, Kessel-Lo (BE); Rudi Rossau, Ekeren (BE); Hugo Van Heuverswyn, Kalken (BE)

(73) Assignee: Innogenetics N.V., Ghent (BE)

( * ) Notice: Subject to any disclaimer, the term of this patent is extended or adjusted under 35 U.S.C. 154(b) by 0 days.

(21) Appl. No.: 09/931,486

(22) Filed: Aug. 17, 2001

(65) Prior Publication Data

US 2003/0215802 A1 Nov. 20, 2003

Related U.S. Application Data

(62) Division of application No. 09/448,894, filed on Nov. 29, 1999, now Pat. No. 6,312,903, which is a division of application No. 08/765,332, filed as application No. PCT/EP95/02452 on Jun. 23, 1995, now Pat. No. 6,025,132.

(30) Foreign Application Priority Data

| Jun. 24, 1994 | (EP) | ............................................ | 94870106 |
| Apr. 7, 1995 | (EP) | ............................................ | 95870032 |
| Jun. 23, 1995 | (EP) | ................................ | PCT/EP95/02452 |

(51) Int. Cl.[7] ............................ C12Q 1/68; C07H 21/04
(52) U.S. Cl. ........................................ 435/6; 536/24.32
(58) Field of Search ............................ 536/24.32; 435/6

(56) References Cited

U.S. PATENT DOCUMENTS

| 4,508,823 | A | * | 4/1985 | Olsen ........................ | 435/172.3 |
| 5,212,059 | A | | 5/1993 | Schwartz | |
| 5,298,392 | A | * | 3/1994 | Atlas et al. .................. | 435/600 |
| 5,358,846 | A | * | 10/1994 | Ohno et al. ...................... | 435/6 |
| 5,521,300 | A | | 5/1996 | Shah | |
| 5,536,638 | A | | 7/1996 | Rossau | |
| 5,545,541 | A | * | 8/1996 | Molin et al. ............. | 435/172.3 |
| 5,574,145 | A | | 11/1996 | Barry | |
| 5,631,130 | A | | 5/1997 | Leckie | |
| 5,712,095 | A | | 1/1998 | Britschgi | |
| 5,726,021 | A | | 3/1998 | Britschgi | |
| 6,025,132 | A | | 2/2000 | Jannes | |

FOREIGN PATENT DOCUMENTS

| EP | A-0395292 | 10/1990 |
| EP | A-0452596 | 10/1991 |
| FR | A2651505 | 3/1991 |
| FR | A-2683227 | 5/1993 |
| WO | WO93/04201 | 3/1993 |
| WO | WO 93/11264 | 6/1993 |
| WO | WO95/34574 | 12/1995 |
| WO | WO96/19585 | 6/1996 |

OTHER PUBLICATIONS

Tyler et al, "Oligonucleotide Primers . . . Transcribed Spacers", Clinical and Diagnostic Laboratory Immunology, Jul. 1995, pp. 448–453; XP 000604143.
Kostman et al, "Molecular Epidemiology . . . Ribotyping", Journal of Clinical Microbiology, Aug., 1992, pp. 2084–2087; XP–000926225.
Gill et al, "Identification of . . . soil isolates", Can. J. Microbiol., vol. 40, 1994.
Microbiology, vol. 140, No. 5, May 1994, Reading GB pp. 1103–1108, J.W. Van Der Giessen et al.
Journal of Bacteriology, vol. 175, No. 10, May 1993, Baltimore US, pp. 2818–2825, R. Frothingham et al.
Microbiology, vol. 140, No. 1, Reading GB, pp. 123–132, Y.JI et al.
Journal of Infectious Diseases, vol. 169, No. 2, Chicago US, pp. 305–312, R. Frothingham et al.
Journal of Bacteriology, vol. 170, No. 6, Baltimore US, pp. 2886–2889, Y. Suzuki et al.
Journal of General Microbiology, vol. 138, No. 8., London GB, pp. 1717–1727, K.E. Kempshell et al.
Methods in Molecular and Cellular Biology, vol. 5, No. 1, 4, New York US, pp. 3–12, T.M. Schmidt.
Edmond et al, "A Ribosomal DNA Fragment of *Listeria monocytogenes* and its Use as Genus–Specific Probe . . . ", Applied and Environmental Microbiology, Aug. 1993, pp. 2690–2697.

* cited by examiner

*Primary Examiner*—Kenneth R. Horlick
(74) *Attorney, Agent, or Firm*—Nixon & Vanderhye P.C

(57) ABSTRACT

The present invention relates to 16S–23S rRNA spacer sequences from Pseudomonas species and their use in a method for detection and/or identification of Pseudomonas species. The invention further it relates to a method for detection and identification of at least one Pseudomonas species, or for the simultaneous detection of several Pseudomonas species in a sample, involving the steps of: (i) optionally releasing, isolating and/or concentrating the polynucleic acids present in the sample; (ii) optionally amplifying the 16S–23S rRNA spacer region, or a part thereof, with at least one primer pair; (iii) detecting the presence of a 16S–23S rRNA spacer sequence; and (iv) identifying the Pseudomonas species present in the sample from the nucleic acid(s) detected in the sample.

19 Claims, 103 Drawing Sheets

Figure 1

AAGGAGCACC ACGAAAACGC CCCAACTGGT GGGGCGTAGG CCGTGAGGGG TTCTTGTCTG TAGTGGGCGA
GAGCCGGGTG CATGACAACA AAGTTGGCCA CCAACACACT GTTGGGTCCT GAGGCAACAC TCGGACTTGT
TCCAGGTGTT GTCCCACCGC CTTGGTGGTG GGGTGTGGTG TTTGAGAACT GGATAGTGGT TGCGAGCATC
AATGGATACG CTGCCGGCTA GCGGTGGCGT GTTCTTTGTG CAATATTCTT TGGTTTTTGT TGTGT (SEQ ID NO 76)

Figure 2

AAGGAGCACC ACGAAAAGCA CCCCAACTGG TGGGGTGCGA GCCGTGAGGG GTTCCCGTCT GTAGTGGACG
GGGGCCGGNT GCGCAACAGC AAATGATTGC CAGACACACT ATTGGGCCCT GAGACAACAC TCGGTCCGTC
CGTGTGGAGT CCCTCCATCT TGGTGGTGGG GTGTGGTGTT TGAGTATTGG ATAGTGGTTG CGAGCATCTA
GATGAGCGCA TGGTCTTCGT GGCCGGCGTT CATCGAAATG TGTAATTTCT TCCTTAACTC TTGTGTGT (SEQ ID NO 77)

Figure 3

AAGGAGCACC ACGAAAAGCA CCCCAACTGG TGGGGTGCGA GCCGTGAGGG GTTCCCGTCT GTAGTGGACG
GGGGCCGGGT GCGCAACAGC AAATGATTGC CAGACACACT ATTGGGCCCT GAGACAACAC TCGGTCCGTC
CGTGTGGAGT CCCTCCATCT TGGTGGTGGG GTGTGGTGTT TGAGTATTGG ATAGTGGTTG CGAGCATCTA
GATGAGCGCA TGGTCTTCGT GGCCGGCGTT CATCGAAATG TGTAATTCT TTTTTAACTC TTGTGTGT (SEQ ID NO 78)

Figure 4

```
AAGGAGCACC ACGAAAAGCA CTCCAATTGG TGGGGTGCCGA GCCGTGAGGG GTTCCCGTCT GTAGTGGACG
GGGGCCGGNT GCACAACAGC AAATGATTGC CAGACACACT ATTGGGCCCT GAGACAACAC TCGGTCGATC
CGTGTGGAGT CCCTCCATCT TGGTGGTGGG GTGTGGTGTT TGAGTATTGG ATAGTGGTTG CGAGCATCTA
GATGAGCCGCA TAGTCCTTGT GGCTGATGCG CTCGTCGAAA TGTGTAATTT CTTCTTTGGT GTNTGTGTGT
```

(SEQ ID NO 79)

Figure 5

```
AAGGAGCACC ACGAAAAGCA TCCCAATTGG TGGGGTGCGA GCCGTGAGGG GTTCTCGTCT GTAGTGGACG
AAACCGGGT GCACAACAGC AAATGATTGC CAGACACACT ATTGGGCCCT GAGACAACAC TCGGTCGATC
CGTGTGGAGT CCCTCCATCT TGGTGGTGGG GTGTGGTGTT TGAGTATTGG ATAGTGGTTG CGAGCATCTA
GATGAGCGCG TAGTCCTTTG TGGCTGATGC GTTCATCAAA ATGTGTAATT TCTTTTTTGG TTTNTGTGTG
T
```

(SEQ ID NO 80)

Figure 6

AAGGAGCACC ACGAAAAGCA CTCCAATTGG TGGGGTGCGA GCCGTGAGGG GTTCCCGTCT GTAGTGGACG
GGGGCCGGGT GCACAACAGC AAATGATTGC CAGACACACT ATTGGGCCCT GAGACAACAC TCGGTCGATC
CGTGTGGAGT CCCTCCATCT TGGTGGTGGG GTGTGGTGTT TGAGTATTGG ATAGTGGTTG CGAGCATCTA
GATGAGCGCA TAGCCCTTGC GGCTGATCCG TTCGNCGAAA TGTGTAATTT CTTCTCTGGT TTCTGTGTGT (SEQ ID NO 81)

Figure 7

AAGGAGCACC ACGAAAAGCA CTCCAATTGG TGGGGTGCGA GCCGTGAGGG GTTCTCGTCT GTAGTGGACG
GNAGCCGGGT GCACAACAGC AAATGATTGC CAGACACACT ATTGGGCCCT GAGACAACAC TCGGTCGATC
CGTGTGGAGT CCCTCCATCT TGGTGGTGGG GTGTGGTGTT TGAGTATTGG ATAGTGGTTG CGAGCATCTA
GATGAGCGCG TAGTCCTTCG TGGCTGATGC GTTCATCGAA ATGTGTAATT TCTTCTTTGG TTTTGGGTGT
GT (SEQ ID NO 82)

Figure 8

AAGGAGCACC ACGAAAAGCA CTCCAATTGG TGGGGTGCGA GCCGTGAGGG GTTCCCGTCT GTAGTGGACG
GGGCCCGGGT GCACAACAGC AAATGATCGC CAGACACACT ATTGGGCCCT GAGACAACAC TCGGTCGATC
CGTGTGGAGT CCCTCCATCT TGGTGGTGGG GTGTGGTGTT TGAGTATTGG ATAGTGGTTG CGAGCATCTA
GATGAGCGCA TAGTCCCTTTG GGGCTGATGT GTTTCATCAA AATGTGTAAT TTCTTTTTNG GTTTTNGTGT
GT (SEQ ID NO 83)

Figure 9

```
AAGGAGCACC ACGAAAAGCA CTCCAATTGG TGGGGTGCGA GCCGTGAGGG GTTCTCGTCT GTAGTGGACG
GGAGCCGGGT GCACAACAGC AAATGATTGC CAGACACACT ATTGGGCCCT GAGACAACAC TCGGTCGATC
CGTGTGGAGT CCCTCCATCT TGGTGGTGGG GTGTGGTGTT TGAGTATTGG ATAGTGGTTG CGAGCATCTA
GATGAGCGCG TAGTCCTTCG TGGCTGATGC GTTCATTGAA ATGTGTAATT TCTTCTCTGG TTTTGTGTG
T
```

(SEQ ID NO 84)

Figure 10

AAGGAGCACC ACGAAAAGCA CTCCAATTGG TGGGGTGCGA GCCCGTGAGGG GTTCCCGTCT GTAGTGGACG
GGGGCCGGGT GCACAACAGC AAATGATTGC CAGACACACT ATTGGGCCCT GAGACAACAC TCGGTCGATC
CGTGTGGAGT CCCTCCATCT TGGTGGTGGG GTGTGGTGTT TGAGTATTGG ATAGTGGTTG CGAGCATCTA
GATGAGCGCA TAGTCCTTGT GGCTGATGCG CTCGTCGAAA TGTGTAATTT CTTCTTTGGT TTTTGTGTGT (SEQ ID NO 85)

Figure 11

AAGGAGCACC ACGAAAAGCA CTCCAATTGG TGGGGTGCGA GCCGTGAGGG GTTCCCGTCT GTAGTGGACG
GGGGCCGGGT GCGCAACAGC AAATGATTGC CAGACACACT ATTGGGCCCT GAGACAACAC TCGGTCGATC
CGTGTGGAGT CCCTCCATCT TGGTGGTGGG GTGTTGGTGT TTGAGTATTG GATAGTGGTT GCGAGCATCT
AGATGAGCGC GTAGTCCTTG TGGCTGATGC GTTCGTCGAA ATGTGTAATT TCTTCTTTGG GTTTTTGTGT
GT (SEQ ID NO 86)

Figure 12

AAGGAGCACC ACGAAAAGCA CCCCAATTGG TGGGGTGCGA GCCGTGAGGG GTTCTCGTCT GTAGTGGACG
GNAGCCGGNT GCGCAACAGC AAATGATTGC CAGACACACT ATTGGGCCCT GAGACAACAC TCGGNCGATC
CGTGTGGAGT CCCTCCATCT TGGTGGTGGG GTGTNGTGTT TGAGTATTGG ATAGTGGTTG CGAGCATCTA
GATGGGCGCG TAGTCCTTTG TGACTGATGC GTTCATCAAA ATGTGTAATT TCTTTTTTGN NTTTNGTGTG
T (SEQ ID NO 87)

Figure 13

AAGGAGCACC ACGAAAAGCA CTCCAATTGG TGGGGTGCGA GCCGTGAGGG GTTCTCGTCT GTAGTGGACG
GGAACCGGGT GCACAACAGC AAATGATTGC CAGACACACT ATTGGGCCCT GAGACAACAC TCGGTCGATC
CGTGTGGAGT CCCTCCATCT TGGTGGTGGG GTGTGGTGTT TGAGTATTGG ATAGTGGTTG CGAGCATCTA
GATGAGCGCA TAGTCCTTTG TGGCTGACGC GTTCATCGAA ATGTGTAATT TCTTCTTTGG TTTTTGTGTG
T (SEQ ID NO 88)

Figure 14

```
AAGGAGCACC ACGAAAAGCA CTCCAATTGG TGGGGTGCGA GCCGTGANGG GTTCCCGTCT GTAGTGGACG
GGGGCCGGGT GCACAACAGC AAATGATTGC CAGACACACT ATTGGGCCCT GAGACAACAC TCGGTCGATC
CGTGTGGAGT CCCTCCATCT TGGTGGTGGG GTGTGGTGTT TGAGTATTGG ATAGTGGTTG CGAGCATCTA
GATGAGCGCA TAGTCCTTAG GGCTGATGCG TTCGTCGNAA TGTGTAATTT CTTCTTTGGT TTTTGTGTGT
```

(SEQ ID NO 89)

Figure 15

AAGGAGCACC ACGAAAAGCA TCCCAATTGG TGGGGTGCGA GCCGTGAGGG GTTCTCGTCT GTAGTGGACG
AAACCGGGT GCACAACAGC AAATAATTGC CAGACACACT ATTGGGCCCT GAGACAACAC TCGGTCGATC
CGTGTGGTGT CCCTCCATCT TGGTGGTGGG GTGTGGTGTT TGAGTATTGG ATAGTGGTTG CGAGCATCTA
GATGAACGCG TAGTCCTTCG TGGCTGACGT GTTCATCGAA ATGTGTAATT TCTTNTNTTA ACTCTTGTGT
GT (SEQ ID NO 90)

Figure 16

AAGGAGCACC ACGAAAAGCA CCCCAATTGG TGGGGTGCGA GCCGTGAGGG GTTCTCGTCT GTAGTGGACG
GGAGCCGGGT GCACAACAGC AAATGATTGC CAGACACACT ATTGGGCCCT GAGACAACAC TCGGTCAGTC
CGTGTGGTGT CCCTCCATCT TGGTGGTGGG GTGTGGTGTT TGAGTATTGG ATAGTGGTTG CGAGCATCTA
GATGAACGCG TAGTCCTTGT GACTGACGTG TTCATCGAAA TGTGTAATTT CTTTTCTAAC TCTTGTGTGT (SEQ ID NO 91)

Figure 17

AAGGAGCACC ACGAAAAGCA CTTCAATTGG TGAAGTGCGA GCCGTGAGGG GTTCTCGTCT GTAGTGGACG
AAAGCCGGGT GCACAACAGC AAATGATTGC CAGACACACT ATTGGGCCCT GAGACAACAC TCGGTCGAAC
CGTGTGGAGT CCCTCCATCT TGGTGGTCGG GTGTGGTGTT TGAGTATTGG ATAGTGGTTG CGAGCATCTA
GATGAACGCG TGGTCTTCAT GGCCGGGCGTG TTCATCGAAA TGTGTAATAT CTTCTCTGGT TTTCGGTGTG
T (SEQ ID NO 92)

Figure 18

AAGGAGCACC ACGAAAAGCA CTTCAATTGG TGAAGTGCGA GCCGTGAGGG GTTCTCGTCT GTAGTGGACG
AAAACCGGNT GCACAACAGC AAATGATTGC CAGACACACT ATTGGGCCCT GAGACAACAC TCGGTCGATC
CGTGTGGAGT CCCTCCATCT TGGTGGTGGG GTGTGGTGTT TGAGTATTGG ATAGTGGTTG CGAGCATCTA
GATGAACGCG TGGTCTTCAT GGCCGGCGTG TTCATCGAAA TGTGTAATTT CTTTTNNAC TCTTGTGTGT (SEQ ID NO 93)

Figure 19

AAGGAGCACC ACGAAAAGCA CTTCAATTGG TGAAGTGCGA GCCGTGAGGG GTTCTCGTCT GTAGTGGACG
AAGCCGGGT GCACAACAGC AAATGATTGC CAGACACACT ATTGGGCCCT GAGACAACAC TCGGTCGAAC
CGTGTGGAGT CCCTCCATCT TGGTGGGTGGG GTGTGGTGTT TGAGTATTGG ATAGTGGTTG CGAGCATCTA
GATGAACGCG TGGTCTTCAT GGCCGGCGTG TTCATCGAAA TGTGTAATTT CTTCTTTGGT TTTNGTGTGT (SEQ ID NO 94)

Figure 20

AAGGAGCACC ACGAAAAGCA CTTCAATTGG TGAAGTGCGA GCCGTGAGGG GTTCTCGTCT GTAGTGGACG
AAACCGGGT GCACAACAGC AAATGATTGC CAGACACACT ATTGGGCCCT GAGACAACAC TCGGTCGATC
CGTGTGGAGT CCCTCCATCT TGGTGGTGGG GTGTGGTGTT TGAGTATTGG ATAGTGGTTG CGAGCATCTA
GATGAACGCG TAGTCCTTCG NGGNCNGCGT GTTCATCGAA ATGTGTAATT TCTNTTNTAA CTCTNGTGTG
T (SEQ ID NO 95)

Figure 21

AAGGAGCACC ACGAAAAGCA TCCCAATTGG TGGGGTGTGA GCCGTGAGGG GTTCTCGTCT GTAGTGGACG
AAACCGGGT GCACAACAGC AAATGATTGC CAGACACACT ATTGGGCCCT GAGACAACAC TCGGTCGATC
CGTGTGGAGT CCCTCCATCT TGGTGGTGGG GTGTGGTGTT TGAGTATTGG ATAGTGGTTG CGAGCATCTA
GATGAACGCG TAGTCCTTCG GGGCCGGCGT GTTCATCGAA ATGTGTAATT TCTTTTTTAA CTCTTGTGTG
T (SEQ ID NO 96)

Figure 22

```
AAGGAGCACC ACGAAAAGCA CTTCANTTGG TGAAGTGCGA GCCGTGAGGG GTTCTCGTCT GTAGTGGACG
AAAACCGGGT GCACAACAGC AAATGATTGC CAGACACACT ATTGGGCCCT GAGACAACAC TCGGTCGAAC
CGTGTGGAGT CCCTCCATCT TGGTGGTGGG GTGTGGTGTT TGAGTATTGG ATAGTGGTTG CGAGCATCTA
GATGAACGCG TGGTCTTCAT GGCCGGGCGTG TTCATCGAAA TGTGTAATTT CTTCTTTAAC TCTTGTGTGT
```

(SEQ ID NO 97)

Figure 23

AAGGAGCACC ACGAAAAGCA CTTCAATTGG TGAAGTGCGA GCCGTGAGGG GTTCTCGTCT GTAGTGGACG
AAACCGGGT GCACAACAGN AAATGATTGC CAGACACACT ATTGGGCCCT GAGACAACAC TCGGTCGATC
CGTGTGGAGT CCCTCCATCT TGGTGGTGGG GTGTGGTGTT TGAGTATTGG ATAGTGGTTG CGAGCATCTA
GATGAACGCG TGGTCTTCAT GGCCNGCCGTG TTCATCGAAA TGTGTAATTT CTTTTTTAAC TCTTGTGTGT (SEQ ID NO 98)

Figure 24

AAGGAGCACC ACGAAAAGCA CTTCAATTGG TGAAGTGCGA GCCGTGAGGG GTTCTCGTCT GTAGTGGACG
AAAACCGGGT GCACAACAGC AAATGATTGC CAGACACACT ATTGGGCCCT GAGACAACAC TCGGTCGATC
CGTGTGGAGT CCCTCCATCT TGGTGGTGGG GTGTGGGTGTT TGAGTATTGG ATAGTGGTTG CGAGCATCTA
GATGAACGCG TGGTCTTCAT GGCCGGGCGTG TTCATCGAAA TGTGTAATTT CTTTTTTAAC TCTTGTGTGT (SEQ ID NO 99)

Figure 25

AAGGAGCACC ACGAAAAGCA CCCCAACTTG TGGGGTGCGA GCCGTGAGGG GTCCTCGCCT GTAGTGGGCG
GGGGCCGGGT GCACAACAGC AAATGATTGC CAGACACACT ATTGGGCCCT GAGGCAACAC TCGGCTCGTT
CTGAGTGGTG TCCCTCCATC TTGGTGGTGG GGTGTGGTGT TTGAGTATTG GATAGTGGTT GCGAGCATCT
AAACGGATGC GTGGCCGGCA ACGGTGGCGT GTTCGTTGAA ATGTGTAATT TCTTTTTTGG TTTTTGTGTG
T (SEQ ID NO 100)

Figure 26

AAGGAGCACC ACGAAAAGCA TCCCAACAAG TGGGGTGCAA NCCGTGAGGG GTTCTCGTCT GTAGTGGACG
AAAGCCGGGT GCACGACAAC AAGCAAAGCC AGACACACTA TTGGGTCCTG AGGCAACACT CGGGCTCTGT
TCGAGAGTTG TCCCACCATC TTGGTGGTGG GGTGTGGTGT TTGAGAATTG GATAGTGGTT GCGAGCATCA
AATGGATGCG TTGCCCTACG GGTAGCGTGT TCTTTTGTGC AATTTTATTC TTTGGTTTTT GTGT (SEQ ID NO 101)

Figure 27

AAGGAGCACC ATTTCCCAGT CGATGAACTA GGGAACATAA AGTAGGCATC TGTAGTGGAT ATCTACTTGG
TGAATATGTT TTGTAAATCC TGTCCACCCC GTGGATGGGT AGTCGGCAAA ACGTCGGACT GTCATAAGAA
TTGAAACGCT GGCACACTGT TGGGTCCTGA GGCAACACGT TGTGTTGTCA CCCTGCTTGG TGGTGGGGTG
TGGACTTTGA CTTCTGAATA GTGGTTGCGA GCATCTAAAC ATAGCCTCGC TCGTTTTCGA GTGGGGCTGG
TTTTGCAATT TTA (SEQ ID NO 102)

Figure 28

AAGGAGCACC ATTTCCCAGT CGGATGAACT AGGGAACATA AAGTAGGCAT CTGTAGTGGG TATCTACTTG
GTGAATATGT TTTGTAAATC CTGTCCACCC CCGTGGATGG GTAGTCGGCA AAACGTCGGA CTGTCATAAG
AATTGAAACG CTGGCACACT GTTGGGTCCT GAGGCAACAC GTTGTGTTGT CACCCTGCTT GGTGGTGGGG
TGTGGACTTT GACTTCTGAA TAGTGGTTGC GAGCATCTAA ACATAGCCTC GCTCGTTTTC GAGTGAGGCT
GGTTTTTGCA ATTTTA (SEQ ID NO 103)

Figure 29

AAGGAGCACC ACGAAGAGCA CTCCAATTGG TGGGGTGCGA GCCGTGAGGG GTCATCGTCT GTAGTGGACG
AAGACCGGGT GCACGACAAC AAGCTAAGCC AGACACACTA TTGGGTCCTG AGGCAACACC CTCGGGTGCT
GTCCCCCCAT CTTGGTGGTG GGGTGTGGTG TTTGAGAATT GGATAGTGGT TGCGAGCATC AAAATGTATG
CGTTGTCGTT CTCGGCAACG TGTTCTTTTT GTGCAATTTA TTCTTTGGTT TTTGTAGTGT TTGT (SEQ ID NO 104)

Figure 30

AAGGAGCACC ACGAAGAGCA CTCCAATTGG TGGGGTGCCGA GCCGNGAGGG GTCATCGTCT GTAGTGGACG
AAGACTGGGT GCACGACAAC AAAGCAAGCC AGACACACTA TTGGGTCCTG AGGCAACACC CTCGGGTGCT
GCCCCTCCAT CTTGGTGGTG GGGTGTGGTG TTTGAGAACT GGATAGTGGT TGCGAGCATC AAAAATGTAT
GCGTTGTCGT TCGCGACAAC GTGTTCTTTT TGTGCAATTT TAATTCTTTT GGTTTTGGTA GTGTTTGT (SEQ ID NO 105)

Figure 31

AAGGAGCACC ACGAGAAGCA CTCCAATTGG TGGGGTGCAA GCCGTGAGGG GTCATCGTCT GTAGTGGACG
AAGACCGGGT GCACGACAAC AAGCAAAGCC AGACACACTA TTGGGTCCTG AGGCAACACC CTCGGGTGCT
GTCCCCCAT CTTGGTGGTG GGGTGTGGTG TTTGAGAACT GGATAGTGGT TGCCAGCATC AAAATGTATG
CGTTGTCGTT CGCGGCAACG TGTTCTTTT GTGCAATTTT TATTCTTTGG TTTTTGTAGT GTTTGT (SEQ ID NO 106)

Figure 32

AAGGAGCACC ACGAAAAGCA CCCCAATTGG TGGGGTGCAA GCCGTGAGGG GTTCCCGCCT GTAGTGGGCG
GGGCCGGGTG CGCAACAGCA AATGATTGCC AGACACACTA TTGGGCCCTG AGGCAACACT CGGATCGATT
GAGTGCTTGT CCCCCATCT TGGTGGTGG GTGTGGTGTT TGAGAACTGG ATAGTGGTTG CGAGCATCTA
AATGAACGCA CTGCCGATGG TGGTGTGTTC GTTTGTGTA ATTTATTCT TTGGTTTTTG TGTTTGT (SEQ ID NO 107)

Figure 33

AAGGAGCACC ACGAAAAGCA CTCCAATTGG TGGGGTGCGA GCCGTNAGGG GTTCTCGTCT GTAGTGGATG
GCAGCCGGGT GCACANCAGC AAATGATTGC CAGACACACT ATTGGGCCCT GAGACAACAC TCGGTCAGTC
CGTGTGGAGT CCCTCCATCT TGGTGGTGGG GTGTGGNGTT TGAGTATTGG ATAGTGGTTG CGANCATCTA
GATGAACGCG TAGTCCTCNG TGGCTGACGT GTTCATCAAA ATGTGTAATT TCTTTTANGG GTTTNGGTGT
CT (SEQ ID NO 108)

Figure 34

```
AAGGAGCACC ACGAAAGCA CTCCAATTGG TGGGGTGCGA GCCGNGAGGG GTTCTCGCCT GTAGTGGNCG
AGGGCCGGAT GCACAACAAC ACATGATTGC CAGACACACT ATTGGGCCCT GANACAACAC TCGGCCAGTC
CGTGGGTGT CCCTCCATCT TGGTGGTGGG GTGTGGTGTT TGAGTATNGG ATAGTNGTTG NGANCATCTA
AACGGCTGCG TNGNCNNGAA CGGTGGCGTG TTCGNTAAAA TGTGTAATTT CTTTTNNGGT TTGGGTGTNT
```

(SEQ ID NO 109)

Figure 35

```
AAGGAGCACC ACGAAAAGCA CTCCAATTGG TGGGGTGCCGA GCCGTGAGGG GTTCTCGCCT GTAGTGGGCG
ANGGCCGGGT GCACAACAAC AAATGATTGC CAGACACACT ATTGGGCCCT GAGACAACAC TCGGCCAGTC
CGTGTGGTGT CCCNCCATCT TGGTGGTGGG GTGTGGTGTT TGAGTATTGG ATAGTGGTTG CGAGCATCTA
AANGGNTGCG TTGCCGNNAN CNGTGGCGTN TTCGNTAAAA TGTGTAANTT CTTTTTNGGT TTGTGTGTGT
```

(SEQ ID NO 110)

Figure 36

```
ATCGAAGATC CCGGCTTCTT CATAAGCTCC CACACGAATT GCTTGATTCA CTGGTTAGAC GATTGGGTCT
GTAGCTCAGT TGGTTAGAGC GCACCCCTGA TAAGGGTGAG GTCGGCAGTT CGAATCTGCC CAGACCCACC
AATTGTTGGT GTGCTGCGTG ATCCGATACG GGCCATAGC TCAGCTGGGA GAGCGCCTGC TTTGCACGCA
GGAGGTCAGG AGTTCGATCC TCCTTGGCTC CACCATCTAA AACAATCGTC GAAAGCTCAG AAATGAATGT
TCGTGGATGA ACATTGATTT CTGGTCTTTG CACCAGAAACT GTTCTTAAA AATTCGGGTA TGTGATAGAA
GTAAGACTGA ATGATCTCTT TCACTGGTGA TCATTCAAGT CAAGGTAAAA TTTGCGAGTT CAAGGCGAA
TTTCGGGCGA ATGTCGTCTT CACAGTATAA CCAGATTGCT TGGGGTTATA T
```

(SEQ ID NO 111)

Figure 37

```
ATCGAAGACA TCAGCTTCTT CATAAGTATC CACACGAATT GCTTGATTCA TAGTCGAACG AATGCTGTAA
CGCGACCCGT GTTATAGGTC TGTAGCTCAG TTGGTTAGAG CGCACCCCTG ATAAGGGTGA GGTCGGCAGT
TCAAATCTGC CCAGACCTAC CAATTGCTTG GTCGAGAAGA ATACGGGGCC ATAGCTCAGC TGGGAGAGCG
CCTGCCTTGC ACGCAGGAGG TCAGCGGGTC GATCCCGCTT GGCTCCACCA CTCTCTCGTG TTGCGGTGAG
TGTTAAAGAG TTCAGAAATG ATGCCGCTTC AGGTTTGTCC TGTTGAGTGC TGATTTCTGG TCTTTTGACC
GGTACGAAAA TCGTTCTTTA AAAATTGGA TATGTGATAG AAGTGACTGA TTAATTGCTT TCACTGGCAA
TTGATCTGGT CAAGGTAAAA TTTGTAGTTC TCAAGACGCA AATTTTCGGC GAATGTCGTC TTCACGATTG
AGACAGTAAC CAGATTGCTT GGGGTTATAT
```

(SEQ ID NO 112)

Figure 38

ATCGAAGACA CCGGCTTCGT CATAAGCTCC CACACGAATT GCTTGATTCA CTTGCGAAAG GCGATTGGGT
TTAGACCCGA GAGTAACGAT TGGGTCTGTA GCTCAGTTGG TTAGAGCGCA CCCCTGATAA GGGTGAGGTC
GGCAGTTCGA ATCTGCCCAG ACCCACCAAT CGAAGGGGCC ATAGCTCAGC TGGGAGAGCG CCTGCTTTGC
ACGCAGGAGG TCAGCGGTTC GATCCCGCTT GGCTCCACCA TTAACTCTAG TCGCCGAAAG CTCAGAAATG
AGTGTTTACC AGGATGAGGT TGATTGCCTG GGTTGAACAT TGATTTCTGG ACTTTGCGCC AGAACTGTTC
TTTAAAAATT TGGGTATGTG ATAGAAGTAG ACCGATGTGT TGCTTTCACT GGCAGCATGT CGCGTCAAGG
TAAATTTGC GTGTTCTCTA TGCAAATTTT CGGCGAATGT CGTCTTCACG TTATAGACAG TAACCAGATT
GCTTGGGGTT ATAT (SEQ ID NO 113)

Figure 39

ATCGAAGACT TCAGCTTCTT CATAAGTTCC CACACGAATT GCTTGATTCA CTTGCGAAAA GCGATTGGGT
TGAGACCCGA GAGTGACGAT TGGGTCTGTA GCTCAGTTGG TTAGAGCGCA CCCCTGATAA GGGTGAGGTC
GCCAGTTCGA ATCTGCCCAG ACCCACCAAT TGTCGGGATG GCCAGTGTCA AATGGGGCCA TAGCTCAGCT
GGGAGAGCGC CTGCTTTGCA CGCAGGAGGT CAGGAGTTCG ATCCTCCTTG GCTCCACCAT CAACTCACGA
TCGCTGAAAG CTCAGAAATG AACATTGGTA GTTCAATGTT GATTTCTGGT CTTTGCGCCA GAACTGTTCT
TTAAAAATTT GGGTATGTGA TAGAAGTGAC TAACAGCCGT TTTCACTGCA CGTTGTTAAT CAAGGCAAAA
TTTGCGAGTT CAAGCGCGAA TTTTCGGCGA ATGTCGTCTT CACGTTACGA ATCTATAACC AGATTGCTTG
GGGTTATAT (SEQ ID NO 114)

Figure 40

```
ATCGACGACA TCAGCTGTCT CATAAGCTCC CACACGAATT GCTTGATTCA TTGAAGAAGA CGATTAGGTT
AGCAACCTTC GATTGGGTCT GTAGCTCAGT TGGTTAGAGC GCACCCCTGA TAAGGGTGAG GTCGGCAGTT
CGAATCTGCC CAGACCCACC AATTTGCTGG GGCCATAGCT CAGCTGGGAG AGCGCCTGCC TTGCACGCAG
GAGGTCAGCG GTTCGATCCC GCTTGGCTCC ACCACCCCGC TTGCCAGTTT GTCAAAGCTT AGAAATGAAT
ATTCGCGTCG AATATTGATT TCTGAACTTT ATCAGAATCG TTCTTTAAAA ATTTGGGTAT GTGATAGAAA
GATAGACTGG ACAGCACTTT CACTGGTGTG TGTTCAGGCT AAGGTAAAAT TTGTGAGTAA TTACAAGTTT
TCGGCGAATG TTGTCTTCAC AGTATAACCA GATTGCTTGG GGTTATAT
```

(SEQ ID NO 115)

Figure 41

TAAGGAAAAG GAAACCTGTG AGTTTTCGTT CTTCTCTGTT TGTTCAGTTT TGAGAGGTTA ATTCTTCTCT
ATACTGTTTG TTCTTTGAAA ACTAGATAAG AAAGTTAGTA AAGTTAGCAT AAATAGGTAA CTATTTATGA
CACAAGTAAC CGAGAATCAT CTGAAAGTGA ATCTTTCATC TGATTGGAAG TATCATCGCT GATACGAAAA
ATCAGAAAAA CAACCTTTAC TTCATCGAAG TAAATT (SEQ ID NO 116)

Figure 42

CTAAGGAAAA GGAAACCTGT GAGTTTTCGT TCTTCTCTAT TTGTTCAGTT TTGAGAGGTT AGTACTTCTC
AGTATGTTTG TTCTTTGAAA ACTAGATAAG AAAGTTAGTA AAGTTAGCAT AGATAATTTA TTATTTATGA
CACAAGTAAC CGAGAATCAT CTGAAAGTGA ATCTTTCATC TGATTGGAAG TATCATCGCT GATACGGAAA
ATCAGAAAAA CAACCTTTAC TTCGTAGAAG TAAATT (SEQ ID NO 117)

Figure 43

TAAGGAAAAG GAAACCTGTG AGTTTTCGTT CTTCTCTGTT TGTTCAGTTT TGAGAGGTTA TTACTTCTCT
GTATGTTTGT TCTTTGAAAA CTAGATAAGA AAGTTAGTAA AGTTAGCATA AGTAGTGTAA CTATTTATGA
CACAAGTAAC CGAGAATCAT CTGAAAGTGA ATCTTTCATC TAATTCGACG TATCATCGCT GATACAGACA
ATTAGAAAAA CAACCTTTAC TTCGACGAAG TAAATT (SEQ ID NO 118)

Figure 44

GGCCTATAGC TCAGCTGGTT AGAGCGCACG CCTGATAAGC GTGAGGTCGA TGGTTCGAGT CCATTTAGGC
CCACTTTTC TTTCTGACAG AAGAAACACT GTATAACCTA TTTAAGGGGC CTTAGCTCAG CTGGGAGAGC
GCCTGCTTTG CACGCAGGAG GTCAGCGGTT CGATCCCGCT AGGCTCCACC AAAATTGTTC TTTGAAAACT
AGATAAGAAA GTTAGTAAAG TTAGCATAAA TAGGTAACTA TTTATGACAC AAGTAACCGA GAATCATCTG
AAGTGAATC TTTCATCTGA TTGGAAGTAT CATCGCTGAT ACGAAAAATC AGAAAAACAA CCTTTACTTC
ATCGAAGTAA ATT (SEQ ID NO 119)

Figure 45

TAAGGAAAAG GAAACCTGTG AGTTTTCGTT CTTCTCTATT TGTTCAGTTT TGAGAGGTTA CTCTCTTTTA
TGTCAGATAA AGTATGCAAG GCACTATGCT TGAAGCATCG CGCCACTACA TTTTTGACGG GCCTATAGCT
CAGCTGGTTA GAGCGCACGC CTGATAAGCG TGAGGTCGAT GGTTCGAGTC CATTTAGGCC CACTTTTTCT
TTCTGACATA AGAAATACAA ATAATCATAC CCTTTTACGG GGCCTTAGCT CAGCTGGGAG AGCGCCTGCT
TTGCACGCAG GAGGTCAGCG GTTCGATCCC GCTAGGCTCC ACCAAAATTG TTCTTTGAAA ACTAGATAAG
AAAGTTAGTA AAGTTAGCAT AGATAATTTA TTATTTATGA CACAAGTAAC CGAGAATCAT CTGAAAGTGA
ATCTTTCATC TGATTGGAAG TATCATCGCT GATACGGAAA ATCAGAAAAA CAACCTTTAC TTCGTAGAAG
TAAATT (SEQ ID NO 120)

Figure 46

```
TAAGGAAAAG GAAACCTGTN AGTTTNCGTN CTTCTCTGTT TGTNCAGTTT TNAGAGGTTA CTCTCTTTNA
TGTCAGATAA AGTACGCACG GCACGTTGCC TTGGGCAAAG AGCCACTACA TTATTGACGG GCCTATAGCT
CAGCTGGTTA GAGCGCACGC CTGATAAGCG TGAGGTCGAT GGTTCGAGTC CATTTAGGCC CACTTTTCT
TTCTGACAGA AGAAATCATT TGCACATCCT ATTAATAAGG GNCCTTAGCT CAGCTGGGAG AGCGCCTGCT
TTGCACGCAG GAGGTCAGCG GTTCGATCCC GCTAGGCTCC ACCCAAAATT GTTCTTTGAA AACTAGATAA
GAAAGTTAGT AAAGTTAGCA TAAGTAGTAT AACTATTTAT GACACAAGTA ACCGAGAATC ATCTGAAAGT
GAATCTTTCA TCTAATTCGA CGTATCATCG CTGATACAGA CAATTNGAAA AACAACCTTT ACTTCGACGA
AGTAAATT
```

(SEQ ID NO 121)

Figure 47

TAAGGATAAG GATAACTGTC TTAGGACGGT TTGACTAGGT TGGGCAAGCG TTTTTTTAAT CTTGTATTCT
ATTCCTTTTG CATTGTTAAG CGTTGTTTCC AAAACATTTA GTTACGATC AAGTATGTTA TGTAAATAAT
ATGGTAACAA GTAAATTCAC ATATAATAAT AGACGTTTAA GAATATATGT CTTTAGGTGA TGTTAACTTG
CATGGATCAA TAATTTACA (SEQ ID NO 122)

Figure 48

TAAGGATAAG GAAGAAGCCT GAGAAGGTTT CTGACTAGGT TGGGCAAGCA TTTATATGTA AGAGCAAGCA
TTCTATTTCA TTTGTGTTGT TAAGAGTAGC GTGGTGAGGA CGAGACATAT AGTTTGTGAT CAAGTATGTT
ATTGTAAAGA AATAATCATG GTAACAAGTA TATTTCACGC ATAATAATAG ACGTTTAAGA GTATTTGTCT
TTTAGGTGAA GTGCTTGCAT GGATCTATAG AAATTACA (SEQ ID NO 123)

Figure 49

CAAATGGAGT TTTTATTTTT TATTTATCTT AAACACCCAT TAATTTTTTC GGTGTTAAAA CCCAAATCAA
TGTTTGGTCT CACAACTAAC ACATTGGTC AGTTGTATC CAGTTCTGAA AGAATGTTTT TGAACAGTTC
TTTCAAAACT GAAAACGACA ATCTTTCTAG TTCCAAAAAT AAATACCAAA GGATCAATAC AATAAGTTAC
TAAGGGCTTA TGGT (SEQ ID NO 124)

Figure 50

CTAATGAAGT TTTTTACTTT TTCTTTTCAT CTTTAATAAA GATAAATACT AAACAAAACA TCAAAATCCA
TTTATTTATC GGTGGTAAAT TAAACCCAAA TCCCTGTTTG GTCTCACAAC TAACATATTT GGTCAGATTG
TATCCAGTTC TGAAAGAACA TTTCCGCTTC TTTCAAAACT GAAAACGACA ATCTTTCTAG TTCCAAATAA
ATACCAAAGG ATCAATACAA TAAGTTACTA AGGGCTTATG GT (SEQ ID NO 125)

Figure 51

AACGAAAGAT TGACGATTGG TAAGAATCCA CAACAAGTTG TTCTTCATAG ATGTATCTGA GGGTCTGTAG
CTCAGTTGGT TAGAGCACAC GCTTGATAAG CGTGGGGTCA CAAGTTCAAG TCTTGTCAGA CCCACCATGA
CTTTGACTGG TTGAAGTTAT AGATAAAAGA TACATGATTG ATGATGTAAG CTGGGGACTT AGCTTAGTTG
GTAGAGCGCC TGCTTTGCAC GCAGGAGGTC AGGAGTTCGA CTCTCCCTAGT CTCCACCAGA ACTTAAGATA
AGTTCGGATT ACAGAAATTA GTAAATAAAG ATTGAGATCT TGGTTTATTA ACTTCTGTGA TTTCATTATC
ACGGTAATTA GTGTGATCTG ACGAAGACAC ATTAACTCAT TAACAGATTG GCAAAATGA GTCTGAAATA
AATTGTTCAC TCAAGAGTTT AGGTTAAGCA ATTAATCTAG ATGAATTGAG AACTAGCAAA TTAACTGAAT
CAAGCGTTTT GGTATGTGAA TTTAGATTGA AGCTGTACAG TGCTTAAGTG CACAGTGCTC TAAACTGAAA
TGTTGAAGTT ACTAACTTGT AGTAACATC GACTGTTTGG GGTTGTAT (SEQ ID NO 126)

Figure 52

AACGAAAGAT TGACGATTGG TAAGAATCCA CGACAAGTTG TTCTTCATAG ATGTATCTGA GGGTCTGTAG
CTCAGTTGGT TAGAGCACAC GCTTGATAAG CGTGGGGTCA CAAGTTCAAG TCTTGTCAGA CCCACCATGA
CTTTGACTGG TTGAAGTTAT AGAAAAGAAG ATACATAACT GATGATGTAA GCTGGGGACT TAGCTTAGTT
GGTAGAGCGC CTGCTTTGCA CGCAGGAGGT CAGGAGTTCG ACTCTCCCTAG TCTCCACCA (SEQ ID NO 127)

Figure 53

AACGAAAGAT TGATGGCCGG TAAGAATCCA CAACAAGTTG TTCTTCGAAG ATGTATCTGA GGGTCTGTAG
CTCAGTTGGT TAGAGCACAC GCTTGATAAG CGTGGGGTCA CAAGTTCAAG TCTTGTCAGA CCCACCAAAT
CTGAAAGATA TGTCGTTCAT TATGATTAAA GCTGGGGACT TAGCTTAGTT GGTAGAGCGC CTGCTTTGCA
CGCAGGAGGT CAGGAGTTCG ACTCTCCCTAG TCTCCACCA (SEQ ID NO 128)

Figure 54

AACGAAAGAT TGACGATTGG TAAGAATCCA CAACAAGTTG TTCTTCATGA CGATGTATCT GAGGGTCTGT
AGCTCAGTTG GTTAGAGCAC ACGCTTGATA AGCGTGGGGT CACAAGTTCA AGTCTTGTCA GACCCACCAA
ATCTGACTAA CAAGCATTAT TAAATGCTGA ATACAGAAAA ACAGAGACAT TGACTTATTG ATAAGCTGGG
GACTTAGCTT AGTTGGTAGA GCGCCTGCTT TGCACGCAGG AGGTCAGGAG TTCGACTCTC CTAGTCTCCA
CCA (SEQ ID NO 129)

Figure 55

AACGAAAGAT TGGTGACCGG TAAGAATCCA CAACAAGTTG TTCTTCGAAG ATGTATCTGA GGGTCTGTAG
CTCAGTTGGT TAGAGCACAC GCTTGATAAG CGTGGGGTCA CAAGTTCAAG TCTTGTCAGA CCCACCACTA
CTGACGAAGT GATGAATAAT CACAAGCTGC TAGATGAAAA GATATGTCGT TCATTATGAT TAAAGCTGGG
GACTTAGCTT AGTTGGTAGA GCGCCTGCTT TGCACGCCAGG AGGTCAGGAG TTCGACTCTC CTAGTCTCCA
CCA (SEQ ID NO 130)

Figure 56

```
TAAGGAAGAT CGAGAATTGG AAAGAGGTCG GATTTATCCG GATGATCCTT CTCCATCTTA TTAGAACATA
GATCGCAGGC CAGTCAGCCT GACGATCGCT TGCAGGCGTG CCGCCTTCGT TTCTCTTTCT TCATTGTTGA
TTGCTCACGG GCCGTACCGC AGCTGACGCT GCTGGCCCTG CGCAGGCGCG GCCCATCAGG GCCGACGGCC
GGTCGGCCTT GCNAAGCTTC GCTTCGGGGT GGATCTGTGG ATCGCGTAGT AGCGTTTGCG TCGGTATCTG
GGCTTGTAGC TCAGTTGGTT AGAGCACACG CTTGATAAGC GTGGGGTCGG AGGTTCAAGT CCTCCCAGGC
CCACCAAGTT ACTTGATGAG GGGCCGTAGC TCAGCTGGGA GAGCACCTGC TTTGCAAGCA GGGGTCGTC
GGTTCGATCC CGTCCGGCTC CACCATCATG TTGGTGTTGA GACGGATATT GGCAATCAAC AAAGAAAGA
AACAAGTTTG CGGACTNTTA CGAAAGTCTG CCTGTTCTGT ATGAAATCGT GAAGAGAAGA TGTAATCGGA
TCAACTGAAG AGTTGATGTC GCAAGAAGCT TGCTCAAGCC TTGCATAATG ATTGATGTGT TTAACCGCCA
TCACCGATTG TATCTCGAGA AGCTGGTCTT TCTGCTGATA CTGTTGAAAC GAGCATTGC AGTCGAATGG
CAACATTCGG CGTCGCATAA TGCGGCTTTA AGAGCTGAGT TTTGATGGAT ATTGGCAATG AGAGTGATCA
AGTGTCTTAA GGGCCATTGG GGATGCCCTTG GCATGCAC
```

(SEQ ID NO 131)

Figure 57

```
TAAGGAGGAT CGAGAATTGG AAAGAGGCCG GATTTATCCG GATGATCCTT CTCCATCTTA TTAGAACATA
GATCGCAGNC CAGTCAGCCT GACGATCGCT TGCAGGCGTG CCGCCTTCGT TTCTCTTTCT TCATTGTTGA
TTGCTCACGG GCCGTACCGC AGCTGACGCT GCTGGCCCTG CGCAGGCGCG GNCCATCAGG GCCGACGGCC
GGTCGGCCTT GCGAAGCTTC GCTTCGGGGT GGATCTGTGT AGCGCGTAGT AGCGTTTGCG TCGGTATCTG
GGCTTGTAGC TCAGTTGGTT AGAGCACACG CTTGATAAGC GTGGGGTCGG AGGTTCAAGT CCTCCCAGGC
CCACCAAGTT ACTTGATGAG GGGCCGTAGC TCAGCTGGGA GAGCACCTGC TTTGCAAGCA GGGGTCGTC
GGTTCGATCC CGTCCGGCTC CACCATCATG TTGGTGTTGA GACGGATATT GGCAATCAAC AAAAGAAAGA
AACAAGTTTG CGGACTNTTA CGAAAGTCTG CCTGTTCTGT ATGAAATCGT GAAGAGAAGA TGTAATCGGA
TCAACTGAAG AGTTGATGTC GCAAGAAGCT TGCTCAAGCC TTGCATAATG ATTGATGTGT TTAACCGCCA
TCACCGATTG TATCTCGAGA AGCTGGTCTT TCTGCTGATA CTGTTGAAAC GAGCATTTGC AGTCGAATGG
CAACATTCGG CGTCGCATAA TGCGGCTTTA AGAGCTGAGT TTTGATGGAT ATTGGCAATG AGAGTGATCA
AGTGTCTTAA GGGCCATTGG TGGATGCCTTG GCATGCAC
```

(SEQ ID NO 132)

Figure 58

CCTTAAAGAA CTGTTCTTTG CAGTGCTCAC ACAGATTGTC TGATGAAAAG TAAATAGCAA GGCGTCTTGC
GAAGCAGACT GATACGTCCC CTTCGTCTAG AGGCCCAGGA CACCGCCCTT TCACGGCGGT AACAGGGGTT
CGAATCCCCT AGGGACGCC ACTTGCGCGG TAATGTGTGA AAGCGTTGCC ATCAGTATCT CAAAACTGAC
TTACGAGTCA CGTTTGAGAT ATTTGCTCTT TAAAAATCTG GATCAAGCTG AAAATTGAAA CACAGAACAA
CGAAAGTTGT TCGTGAGTCT CTCAAATTTT CGCAACACGA TGATGAATCG TAAGAAACAT CTTCGGGTTG
TGA (SEQ ID NO 133)

Figure 59

CCTTAAAGAA CTGTTCTTTG CAGTGCTCAC ACAGATTGTC TGATGAAAAA CGAGCAGTAA AACCTCTACA
GGCTTGTAGC TCAGGTGGTT AGAGCGCACC CCTGATAAGG GTGAGGTCGG TGGTTCAAGT CCACTCAGGC
CTACCAAATT TTCCCTGAAT ACTGCGTTGT GAAATAACTC ACATACTGAT GTATGCTTCG TTATTCCACG
CCTTGTCTCA GGAAAAATTA TCGGTAAAGA GGTTCTGACT ACACGATGGG GCTATAGCTC AGCTGGGAGA
GCGCCTGCTT TGCACGCAGG AGGTCTGCGG TTCGATCCCG CATAGCTCCA CCATATCGTG AGTGTTTACG
AAAAATACT TCAGAGTGTA CCTGAAAGGG TTCACTGCGA AGTTTTGCTC TTTAAAAATC TGGATCAAGC
TGAAATTGA AACACAGAAC AACGAAAGTT GTTCGTGAGT CTCTCAAATT TTCGCAACAC GATGATGAAT
CGTAAGAAAC ATCTTCGGGT TGTGA (SEQ ID NO 134)

Figure 60

CCTTAAAGAA GCGTACTTTG CAGTGCTCAC ACAGATTGTC TGATGAAAAG TAAATAGCAA GGCGTCTTGC
GAAGCAGACT GATACGTCCC CTTCGTCTAG AGGCCCAGGA CACCGCCCTT TCACGGCGGT AACAGGGGTT
CGAATCCCCT AGGGGACGCC ACTTGCGCGG TAATGTGTGA AAGCGTTGCC ATCAGTATCT CAAAACTGAC
TTACGAGTCA CGTTTGAGAT ATTTGCTCTT TAAAAATCTG GATCAAGCTG AAAATTGAAA CACAGAACAA
CGAAAGTTGT TCGTGAGTCT CTCAAATTTT CGCAACACGA TGATGAATCG TAAGAAACAT CTTCGGGTTG
TGA (SEQ ID NO 135)

Figure 61

CCTTAAAGAA CTGTTCTTTG AAGTGCTCAC ACAGATTGTC TGATGAAAAA CGAGCAGTAA AACCCTCTACA
GGCTTGTAGC TCAGGTGGTT AGAGCGCACC CCTGATAAGG GTGAGGTCGG TGGTTCAAGT CCACTCAGGC
CTACCAAATT TTCCCTGAAT ACTGCGTTGT GAAATAACTC ACATACTGAT GTATGCTTCG TTATTCCACG
CCTTGTCTCA GGAAAAATTA TCGGTAAAGA GGTTCTGACT ACACGATGGG GCTATAGCTC AGCTGGGAGA
GCGCCTGCTT TGCACGCAGG AGGTCTGCGG TTCGATCCCG CATAGCTCCA CCATCTCGTG AGTGTTTACG
AAAAATACT TCAGAGTGTA CCTGAAAGGG TTCACTGCGA AGTTTGCTC TTTAAAAATC TGGATCAAGC
TGAAAATTGA AACACAGAAC AACGAAAGTT GTTCGTGAGT CTCTCAAATT TTCGCAACAC G (SEQ ID NO 136)

Figure 62

CCTTAAAGAA GCGTACTTTG AAGTGCTCAC ACAGATTGTC TGATGAAAAG TGAATAGCAA GGCGTCTTGC
GATTGAGACT TCAGTGTCCC CTTCGTCTAG AGGCCCAGGA CACCGCCTT TCACGGCGGT AACAGGGGTT
CGAATCCCCT AGGGACGCC AGCGTTCAAA CTGATGAGGT CAAACCTCCA GGGACGCCAC TTGCTGGTTT
GTGAGTGAAA GTCACCTGCC TTAATATCTC AAAACTGACT TACGAGTCAC GTTTGAGATA TTTGCTCTTT
AAAAATCTGG ATCAAGCTGA AAATTGAAAC ACAGAACAAC GAAAGTTGTT CGTGAGTCTC TCAAATTTTC
GCAACACGAT GATGAATCGT AAGAAACATC TTCGGGTTGT GA (SEQ ID NO 137)

Figure 63

CCTTAAAGAA ACGGTCTTTG AAGTGCTCAC ACAGATTGTC TGATGAAAAA CGACCAGTAA AACCCTCTACA
GGCTTGTAGC TCAGGTGGTT AGAGCGCACC CCTGATAAGG GTGAGGTCGG TGGTTCAAGT CCACTCAGGC
CTACCAAATT TTCCCTGAAT ACTGCGTTGT GAAATAACTC ACATACTGAT GTATGCTTCG TTATTCCACG
CCTTGTCTCA GGAAAAATTA TCGGTAAGA GGTTCTGACT ACACGATGGG GCTATAGCTC AGCTGGGAGA
GCGCCTGCTT TGCACGCAGG AGGTCTGCGG TTCGATCCCG CATAGCTCCA CCATCTCGTG AGTGTTTACG
AAAAATACT TCAGAGTGTA CCTGAAAGGG TTCACTGCGA AGTTTTGCTC TTTAAAAATC TGGATCAAGC
TGAAAATTGA AACACAGAAC AACGAAAGTT GTTCGTGAGT CTCTCAAATT TTCGCAACAC GATGATGAAT
CGTAAGAAAC ATCTTCGGGT TGTGA (SEQ ID NO 138)

Figure 64

CTAAGGATAT ATTCGGAACA TCTTCTTCGG AAGATGCGGA ATAACGTGAC ATATTGTATT CAGTTTTGAA
TGTTTATTTA ACATTCAAAT ATTTTTGGT TAAAGTGATA TTGCTTTTGA AAATAAAGCA GTATGCGAGC
GCTTGACTAA AAAAAATTGT ACATTGAAAA CTAGATAAGT AAGTAAAATA TAGATTTTAC CAAGCAAAAC
CGAGTGAATA AAGAGTTTTA AATAAGCTTG AATTCATAAG AAATAATCGC TAGTGTTCGA AAGAACACTC
ACAAGATTAA TAACGCGTTT AAATCTTTTT ATAAAAGAAC GTAACTTCAT GTTAACGTTT GACTTATAAA
AATGGTGGAA ACATA (SEQ ID NO 139)

Figure 65

CTAAGGATAT ATTCGGAACA TCTTCTTCAG AAGATGCGGA ATAACGTGAC ATATTGTATT CAGTTTTGAA
TGTTTATTTA ACATTCAAAT ATTTTTTGGT TAAAGTGATA TTGCTTATGC GAGCNCTTGA CAATCTATTC
TTTTGATTT AAGA AAGCGCTTGT CAGACAATGC ATTAAGAAAA ATTAAGCCGG AGTTTACTTT TGTAAATGAG
CATTTGATTT TTTGAAAATA AAGCAGTATG CGAGCGCTTG ACTAAAAAGA AATGTACAT TGAAAACTAG
ATAAGTAAGT AAAATATAGA TTTTACCAAG CAAAACCGAG TGAATAAAGA GTTTAAATA AGCTTGAATT
CATAAGAAAT AATCGCTAGT GTTCGAAAGA ACACTCACAA GATTAATAAC GCGTTTAAAT CTTTTTATAA
AAGAAAACGT TTAGCAGACA ATGAGTTAAA TTATTTTAAA GCAGAGTTTA CTTATGTAAA TGAGCATTTA
AAATAATGAA AACGAAGCCG TATGTGAGCA TTTGACTTAT AAAATGGTG GAAACATA (SEQ ID NO 140)

Figure 66

```
CTAAGGATAT ATTCGGAACA TCTTCTTCAG AAGATGCGGA ATAACGTGAC ATATTGTATT CAGTTTTGAA
TGTTTATTTA ACATTCAAAT ATTTTTGGT TAAAGTGATA TTGCTTATGC GAGCGCTTGA CAATCTATTC
TTTTAAAGA AAGCGGTTGT CAGACAATGC ATTAAGAAAA ATTAAAGCGG AGTTTACTTT TGTAAATGAG
CATTTGATTT TTTGAAAATA AAGCAGTATG CGAGCGCTTG ACTAAAANGA AATTGTACAT TGAAAACTAG
ATAAGTAAGT AAAATATAGA TTTTACCAAG CAAAACCGAG TGAATAAAGA GTTTTGAATA AGCTTGAATT
CATAAGAAAT AATCGCTAGT GTTCGAAAGA ACACTCACAA GATTAATAAC GCGTTTAAAT CTTTTTATAA
AAGAACGTAA CTTCATGTTA ACGTTTGACT TATAAAAATG GTGGAAACAT A
```

(SEQ ID NO 141)

Figure 67

CTAAGGATAT ATTCGGAACA TCTTCTTCAG AAGATGCGGA ATAACGTGAC ATATTGTATT CAGNTTTGAA
TGTTTATTTA ACATTCAAAA AATGGGCCTA TAGCTCAGCT GGTTAGAGCG CACGCCTGAT AAGCGTGAGG
TCGGTGGTTC GAGTCCACTT AGGCCCACCA TTATTTGTAC ATTGAAAACT AGATAAGTAA GTAAAATATA
GATTTACCA AGCAAAACCG AGTGAATAAA GAGTTTAAA TAAGCTTGAA TTCATAAGAA ATAATCGCTA
GTGTTCGAAA GAACACTCAC AAGATTAATA ACGCGTTTAA ATCTTTTTAT AAAAGAACGT AACTTCATGT
TAACGTTTGA CTTATAAAAA TGGTGGAAAC ATA (SEQ ID NO 142)

Figure 68

CTAAGGATAT ATTCGGAACA TCTTCYTCAG AAGATGCGGA ATAATGTGAC ATATTGTATT CAGTTTTGAA
TGTTTATTTA ACATTCAAAT ATTTTTGGT TAAAGTGATA TTGCTTATGC GAGCGCTTGA CTAAAAAGAA
ATTGTACATT GAAAACTAGA TAAGTAAGTA AAANTATAGA TTTTACCAAG CAAAACCGAG TGAATAAAGA
GTTTAAATA AGCTTGAATT CATAAGAAAT AATCGCTAGT GTTCGAAAGA ACACTCACAA GATTAATAAC
GCGTTAAAT CTTTTTATAA AAGAACGTAA CTTCATGTTA ACGTTTGACT TATAAAAATG GTGGAAACAT
A (SEQ ID NO 143)

Figure 69

CTAAGGATAT ATTCGGAACA TCTTCTACGA AGATGAGGGA ATAACGTGAC ATATTGTATT CAGTTTTGAA
TGTTTATTAA CATTCATTTG TACATTGAAA ACTAGATAAG TAAGTAAGAT TTTACCAAGC AAAACCGAGT
GAATAGAGTT TTAAATAAGC TTGAATTCAT AAATAATCGC TAGTGTTCGA AAGACNTCCA CAAGATTAAT
AACTAGTTTT AGCTATTTAT TTTGAATAAC AATTCAAAAT ATGGTGGGAC ATA (SEQ ID NO 144)

Figure 70

AAGGATAAGG AACTGCACAT TGGTCTTGTT TAGTCTTGAG AGGTCTTGTG GGGCCTTAGC TCAGCTGGGA
GAGCGCCTGC TTTGCACGCA GGAGGTCAGC GGTTCGATCC CGCTAGGCTC CGCTAGGCTC CATTGGTGAG AGATCACCAA
GTAATGCACA TTGAAAATTG AATATCTATA TCAAATAGTA ACAAGAAAAT AAACCGAAAA CGCTGTAGTA
TTAATAAAGA GTTTATGACT GAAAGGTCAA AAAATAA (SEQ ID NO 145)

Figure 71

AAGGAAATGG AACACGTTTA TCGTCTTATT TAGTTTTGAG AGGTCTTGTG GGGCCTTAGC TCAGCTGGGA
GAGCGCCTGC TTNGCACGCA GGAGGTCAGC GGTTCGATCC CGCTAGGCTC CATCAGGATA CANTCCTACT
AAACTTAATA CAAGTGAAGT TGAACACGCA ACTCACTTCC TAGGAAAATA GACAATCTTC GCTTGTGTGC
AAGGCACACA TGGTCAGATT CCTAATTTTC TACAGAAGTT TCGCTAAAGC GAGCGTTGCT TAGTATCCTA
TATAATAGTC CATNGAAAAT TGAATATCTA TATCAAATTC CACGATCTAG AAATAGATTG TGGAAACGTA
ACAAGAAATT AACCCGNAAA CGCTG (SEQ ID NO 146)

Figure 72

AAGGATAAGG AACTGCACAT TGGTCTTGTT TAGTCTTGAG AGGTCTTGTG GGGCCTTAGC TCAGCTGGGA
GAGCGCCTGC TTTGCACGCA GGAGGTCAGC GGTTCGATCC CGCTAGGCTC CATTGGTGAG AGATCACCAA
GTAATGCACA TTGAAAATTG AATATCTATA TCAAATAGTA ACAAGAAAT AAACCGAAAC GCTGTAGTAT
TAAAAGAGTT TATGACTGAA AGGTCAGAAA ATAA (SEQ ID NO 147)

Figure 73

CTAAGGATAT ATTCGGAACA TCTTCTTACG AAGATGCAGG AATAACATTG ACATATTGTA TTCAGNTGTG
AATGCTCATT GGAGNATTCA TNGCATNATT TGGTNCATTG ACANCTAGAT AAGNAAGTAA AATTTATGAT
TTTACCAAGC AAAACCGAGT GAATTAGAGT TNTNNAACAA GCTTTGATTT CAAAAAGAAA TAATCGCTAG
TGTTCGAAAG AACACTCACA ATCTTGGGTT TTCACCCGAC TTGTTCGTNT CGAAAGTCAA
AAAA (SEQ ID NO 148)

Figure 74

AAGGATAAGG AACTGCGCAT TGGTCTTGTT TAGTCTTGAG AGGTCTTGTG GGGCCTTAGC TCAGCTGGGA
GAGCGCCTGC TTTGCACGCA GGAGGTCAGC GGTTCGATCC CGCTAGGCTC CATTGGTGAG AGATCACCAA
GTAATGCACA TTGAAAATTG AATATCTATA TCAAATAGTA ACAAGAAAAT AAACCGAAAA CGCTGTAGTA
TTAATAAGAG TTTATGACTG AAAGGTCAAA AAATAA (SEQ ID NO 149)

Figure 75

AAGGATAAGG AACTGCGCAT TGGTCTTGTT TAGTCTTGAG AGGTCTTGTG GGGCCTTAGC TCAGCTGGGA
GAGCGCCTGC TTTGCACGCA GGAGGTCAGC GGTTCGATCC CGCTAGGCTC CATTGGTGAG AGATCACCAA
GTAATGCACA TTGAAAATTG AATATCTATA TCAAATAGTA ACAAGAAAAT AAACCGAAAA CGCTGTAGTA
TTAATAAGAG TTTATGACTG AAAGGTCAGA AAAATAA (SEQ ID NO 150)

Figure 76

AAGGAAAAGG AACTGCGCAT TGGTCTTGTT TAGTCTTGAG AGGTCTTGTG GGGCCTTAGC TCAGCTGGGA
GAGCGCCTGC TTTGCACGCA GGAGGTCAGC GGTTCGATCC CGCTAGGCTC CGCTAGGTGAG AGATCACCAA
GTAATGCACA TTGAAAATTG AATATCTATA TCAAATAGTA ACAAGAAAAT AAACCGAAAA CGCTGTAGTA
TTAATAAGAG TTTATGACTG AAAGGTCAGA AAATAA (SEQ ID NO 151)

Figure 77

AAGGATAAGG AACTGCGCAT TGGTCTTGTT TAGTCTTGAG AGGTCTTGTG GGGCCTTAGC TCAGCTGGGA
GACCGCCTGC TTTGCACGCA GGAGGTCAGC GGTTCGATCC CGCTAGGCTC CATTGGTGAG AGATCACCAA
GTAATGCACA TTGAAAATTG AATATCTATA TCAAATAGTA ACAAGAAAAT AAACCGAAAC GCTGTAGTAT
TAAAAGAGTT TATGACTGAA AGGTCAGAAA ATAA (SEQ ID NO 152)

Figure 78

AAGGATAAGG AACTGCGCAT TGGTCTTGTT TAGTCTTGAG AGGTCTTGTG GGGCCTTAGC TCAGCTGGGA
GAGCGCCTGC TTTGCACGCA GGAGGTCAGC GGTTCGATCC CGCTAGGCTC CATTGGTGAG AGATCACCAA
GTAATGCACA TTGAAAATTG AATATCTATA TCAAATAGTA ACAAGAAAAT AAACCGAAAC GCTGTAGTAT
TAAAAGAGTT TATGACTGAA AGGTCAAAAA TAA (SEQ ID NO 153)

Figure 79

TAAGGAAGAT CGAGAATTGG AAAGAGGTCG GATTTATCCG GATGATCCTT CTCCATCTTA TTAGAACATA
GATCGCAGGC CAGTCAGCCT GACGATCGCT TGCAGGCGTG CCGCCTTCGT TTCTCTTTCT TCATTGTTGA
TTGCTCACGG GCCGTACCGC AGCTGACGCT GCTGGCCCTG CGCAGGCGCG GCCCATCAGG GCCGAACGGC
CGGTCGGCCT TGCNAAGCTT CGCTTCGGGG TGGATCTGTG GATCGCGTAG TAGCGTTTGC GTCGGTATCT
GGGCTTGTAG CTCAGTTGGT TAGAGCACAC GCTTGATAAG CGTGGGGTCG GAGGTTCAAG TCCTCCCAGG
CCCACCAAGT TACTTGATGA GGGGCCGTAG CTCAGCTGGG AGAGCACCTG CTTTGCAAGC AGGGGTCGT
CGGTTCGATC CCGTCCGGCT CCACCATCAT GTTGGTGTTG AGACGGATAT TGGCAATCAA CAAAAGAAAG
AACAAGTTT GCGGACTNTT ACGAAAGTCT GCCTGTTCTG TATGAAATCG TGAAGAGAAG ATGTAATCGG
ATCAACTGAA GAGTTGATGT CGCAAGAAGC TTGCTCAAGC CTTGCATAAT GATTGATGTG TTTAACCGCC
ATCACCGATT GTATCTCGAG AAGCTGGTCT TTCTCTGCTGAT ACTGTTGAAA CGAGCATTTG CAGTCGAATG
GCAACATTCG GCGTCGCATA ATGCGGCTTT AAGAGCTGAG TTTTGATGGA TATTGGCAAT GAGAGTGATC
AAGTGTCTTA AGGGCATTGG TGGATGCCTT GGCATGCAC (SEQ ID NO 154)

Figure 80

```
AAGGAGCACC ACGAGAAACA CTCCAATTGG TGGGGTGTAA GCCGTGAGGG GTTCTCGTCT GTAGTGGACG
GAAGCCGGGT GCACAACAAC AAGCAAGCCA GACACACTAT TGGGTCCTGA GGCAACATCT CTGTTGGTTT
CGGGATGTTG TCCCACCATC TTGGTGGTGG GGTGTGGTGT TTGAGAATTG GATAGTGGTT GCGAGCATCA
ATTGGATGCG CTGCCTTTTG GTGGCGTGTT CTGTTGTGCA ATTTTATTCT TTGGTTTTTG TGTTTAT
```

(SEQ ID NO 157)

Figure 81

AAGGAGCACC ACGAGAAACA CCCCAATTGG TGGGGTGTGA GCCGTGAGGG GTTCTCGTCT GTAGTGGACG
AGGGCCGGGT GCACAACAAC AGGCAATCGC CGGACACACT ATTGGGCCCT GAGACAACAC TCGGCCGACT
GAGGTCGACG TGGTGTCCCT CCATCTTGGT GGTGGGGTGT GGTGTTTGAG CATTGAATAG TGGTTGCGAG
CATCTAGCCG GATGCGTTCC CCAGTGGTGC GCGTTCGTCA AAAATGTGTA ATTTTTCTTT TGGTTTTTGT
GTTCGT (SEQ ID NO 158)

Figure 82

AAGGAGCACC ACGAGAAACA CCCCAATTGG TGGGGTGTGA GCCGTGAGGG GTTCTCGTCT GTAGTGGACG
AGGGCCGGGT GCACAACAAC AGGCAATCGC CGGACACACT ATTGGGCCCT GAGACAACAC TCGGCCGACT
GAGGTCGACG TGGTGTCCCT CCATCTTGGT GGTGGGGTGT GGTGTTTGAG CATTGAATAG TGGTTGCGAG
CATCTAGACG GATGCGTTCC CCAGTGGTGC GCGTTCGTCA AAAATGTGTA ATTTTTCTTT TGGTTTTTGT
GTTCGT (SEQ ID NO 159)

Figure 83

AAGGAGCACC ACGAGAAACA CCCCAATTGG TGGGGTGTGA GCCGTGAGGG GTTCTCGTCT GTAGTGGACG
AGGNNCGGGT NNACAACAAC NGCCAATCGC CGGACACACT ATTGGGNCCT GAGACAACAC TCGGCCGACT
GAGGTCGACG TGGTGTCCCT CCATCTTGGT GGTGGGGTGT GGTGTTTGAG CATTGAATAG TGGTTGCGAG
CATCTAGCCG GATGCGTTCC CCAGTGGGTGC GCGTTCGTCA AAAATGTGTA ATTTTTCTNT TGGTTTTTGT
GTTCGT (SEQ ID NO 160)

Figure 84

AAGGAGCACC ACGAGAAACA CTCCAATTGG TGGAGTGTGA GCCGTGAGGG GTTCTCGTCT GTAGTGGACG
AGGCCCGGGT GCACAACAGC AGACAATCGC CAGACACACT ATTGGCCCT GAGACAACAC TCGGCCGACT
TTGGTCGACG TGGTGTCCCT CCATCTTGGT GGTGGGGTGT GGTGTTTGAG CATTGAATAG TGGTTGCGAG
CATCTAGACG GATGCGTTGC CCTCGGGCCG CGTGTTCGTC AAAAATGTGT AATTTTTTCT TTTGGTTTTT
GTGTTCGT (SEQ ID NO 161)

Figure 85

AAGGAGCACC ACGAGAAACA CTCCAATTGG TGGAGTGTGA GCCGTGAGGG GTTCTCGTCT GTAGTGGACG
GGAGCCGGGT GCACAACAAC AGGCAATCGC CAGACACACT ATTGGGCCCT GAGACAACAC TCGGCCGGCT
TTGAGTCGAA GTGGTGTCCC TCCATCTTGG TGGTGGGGTG TGGTGTTTGA GCATTGAATA GTGGTTGCGA
GCATCTAGAC GGATGCGTTG CCTTCGGGCC GCGTGTTCGT CAAAAATGTG TAATTTTTC TTTTGGTTTT
TGTGTTCGT (SEQ ID NO 162)

Figure 86

AGGGAGCACC GNAAACGCAT CCCGCGTGGG GTGTGGGTTC GGCGTGTTGT GGCGTCGGNC CGAGGTGTTG
GGCAGCAGGC AGTAACCNCC GGAACACTGT TGGGTTTTGA GNNAACACCC GTGGTGGTGT TGTGCTCCCC
GTGGTGNCGG GGTGTGGTGT TTGAGTGTTG GATAGTGGTT GCGAGCATCT GGCAAAGACT GTGGTAAGCG
GTTTTGTTG ANTGTTTTCT GGTGTTTGT (SEQ ID NO 163)

Figure 87

AAGGAGCACC ACGAGAAACA CTCCAATTGG TGGGGTGTGA GCCGTGAGGG GTTCTCGTCT GTAGTGGACG
AGGGNCGGGT GCACAACAAC AGNCAATCGC CAGACACACT ATTGGNCCCT GAGACAACAC TCGGCCGACT
TNGGTTGAAG TGGTGTCCCT CCATCTTCGT GGTGGGGTGT GGTGTTTGAG TATTGGATAG TGGTTGCGAG
CATCTAANTG AACGCGTCGC CGNCAACGGT TACGTGTTCG TTTTGTGTAA TTNTTTCTAT TGGTTTTTGT
GTTCGT (SEQ ID NO 164)

Figure 88

AAGGAGCACC ACGAGAAACA CTCCAATTGG TGGGGTGTGA GCCGTGAGGG GTTCTCGTCT GTAGTGGACG
AGGGCCGGGT GCACAACAAC AGGCAATCGC CAGACACACT ATTGGNCCCT GAGACAACAC TCGGCCGACT
TTGGTCGAAG TGGTGTCCCC CCATCTTGGT GGTGGGGTGT GGTGTTTGAG TATTGGATAG TGGTTGCGAA
CATCTAAATG AACGCGTTGC CGGCAACGGT TACGTGTTCG TTTTAGTGTA ATTNTTTCTA ATGGTTTTTG
TGTTCGT (SEQ ID NO 165)

Figure 89

AAGGAGCACC ACGAGACCTG GGCCGGCCCC GCAGATCGCG GGATCAGCTG AGCTTTCAGG CGATTCGTTG
GATGGCCTCG CACCTGTAGT GGGTGGGGGT CTGGTGCACT CAACAAACTT GGCGTGGGAT GCGGGAAAGC
ATCTGCGGAA AATCATCAGA CACACTATTG GGCTTTGAGA CAACAGGCCC GCAGNCCTGN CCCGTTGGGG
GCAGNGGGTG TGTTGTTGCC TCACTTTGGT GGTGGGGGTG GTGTTTGATT TGTGGATAGT GGTTGCGAGC
ATCTAGCGCG CAGAATGTGT GGTCTCACTC CTTGTGGGTG GGGCCTGGTT TTGTGTGCGA TTGATGTGCA
ATTTCTTTTG AAACTCATTT TTTGGTTTTT GTGTTGT (SEQ ID NO 166)

Figure 90

AAGGAGCACC ACGAAAAACT CCCCAATTGG TGGGGTGTAA GCCCGTGAGGG GTTCCCGTCT GTAGTGGACG
GGGGCCGGGT GCGCAACAGC AAGCGAAACG CCGGACACAC TATTGGGTCC TGAGGCAACA CTCGGGTTTG
TCCCCCTCAG GGATTTTCTG GGTGTTGTCC CACCATCTTG GTGGTGGGGT GTGGTGTTTG AGAATTGGAT
AGTGGTTGCG AGCATCAAAT GGATGCGGTTG CCCCTACGGG TAGCGTGTTC TTTTGTGCAA TTTTATTCNT
TGGTTTTTGT GTTTGT (SEQ ID NO 167)

Figure 91

AAGGAGCACC ACGAGAAGCA CTCCAACTGG TGGGGTGCAA GCCGTGAGGG GTTCTCGTCT GTAGTGGACG
AGAGCCGGGT GCGCGACAAC GAACGAGCCA GACACACTAT TGGGTCCTGA GGCAACACTC GGGCTTGGCC
ACAGCTGTTG TCCCACCATC TTGGTGGTGG GGTGTGGTGT TTGAGAATTG GATAGTGGTT GCGAGCATCA
AATGGATGCG TTGCCCCTAC GGGTGGCGTG TTCTTTTCTG CAATTTATT CTTTGGTTTT TGTGTTTGT (SEQ ID NO 168)

Figure 92

AAGGAGCACC ACGAAAAACA CCCCAACTGG TGGGGTGTAA GCCGTGAGGG GCTCCCGTCT GTAGTAGACG
GGCGCCGGGT GCGCAACAGC AAGCGAGCCA GACACACTAT TGGGTCCTGA GGCAACACTC GGGCTTGTCT
TGGACTCGTC CAAGAGTGTT GTCCCACCAT CTTGGTGGTG GGGTGTGGTG TTTGAGAATT GGATAGTGGT
TGCGAGCATC ANCTGGATGC GTGCCCCCA GGGGTAGCGT GTTCTTTTGT GCAATTNTAT TCNNTGGTTT
TTGTGTTAGT (SEQ ID NO 169)

Figure 93

AAGGAGCACC ACGAAAAACA CTCCGCATCC GGTGGGGTGT GAGCCGTGAG GGAGCCCGTG CCTGTAGTGG
GTGTGGGTTG GGTGCGCGAC AACAAATGGG AAAAATCGCT GGGCACACTA TTGGGCTTTG AGGCAACACC
TGGTTTGTTT TGGGTGGTGT CGCTCCATCT TGGTGGTGGG GTGTGGTGTT TGAGTTGTGG ATAGTGGTTG
CGAGCATCTA AGCAAAAGCT GTTGTTTGAC GGTTTTTGTC GAGTGTTGTG TGTGT (SEQ ID NO 170)

Figure 94

AAGGAGCACC ACGAAAAACA CTCCAATTGG TGGGGTGTAA GCCGTGAGGG GTTCTCATCT GTAGTGGACG
AGAGCCGGGT GCACAACAGC AAATGAATCG CCAGACACAC TGTTGGGTCC TGAGGCAACA CTCAGGCTTG
TCCCATGTTG GGCTTGATCG GGTGCTGTCC CCCCATCTTG GTGGTGGGGT GTGGTGTTTG AGTATTGGAT
AGTGGTTGCG AGCATCTAAA TGGATACGTT GCCAGTAATG GTGGCGTATT CATTGAAAAT GTGTAATTTT
CTTCTTTGGT TTTGTGTGT (SEQ ID NO 171)

Figure 95

AAGGAGCACC ACGAAAAACA CTCCAATTGG TGGGGTGTAA GCCGTGAGGG GTTCTCATCT GTAGTGGACG
AGAGCCGGGT GCACAACAGC AAATGAATCG CCAGACACAC TGTTGGGTCC TGAGGCAACA CTCAGGCTTG
TCCCATGTTG GGCTTGATCG GGTGCTGTCC CCCCATCTTG GTGGTGGGT GTGGTGTTTG AGTATTGGAT
AGTGGTTGCG AGCATCTAAA TGGATACGTT GCCAGTAATG GTGGCCGTGTT CATTGAAAAT GTGTAATTTT
CTTCTTTGGT TTTGTGTGT (SEQ ID NO 172)

Figure 96

AAGGAGCACC ACGAAAAACA CTCCAATTGG TGGGGTGTAA GCCGTGAGGG GTTCTCATCT GTAGTGGACG
AGAGCCGGGT GCACAACAGC AAATGAATCG CCAGACACAC TGTTGGGTCC TGAGGCAACA CTCAGGCTTG
TCCCATGTTG GGCTTGATCG GGTGCTGTCC CCCCATCTTG GTGGTGGGGT GTGGTGTTTG AGTATTGGAT
AGTGGTTGCG AGCATCTAAA TGGANACCTT GCCAGTAATG GTGGCGTGTT CATTGAAAAT GTGTAATTTT
CTTCTTTGGT TTTGTGTGT (SEQ ID NO 173)

Figure 97

AAGGAGCACC ATTTCTCAGT CGAATGAACT GAGAACATAA AGCGAGTATC TGTAGTGGAT ACATGCTTGG
TGAATATGTT TTATAAATCC TGTCCACCCC GTGGATAGGT AGTCGGCAAA ACGTCGGACT GTCATAAGAA
TTGAAACGCT GGCACACTGT TGGGTCCTGA GGCAACACAT TGTGTTGTCA CCCTGCTTGG TGGTGGGGTG
TGGTCCTTGA CTTATGGATA GTGGTTGCGA GCATCTAAAC ATAGCCTCGC TCGTTTTCGA GTGAGGCTGG
TTTTTGCAAT TTTATTAGCT (SEQ ID NO 174)

Figure 98

```
CCTAATGATA TTGATTCGCG TGAAGTGCTC ACACAGATTG TCTGATGAAA AAGTAACGAG CAGAAATACC
TTTATAGGCT TGTAGCTCAG GTGGTTAGAG CGCACCCCTG ATAAGGGTGA GGTCGGTGGT TCAAGTCCAC
TCAGGCCTAC CACTTCTCGA AGTGGAAAAG GTACTGCACG TGACTGTATG GGGCTATAGC TCAGCTGGGA
GAGCGCCTGC CTTGCACGCA GGAGGTCAGC GGTTCGATCC CGCTTAGCTC CACCATATAG TCCTGTATTT
CAATACTTCA GAGTGTACTG GCAACAGTAT GCTGCGAAGT ATTTGCTCT TTAACAATCT GGAACAAGCT
GAAAATTGAA ACATGACAGC TGAAACTTAT CCCTCCGTAG AAGTATTGGG GTAAGGATTA ACCTGTCATA
GAGTCTCTCA AATGTAGCAG CACGAAAGTG GAAACACCTT CGGGTTGTGA
```

(SEQ ID NO 195)

Figure 99

CCTAATGATA TTGATTCGCG TGAAGTGCTC ACACAGATTG TTTGATAGAA ACGTAATGAG CAAAAGCGCT
ACCTGTTGAT GTAATGAGTC ACTGACTCAT GCTGATACGA ACCGATTAAG ACAGTCAGTT TAATCGGATT
TTCGTGTCCC CATCGTCTAG AGGCCTAGGA CACTGCCCTT TCACGGCTGT AACAGGGGTT CGAATCCCCT
TGGGACGCC ATTCGATAAT GAGTGAAAGA CATTATCACC GGTTCTTGGA ACCGAAAACA TCTTAAAGAT
GACTCTTGCG AGTCGTGTTT AAGATATTGC TCTTTAACAA TCTGGAACAA GCTGAAAATT GAAACATGAC
AGCTGAAACT TATCCCTCCG TAGAAGTATT GGGGTAAGGA TTAACCTGTC ATAGAGTCTC TCAAATGTAG
CAGCACGAAA GTGGAAACAC CTTCGGGTTG TGA (SEQ ID NO 196)

Figure 100

TAAGGATAAG GAAGAAGCCT GAGAAGGTTT CTGACTAGGT TGGGCAAGCA TTTATATGTA AGAGCAAGCA
TTCTATTCA TTTGTGTTGT TAAGAGTAGC GCGGTGAGGA CGAGACATAT AGTTTGTGAT CAAGTATGTT
ATTGTAAAGA AATAATCATG GTAACAAGTA TATTTCACGC ATAATAAATAG ACGTTAAGA GTATTGTCT
TTTAGGTGAA GTGCTTGCAT GGATCTATAG AAATTACA (SEQ ID NO 197)

Figure 101

TAAGGATAAG GAAACCTGTG AATCTTTTTC CCTTCTTTTG TTCAGTTTTG AGAGGTTCAT CTCTCAAAAC
GTGTTCTTTG AAAACTAGAT AAGAAAAGTT AGTGTAAAAA GACGAAGAGA AACCGTAGGT TTTTCTTCAA
CCAAAACCGA GAATCAAACC GAGAAAGAAT CTTTCCGTTT TCATAAGCGA TCGCACGTTT ATGAAAACAC
AACAACACCT TCGTAAGAAG GATGA (SEQ ID NO 213)

Figure 102

TAAGGATAAG GAAACCTGTG AATCTTTTTC CCTTCTTTTG TTCAGTTTTG AGAGGTCAAT GACGCTCATA
CTGAGTACCA GGTGACACGT TTTGAGGTG TCTCTTCGTA TGAGGGGCCT ATAGCTCAGC TGGTTAGAGC
GCACGCCTGA TAAGCGTGAG GTCGGTGGTT CGAGTCCACT TAGGCCCACT TTTTGAATA AACCTTTCTT
TTTTATATGT TAATAAGGGG CCTTAGCTCA GCTGGGAGAG CGCCTGCTTT GCACGCAGGA GGTCAGCGGT
TCGATCCCGC TAGGCTCCAC CAAAGATAGT TTGTTCTTTG AAAACTAGAT AAGAAAAGTT AGTGTAAAAA
GACGAAGAGA AACCGTAGGT TTTTCTTCAA CCAAAACCGA GAATCAAACC GAGAAAGAAT CTTTCCGTTT
TCATAAGCGA TCGCACGTTT ATGAAAACAC AACAACACCT TCGTAAGAAG GATGA (SEQ ID NO 214)

Figure 103

TAAGGATAAG GAAACCTGTG AATCTTTTTC CCTTCTTTTG TTCAGTTTTG AGAGGTCAAT GACGCTCATA
CTGAGTACCA GGTGACACGT TTTGAGGTG TCTCTTCGTA TGAGGGGCCT ATAGCTCAGC TGGTTAGAGC
GCACGCCTGA TAAGCGTGAG GTCGGTGGTT CGAGTCCACT TAGGCCCACT TTTTGAATA AACCTTTCTT
TTTTATATGT TAATAAGGGG CCTTAGCTCA GCTGGGAGAG CGCCTGCTTT GCACGCAGGA GGTCAGCGGT
TCGATCCCGC TAGGCTCCAC CAAAGATAGT TTGTTCTTTG AAAACTAGAT AAGAAAAGTT AGTGTAAAAA
GACGAAGAGA AACCGTAGGT TTTTCTTCAA CCAAAAACCGA GAAAGAATCT TTCCGTTTTC ATAAGCGATC
GCACGTTTAT GAAAACACAA CAACACCTTC GTAAGAAGGA TGA (SEQ ID NO 215)

SEQUENCE LISTING (1) GENERAL INFORMATION:

(iii) NUMBER OF SEQUENCES: 216

(2) INFORMATION FOR SEQ ID NO: 1:

(i) SEQUENCE CHARACTERISTICS:
      (A) LENGTH: 25 base pairs
      (B) TYPE: nucleic acid
      (C) STRANDEDNESS: single
      (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 1:

ACTGGATAGT GGTTGCGAGC ATCTA       25

(2) INFORMATION FOR SEQ ID NO: 2:

(i) SEQUENCE CHARACTERISTICS:
            (A) LENGTH: 26 base pairs
            (B) TYPE: nucleic acid
            (C) STRANDEDNESS: single
            (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 2:

CTTCTGAATA GTGGTTGCGA GCATCT                                            26

(2) INFORMATION FOR SEQ ID NO: 3:

(i) SEQUENCE CHARACTERISTICS:
            (A) LENGTH: 25 base pairs
            (B) TYPE: nucleic acid
            (C) STRANDEDNESS: single
            (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 3:

GGGTGCATGA CAACAAAGTT GGCCA                                             25

(2) INFORMATION FOR SEQ ID NO: 4:

(i) SEQUENCE CHARACTERISTICS:
            (A) LENGTH: 24 base pairs
            (B) TYPE: nucleic acid
            (C) STRANDEDNESS: single
            (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 4:

GACTTGTTCC AGGTGTTGTC CCAC                                              24

(2) INFORMATION FOR SEQ ID NO: 5:

(i) SEQUENCE CHARACTERISTICS:
            (A) LENGTH: 21 base pairs
            (B) TYPE: nucleic acid
            (C) STRANDEDNESS: single
            (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 5:

CGGCTAGCGG TGGCGTGTTC T                                                 21

(2) INFORMATION FOR SEQ ID NO: 6:

(i) SEQUENCE CHARACTERISTICS:
            (A) LENGTH: 26 base pairs
            (B) TYPE: nucleic acid -continued

```
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 6:

CAACAGCAAA TGATTGCCAG ACACAC                                    26

(2) INFORMATION FOR SEQ ID NO: 7:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 7:

GAGGGGTTCC CGTCTGTAGT G                                         21

(2) INFORMATION FOR SEQ ID NO: 8:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 8:

TGAGGGGTTC TCGTCTGTAG TG                                        22

(2) INFORMATION FOR SEQ ID NO: 9:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 9:

CACTCGGTCG ATCCGTGTGG A                                         21

(2) INFORMATION FOR SEQ ID NO: 10:

(i) SEQUENCE CHARACTERISTICS:
        (A) LENGTH: 21 base pairs
        (B) TYPE: nucleic acid
        (C) STRANDEDNESS: single
        (D) TOPOLOGY: linear
```

(ii) MOLECULE TYPE: cDNA (iii) HYPOTHETICAL: NO (iv) ANTI-SENSE: NO (xi) SEQUENCE DESCRIPTION: SEQ ID NO: 10:

TCGGTCCGTC CGTGTGGAGT C                                                        21

(2) INFORMATION FOR SEQ ID NO: 11:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 11:

GTGGCCGGCG TTCATCGAAA                                                          20

(2) INFORMATION FOR SEQ ID NO: 12:

(i) SEQUENCE CHARACTERISTICS:
            (A) LENGTH: 25 base pairs
            (B) TYPE: nucleic acid
            (C) STRANDEDNESS: single
            (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 12:

GCATAGTCCT TAGGGCTGAT GCGTT                                                    25

(2) INFORMATION FOR SEQ ID NO: 13:

(i) SEQUENCE CHARACTERISTICS:
            (A) LENGTH: 25 base pairs
            (B) TYPE: nucleic acid
            (C) STRANDEDNESS: single
            (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 13:

GCTGATGCGT TCGTCGAAAT GTGTA                                                    25

(2) INFORMATION FOR SEQ ID NO: 14:

(i) SEQUENCE CHARACTERISTICS:
            (A) LENGTH: 23 base pairs
            (B) TYPE: nucleic acid
            (C) STRANDEDNESS: single
            (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 14:

CTGATGCGTT CGTCGAAATG TGT                                                    23

(2) INFORMATION FOR SEQ ID NO: 15:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 15:

TGATGCGTTC GTCGAAATGT GT                                                     22

(2) INFORMATION FOR SEQ ID NO: 16:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 16:

GGCTGATGCG TTCGTCGAAA TGTGTAA                                                27

(2) INFORMATION FOR SEQ ID NO: 17:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 17:

ACTAGATGAA CGCGTAGTCC TTGT                                                   24

(2) INFORMATION FOR SEQ ID NO: 18:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 18:

TGGACGAAAA CCGGGTGCAC AA                                                      22

(2) INFORMATION FOR SEQ ID NO: 19:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 19:

GTGTAATTTC TTTTTTAACT CTTGTGTGTA AGTAAGTG                                      38

(2) INFORMATION FOR SEQ ID NO: 20:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 20:

TGGCCGGCGT GTTCATCGAA A                                                       21

(2) INFORMATION FOR SEQ ID NO: 21:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 21:

GCACTTCAAT TGGTGAAGTG CGAGCC                                                  26

(2) INFORMATION FOR SEQ ID NO: 22:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 22:

GCGTGGTCTT CATGGCCGG                                                          19

(2) INFORMATION FOR SEQ ID NO: 23:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 23:

ACGCGTGGTC CTTCGTGG                                                      18

(2) INFORMATION FOR SEQ ID NO: 24:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 24:

TCGGCTCGTT CTGAGTGGTG TC                                          22

(2) INFORMATION FOR SEQ ID NO: 25:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 25:

GATGCGTTTG CTACGGGTAG CGT                                        23

(2) INFORMATION FOR SEQ ID NO: 26:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 26:

GATGCGTTGC CTACGGGTAG CGT                                        23

(2) INFORMATION FOR SEQ ID NO: 27:

(i) SEQUENCE CHARACTERISTICS:
    (A) LENGTH: 23 base pairs
    (B) TYPE: nucleic acid
    (C) STRANDEDNESS: single
    (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 27:

ATGCGTTGCC CTACGGGTAG CGT                                           23

(2) INFORMATION FOR SEQ ID NO: 28:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 28:

CGGGCTCTGT TCGAGAGTTG TC                                            22

(2) INFORMATION FOR SEQ ID NO: 29:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 29:

GGTGTGGACT TTGACTTCTG AATAG                                         25

(2) INFORMATION FOR SEQ ID NO: 30:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 30:

CGGCAAAACG TCGGACTGTC A                                             21

(2) INFORMATION FOR SEQ ID NO: 31:

(i) SEQUENCE CHARACTERISTICS:
        (A) LENGTH: 20 base pairs (B) TYPE: nucleic acid
            (C) STRANDEDNESS: single
            (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 31:

AACACCCTCG GGTGCTGTCC                                              20

(2) INFORMATION FOR SEQ ID NO: 32:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 32:

GTATGCGTTG TCGTTCGCGG C                                            21

(2) INFORMATION FOR SEQ ID NO: 33:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 33:

CGTGAGGGGT CATCGTCTGT AG                                           22

(2) INFORMATION FOR SEQ ID NO: 34:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 34:

TGGTGTGCTG CGTGATCCGA T                                            21

(2) INFORMATION FOR SEQ ID NO: 35:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 35:

TGAATGTTCG TGGATGAACA TTGATT                                            26

(2) INFORMATION FOR SEQ ID NO: 36:

(i) SEQUENCE CHARACTERISTICS:
            (A) LENGTH: 23 base pairs
            (B) TYPE: nucleic acid
            (C) STRANDEDNESS: single
            (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 36:

CACTGGTGAT CATTCAAGTC AAG                                               23

(2) INFORMATION FOR SEQ ID NO: 37:

(i) SEQUENCE CHARACTERISTICS:
            (A) LENGTH: 33 base pairs
            (B) TYPE: nucleic acid
            (C) STRANDEDNESS: single
            (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 37:

TGAATGTTCG TVVATGAACA TTGATTTCTG GTC                                    33

(2) INFORMATION FOR SEQ ID NO: 38:

(i) SEQUENCE CHARACTERISTICS:
            (A) LENGTH: 29 base pairs
            (B) TYPE: nucleic acid
            (C) STRANDEDNESS: single
            (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 38:

CTCTTTCACT GGTGATCATT CAAGTCAAG                                         29

(2) INFORMATION FOR SEQ ID NO: 39:

(i) SEQUENCE CHARACTERISTICS:
            (A) LENGTH: 31 base pairs
            (B) TYPE: nucleic acid
            (C) STRANDEDNESS: single
            (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 39:

CAAGTAACCG AGAATCATCT GAAAGTGAAT C                                          31

(2) INFORMATION FOR SEQ ID NO: 40:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 40:

AAACAACCTT TACTTCGTAG AAGTAAATTG GTTAAG                                     36

(2) INFORMATION FOR SEQ ID NO: 41:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 41:

TGAGAGGTTA GTACTTCTCA GTATGTTTGT TC                                         32

(2) INFORMATION FOR SEQ ID NO: 42:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 42:

AGGCACTATG CTTGAAGCAT CGC                                                   23

(2) INFORMATION FOR SEQ ID NO: 43:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 43:

GTTAGCATAA ATAGGTAACT ATTTATGACA CAAGTAAC                                38

(2) INFORMATION FOR SEQ ID NO: 44:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 44:

AGTTAGCATA AGTAGTGTAA CTATTTATGA CACAAG                                  36

(2) INFORMATION FOR SEQ ID NO: 45:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 45:

GGAAGAAGCC TGAGAAGGTT TCTGAC                                             26

(2) INFORMATION FOR SEQ ID NO: 46:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 46:

GCATTTATAT GTAAGAGCAA GCATTCTATT TCA                                     33

(2) INFORMATION FOR SEQ ID NO: 47:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 47:

```
GAGTAGCGTG GTGAGGACGA GA                                                    22

(2) INFORMATION FOR SEQ ID NO: 48:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 48:

GGATAACTGT CTTAGGACGG TTTGAC                                                26

(2) INFORMATION FOR SEQ ID NO: 49:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 49:

ATCGGTGGTA AATTAAACCC AAATCCCTGT                                            30

(2) INFORMATION FOR SEQ ID NO: 50:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 50:

CAGTTCTGAA AGAACATTTC CGCTTCTTTC                                            30

(2) INFORMATION FOR SEQ ID NO: 51:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 51:

CACCCATTAA TTTTTTCGGT GTTAAAACCC                                            30
```

(2) INFORMATION FOR SEQ ID NO: 52:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 52:

CAAAACTGAA AACGACAATC TTTCTAGTTC C                              31

(2) INFORMATION FOR SEQ ID NO: 53:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 53:

TACCAAGCAA AACCGAGTGA ATAAAGAGTT                              30

(2) INFORMATION FOR SEQ ID NO: 54:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 54:

CAGAAGATGC GGAATAACGT GAC                                      23

(2) INFORMATION FOR SEQ ID NO: 55:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 55:

AACGAAGCCG TATGTGAGCA TTTGAC                                  26

(2) INFORMATION FOR SEQ ID NO: 56:

(i) SEQUENCE CHARACTERISTICS:

```
        (A) LENGTH: 31 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 56:

GAACGTAACT TCATGTTAAC GTTTGACTTA T                              31

(2) INFORMATION FOR SEQ ID NO: 57:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 57:

GCTTAAGTGC ACAGTGCTCT AAACTGA                                   27

(2) INFORMATION FOR SEQ ID NO: 58:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 58:

CACGGTAATT AGTGTGATCT GACGAAG                                   27

(2) INFORMATION FOR SEQ ID NO: 59:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 59:

CGTGCCGCCT TCGTTTCTCT TT                                        22

(2) INFORMATION FOR SEQ ID NO: 60:

(i) SEQUENCE CHARACTERISTICS:
        (A) LENGTH: 22 base pairs
        (B) TYPE: nucleic acid
        (C) STRANDEDNESS: single
```

(D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 60:

TTCGCTTCGG GGTGGATCTG TG                                          22

(2) INFORMATION FOR SEQ ID NO: 61:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 61:

CAAAACTGAC TTACGAGTCA CGTTTGAG                                    28

(2) INFORMATION FOR SEQ ID NO: 62:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 62:

GATGTATGCT TCGTTATTCC ACGCC                                       25

(2) INFORMATION FOR SEQ ID NO: 63:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 63:

GGTCAAACCT CCAGGGACGC C                                           21

(2) INFORMATION FOR SEQ ID NO: 64:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 64:

GCGGTAATGT GTGAAAGCGT TGCC                    24

(2) INFORMATION FOR SEQ ID NO: 65:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 65:

TCCCTTGTGG CCTGTGTG                           18

(2) INFORMATION FOR SEQ ID NO: 66:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 66:

TCCTTCATCG GCTCTTCGA                          19

(2) INFORMATION FOR SEQ ID NO: 67:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 67:

GATGCCAAGG CATCCACC                           18

(2) INFORMATION FOR SEQ ID NO: 68:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: cDNA (iii) HYPOTHETICAL: NO -continued (iv) ANTI-SENSE: NO (xi) SEQUENCE DESCRIPTION: SEQ ID NO: 68:

CCTCCCACGT CCTTCATCG                                                    19

(2) INFORMATION FOR SEQ ID NO: 69:

(i) SEQUENCE CHARACTERISTICS:
            (A) LENGTH: 22 base pairs
            (B) TYPE: nucleic acid
            (C) STRANDEDNESS: single
            (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 69:

AAGGTTTCTG ACTAGGTTGG GC                                                22

(2) INFORMATION FOR SEQ ID NO: 70:

(i) SEQUENCE CHARACTERISTICS:
            (A) LENGTH: 22 base pairs
            (B) TYPE: nucleic acid
            (C) STRANDEDNESS: single
            (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 70:

GGTGAAGTGC TTGCATGGAT CT                                                22

(2) INFORMATION FOR SEQ ID NO: 71:

(i) SEQUENCE CHARACTERISTICS:
            (A) LENGTH: 23 base pairs
            (B) TYPE: nucleic acid
            (C) STRANDEDNESS: single
            (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 71:

ACCTGTGAGT TTTCGTTCTT CTC                                               23

(2) INFORMATION FOR SEQ ID NO: 72:

(i) SEQUENCE CHARACTERISTICS:
            (A) LENGTH: 24 base pairs
            (B) TYPE: nucleic acid
            (C) STRANDEDNESS: single
            (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 72:

```
CTATTTGTTC AGTTTTGAGA GGTT                                              24
```

(2) INFORMATION FOR SEQ ID NO: 73:

(i) SEQUENCE CHARACTERISTICS:
       (A) LENGTH: 23 base pairs
       (B) TYPE: nucleic acid
       (C) STRANDEDNESS: single
       (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 73:

```
ATTTTCCGTA TCAGCGATGA TAC                                               23
```

(2) INFORMATION FOR SEQ ID NO: 74:

(i) SEQUENCE CHARACTERISTICS:
       (A) LENGTH: 22 base pairs
       (B) TYPE: nucleic acid
       (C) STRANDEDNESS: single
       (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 74:

```
ACGAAGTAAA GGTTGTTTTT CT                                                22
```

(2) INFORMATION FOR SEQ ID NO: 75:

(i) SEQUENCE CHARACTERISTICS:
       (A) LENGTH: 25 base pairs
       (B) TYPE: nucleic acid
       (C) STRANDEDNESS: single
       (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 75:

```
GAGAGGTTAC TCTCTTTTAT GTCAG                                             25
```

(2) INFORMATION FOR SEQ ID NO: 76:

(i) SEQUENCE CHARACTERISTICS:
       (A) LENGTH: 275 base pairs
       (B) TYPE: nucleic acid
       (C) STRANDEDNESS: single
       (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 76:

```
AAGGAGCACC ACGAAAACGC CCCAACTGGT GGGGCGTAGG CCGTGAGGGG TTCTTGTCTG        60
```

```
TAGTGGGCGA GAGCCGGGTG CATGACAACA AAGTTGGCCA CCAACACACT GTTGGGTCCT    120

GAGGCAACAC TCGGACTTGT TCCAGGTGTT GTCCCACCGC CTTGGTGGTG GGGTGTGGTG    180

TTTGAGAACT GGATAGTGGT TGCGAGCATC AATGGATACG CTGCCGGCTA GCGGTGGCGT    240

GTTCTTTGTG CAATATTCTT TGGTTTTTGT TGTGT                              275
```

(2) INFORMATION FOR SEQ ID NO: 77:

(i) SEQUENCE CHARACTERISTICS:
        (A) LENGTH: 278 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 77:

```
AAGGAGCACC ACGAAAAGCA CCCCAACTGG TGGGGTGCGA GCCGTGAGGG GTTCCCGTCT     60

GTAGTGGACG GGGGCCGGNT GCGCAACAGC AAATGATTGC CAGACACACT ATTGGGCCCT    120

GAGACAACAC TCGGTCCGTC CGTGTGGAGT CCCTCCATCT TGGTGGTGGG GTGTGGTGTT    180

TGAGTATTGG ATAGTGGTTG CGAGCATCTA GATGAGCGCA TGGTCTTCGT GGCCGGCGTT    240

CATCGAAATG TGTAATTTCT TCCTTAACTC TTGTGTGT                           278
```

(2) INFORMATION FOR SEQ ID NO: 78:

(i) SEQUENCE CHARACTERISTICS:
        (A) LENGTH: 278 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 78:

```
AAGGAGCACC ACGAAAAGCA CCCCAACTGG TGGGGTGCGA GCCGTGAGGG GTTCCCGTCT     60

GTAGTGGACG GGGGCCGGGT GCGCAACAGC AAATGATTGC CAGACACACT ATTGGGCCCT    120

GAGACAACAC TCGGTCCGTC CGTGTGGAGT CCCTCCATCT TGGTGGTGGG GTGTGGTGTT    180

TGAGTATTGG ATAGTGGTTG CGAGCATCTA GATGAGCGCA TGGTCTTCGT GGCCGGCGTT    240

CATCGAAATG TGTAATTTCT TTTTTAACTC TTGTGTGT                           278
```

(2) INFORMATION FOR SEQ ID NO: 79:

(i) SEQUENCE CHARACTERISTICS:
        (A) LENGTH: 280 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 79:

```
AAGGAGCACC ACGAAAAGCA CTCCAATTGG TGGGGTGCGA GCCGTGAGGG GTTCCCGTCT        60

GTAGTGGACG GGGGCCGGNT GCACAACAGC AAATGATTGC CAGACACACT ATTGGGCCCT       120

GAGACAACAC TCGGTCGATC CGTGTGGAGT CCCTCCATCT TGGTGGTGGG GTGTGGTGTT       180

TGAGTATTGG ATAGTGGTTG CGAGCATCTA GATGAGCGCA TAGTCCTTGT GGCTGATGCG       240

CTCGTCGAAA TGTGTAATTT CTTCTTTGGT GTNTGTGTGT                            280

(2) INFORMATION FOR SEQ ID NO: 80:

(i) SEQUENCE CHARACTERISTICS:
        (A) LENGTH: 281 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 80:

AAGGAGCACC ACGAAAAGCA TCCCAATTGG TGGGGTGCGA GCCGTGAGGG GTTCTCGTCT        60

GTAGTGGACG AAAACCGGGT GCACAACAGC AAATGATTGC CAGACACACT ATTGGGCCCT       120

GAGACAACAC TCGGTCGATC CGTGTGGAGT CCCTCCATCT TGGTGGTGGG GTGTGGTGTT       180

TGAGTATTGG ATAGTGGTTG CGAGCATCTA GATGAGCGCG TAGTCCTTTG TGGCTGATGC       240

GTTCATCAAA ATGTGTAATT TCTTTTTTGG TTTNTGTGTG T                          281

(2) INFORMATION FOR SEQ ID NO: 81:

(i) SEQUENCE CHARACTERISTICS:
        (A) LENGTH: 280 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 81:

AAGGAGCACC ACGAAAAGCA CTCCAATTGG TGGGGTGCGA GCCGTGAGGG GTTCCCGTCT        60

GTAGTGGACG GGGGCCGGGT GCACAACAGC AAATGATTGC CAGACACACT ATTGGGCCCT       120

GAGACAACAC TCGGTCGATC CGTGTGGAGT CCCTCCATCT TGGTGGTGGG GTGTGGTGTT       180

TGAGTATTGG ATAGTGGTTG CGAGCATCTA GATGAGCGCA TAGCCCTTGC GGCTGATGCG       240

TTCGNCGAAA TGTGTAATTT CTTCTCTGGT TTCTGTGTGT                            280

(2) INFORMATION FOR SEQ ID NO: 82:

(i) SEQUENCE CHARACTERISTICS:
        (A) LENGTH: 282 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO
```

(xi) SEQUENCE DESCRIPTION: SEQ ID NO: 82:

AAGGAGCACC ACGAAAAGCA CTCCAATTGG TGGGGTGCGA GCCGTGAGGG GTTCTCGTCT    60

GTAGTGGACG GNAGCCGGGT GCACAACAGC AAATGATTGC CAGACACACT ATTGGGCCCT   120

GAGACAACAC TCGGTCGATC CGTGTGGAGT CCCTCCATCT TGGTGGTGGG GTGTGGTGTT   180

TGAGTATTGG ATAGTGGTTG CGAGCATCTA GATGAGCGCG TAGTCCTTCG TGGCTGATGC   240

GTTCATCGAA ATGTGTAATT TCTTCTTTGG TTTTGGGTGT GT                     282

(2) INFORMATION FOR SEQ ID NO: 83:

(i) SEQUENCE CHARACTERISTICS:
        (A) LENGTH: 282 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 83:

AAGGAGCACC ACGAAAAGCA CTCCAATTGG TGGGGTGCGA GCCGTGAGGG GTTCCCGTCT    60

GTAGTGGACG GGGGCCGGGT GCACAACAGC AAATGATCGC CAGACACACT ATTGGGCCCT   120

GAGACAACAC TCGGTCGATC CGTGTGGAGT CCCTCCATCT TGGTGGTGGG GTGTGGTGTT   180

TGAGTATTGG ATAGTGGTTG CGAGCATCTA GATGAGCGCA TAGTCCTTTG GGGCTGATGT   240

GTTTCATCAA AATGTGTAAT TTCTTTTTNG GTTTTNGTGT GT                     282

(2) INFORMATION FOR SEQ ID NO: 84:

(i) SEQUENCE CHARACTERISTICS:
        (A) LENGTH: 281 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 84:

AAGGAGCACC ACGAAAAGCA CTCCAATTGG TGGGGTGCGA GCCGTGAGGG GTTCTCGTCTT   60

GTAGTGGACG GGAGCCGGGT GCACAACAGC AAATGATTGC CAGACACACT ATTGGGCCCT   120

GAGACAACAC TCGGTCGATC CGTGTGGAGT CCCTCCATCT TGGTGGTGGG GTGTGGTGTT   180

TGAGTATTGG ATAGTGGTTG CGAGCATCTA GATGAGCGCG TAGTCCTTCG TGGCTGATGC   240

GTTCATTGAA ATGTGTAATT TCTTCTCTGG TTTTTGTGTG T                      281

(2) INFORMATION FOR SEQ ID NO: 85:

(i) SEQUENCE CHARACTERISTICS:
        (A) LENGTH: 280 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 85:

| | | | | | |
|---|---|---|---|---|---|
| AAGGAGCACC | ACGAAAAGCA | CTCCAATTGG | TGGGGTGCGA | GCCGTGAGGG | GTTCCCGTCT | 60
| GTAGTGGACG | GGGGCCGGGT | GCACAACAGC | AAATGATTGC | CAGACACACT | ATTGGGCCCT | 120
| GAGACAACAC | TCGGTCGATC | CGTGTGGAGT | CCCTCCATCT | TGGTGGTGGG | GTGTGGTGTT | 180
| TGAGTATTGG | ATAGTGGTTG | CGAGCATCTA | GATGAGCGCA | TAGTCCTTGT | GGCTGATGCG | 240
| CTCGTCGAAA | TGTGTAATTT | CTTCTTTGGT | TTTTGTGTGT | | | 280

(2) INFORMATION FOR SEQ ID NO: 86:

(i) SEQUENCE CHARACTERISTICS:
        (A) LENGTH: 282 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 86:

| | | | | | |
|---|---|---|---|---|---|
| AAGGAGCACC | ACGAAAAGCA | CTCCAATTGG | TGGGGTGCGA | GCCGTGAGGG | GTTCCCGTCT | 60
| GTAGTGGACG | GGGGCCGGGT | GCGCAACAGC | AAATGATTGC | CAGACACACT | ATTGGGCCCT | 120
| GAGACAACAC | TCGGTCGATC | CGTGTGGAGT | CCCTCCATCT | TGGTGGTGGG | GTGTTGGTGT | 180
| TTGAGTATTG | GATAGTGGTT | GCGAGCATCT | AGATGAGCGC | GTAGTCCTTG | TGGCTGATGC | 240
| GTTCGTCGAA | ATGTGTAATT | TCTTCTTTGG | GTTTTTGTGT | GT | | 282

(2) INFORMATION FOR SEQ ID NO: 87:

(i) SEQUENCE CHARACTERISTICS:
        (A) LENGTH: 281 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 87:

| | | | | | |
|---|---|---|---|---|---|
| AAGGAGCACC | ACGAAAAGCA | CCCCAATTGG | TGGGGTGCGA | GCCGTGAGGG | GTTCTCGTCT | 60
| GTAGTGGACG | GNAGCCGGNT | GCGCAACAGC | AAATGATTGC | CAGACACACT | ATTGGGCCCT | 120
| GAGACAACAC | TCGGNCGATC | CGTGTGGAGT | CCCTCCATCT | TGGTGGTGGG | GTGTNGTGTT | 180
| TGAGTATTGG | ATAGTGGTTG | CGAGCATCTA | GATGGGCGCG | TAGTCCTTTG | TGACTGATGC | 240
| GTTCATCAAA | ATGTGTAATT | TCTTTTTTGN | NTTTNGTGTG | T | | 281

(2) INFORMATION FOR SEQ ID NO: 88:

(i) SEQUENCE CHARACTERISTICS:
        (A) LENGTH: 281 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 88:

AAGGAGCACC ACGAAAAGCA CTCCAATTGG TGGGGTGCGA GCCGTGAGGG GTTCTCGTCT      60

GTAGTGGACG GGAACCGGGT GCACAACAGC AAATGATTGC CAGACACACT ATTGGGCCCT     120

GAGACAACAC TCGGTCGATC CGTGTGGAGT CCCTCCATCT TGGTGGTGGG GTGTGGTGTT     180

TGAGTATTGG ATAGTGGTTG CGAGCATCTA GATGAGCGCA TAGTCCTTTG TGGCTGACGC     240

GTTCATCGAA ATGTGTAATT TCTTCTTTGG TTTTTGTGTG T                        281

(2) INFORMATION FOR SEQ ID NO: 89:

(i) SEQUENCE CHARACTERISTICS:
        (A) LENGTH: 280 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 89:

AAGGAGCACC ACGAAAAGCA CTCCAATTGG TGGGGTGCGA GCCGTGANGG GTTCCCGTCT      60

GTAGTGGACG GGGGCCGGGT GCACAACAGC AAATGATTGC CAGACACACT ATTGGGCCCT     120

GAGACAACAC TCGGTCGATC CGTGTGGAGT CCCTCCATCT TGGTGGTGGG GTGTGGTGTT     180

TGAGTATTGG ATAGTGGTTG CGAGCATCTA GATGAGCGCA TAGTCCTTAG GGCTGATGCG     240

TTCGTCGNAA TGTGTAATTT CTTCTTTGGT TTTTGTGTGT                          280

(2) INFORMATION FOR SEQ ID NO: 90:

(i) SEQUENCE CHARACTERISTICS:
        (A) LENGTH: 282 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 90:

AAGGAGCACC ACGAAAAGCA TCCCAATTGG TGGGGTGCGA GCCGTGAGGG GTTCTCGTCT      60

GTAGTGGACG AAAACCGGGT GCACAACAGC AAATAATTGC CAGACACACT ATTGGGCCCT     120

GAGACAACAC TCGGTCGATC CGTGTGGTGT CCCTCCATCT TGGTGGTGGG GTGTGGTGTT     180

TGAGTATTGG ATAGTGGTTG CGAGCATCTA GATGAACGCG TAGTCCTTCG TGGCTGACGT     240

GTTCATCGAA ATGTGTAATT TCTTNTNTTA ACTCTTGTGT GT                       282

(2) INFORMATION FOR SEQ ID NO: 91:

(i) SEQUENCE CHARACTERISTICS:
        (A) LENGTH: 280 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 91:

AAGGAGCACC ACGAAAAGCA CCCCAATTGG TGGGGTGCGA GCCGTGAGGG GTTCTCGTCT        60

GTAGTGGACG GGAGCCGGGT GCACAACAGC AAATGATTGC CAGACACACT ATTGGGCCCT       120

GAGACAACAC TCGGTCAGTC CGTGTGGTGT CCCTCCATCT TGGTGGTGGG GTGTGGTGTT       180

TGAGTATTGG ATAGTGGTTG CGAGCATCTA GATGAACGCG TAGTCCTTGT GACTGACGTG       240

TTCATCGAAA TGTGTAATTT CTTTTCTAAC TCTTGTGTGT                            280

(2) INFORMATION FOR SEQ ID NO: 92:

(i) SEQUENCE CHARACTERISTICS:
            (A) LENGTH: 281 base pairs
            (B) TYPE: nucleic acid
            (C) STRANDEDNESS: single
            (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 92:

AAGGAGCACC ACGAAAAGCA CTTCAATTGG TGAAGTGCGA GCCGTGAGGG GTTCTCGTCT        60

GTAGTGGACG AAAGCCGGGT GCACAACAGC AAATGATTGC CAGACACACT ATTGGGCCCT       120

GAGACAACAC TCGGTCGAAC CGTGTGGAGT CCCTCCATCT TGGTGGTGGG GTGTGGTGTT       180

TGAGTATTGG ATAGTGGTTG CGAGCATCTA GATGAACGCG TGGTCTTCAT GGCCGGCGTG       240

TTCATCGAAA TGTGTAATAT CTTCTCTGGT TTTCGGTGTG T                          281

(2) INFORMATION FOR SEQ ID NO: 93:

(i) SEQUENCE CHARACTERISTICS:
            (A) LENGTH: 280 base pairs
            (B) TYPE: nucleic acid
            (C) STRANDEDNESS: single
            (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 93:

AAGGAGCACC ACGAAAAGCA CTTCAATTGG TGAAGTGCGA GCCGTGAGGG GTTCTCGTCT        60

GTAGTGGACG AAAACCGGNT GCACAACAGC AAATGATTGC CAGACACACT ATTGGGCCCT       120

GAGACAACAC TCGGTCGATC CGTGTGGAGT CCCTCCATCT TGGTGGTGGG GTGTGGTGTT       180

TGAGTATTGG ATAGTGGTTG CGAGCATCTA GATGAACGCG TGGTCTTCAT GGCCGGCGTG       240

TTCATCGAAA TGTGTAATTT CTTTTTNNAC TCTTGTGTGT                            280

(2) INFORMATION FOR SEQ ID NO: 94:

(i) SEQUENCE CHARACTERISTICS:
            (A) LENGTH: 280 base pairs
            (B) TYPE: nucleic acid
            (C) STRANDEDNESS: single (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 94:

AAGGAGCACC ACGAAAAGCA CTTCAATTGG TGAAGTGCGA GCCGTGAGGG GTTCTCGTCT      60

GTAGTGGACG AAAGCCGGGT GCACAACAGC AAATGATTGC CAGACACACT ATTGGGCCCT     120

GAGACAACAC TCGGTCGAAC CGTGTGGAGT CCCTCCATCT TGGTGGTGGG GTGTGGTGTT     180

TGAGTATTGG ATAGTGGTTG CGAGCATCTA GATGAACGCG TGGTCTTCAT GGCCGGCGTG     240

TTCATCGAAA TGTGTAATTT CTTCTTTGGT TTTNGTGTGT                          280

(2) INFORMATION FOR SEQ ID NO: 95:

(i) SEQUENCE CHARACTERISTICS:
           (A) LENGTH: 281 base pairs
           (B) TYPE: nucleic acid
           (C) STRANDEDNESS: single
           (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 95:

AAGGAGCACC ACGAAAAGCA CTTCAATTGG TGAAGTGCGA GCCGTGAGGG GTTCTCGTCT      60

GTAGTGGACG AAAACCGGGT GCACAACAGC AAATGATTGC CAGACACACT ATTGGGCCCT     120

GAGACAACAC TCGGTCGATC CGTGTGGAGT CCCTCCATCT TGGTGGTGGG GTGTGGTGTT     180

TGAGTATTGG ATAGTGGTTG CGAGCATCTA GATGAACGCG TAGTCCTTCG NGGNCNGCGT     240

GTTCATCGAA ATGTGTAATT TCTNTTNTAA CTCTNGTGTG T                        281

(2) INFORMATION FOR SEQ ID NO: 96:

(i) SEQUENCE CHARACTERISTICS:
           (A) LENGTH: 281 base pairs
           (B) TYPE: nucleic acid
           (C) STRANDEDNESS: single
           (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 96:

AAGGAGCACC ACGAAAAGCA TCCCAATTGG TGGGGTGTGA GCCGTGAGGG GTTCTCGTCT      60

GTAGTGGACG AAAACCGGGT GCACAACAGC AAATGATTGC CAGACACACT ATTGGGCCCT     120

GAGACAACAC TCGGTCGATC CGTGTGGAGT CCCTCCATCT TGGTGGTGGG GTGTGGTGTT     180

TGAGTATTGG ATAGTGGTTG CGAGCATCTA GATGAACGCG TAGTCCTTCG GGGCCGGCGT     240

GTTCATCGAA ATGTGTAATT TCTTTTTTAA CTCTTGTGTG T                        281

(2) INFORMATION FOR SEQ ID NO: 97:

(i) SEQUENCE CHARACTERISTICS:
           (A) LENGTH: 280 base pairs (B) TYPE: nucleic acid
            (C) STRANDEDNESS: single
            (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 97:

AAGGAGCACC ACGAAAAGCA CTTCANTTGG TGAAGTGCGA GCCGTGAGGG GTTCTCGTCT      60

GTAGTGGACG AAAACCGGGT GCACAACAGC AAATGATTGC CAGACACACT ATTGGGCCCT     120

GAGACAACAC TCGGTCGAAC CGTGTGGAGT CCCTCCATCT TGGTGGTGGG GTGTGGTGTT     180

TGAGTATTGG ATAGTGGTTG CGAGCATCTA GATGAACGCG TGGTCTTCAT GGCCGGCGTG     240

TTCATCGAAA TGTGTAATTT CTTCTTTAAC TCTTGTGTGT                          280

(2) INFORMATION FOR SEQ ID NO: 98:

(i) SEQUENCE CHARACTERISTICS:
            (A) LENGTH: 280 base pairs
            (B) TYPE: nucleic acid
            (C) STRANDEDNESS: single
            (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 98:

AAGGAGCACC ACGAAAAGCA CTTCAATTGG TGAAGTGCGA GCCGTGAGGG GTTCTCGTCT      60

GTAGTGGACG AAAACCGGGT GCACAACAGN AAATGATTGC CAGACACACT ATTGGGCCCT     120

GAGACAACAC TCGGTCGATC CGTGTGGAGT CCCTCCATCT TGGTGGTGGG GTGTGGTGTT     180

TGAGTATTGG ATAGTGGTTG CGAGCATCTA GATGAACGCG TGGTCTTCAT GGCCNGCGTG     240

TTCATCGAAA TGTGTAATTT CTTTTTTAAC TCTTGTGTGT                          280

(2) INFORMATION FOR SEQ ID NO: 99:

(i) SEQUENCE CHARACTERISTICS:
            (A) LENGTH: 280 base pairs
            (B) TYPE: nucleic acid
            (C) STRANDEDNESS: single
            (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 99:

AAGGAGCACC ACGAAAAGCA CTTCAATTGG TGAAGTGCGA GCCGTGAGGG GTTCTCGTCT      60

GTAGTGGACG AAAACCGGGT GCACAACAGC AAATGATTGC CAGACACACT ATTGGGCCCT     120

GAGACAACAC TCGGTCGATC CGTGTGGAGT CCCTCCATCT TGGTGGTGGG GTGTGGTGTT     180

TGAGTATTGG ATAGTGGTTG CGAGCATCTA GATGAACGCG TGGTCTTCAT GGCCGGCGTG     240

TTCATCGAAA TGTGTAATTT CTTTTTTAAC TCTTGTGTGT                          280

(2) INFORMATION FOR SEQ ID NO: 100:

(i) SEQUENCE CHARACTERISTICS:
            (A) LENGTH: 281 base pairs
            (B) TYPE: nucleic acid
            (C) STRANDEDNESS: single
            (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 100:

| | |
|---|---|
| AAGGAGCACC ACGAAAAGCA CCCCAACTGG TGGGGTGCGA GCCGTGAGGG GTCCTCGCCT | 60 |
| GTAGTGGGCG GGGGCCGGGT GCACAACAGC AAATGATTGC CAGACACACT ATTGGGCCCT | 120 |
| GAGGCAACAC TCGGCTCGTT CTGAGTGGTG TCCCTCCATC TTGGTGGTGG GGTGTGGTGT | 180 |
| TTGAGTATTG GATAGTGGTT GCGAGCATCT AAACGGATGC GTGGCCGGCA ACGGTGGCGT | 240 |
| GTTCGTTGAA ATGTGTAATT TCTTTTTTGG TTTTTGTGTG T | 281 |

(2) INFORMATION FOR SEQ ID NO: 101:

(i) SEQUENCE CHARACTERISTICS:
            (A) LENGTH: 274 base pairs
            (B) TYPE: nucleic acid
            (C) STRANDEDNESS: single
            (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 101:

| | |
|---|---|
| AAGGAGCACC ACGAAAAGCA TCCCAACAAG TGGGGTGCAA NCCGTGAGGG GTTCTCGTCT | 60 |
| GTAGTGGACG AAAGCCGGGT GCACGACAAC AAGCAAAGCC AGACACACTA TTGGGTCCTG | 120 |
| AGGCAACACT CGGGCTCTGT TCGAGAGTTG TCCCACCATC TTGGTGGTGG GGTGTGGTGT | 180 |
| TTGAGAATTG GATAGTGGTT GCGAGCATCA AATGGATGCG TTGCCCTACG GGTAGCGTGT | 240 |
| TCTTTTGTGC AATTTTATTC TTTGGTTTTT GTGT | 274 |

(2) INFORMATION FOR SEQ ID NO: 102:

(i) SEQUENCE CHARACTERISTICS:
            (A) LENGTH: 293 base pairs
            (B) TYPE: nucleic acid
            (C) STRANDEDNESS: single
            (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 102:

| | |
|---|---|
| AAGGAGCACC ATTTCCCAGT CGATGAACTA GGGAACATAA AGTAGGCATC TGTAGTGGAT | 60 |
| ATCTACTTGG TGAATATGTT TTGTAAATCC TGTCCACCCC GTGGATGGGT AGTCGGCAAA | 120 |
| ACGTCGGACT GTCATAAGAA TTGAAACGCT GGCACACTGT TGGGTCCTGA GGCAACACGT | 180 |
| TGTGTTGTCA CCCTGCTTGG TGGTGGGGTG TGGACTTTGA CTTCTGAATA GTGGTTGCGA | 240 |
| GCATCTAAAC ATAGCCTCGC TCGTTTTCGA GTGGGCTGG TTTTGCAATT TTA | 293 |

(2) INFORMATION FOR SEQ ID NO: 103:

(i) SEQUENCE CHARACTERISTICS:
       (A) LENGTH: 296 base pairs
       (B) TYPE: nucleic acid
       (C) STRANDEDNESS: single
       (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 103:

| | |
|---|---|
| AAGGAGCACC ATTTCCCAGT CGGATGAACT AGGGAACATA AAGTAGGCAT CTGTAGTGGG | 60 |
| TATCTACTTG GTGAATATGT TTTGTAAATC CTGTCCACCC CCGTGGATGG GTAGTCGGCA | 120 |
| AAACGTCGGA CTGTCATAAG AATTGAAACG CTGGCACACT GTTGGGTCCT GAGGCAACAC | 180 |
| GTTGTGTTGT CACCCTGCTT GGTGGTGGGG TGTGGACTTT GACTTCTGAA TAGTGGTTGC | 240 |
| GAGCATCTAA ACATAGCCTC GCTCGTTTTC GAGTGAGGCT GGTTTTTGCA ATTTTA | 296 |

(2) INFORMATION FOR SEQ ID NO: 104:

(i) SEQUENCE CHARACTERISTICS:
       (A) LENGTH: 274 base pairs
       (B) TYPE: nucleic acid
       (C) STRANDEDNESS: single
       (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 104:

| | |
|---|---|
| AAGGAGCACC ACGAAGAGCA CTCCAATTGG TGGGGTGCGA GCCGTGAGGG GTCATCGTCT | 60 |
| GTAGTGGACG AAGACCGGGT GCACGACAAC AAGCTAAGCC AGACACACTA TTGGGTCCTG | 120 |
| AGGCAACACC CTCGGGTGCT GTCCCCCCAT CTTGGTGGTG GGGTGTGGTG TTTGAGAATT | 180 |
| GGATAGTGGT TGCGAGCATC AAAATGTATG CGTTGTCGTT CTCGGCAACG TGTTCTTTTT | 240 |
| GTGCAATTTA TTCTTTGGTT TTTGTAGTGT TTGT | 274 |

(2) INFORMATION FOR SEQ ID NO: 105:

(i) SEQUENCE CHARACTERISTICS:
       (A) LENGTH: 278 base pairs
       (B) TYPE: nucleic acid
       (C) STRANDEDNESS: single
       (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 105:

| | |
|---|---|
| AAGGAGCACC ACGAAGAGCA CTCCAATTGG TGGGGTGCGA GCCGNGAGGG GTCATCGTCT | 60 |
| GTAGTGGACG AAGACTGGGT GCACGACAAC AAAGCAAGCC AGACACACTA TTGGGTCCTG | 120 |
| AGGCAACACC CTCGGGTGCT GCCCCTCCAT CTTGGTGGTG GGGTGTGGTG TTTGAGAACT | 180 |
| GGATAGTGGT TGCGAGCATC AAAAATGTAT GCGTTGTCGT TCGCGACAAC GTGTTCTTTT | 240 |
| TGTGCAATTT TAATTCTTTT GGTTTTGGTA GTGTTTGT | 278 |

(2) INFORMATION FOR SEQ ID NO: 106:

(i) SEQUENCE CHARACTERISTICS:
        (A) LENGTH: 276 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 106:

```
AAGGAGCACC ACGAGAAGCA CTCCAATTGG TGGGGTGCAA GCCGTGAGGG GTCATCGTCT      60
GTAGTGGACG AAGACCGGGT GCACGACAAC AAGCAAAGCC AGACACACTA TTGGGTCCTG     120
AGGCAACACC CTCGGGTGCT GTCCCCCCAT CTTGGTGGTG GGGTGTGGTG TTTGAGAACT     180
GGATAGTGGT TGCGAGCATC AAAATGTATG CGTTGTCGTT CGCGGCAACG TGTTCTTTTT     240
GTGCAATTTT TATTCTTTGG TTTTTGTAGT GTTTGT                               276
```

(2) INFORMATION FOR SEQ ID NO: 107:

(i) SEQUENCE CHARACTERISTICS:
        (A) LENGTH: 277 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 107:

```
AAGGAGCACC ACGAAAAGCA CCCCAATTGG TGGGGTGCAA GCCGTGAGGG GTTCCCGCCT      60
GTAGTGGGCG GGGCCGGGTG CGCAACAGCA AATGATTGCC AGACACACTA TTGGGCCCTG     120
AGGCAACACT CGGATCGATT GAGTGCTTGT CCCCCCATCT TGGTGGTGGG GTGTGGTGTT     180
TGAGAACTGG ATAGTGGTTG CGAGCATCTA AATGAACGCA CTGCCGATGG TGGTGTGTTC     240
GTTTTGTGTA ATTTTATTCT TTGGTTTTTG TGTTTGT                              277
```

(2) INFORMATION FOR SEQ ID NO: 108:

(i) SEQUENCE CHARACTERISTICS:
        (A) LENGTH: 282 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 108:

```
AAGGAGCACC ACGAAAAGCA CTCCAATTGG TGGGGTGCGA GCCGTNAGGG GTTCTCGTCT      60
GTAGTGGATG GCAGCCGGGT GCACANCAGC AAATGATTGC CAGACACACT ATTGGGCCCT     120
GAGACAACAC TCGGTCAGTC CGTGTGGAGT CCCTCCATCT TGGTGGTGGG GTGTGGNGTT     180
TGAGTATTGG ATAGTGGTTG CGANCATCTA GATGAACGCG TAGTCCTCNG TGGCTGACGT     240
```

```
GTTCATCAAA ATGTGTAATT TCTTTTANGG GTTTNGGTGT CT                  282

(2) INFORMATION FOR SEQ ID NO: 109:

(i) SEQUENCE CHARACTERISTICS:
        (A) LENGTH: 280 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 109:

AAGGAGCACC ACGAAAAGCA CTCCAATTGG TGGGGTGCGA GCCGNGAGGG GTTCTCGCCT   60

GTAGTGGNCG AGGGCCGGAT GCACAACAAC ACATGATTGC CAGACACACT ATTGGGCCCT  120

GANACAACAC TCGGCCAGTC CGTGTGGTGT CCCTCCATCT TGGTGGTGGG GTGTGGTGTT  180

TGAGTATNGG ATAGTNGTTG NGANCATCTA AACGGCTGCG TNGNCNNGAA CGGTGGCGTG  240

TTCGNTAAAA TGTGTAATTT CTTTTNNGGT TTGGGTGTNT                       280

(2) INFORMATION FOR SEQ ID NO: 110:

(i) SEQUENCE CHARACTERISTICS:
        (A) LENGTH: 280 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 110:

AAGGAGCACC ACGAAAAGCA CTCCAATTGG TGGGGTGCGA GCCGTGAGGG GTTCTCGCCT   60

GTAGTGGGCG ANGGCCGGGT GCACAACAAC AAATGATTGC CAGACACACT ATTGGGCCCT  120

GAGACAACAC TCGGCCAGTC CGTGTGGTGT CCCNCCATCT TGGTGGTGGG GTGTGGTGTT  180

TGAGTATTGG ATAGTGGTTG CGAGCATCTA AANGGNTGCG TTGCCGNNAN CNGTGGCGTN  240

TTCGNTAAAA TGTGTAATTT CTTTTTNGGT TTGTGTGTGT                       280

(2) INFORMATION FOR SEQ ID NO: 111:

(i) SEQUENCE CHARACTERISTICS:
        (A) LENGTH: 471 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 111:

ATCGAAGATC CCGGCTTCTT CATAAGCTCC CACACGAATT GCTTGATTCA CTGGTTAGAC   60

GATTGGGTCT GTAGCTCAGT TGGTTAGAGC GCACCCCTGA TAAGGGTGAG GTCGGCAGTT  120

CGAATCTGCC CAGACCCACC AATTGTTGGT GTGCTGCGTG ATCCGATACG GGGCCATAGC  180
```

```
TCAGCTGGGA GAGCGCCTGC TTTGCACGCA GGAGGTCAGG AGTTCGATCC TCCTTGGCTC      240

CACCATCTAA AACAATCGTC GAAAGCTCAG AAATGAATGT TCGTGGATGA ACATTGATTT      300

CTGGTCTTTG CACCAGAACT GTTCTTTAAA AATTCGGGTA TGTGATAGAA GTAAGACTGA      360

ATGATCTCTT TCACTGGTGA TCATTCAAGT CAAGGTAAAA TTTGCGAGTT CAAGCGCGAA      420

TTTTCGGCGA ATGTCGTCTT CACAGTATAA CCAGATTGCT TGGGGTTATA T              471
```

(2) INFORMATION FOR SEQ ID NO: 112:

(i) SEQUENCE CHARACTERISTICS:
        (A) LENGTH: 520 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 112:

```
ATCGAAGACA TCAGCTTCTT CATAAGTATC CACACGAATT GCTTGATTCA TAGTCGAACG       60

AATGCTGTAA CGCGACCCGT GTTATAGGTC TGTAGCTCAG TTGGTTAGAG CGCACCCCTG      120

ATAAGGGTGA GGTCGGCAGT TCAAATCTGC CCAGACCTAC CAATTGCTTG GTCGAGAAGA      180

ATACGGGGCC ATAGCTCAGC TGGGAGAGCG CCTGCCTTGC ACGCAGGAGG TCAGCGGTTC      240

GATCCCGCTT GGCTCCACCA CTCTCTCGTG TTGCGGTGAG TGTTAAAGAG TTCAGAAATG      300

ATGCCGCTTC AGGTTTGTCC TGTTGAGTGC TGATTTCTGG TCTTTTGACC GGTACGAAAA      360

TCGTTCTTTA AAAATTTGGA TATGTGATAG AAGTGACTGA TTAATTGCTT TCACTGGCAA      420

TTGATCTGGT CAAGGTAAAA TTTGTAGTTC TCAAGACGCA AATTTTCGGC GAATGTCGTC      480

TTCACGATTG AGACAGTAAC CAGATTGCTT GGGGTTATAT                           520
```

(2) INFORMATION FOR SEQ ID NO: 113:

(i) SEQUENCE CHARACTERISTICS:
        (A) LENGTH: 504 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 113:

```
ATCGAAGACA CCGGCTTCGT CATAAGCTCC CACACGAATT GCTTGATTCA CTTGCGAAAG       60

GCGATTGGGT TTAGACCCGA GAGTAACGAT TGGGTCTGTA GCTCAGTTGG TTAGAGCGCA      120

CCCCTGATAA GGGTGAGGTC GGCAGTTCGA ATCTGCCCAG ACCCACCAAT CGAAGGGGCC      180

ATAGCTCAGC TGGGAGAGCG CCTGCTTTGC ACGCAGGAGG TCAGCGGTTC GATCCCGCTT      240

GGCTCCACCA TTAACTCTAG TCGCCGAAAG CTCAGAAATG AGTGTTTACC AGGATGAGGT      300

TGATTGCCTG GGTTGAACAT TGATTTCTGG ACTTTGCGCC AGAACTGTTC TTTAAAAATT      360

TGGGTATGTG ATAGAAGTAG ACCGATGTGT TGCTTTCACT GGCAGCATGT CGCGTCAAGG      420

TAAAATTTGC GTGTTCTCTA TGCAAATTTT CGGCGAATGT CGTCTTCACG TTATAGACAG      480
```

```
TAACCAGATT GCTTGGGGTT ATAT                                               504

(2) INFORMATION FOR SEQ ID NO: 114:

(i) SEQUENCE CHARACTERISTICS:
        (A) LENGTH: 499 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 114:

ATCGAAGACT TCAGCTTCTT CATAAGTTCC CACACGAATT GCTTGATTCA CTTGCGAAAA         60

GCGATTGGGT TGAGACCCGA GAGTGACGAT TGGGTCTGTA GCTCAGTTGG TTAGAGCGCA        120

CCCCTGATAA GGGTGAGGTC GGCAGTTCGA ATCTGCCCAG ACCCACCAAT TGTCGGGATG        180

GCCAGTGTCA AATGGGGCCA TAGCTCAGCT GGGAGAGCGC CTGCTTTGCA CGCAGGAGGT        240

CAGGAGTTCG ATCCTCCTTG GCTCCACCAT CAACTCACGA TCGCTGAAAG CTCAGAAATG        300

AACATTGGTA GTTCAATGTT GATTTCTGGT CTTTGCGCCA GAACTGTTCT TTAAAAATTT        360

GGGTATGTGA TAGAAGTGAC TAACAGCGTG TTTCACTGCA CGTTGTTAAT CAAGGCAAAA        420

TTTGCGAGTT CAAGCGCGAA TTTTCGGCGA ATGTCGTCTT CACGTTACGA ATCTATAACC        480

AGATTGCTTG GGGTTATAT                                                    499

(2) INFORMATION FOR SEQ ID NO: 115:

(i) SEQUENCE CHARACTERISTICS:
        (A) LENGTH: 468 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 115:

ATCGACGACA TCAGCTGTCT CATAAGCTCC CACACGAATT GCTTGATTCA TTGAAGAAGA         60

CGATTAGGTT AGCAACCTTC GATTGGGTCT GTAGCTCAGT TGGTTAGAGC GCACCCCTGA        120

TAAGGGTGAG GTCGGCAGTT CGAATCTGCC CAGACCCACC AATTTGCTGG GGCCATAGCT        180

CAGCTGGGAG AGCGCCTGCC TTGCACGCAG GAGGTCAGCG GTTCGATCCC GCTTGGCTCC        240

ACCACCCCGC TTGCCAGTTT GTCAAAGCTT AGAAATGAAT ATTCGCGTCG AATATTGATT        300

TCTGAACTTT ATCAGAATCG TTCTTTAAAA ATTTGGGTAT GTGATAGAAA GATAGACTGG        360

ACAGCACTTT CACTGGTGTG TGTTCAGGCT AAGGTAAAAT TTGTGAGTAA TTACAAGTTT        420

TCGGCGAATG TTGTCTTCAC AGTATAACCA GATTGCTTGG GGTTATAT                     468

(2) INFORMATION FOR SEQ ID NO: 116:

(i) SEQUENCE CHARACTERISTICS:
        (A) LENGTH: 246 base pairs
        (B) TYPE: nucleic acid
        (C) STRANDEDNESS: single
        (D) TOPOLOGY: linear
```

(ii) MOLECULE TYPE: cDNA (iii) HYPOTHETICAL: NO (iv) ANTI-SENSE: NO (xi) SEQUENCE DESCRIPTION: SEQ ID NO: 116:

TAAGGAAAAG GAAACCTGTG AGTTTTCGTT CTTCTCTGTT TGTTCAGTTT TGAGAGGTTA     60

ATTCTTCTCT ATACTGTTTG TTCTTTGAAA ACTAGATAAG AAAGTTAGTA AAGTTAGCAT    120

AAATAGGTAA CTATTTATGA CACAAGTAAC CGAGAATCAT CTGAAAGTGA ATCTTTCATC    180

TGATTGGAAG TATCATCGCT GATACGAAAA ATCAGAAAAA CAACCTTTAC TTCATCGAAG    240

TAAATT                                                              246

(2) INFORMATION FOR SEQ ID NO: 117:

(i) SEQUENCE CHARACTERISTICS:
            (A) LENGTH: 246 base pairs
            (B) TYPE: nucleic acid
            (C) STRANDEDNESS: single
            (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 117:

CTAAGGAAAA GGAAACCTGT GAGTTTTCGT TCTTCTCTAT TTGTTCAGTT TTGAGAGGTT     60

AGTACTTCTC AGTATGTTTG TTCTTTGAAA ACTAGATAAG AAAGTTAGTA AAGTTAGCAT    120

AGATAATTTA TTATTTATGA CACAAGTAAC CGAGAATCAT CTGAAAGTGA ATCTTTCATC    180

TGATTGGAAG TATCATCGCT GATACGGAAA ATCAGAAAAA CAACCTTTAC TTCGTAGAAG    240

TAAATT                                                              246

(2) INFORMATION FOR SEQ ID NO: 118:

(i) SEQUENCE CHARACTERISTICS:
            (A) LENGTH: 246 base pairs
            (B) TYPE: nucleic acid
            (C) STRANDEDNESS: single
            (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 118:

TAAGGAAAAG GAAACCTGTG AGTTTTCGTT CTTCTCTGTT TGTTCAGTTT TGAGAGGTTA     60

TTACTTCTCT GTATGTTTGT TCTTTGAAAA CTAGATAAGA AAGTTAGTAA AGTTAGCATA    120

AGTAGTGTAA CTATTTATGA CACAAGTAAC CGAGAATCAT CTGAAAGTGA ATCTTTCATC    180

TAATTCGACG TATCATCGCT GATACAGACA ATTAGAAAAA CAACCTTTAC TTCGACGAAG    240

TAAATT                                                              246

(2) INFORMATION FOR SEQ ID NO: 119:

(i) SEQUENCE CHARACTERISTICS:
            (A) LENGTH: 363 base pairs
            (B) TYPE: nucleic acid
            (C) STRANDEDNESS: single (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 119:

| | |
|---|---|
| GGCCTATAGC TCAGCTGGTT AGAGCGCACG CCTGATAAGC GTGAGGTCGA TGGTTCGAGT | 60 |
| CCATTTAGGC CCACTTTTTC TTTCTGACAG AAGAAACACT GTATAACCTA TTTAAGGGGC | 120 |
| CTTAGCTCAG CTGGGAGAGC GCCTGCTTTG CACGCAGGAG GTCAGCGGTT CGATCCCGCT | 180 |
| AGGCTCCACC AAAATTGTTC TTTGAAAACT AGATAAGAAA GTTAGTAAAG TTAGCATAAA | 240 |
| TAGGTAACTA TTTATGACAC AAGTAACCGA GAATCATCTG AAAGTGAATC TTTCATCTGA | 300 |
| TTGGAAGTAT CATCGCTGAT ACGAAAAATC AGAAAAACAA CCTTTACTTC ATCGAAGTAA | 360 |
| ATT | 363 |

(2) INFORMATION FOR SEQ ID NO: 120:

(i) SEQUENCE CHARACTERISTICS:
        (A) LENGTH: 496 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 120:

| | |
|---|---|
| TAAGGAAAAG GAAACCTGTG AGTTTTCGTT CTTCTCTATT TGTTCAGTTT TGAGAGGTTA | 60 |
| CTCTCTTTTA TGTCAGATAA AGTATGCAAG GCACTATGCT TGAAGCATCG CGCCACTACA | 120 |
| TTTTTGACGG GCCTATAGCT CAGCTGGTTA GAGCGCACGC CTGATAAGCG TGAGGTCGAT | 180 |
| GGTTCGAGTC CATTTAGGCC CACTTTTTCT TTCTGACATA AGAAATACAA ATAATCATAC | 240 |
| CCTTTTACGG GGCCTTAGCT CAGCTGGGAG AGCGCCTGCT TTGCACGCAG GAGGTCAGCG | 300 |
| GTTCGATCCC GCTAGGCTCC ACCAAAATTG TTCTTTGAAA ACTAGATAAG AAAGTTAGTA | 360 |
| AAGTTAGCAT AGATAATTTA TTATTTATGA CACAAGTAAC CGAGAATCAT CTGAAAGTGA | 420 |
| ATCTTTCATC TGATTGGAAG TATCATCGCT GATACGGAAA ATCAGAAAAA CAACCTTTAC | 480 |
| TTCGTAGAAG TAAATT | 496 |

(2) INFORMATION FOR SEQ ID NO: 121:

(i) SEQUENCE CHARACTERISTICS:
        (A) LENGTH: 498 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 121:

| | |
|---|---|
| TAAGGAAAAG GAAACCTGTN AGTTTNCGTN CTTCTCTGTT TGTNCAGTTT TNAGAGGTTA | 60 |
| CTCTCTTTNA TGTCAGATAA AGTACGCACG GCACGTTGCC TTGGGCAAAG AGCCACTACA | 120 |

TTATTGACGG GCCTATAGCT CAGCTGGTTA GAGCGCACGC CTGATAAGCG TGAGGTCGAT    180

GGTTCGAGTC CATTTAGGCC CACTTTTTCT TTCTGACAGA AGAAATCATT TGCACATCCT    240

ATTAATAAGG GNCCTTAGCT CAGCTGGGAG AGCGCCTGCT TTGCACGCAG GAGGTCAGCG    300

GTTCGATCCC GCTAGGCTCC ACCCAAAATT GTTCTTTGAA AACTAGATAA GAAAGTTAGT    360

AAAGTTAGCA TAAGTAGTAT AACTATTTAT GACACAAGTA ACCGAGAATC ATCTGAAAGT    420

GAATCTTTCA TCTAATTCGA CGTATCATCG CTGATACAGA CAATTNGAAA AACAACCTTT    480

ACTTCGACGA AGTAAATT                                                  498

(2) INFORMATION FOR SEQ ID NO: 122:

(i) SEQUENCE CHARACTERISTICS:
        (A) LENGTH: 229 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 122:

TAAGGATAAG GATAACTGTC TTAGGACGGT TTGACTAGGT TGGGCAAGCG TTTTTTTAAT     60

CTTGTATTCT ATTCCTTTTG CATTGTTAAG CGTTGTTTCC AAAACATTTA GTTTACGATC    120

AAGTATGTTA TGTAAATAAT ATGGTAACAA GTAAATTCAC ATATAATAAT AGACGTTTAA    180

GAATATATGT CTTTAGGTGA TGTTAACTTG CATGGATCAA TAATTTACA               229

(2) INFORMATION FOR SEQ ID NO: 123:

(i) SEQUENCE CHARACTERISTICS:
        (A) LENGTH: 248 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 123:

TAAGGATAAG GAAGAAGCCT GAGAAGGTTT CTGACTAGGT TGGGCAAGCA TTTATATGTA     60

AGAGCAAGCA TTCTATTTCA TTTGTGTTGT TAAGAGTAGC GTGGTGAGGA CGAGACATAT    120

AGTTTGTGAT CAAGTATGTT ATTGTAAAGA AATAATCATG GTAACAAGTA TATTTCACGC    180

ATAATAAATAG ACGTTTAAGA GTATTTGTCT TTTAGGTGAA GTGCTTGCAT GGATCTATAG   240

AAATTACA                                                             248

(2) INFORMATION FOR SEQ ID NO: 124:

(i) SEQUENCE CHARACTERISTICS:
        (A) LENGTH: 224 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 124:

CAAATGGAGT TTTTATTTTT TATTTATCTT AAACACCCAT TAATTTTTTC GGTGTTAAAA      60

CCCAAATCAA TGTTTGGTCT CACAACTAAC ACATTTGGTC AGTTTGTATC CAGTTCTGAA     120

AGAATGTTTT TGAACAGTTC TTTCAAAACT GAAAACGACA ATCTTTCTAG TTCCAAAAAT     180

AAATACCAAA GGATCAATAC AATAAGTTAC TAAGGGCTTA TGGT                     224

(2) INFORMATION FOR SEQ ID NO: 125:

(i) SEQUENCE CHARACTERISTICS:
            (A) LENGTH: 252 base pairs
            (B) TYPE: nucleic acid
            (C) STRANDEDNESS: single
            (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 125:

CTAATGAAGT TTTTTACTTT TTCTTTTCAT CTTTAATAAA GATAAATACT AAACAAAACA      60

TCAAAATCCA TTTATTTATC GGTGGTAAAT TAAACCCAAA TCCCTGTTTG GTCTCACAAC     120

TAACATATTT GGTCAGATTG TATCCAGTTC TGAAAGAACA TTTCCGCTTC TTTCAAAACT     180

GAAAACGACA ATCTTTCTAG TTCCAAATAA ATACCAAAGG ATCAATACAA TAAGTTACTA     240

AGGGCTTATG GT                                                        252

(2) INFORMATION FOR SEQ ID NO: 126:

(i) SEQUENCE CHARACTERISTICS:
            (A) LENGTH: 608 base pairs
            (B) TYPE: nucleic acid
            (C) STRANDEDNESS: single
            (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 126:

AACGAAAGAT TGACGATTGG TAAGAATCCA CAACAAGTTG TTCTTCATAG ATGTATCTGA      60

GGGTCTGTAG CTCAGTTGGT TAGAGCACAC GCTTGATAAG CGTGGGGTCA CAAGTTCAAG     120

TCTTGTCAGA CCCACCATGA CTTTGACTGG TTGAAGTTAT AGATAAAAGA TACATGATTG     180

ATGATGTAAG CTGGGGACTT AGCTTAGTTG GTAGAGCGCC TGCTTTGCAC GCAGGAGGTC     240

AGGAGTTCGA CTCTCCTAGT CTCCACCAGA ACTTAAGATA AGTTCGGATT ACAGAAATTA     300

GTAAATAAAG ATTGAGATCT TGGTTTATTA ACTTCTGTGA TTTCATTATC ACGGTAATTA     360

GTGTGATCTG ACGAAGACAC ATTAACTCAT TAACAGATTG GCAAAATTGA GTCTGAAATA     420

AATTGTTCAC TCAAGAGTTT AGGTTAAGCA ATTAATCTAG ATGAATTGAG AACTAGCAAA     480

TTAACTGAAT CAAGCGTTTT GGTATGTGAA TTTAGATTGA AGCTGTACAG TGCTTAAGTG     540

CACAGTGCTC TAAACTGAAA TGTTGAAGTT ACTAACTTGT AGGTAACATC GACTGTTTGG     600

GGTTGTAT                                                             608

(2) INFORMATION FOR SEQ ID NO: 127:

(i) SEQUENCE CHARACTERISTICS:
        (A) LENGTH: 269 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 127:

```
AACGAAAGAT TGACGATTGG TAAGAATCCA CGACAAGTTG TTCTTCATAG ATGTATCTGA      60
GGGTCTGTAG CTCAGTTGGT TAGAGCACAC GCTTGATAAG CGTGGGGTCA CAAGTTCAAG     120
TCTTGTCAGA CCCACCATGA CTTTGACTGG TTGAAGTTAT AGAAAAGAAG ATACATAACT     180
GATGATGTAA GCTGGGGACT TAGCTTAGTT GGTAGAGCGC CTGCTTTGCA CGCAGGAGGT     240
CAGGAGTTCG ACTCTCCTAG TCTCCACCA                                      269
```

(2) INFORMATION FOR SEQ ID NO: 128:

(i) SEQUENCE CHARACTERISTICS:
        (A) LENGTH: 249 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 128:

```
AACGAAAGAT TGATGGCCGG TAAGAATCCA CAACAAGTTG TTCTTCGAAG ATGTATCTGA      60
GGGTCTGTAG CTCAGTTGGT TAGAGCACAC GCTTGATAAG CGTGGGGTCA CAAGTTCAAG     120
TCTTGTCAGA CCCACCAAAT CTGAAAGATA TGTCGTTCAT TATGATTAAA GCTGGGGACT     180
TAGCTTAGTT GGTAGAGCGC CTGCTTTGCA CGCAGGAGGT CAGGAGTTCG ACTCTCCTAG     240
TCTCCACCA                                                             249
```

(2) INFORMATION FOR SEQ ID NO: 129:

(i) SEQUENCE CHARACTERISTICS:
        (A) LENGTH: 283 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 129:

```
AACGAAAGAT TGACGATTGG TAAGAATCCA CAACAAGTTG TTCTTCATGA CGATGTATCT      60
GAGGGTCTGT AGCTCAGTTG GTTAGAGCAC ACGCTTGATA AGCGTGGGGT CACAAGTTCA     120
AGTCTTGTCA GACCCACCAA ATCTGACTAA CAAGCATTAT TAAATGCTGA ATACAGAAAA     180
ACAGAGACAT TGACTTATTG ATAAGCTGGG GACTTAGCTT AGTTGGTAGA GCGCCTGCTT     240
```

```
TGCACGCAGG AGGTCAGGAG TTCGACTCTC CTAGTCTCCA CCA              283

(2) INFORMATION FOR SEQ ID NO: 130:

(i) SEQUENCE CHARACTERISTICS:
        (A) LENGTH: 283 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 130:

AACGAAAGAT TGGTGACCGG TAAGAATCCA CAACAAGTTG TTCTTCGAAG ATGTATCTGA    60

GGGTCTGTAG CTCAGTTGGT TAGAGCACAC GCTTGATAAG CGTGGGGTCA CAAGTTCAAG   120

TCTTGTCAGA CCCACCACTA CTGACGAAGT GATGAATAAT CACAAGCTGC TAGATGAAAA   180

GATATGTCGT TCATTATGAT TAAAGCTGGG GACTTAGCTT AGTTGGTAGA GCGCCTGCTT   240

TGCACGCAGG AGGTCAGGAG TTCGACTCTC CTAGTCTCCA CCA                     283

(2) INFORMATION FOR SEQ ID NO: 131:

(i) SEQUENCE CHARACTERISTICS:
        (A) LENGTH: 808 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 131:

TAAGGAAGAT CGAGAATTGG AAAGAGGTCG GATTTATCCG GATGATCCTT CTCCATCTTA    60

TTAGAACATA GATCGCAGGC CAGTCAGCCT GACGATCGCT TGCAGGCGTG CCGCCTTCGT   120

TTCTCTTTCT TCATTGTTGA TTGCTCACGG GCCGTACCGC AGCTGACGCT GCTGGCCCTG   180

CGCAGGCGCG GCCCATCAGG GCCGACGGCC GGTCGGCCTT GCNAAGCTTC GCTTCGGGGT   240

GGATCTGTGG ATCGCGTAGT AGCGTTTGCG TCGGTATCTG GGCTTGTAGC TCAGTTGGTT   300

AGAGCACACG CTTGATAAGC GTGGGGTCGG AGGTTCAAGT CCTCCCAGGC CCACCAAGTT   360

ACTTGATGAG GGGCCGTAGC TCAGCTGGGA GAGCACCTGC TTTGCAAGCA GGGGGTCGTC   420

GGTTCGATCC CGTCCGGCTC CACCATCATG TTGGTGTTGA GACGGATATT GGCAATCAAC   480

AAAAGAAAGA AACAAGTTTG CGGACTNTTA CGAAAGTCTG CCTGTTCTGT ATGAAATCGT   540

GAAGAGAAGA TGTAATCGGA TCAACTGAAG AGTTGATGTC GCAAGAAGCT TGCTCAAGCC   600

TTGCATAATG ATTGATGTGT TTAACCGCCA TCACCGATTG TATCTCGAGA AGCTGGTCTT   660

TCTGCTGATA CTGTTGAAAC GAGCATTTGC AGTCGAATGG CAACATTCGG CGTCGCATAA   720

TGCGGCTTTA AGAGCTGAGT TTTGATGGAT ATTGGCAATG AGAGTGATCA AGTGTCTTAA   780

GGGCATTGGT GGATGCCTTG GCATGCAC                                     808

(2) INFORMATION FOR SEQ ID NO: 132:

(i) SEQUENCE CHARACTERISTICS:
        (A) LENGTH: 808 base pairs
```

(B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 132:

```
TAAGGAGGAT CGAGAATTGG AAAGAGGCCG GATTTATCCG GATGATCCTT CTCCATCTTA      60

TTAGAACATA GATCGCAGNC CAGTCAGCCT GACGATCGCT TGCAGGCGTG CCGCCTTCGT     120

TTCTCTTTCT TCATTGTTGA TTGCTCACGG GCCGTACCGC AGCTGACGCT GCTGGCCCTG     180

CGCAGGCGCG GNCCATCAGG GCCGACGGCC GGTCGGCCTT GCGAAGCTTC GCTTCGGGGT     240

GGATCTGTGG ATCGCGTAGT AGCGTTTGCG TCGGTATCTG GCTTGTAGC  TCAGTTGGTT     300

AGAGCACACG CTTGATAAGC GTGGGGTCGG AGGTTCAAGT CCTCCCAGGC CCACCAAGTT     360

ACTTGATGAG GGGCCGTAGC TCAGCTGGGA GAGCACCTGC TTTGCAAGCA GGGGGTCGTC     420

GGTTCGATCC CGTCCGGCTC CACCATCATG TTGGTGTTGA GACGGATATT GGCAATCAAC     480

AAAAGAAAGA AACAAGTTTG CGGACTNTTA CGAAAGTCTG CCTGTTCTGT ATGAAATCGT     540

GAAGAGAAGA TGTAATCGGA TCAACTGAAG AGTTGATGTC GCAAGAAGCT TGCTCAAGCC     600

TTGCATAATG ATTGATGTGT TTAACCGCCA TCACCGATTG TATCTCGAGA AGCTGGTCTT     660

TCTGCTGATA CTGTTGAAAC GAGCATTTGC AGTCGAATGG CAACATTCGG CGTCGCATAA     720

TGCGGCTTTA AGAGCTGAGT TTTGATGGAT ATTGGCAATG AGAGTGATCA AGTGTCTTAA     780

GGGCATTGGT GGATGCCTTG GCATGCAC                                       808
```

(2) INFORMATION FOR SEQ ID NO: 133:

(i) SEQUENCE CHARACTERISTICS:
        (A) LENGTH: 353 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 133:

```
CCTTAAAGAA CTGTTCTTTG CAGTGCTCAC ACAGATTGTC TGATGAAAAG TAAATAGCAA      60

GGCGTCTTGC GAAGCAGACT GATACGTCCC CTTCGTCTAG AGGCCCAGGA CACCGCCCTT     120

TCACGGCGGT AACAGGGGTT CGAATCCCCT AGGGGACGCC ACTTGCGCGG TAATGTGTGA     180

AAGCGTTGCC ATCAGTATCT CAAAACTGAC TTACGAGTCA CGTTTGAGAT ATTTGCTCTT     240

TAAAAATCTG GATCAAGCTG AAAATTGAAA CACAGAACAA CGAAAGTTGT TCGTGAGTCT     300

CTCAAATTTT CGCAACACGA TGATGAATCG TAAGAAACAT CTTCGGGTTG TGA            353
```

(2) INFORMATION FOR SEQ ID NO: 134:

(i) SEQUENCE CHARACTERISTICS:
        (A) LENGTH: 515 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 134:

CCTTAAAGAA CTGTTCTTTG CAGTGCTCAC ACAGATTGTC TGATGAAAAA CGAGCAGTAA      60

AACCTCTACA GGCTTGTAGC TCAGGTGGTT AGAGCGCACC CCTGATAAGG GTGAGGTCGG     120

TGGTTCAAGT CCACTCAGGC CTACCAAATT TTCCCTGAAT ACTGCGTTGT GAAATAACTC     180

ACATACTGAT GTATGCTTCG TTATTCCACG CCTTGTCTCA GGAAAAATTA TCGGTAAAGA     240

GGTTCTGACT ACACGATGGG GCTATAGCTC AGCTGGGAGA GCGCCTGCTT TGCACGCAGG     300

AGGTCTGCGG TTCGATCCCG CATAGCTCCA CCATATCGTG AGTGTTTACG AAAAAATACT     360

TCAGAGTGTA CCTGAAAGGG TTCACTGCGA AGTTTTGCTC TTTAAAAATC TGGATCAAGC     420

TGAAAATTGA AACACAGAAC AACGAAAGTT GTTCGTGAGT CTCTCAAATT TTCGCAACAC     480

GATGATGAAT CGTAAGAAAC ATCTTCGGGT TGTGA                                515

(2) INFORMATION FOR SEQ ID NO: 135:

(i) SEQUENCE CHARACTERISTICS:
            (A) LENGTH: 353 base pairs
            (B) TYPE: nucleic acid
            (C) STRANDEDNESS: single
            (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 135:

CCTTAAAGAA GCGTACTTTG CAGTGCTCAC ACAGATTGTC TGATGAAAAG TAAATAGCAA      60

GGCGTCTTGC GAAGCAGACT GATACGTCCC CTTCGTCTAG AGGCCCAGGA CACCGCCCTT     120

TCACGGCGGT AACAGGGGTT CGAATCCCCT AGGGGACGCC ACTTGCGCGG TAATGTGTGA     180

AAGCGTTGCC ATCAGTATCT CAAAACTGAC TTACGAGTCA CGTTTGAGAT ATTTGCTCTT     240

TAAAAATCTG GATCAAGCTG AAAATTGAAA CACAGAACAA CGAAAGTTGT TCGTGAGTCT     300

CTCAAATTTT CGCAACACGA TGATGAATCG TAAGAAACAT CTTCGGGTTG TGA            353

(2) INFORMATION FOR SEQ ID NO: 136:

(i) SEQUENCE CHARACTERISTICS:
            (A) LENGTH: 481 base pairs
            (B) TYPE: nucleic acid
            (C) STRANDEDNESS: single
            (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 136:

CCTTAAAGAA CTGTTCTTTG AAGTGCTCAC ACAGATTGTC TGATGAAAAA CGAGCAGTAA      60

AACCTCTACA GGCTTGTAGC TCAGGTGGTT AGAGCGCACC CCTGATAAGG GTGAGGTCGG     120

TGGTTCAAGT CCACTCAGGC CTACCAAATT TTCCCTGAAT ACTGCGTTGT GAAATAACTC     180

ACATACTGAT GTATGCTTCG TTATTCCACG CCTTGTCTCA GGAAAAATTA TCGGTAAAGA     240

-continued

```
GGTTCTGACT ACACGATGGG GCTATAGCTC AGCTGGGAGA GCGCCTGCTT TGCACGCAGG      300

AGGTCTGCGG TTCGATCCCG CATAGCTCCA CCATCTCGTG AGTGTTTACG AAAAAATACT      360

TCAGAGTGTA CCTGAAAGGG TTCACTGCGA AGTTTTGCTC TTTAAAAATC TGGATCAAGC      420

TGAAAATTGA AACACAGAAC AACGAAAGTT GTTCGTGAGT CTCTCAAATT TTCGCAACAC      480

G                                                                      481
```

(2) INFORMATION FOR SEQ ID NO: 137:

(i) SEQUENCE CHARACTERISTICS:
        (A) LENGTH: 392 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 137:

```
CCTTAAAGAA GCGTACTTTG AAGTGCTCAC ACAGATTGTC TGATGAAAAG TGAATAGCAA       60

GGCGTCTTGC GATTGAGACT TCAGTGTCCC CTTCGTCTAG AGGCCCAGGA CACCGCCCTT      120

TCACGGCGGT AACAGGGGTT CGAATCCCCT AGGGGACGCC AGCGTTCAAA CTGATGAGGT      180

CAAACCTCCA GGGACGCCAC TTGCTGGTTT GTGAGTGAAA GTCACCTGCC TTAATATCTC      240

AAAACTGACT TACGAGTCAC GTTTGAGATA TTTGCTCTTT AAAAATCTGG ATCAAGCTGA      300

AAATTGAAAC ACAGAACAAC GAAAGTTGTT CGTGAGTCTC TCAAATTTTC GCAACACGAT      360

GATGAATCGT AAGAAACATC TTCGGGTTGT GA                                    392
```

(2) INFORMATION FOR SEQ ID NO: 138:

(i) SEQUENCE CHARACTERISTICS:
        (A) LENGTH: 515 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 138:

```
CCTTAAAGAA ACGGTCTTTG AAGTGCTCAC ACAGATTGTC TGATGAAAAA CGAGCAGTAA       60

AACCTCTACA GGCTTGTAGC TCAGGTGGTT AGAGCGCACC CCTGATAAGG GTGAGGTCGG      120

TGGTTCAAGT CCACTCAGGC CTACCAAATT TTCCCTGAAT ACTGCGTTGT GAAATAACTC      180

ACATACTGAT GTATGCTTCG TTATTCCACG CCTTGTCTCA GGAAAAATTA TCGGTAAAGA      240

GGTTCTGACT ACACGATGGG GCTATAGCTC AGCTGGGAGA GCGCCTGCTT TGCACGCAGG      300

AGGTCTGCGG TTCGATCCCG CATAGCTCCA CCATCTCGTG AGTGTTTACG AAAAAATACT      360

TCAGAGTGTA CCTGAAAGGG TTCACTGCGA AGTTTTGCTC TTTAAAAATC TGGATCAAGC      420

TGAAAATTGA AACACAGAAC AACGAAAGTT GTTCGTGAGT CTCTCAAATT TTCGCAACAC      480

GATGATGAAT CGTAAGAAAC ATCTTCGGGT TGTGA                                 515
```

(2) INFORMATION FOR SEQ ID NO: 139:

(i) SEQUENCE CHARACTERISTICS:
            (A) LENGTH: 365 base pairs
            (B) TYPE: nucleic acid
            (C) STRANDEDNESS: single
            (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 139:

CTAAGGATAT ATTCGGAACA TCTTCTTCGG AAGATGCGGA ATAACGTGAC ATATTGTATT       60

CAGTTTTGAA TGTTTATTTA ACATTCAAAT ATTTTTTGGT TAAAGTGATA TTGCTTTTGA      120

AAATAAAGCA GTATGCGAGC GCTTGACTAA AAAAAATTGT ACATTGAAAA CTAGATAAGT      180

AAGTAAAATA TAGATTTTAC CAAGCAAAAC CGAGTGAATA AAGAGTTTTA AATAAGCTTG      240

AATTCATAAG AAATAATCGC TAGTGTTCGA AGAACACTC ACAAGATTAA TAACGCGTTT       300

AAATCTTTTT ATAAAAGAAC GTAACTTCAT GTTAACGTTT GACTTATAAA AATGGTGGAA      360

ACATA                                                                 365

(2) INFORMATION FOR SEQ ID NO: 140:

(i) SEQUENCE CHARACTERISTICS:
            (A) LENGTH: 548 base pairs
            (B) TYPE: nucleic acid
            (C) STRANDEDNESS: single
            (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 140:

CTAAGGATAT ATTCGGAACA TCTTCTTCAG AAGATGCGGA ATAACGTGAC ATATTGTATT       60

CAGTTTTGAA TGTTTATTTA ACATTCAAAT ATTTTTTGGT TAAAGTGATA TTGCTTATGC      120

GAGCNCTTGA CAATCTATTC TTTTTAAAGA AAGCGGTTGT CAGACAATGC ATTAAGAAAA      180

ATTAAAGCGG AGTTTACTTT TGTAAATGAG CATTTGATTT TTTGAAAATA AAGCAGTATG      240

CGAGCGCTTG ACTAAAAAGA AATTGTACAT TGAAAACTAG ATAAGTAAGT AAAATATAGA      300

TTTTACCAAG CAAAACCGAG TGAATAAAGA GTTTTAAATA AGCTTGAATT CATAAGAAAT      360

AATCGCTAGT GTTCGAAAGA ACACTCACAA GATTAATAAC GCGTTTAAAT CTTTTTATAA      420

AAGAAAACGT TTAGCAGACA ATGAGTTAAA TTATTTTAAA GCAGAGTTTA CTTATGTAAA      480

TGAGCATTTA AAATAATGAA AACGAAGCCG TATGTGAGCA TTTGACTTAT AAAAATGGTG      540

GAAACATA                                                              548

(2) INFORMATION FOR SEQ ID NO: 141:

(i) SEQUENCE CHARACTERISTICS:
            (A) LENGTH: 471 base pairs
            (B) TYPE: nucleic acid
            (C) STRANDEDNESS: single
            (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 141:

```
CTAAGGATAT ATTCGGAACA TCTTCTTCAG AAGATGCGGA ATAACGTGAC ATATTGTATT      60

CAGTTTTGAA TGTTTATTTA ACATTCAAAT ATTTTTTGGT TAAAGTGATA TTGCTTATGC     120

GAGCGCTTGA CAATCTATTC TTTTTAAAGA AAGCGGTTGT CAGACAATGC ATTAAGAAAA     180

ATTAAAGCGG AGTTTACTTT TGTAAATGAG CATTTGATTT TTTGAAAATA AAGCAGTATG     240

CGAGCGCTTG ACTAAAANGA AATTGTACAT TGAAAACTAG ATAAGTAAGT AAAATATAGA     300

TTTTACCAAG CAAAACCGAG TGAATAAAGA GTTTTGAATA AGCTTGAATT CATAAGAAAT     360

AATCGCTAGT GTTCGAAAGA ACACTCACAA GATTAATAAC GCGTTTAAAT CTTTTTATAA     420

AAGAACGTAA CTTCATGTTA ACGTTTGACT TATAAAAATG GTGGAAACAT A             471
```

(2) INFORMATION FOR SEQ ID NO: 142:

(i) SEQUENCE CHARACTERISTICS:
        (A) LENGTH: 383 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 142:

```
CTAAGGATAT ATTCGGAACA TCTTCTTCAG AAGATGCGGA ATAACGTGAC ATATTGTATT      60

CAGNTTTGAA TGTTTATTTA ACATTCAAAA AATGGGCCTA TAGCTCAGCT GGTTAGAGCG     120

CACGCCTGAT AAGCGTGAGG TCGGTGGTTC GAGTCCACTT AGGCCCACCA TTATTTGTAC     180

ATTGAAAACT AGATAAGTAA GTAAAATATA GATTTTACCA AGCAAAACCG AGTGAATAAA     240

GAGTTTTAAA TAAGCTTGAA TTCATAAGAA ATAATCGCTA GTGTTCGAAA GAACACTCAC     300

AAGATTAATA ACGCGTTTAA ATCTTTTTAT AAAAGAACGT AACTTCATGT TAACGTTTGA     360

CTTATAAAAA TGGTGGAAAC ATA                                            383
```

(2) INFORMATION FOR SEQ ID NO: 143:

(i) SEQUENCE CHARACTERISTICS:
        (A) LENGTH: 351 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 143:

```
CTAAGGATAT ATTCGGAACA TCTTCYTCAG AAGATGCGGA ATAATGTGAC ATATTGTATT      60

CAGTTTTGAA TGTTTATTTA ACATTCAAAT ATTTTTTGGT TAAAGTGATA TTGCTTATGC     120

GAGCGCTTGA CTAAAAAGAA ATTGTACATT GAAAACTAGA TAAGTAAGTA AAANTATAGA     180

TTTTACCAAG CAAAACCGAG TGAATAAAGA GTTTTAAATA AGCTTGAATT CATAAGAAAT     240

AATCGCTAGT GTTCGAAAGA ACACTCACAA GATTAATAAC GCGTTTAAAT CTTTTTATAA     300

AAGAACGTAA CTTCATGTTA ACGTTTGACT TATAAAAATG GTGGAAACAT A             351
```

(2) INFORMATION FOR SEQ ID NO: 144:

(i) SEQUENCE CHARACTERISTICS:
        (A) LENGTH: 263 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 144:

```
CTAAGGATAT ATTCGGAACA TCTTCTACGA AGATGAGGGA ATAACGTGAC ATATTGTATT     60
CAGTTTTGAA TGTTTATTAA CATTCATTTG TACATTGAAA ACTAGATAAG TAAGTAAGAT    120
TTTACCAAGC AAAACCGAGT GAATAGAGTT TTAAATAAGC TTGAATTCAT AAATAATCGC    180
TAGTGTTCGA AAGACNTCCA CAAGATTAAT AACTAGTTTT AGCTATTTAT TTTGAATAAC    240
AATTCAAAAT ATGGTGGGAC ATA                                           263
```

(2) INFORMATION FOR SEQ ID NO: 145:

(i) SEQUENCE CHARACTERISTICS:
        (A) LENGTH: 247 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 145:

```
AAGGATAAGG AACTGCACAT TGGTCTTGTT TAGTCTTGAG AGGTCTTGTG GGGCCTTAGC     60
TCAGCTGGGA GAGCGCCTGC TTTGCACGCA GGAGGTCAGC GGTTCGATCC CGCTAGGCTC    120
CATTGGTGAG AGATCACCAA GTAATGCACA TTGAAAATTG AATATCTATA TCAAATAGTA    180
ACAAGAAAAT AAACCGAAAA CGCTGTAGTA TTAATAAAGA GTTTATGACT GAAAGGTCAA    240
AAAATAA                                                             247
```

(2) INFORMATION FOR SEQ ID NO: 146:

(i) SEQUENCE CHARACTERISTICS:
        (A) LENGTH: 375 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 146:

```
AAGGAAATGG AACACGTTTA TCGTCTTATT TAGTTTTGAG AGGTCTTGTG GGGCCTTAGC     60
TCAGCTGGGA GAGCGCCTGC TTNGCACGCA GGAGGTCAGC GGTTCGATCC CGCTAGGCTC    120
CATCAGGATA CANTCCTACT AAACTTAATA CAAGTGAAGT TGAACACGCA ACTCACTTCC    180
TAGGAAAATA GACAATCTTC GCTTGTGTGC AAGGCACACA TGGTCAGATT CCTAATTTTC    240
```

```
TACAGAAGTT TCGCTAAAGC GAGCGTTGCT TAGTATCCTA TATAATAGTC CATNGAAAAT      300

TGAATATCTA TATCAAATTC CACGATCTAG AAATAGATTG TGGAAACGTA ACAAGAAATT      360

AACCCGNAAA CGCTG                                                      375
```

(2) INFORMATION FOR SEQ ID NO: 147:

(i) SEQUENCE CHARACTERISTICS:
        (A) LENGTH: 244 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 147:

```
AAGGATAAGG AACTGCACAT TGGTCTTGTT TAGTCTTGAG AGGTCTTGTG GGGCCTTAGC       60

TCAGCTGGGA GAGCGCCTGC TTTGCACGCA GGAGGTCAGC GGTTCGATCC CGCTAGGCTC      120

CATTGGTGAG AGATCACCAA GTAATGCACA TTGAAAATTG AATATCTATA TCAAATAGTA      180

ACAAGAAAAT AAACCGAAAC GCTGTAGTAT TAAAAGAGTT TATGACTGAA AGGTCAGAAA      240

ATAA                                                                  244
```

(2) INFORMATION FOR SEQ ID NO: 148:

(i) SEQUENCE CHARACTERISTICS:
        (A) LENGTH: 284 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 148:

```
CTAAGGATAT ATTCGGAACA TCTTCTTACG AAGATGCAGG AATAACATTG ACATATTGTA       60

TTCAGNTGTG AATGCTCATT GGAGNATTCA TNGCATNATT TGGTNCATTG ACANCTAGAT      120

AAGNAAGTAA AATTTATGAT TTTACCAAGC AAAACCGAGT GAATTAGAGT TNTNNAACAA      180

GCTTTGATTT CAAAAAGAAA TAATCGCTAG TGTTCGAAAG AACACTCACA GATTANTAAC      240

ATCTTGGGTT TTCACCCGAC TTGTTCGTNT CGAAAGTCAA AAAA                      284
```

(2) INFORMATION FOR SEQ ID NO: 149:

(i) SEQUENCE CHARACTERISTICS:
        (A) LENGTH: 246 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 149:

```
AAGGATAAGG AACTGCGCAT TGGTCTTGTT TAGTCTTGAG AGGTCTTGTG GGGCCTTAGC       60
```

```
TCAGCTGGGA GAGCGCCTGC TTTGCACGCA GGAGGTCAGC GGTTCGATCC CGCTAGGCTC      120

CATTGGTGAG AGATCACCAA GTAATGCACA TTGAAAATTG AATATCTATA TCAAATAGTA      180

ACAAGAAAAT AAACCGAAAA CGCTGTAGTA TTAATAAGAG TTTATGACTG AAAGGTCAAA      240

AAATAA                                                                 246
```

(2) INFORMATION FOR SEQ ID NO: 150:

(i) SEQUENCE CHARACTERISTICS:
        (A) LENGTH: 247 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 150:

```
AAGGATAAGG AACTGCGCAT TGGTCTTGTT TAGTCTTGAG AGGTCTTGTG GGGCCTTAGC       60

TCAGCTGGGA GAGCGCCTGC TTTGCACGCA GGAGGTCAGC GGTTCGATCC CGCTAGGCTC      120

CATTGGTGAG AGATCACCAA GTAATGCACA TTGAAAATTG AATATCTATA TCAAATAGTA      180

ACAAGAAAAT AAACCGAAAA CGCTGTAGTA TTAATAAGAG TTTATGACTG AAAGGTCAGA      240

AAAATAA                                                                247
```

(2) INFORMATION FOR SEQ ID NO: 151:

(i) SEQUENCE CHARACTERISTICS:
        (A) LENGTH: 247 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 151:

```
AAGGAAAAGG AACTGCGCAT TGGTCTTGTT TAGTCTTGAG AGGTCTTGTG GGGCCTTAGC       60

TCAGCTGGGA GAGCGCCTGC TTTGCACGCA GGAGGTCAGC GGTTCGATCC CGCTAGGCTC      120

CATTGGTGAG AGATCACCAA GTAATGCACA TTGAAAATTG AATATCTATA TCAAATAGTA      180

ACAAGAAAAT AAACCGAAAA CGCTGTAGTA TTAATAAGAG TTTATGACTG AAAGGTCAGA      240

AAAATAA                                                                247
```

(2) INFORMATION FOR SEQ ID NO: 152:

(i) SEQUENCE CHARACTERISTICS:
        (A) LENGTH: 244 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 152:

```
AAGGATAAGG AACTGCGCAT TGGTCTTGTT TAGTCTTGAG AGGTCTTGTG GGGCCTTAGC      60

TCAGCTGGGA GAGCGCCTGC TTTGCACGCA GGAGGTCAGC GGTTCGATCC CGCTAGGCTC     120

CATTGGTGAG AGATCACCAA GTAATGCACA TTGAAAATTG AATATCTATA TCAAATAGTA     180

ACAAGAAAAT AAACCGAAAC GCTGTAGTAT TAAAAGAGTT TATGACTGAA AGGTCAGAAA     240

ATAA                                                                  244

(2) INFORMATION FOR SEQ ID NO: 153:

(i) SEQUENCE CHARACTERISTICS:
        (A) LENGTH: 243 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 153:

AAGGATAAGG AACTGCGCAT TGGTCTTGTT TAGTCTTGAG AGGTCTTGTG GGGCCTTAGC      60

TCAGCTGGGA GAGCGCCTGC TTTGCACGCA GGAGGTCAGC GGTTCGATCC CGCTAGGCTC     120

CATTGGTGAG AGATCACCAA GTAATGCACA TTGAAAATTG AATATCTATA TCAAATAGTA     180

ACAAGAAAAT AAACCGAAAC GCTGTAGTAT TAAAAGAGTT TATGACTGAA AGGTCAAAAA     240

TAA                                                                   243

(2) INFORMATION FOR SEQ ID NO: 154:

(i) SEQUENCE CHARACTERISTICS:
        (A) LENGTH: 809 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 154:

TAAGGAAGAT CGAGAATTGG AAAGAGGTCG GATTTATCCG GATGATCCTT CTCCATCTTA      60

TTAGAACATA GATCGCAGGC CAGTCAGCCT GACGATCGCT TGCAGGCGTG CCGCCTTCGT     120

TTCTCTTTCT TCATTGTTGA TTGCTCACGG GCCGTACCGC AGCTGACGCT GCTGGCCCTG     180

CGCAGGCGCG GCCCATCAGG GCCGAACGGC CGGTCGGCCT TGCNAAGCTT CGCTTCGGGG     240

TGGATCTGTG GATCGCGTAG TAGCGTTTGC GTCGGTATCT GGGCTTGTAG CTCAGTTGGT     300

TAGAGCACAC GCTTGATAAG CGTGGGGTCG GAGGTTCAAG TCCTCCCAGG CCCACCAAGT     360

TACTTGATGA GGGGCCGTAG CTCAGCTGGG AGAGCACCTG CTTTGCAAGC AGGGGGTCGT     420

CGGTTCGATC CCGTCCGGCT CCACCATCAT GTTGGTGTTG AGACGGATAT TGGCAATCAA     480

CAAAAGAAAG AAACAAGTTT GCGGACTNTT ACGAAAGTCT GCCTGTTCTG TATGAAATCG     540

TGAAGAGAAG ATGTAATCGG ATCAACTGAA GAGTTGATGT CGCAAGAAGC TTGCTCAAGC     600

CTTGCATAAT GATTGATGTG TTTAACCGCC ATCACCGATT GTATCTCGAG AAGCTGGTCT     660

TTCTGCTGAT ACTGTTGAAA CGAGCATTTG CAGTCGAATG GCAACATTCG GCGTCGCATA     720

ATGCGGCTTT AAGAGCTGAG TTTTGATGGA TATTGGCAAT GAGAGTGATC AAGTGTCTTA     780
```

```
AGGGCATTGG TGGATGCCTT GGCATGCAC                                              809

(2) INFORMATION FOR SEQ ID NO: 155:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 155:

TGGGGTGAAG TCGTAACAAG GTA                                                    23

(2) INFORMATION FOR SEQ ID NO: 156:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 156:

CCTTTCCCTC ACGGTACTGG T                                                      21

(2) INFORMATION FOR SEQ ID NO: 157:

(i) SEQUENCE CHARACTERISTICS:
        (A) LENGTH: 277 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 157:

AAGGAGCACC ACGAGAAACA CTCCAATTGG TGGGGTGTAA GCCGTGAGGG GTTCTCGTCT             60

GTAGTGGACG GAAGCCGGGT GCACAACAAC AAGCAAGCCA GACACACTAT TGGGTCCTGA            120

GGCAACATCT CTGTTGGTTT CGGGATGTTG TCCCACCATC TTGGTGGTGG GGTGTGGTGT            180

TTGAGAATTG GATAGTGGTT GCGAGCATCA ATTGGATGCG CTGCCTTTTG GTGGCGTGTT            240

CTGTTGTGCA ATTTTATTCT TTGGTTTTTG TGTTTAT                                     277

(2) INFORMATION FOR SEQ ID NO: 158:

(i) SEQUENCE CHARACTERISTICS:
        (A) LENGTH: 286 base pairs
        (B) TYPE: nucleic acid
        (C) STRANDEDNESS: single
        (D) TOPOLOGY: linear (ii) MOLECULE TYPE: cDNA
```

(iii) HYPOTHETICAL: NO (iv) ANTI-SENSE: NO (xi) SEQUENCE DESCRIPTION: SEQ ID NO: 158:

AAGGAGCACC ACGAGAAACA CCCCAATTGG TGGGGTGTGA GCCGTGAGGG GTTCTCGTCT        60

GTAGTGGACG AGGGCCGGGT GCACAACAAC AGGCAATCGC CGGACACACT ATTGGGCCCT       120

GAGACAACAC TCGGCCGACT GAGGTCGACG TGGTGTCCCT CCATCTTGGT GGTGGGGTGT       180

GGTGTTTGAG CATTGAATAG TGGTTGCGAG CATCTAGCCG GATGCGTTCC CCAGTGGTGC       240

GCGTTCGTCA AAATGTGTA ATTTTTCTTT TGGTTTTTGT GTTCGT                      286

(2) INFORMATION FOR SEQ ID NO: 159:

(i) SEQUENCE CHARACTERISTICS:
        (A) LENGTH: 286 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 159:

AAGGAGCACC ACGAGAAACA CCCCAATTGG TGGGGTGTGA GCCGTGAGGG GTTCTCGTCT        60

GTAGTGGACG AGGGCCGGGT GCACAACAAC AGGCAATCGC CGGACACACT ATTGGGCCCT       120

GAGACAACAC TCGGCCGACT GAGGTCGACG TGGTGTCCCT CCATCTTGGT GGTGGGGTGT       180

GGTGTTTGAG CATTGAATAG TGGTTGCGAG CATCTAGACG GATGCGTTCC CCAGTGGTGC       240

GCGTTCGTCA AAATGTGTA ATTTTTCTTT TGGTTTTTGT GTTCGT                      286

(2) INFORMATION FOR SEQ ID NO: 160:

(i) SEQUENCE CHARACTERISTICS:
        (A) LENGTH: 279 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 160:

AAGGAGCACC ACGAGAAACA CCCCAATTGG TGGGGTGTGA GCCGTGAGGG GTTCTCGTCT        60

GTAGTGGACG AGGCGGGTAC AACAACGCCA ATCGCCGGAC ACACTATTGG GCCTGAGACA       120

ACACTCGGCC GACTGAGGTC GACGTGGTGT CCCTCCATCT TGGTGGTGGG GTGTGGTGTT       180

TGAGCATTGA ATAGTGGTTG CGAGCATCTA GCCGGATGCG TTCCCCAGTG GTGCGCGTTC       240

GTCAAAAATG TGTAATTTTT CTTTGGTTTT TGTGTTCGT                             279

(2) INFORMATION FOR SEQ ID NO: 161:

(i) SEQUENCE CHARACTERISTICS:
        (A) LENGTH: 288 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 161:

AAGGAGCACC ACGAGAAACA CTCCAATTGG TGGAGTGTGA GCCGTGAGGG GTTCTCGTCT      60

GTAGTGGACG AGGGCCGGGT GCACAACAGC AGACAATCGC CAGACACACT ATTGGGCCCT     120

GAGACAACAC TCGGCCGACT TTGGTCGACG TGGTGTCCCT CCATCTTGGT GGTGGGGTGT     180

GGTGTTTGAG CATTGAATAG TGGTTGCGAG CATCTAGACG GATGCGTTGC CCTCGGGCCG     240

CGTGTTCGTC AAAAATGTGT AATTTTTTCT TTTGGTTTTT GTGTTCGT                  288

(2) INFORMATION FOR SEQ ID NO: 162:

(i) SEQUENCE CHARACTERISTICS:
            (A) LENGTH: 289 base pairs
            (B) TYPE: nucleic acid
            (C) STRANDEDNESS: single
            (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 162:

AAGGAGCACC ACGAGAAACA CTCCAATTGG TGGAGTGTGA GCCGTGAGGG GTTCTCGTCT      60

GTAGTGGACG GGAGCCGGGT GCACAACAAC AGGCAATCGC CAGACACACT ATTGGGCCCT     120

GAGACAACAC TCGGCCGGCT TTGAGTCGAA GTGGTGTCCC TCCATCTTGG TGGTGGGGTG     180

TGGTGTTTGA GCATTGAATA GTGGTTGCGA GCATCTAGAC GGATGCGTTG CCTTCGGGCC     240

GCGTGTTCGT CAAAAATGTG TAATTTTTTC TTTTGGTTTT TGTGTTCGT                 289

(2) INFORMATION FOR SEQ ID NO: 163:

(i) SEQUENCE CHARACTERISTICS:
            (A) LENGTH: 232 base pairs
            (B) TYPE: nucleic acid
            (C) STRANDEDNESS: single
            (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 163:

AGGGAGCACC GAAACGCATC CCGCGTGGGG TGTGGGTTCG GCGTGTTGTG GCGTCGGCCG      60

AGGTGTTGGG CAGCAGGCAG TAACCCCGGA ACACTGTTGG GTTTTGAGAA CACCCGTGGT     120

GGTGTTGTGC TCCCCGTGGT GCGGGGTGTG GTGTTTGAGT GTTGGATAGT GGTTGCGAGC     180

ATCTGGCAAA GACTGTGGTA AGCGGTTTTT GTTGATGTTT TCTGGTGTTT GT             232

(2) INFORMATION FOR SEQ ID NO: 164:

(i) SEQUENCE CHARACTERISTICS:
            (A) LENGTH: 279 base pairs
            (B) TYPE: nucleic acid
            (C) STRANDEDNESS: single
            (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 164:

| | | | | | |
|---|---|---|---|---|---|
| AAGGAGCACC | ACGAGAAACA | CTCCAATTGG | TGGGGTGTGA | GCCGTGAGGG | GTTCTCGTCT | 60 |
| GTAGTGGACG | AGGGCGGGTG | CACAACAACA | GCAATCGCCA | GACACACTAT | TGGCCCTGAG | 120 |
| ACAACACTCG | GCCGACTTGG | TTGAAGTGGT | GTCCCTCCAT | CTTGGTGGTG | GGGTGTGGTG | 180 |
| TTTGAGTATT | GGATAGTGGT | TGCGAGCATC | TAATGAACGC | GTCGCCGCAA | CGGTTACGTG | 240 |
| TTCGTTTTGT | GTAATTTTTC | TATTGGTTTT | TGTGTTCGT | | | 279 |

(2) INFORMATION FOR SEQ ID NO: 165:

(i) SEQUENCE CHARACTERISTICS:
        (A) LENGTH: 285 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 165:

| | | | | | |
|---|---|---|---|---|---|
| AAGGAGCACC | ACGAGAAACA | CTCCAATTGG | TGGGGTGTGA | GCCGTGAGGG | GTTCTCGTCT | 60 |
| GTAGTGGACG | AGGGCCGGGT | GCACAACAAC | AGGCAATCGC | CAGACACACT | ATTGGCCCTG | 120 |
| AGACAACACT | CGGCCGACTT | TGGTCGAAGT | GGTGTCCCCC | CATCTTGGTG | GTGGGGTGTG | 180 |
| GTGTTTGAGT | ATTGGATAGT | GGTTGCGAAC | ATCTAAATGA | ACGCGTTGCC | GGCAACGGTT | 240 |
| ACGTGTTCGT | TTTAGTGTAA | TTTTTCTAAT | GGTTTTTGTG | TTCGT | | 285 |

(2) INFORMATION FOR SEQ ID NO: 166:

(i) SEQUENCE CHARACTERISTICS:
        (A) LENGTH: 384 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 166:

| | | | | | |
|---|---|---|---|---|---|
| AAGGAGCACC | ACGAGACCTG | GGCCGGCCCC | GCAGATCGCG | GGATCAGCTG | AGCTTTCAGG | 60 |
| CGATTCGTTG | GATGGCCTCG | CACCTGTAGT | GGGTGGGGGT | CTGGTGCACT | CAACAAACTT | 120 |
| GGCGTGGGAT | GCGGGAAAGC | ATCTGCGGAA | AATCATCAGA | CACACTATTG | GCTTTGAGA | 180 |
| CAACAGGCCC | GCAGCCTGCC | CGTTGGGGGC | AGGGGTGTGT | TGTTGCCTCA | CTTTGGTGGT | 240 |
| GGGGGTGGTG | TTTGATTTGT | GGATAGTGGT | TGCGAGCATC | TAGCGCGCAG | AATGTGTGGT | 300 |
| CTCACTCCTT | GTGGGTGGGG | CCTGGTTTTG | TGTGCGATTG | ATGTGCAATT | TCTTTTGAAA | 360 |
| CTCATTTTTT | GGTTTTTGTG | TTGT | | | | 384 |

(2) INFORMATION FOR SEQ ID NO: 167:

(i) SEQUENCE CHARACTERISTICS:
        (A) LENGTH: 295 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 167:

| | | | | | |
|---|---|---|---|---|---|
| AAGGAGCACC | ACGAAAAACT | CCCCAATTGG | TGGGGTGTAA | GCCGTGAGGG | GTTCCCGTCT | 60 |
| GTAGTGGACG | GGGGCCGGGT | GCGCAACAGC | AAGCGAAACG | CCGGACACAC | TATTGGGTCC | 120 |
| TGAGGCAACA | CTCGGGTTTG | TCCCCCTCAG | GGATTTTCTG | GGTGTTGTCC | CACCATCTTG | 180 |
| GTGGTGGGGT | GTGGTGTTTG | AGAATTGGAT | AGTGGTTGCG | AGCATCAAAT | GGATGCGTTG | 240 |
| CCCCTACGGG | TAGCGTGTTC | TTTTGTGCAA | TTTTATTCTT | GGTTTTTGTG | TTTGT | 295 |

(2) INFORMATION FOR SEQ ID NO: 168:

(i) SEQUENCE CHARACTERISTICS:
        (A) LENGTH: 279 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 168:

| | | | | | |
|---|---|---|---|---|---|
| AAGGAGCACC | ACGAGAAGCA | CTCCAACTGG | TGGGGTGCAA | GCCGTGAGGG | GTTCTCGTCT | 60 |
| GTAGTGGACG | AGAGCCGGGT | GCGCGACAAC | GAACGAGCCA | GACACACTAT | TGGGTCCTGA | 120 |
| GGCAACACTC | GGGCTTGGCC | AGAGCTGTTG | TCCCACCATC | TTGGTGGTGG | GGTGTGGTGT | 180 |
| TTGAGAATTG | GATAGTGGTT | GCGAGCATCA | AATGGATGCG | TTGCCCCTAC | GGGTGGCGTG | 240 |
| TTCTTTTGTG | CAATTTTATT | CTTTGGTTTT | TGTGTTTGT | | | 279 |

(2) INFORMATION FOR SEQ ID NO: 169:

(i) SEQUENCE CHARACTERISTICS:
        (A) LENGTH: 286 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 169:

| | | | | | |
|---|---|---|---|---|---|
| AAGGAGCACC | ACGAAAAACA | CCCCAACTGG | TGGGGTGTAA | GCCGTGAGGG | GCTCCCGTCT | 60 |
| GTAGTAGACG | GGCGCCGGGT | GCGCAACAGC | AAGCGAGCCA | GACACACTAT | TGGGTCCTGA | 120 |
| GGCAACACTC | GGGCTTGTCT | TGGACTCGTC | CAAGAGTGTT | GTCCCACCAT | CTTGGTGGTG | 180 |
| GGGTGTGGTG | TTTGAGAATT | GGATAGTGGT | TGCGAGCATC | ACTGGATGCG | TTGCCCCCAG | 240 |
| GGGTAGCGTG | TTCTTTTGTG | CAATTTATTC | TGGTTTTTGT | GTTAGT | | 286 |

(2) INFORMATION FOR SEQ ID NO: 170:

(i) SEQUENCE CHARACTERISTICS:
        (A) LENGTH: 265 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 170:

```
AAGGAGCACC ACGAAAAACA CTCCGCATCC GGTGGGGTGT GAGCCGTGAG GGAGCCCGTG      60

CCTGTAGTGG GTGTGGGTTG GGTGCGCGAC AACAAATGGG AAAAATCGCT GGGCACACTA     120

TTGGGCTTTG AGGCAACACC TGGTTTGTTT TGGGTGGTGT CGCTCCATCT TGGTGGTGGG     180

GTGTGGTGTT TGAGTTGTGG ATAGTGGTTG CGAGCATCTA AGCAAAAGCT GTTGTTTGAC     240

GGTTTTTGTC GAGTGTTGTG TGTGT                                          265
```

(2) INFORMATION FOR SEQ ID NO: 171:

(i) SEQUENCE CHARACTERISTICS:
        (A) LENGTH: 299 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 171:

```
AAGGAGCACC ACGAAAAACA CTCCAATTGG TGGGGTGTAA GCCGTGAGGG GTTCTCATCT      60

GTAGTGGACG AGAGCCGGGT GCACAACAGC AAATGAATCG CCAGACACAC TGTTGGGTCC     120

TGAGGCAACA CTCAGGCTTG TCCCATGTTG GGCTTGATCG GGTGCTGTCC CCCCATCTTG     180

GTGGTGGGGT GTGGTGTTTG AGTATTGGAT AGTGGTTGCG AGCATCTAAA TGGATACGTT     240

GCCAGTAATG GTGGCGTATT CATTGAAAAT GTGTAATTTT CTTCTTTGGT TTTGTGTGT     299
```

(2) INFORMATION FOR SEQ ID NO: 172:

(i) SEQUENCE CHARACTERISTICS:
        (A) LENGTH: 299 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 172:

```
AAGGAGCACC ACGAAAAACA CTCCAATTGG TGGGGTGTAA GCCGTGAGGG GTTCTCATCT      60

GTAGTGGACG AGAGCCGGGT GCACAACAGC AAATGAATCG CCAGACACAC TGTTGGGTCC     120

TGAGGCAACA CTCAGGCTTG TCCCATGTTG GGCTTGATCG GGTGCTGTCC CCCCATCTTG     180

GTGGTGGGGT GTGGTGTTTG AGTATTGGAT AGTGGTTGCG AGCATCTAAA TGGATACGTT     240

GCCAGTAATG GTGGCGTGTT CATTGAAAAT GTGTAATTTT CTTCTTTGGT TTTGTGTGT     299
```

(2) INFORMATION FOR SEQ ID NO: 173:

(i) SEQUENCE CHARACTERISTICS:
        (A) LENGTH: 298 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 173:

```
AAGGAGCACC ACGAAAAACA CTCCAATTGG TGGGGTGTAA GCCGTGAGGG GTTCTCATCT      60
GTAGTGGACG AGAGCCGGGT GCACAACAGC AAATGAATCG CCAGACACAC TGTTGGGTCC     120
TGAGGCAACA CTCAGGCTTG TCCCATGTTG GGCTTGATCG GGTGCTGTCC CCCCATCTTG     180
GTGGTGGGGT GTGGTGTTTG AGTATTGGAT AGTGGTTGCG AGCATCTAAA TGGAACGTTG     240
CCAGTAATGG TGGCGTGTTC ATTGAAAATG TGTAATTTTC TTCTTTGGTT TTGTGTGT      298
```

(2) INFORMATION FOR SEQ ID NO: 174:

(i) SEQUENCE CHARACTERISTICS:
        (A) LENGTH: 300 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 174:

```
AAGGAGCACC ATTTCTCAGT CGAATGAACT GAGAACATAA AGCGAGTATC TGTAGTGGAT      60
ACATGCTTGG TGAATATGTT TTATAAATCC TGTCCACCCC GTGGATAGGT AGTCGGCAAA     120
ACGTCGGACT GTCATAAGAA TTGAAACGCT GGCACACTGT TGGGTCCTGA GGCAACACAT     180
TGTGTTGTCA CCCTGCTTGG TGGTGGGGTG TGGTCCTTGA CTTATGGATA GTGGTTGCGA     240
GCATCTAAAC ATAGCCTCGC TCGTTTTCGA GTGAGGCTGG TTTTTGCAAT TTTATTAGCT     300
```

(2) INFORMATION FOR SEQ ID NO: 175:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 175:

```
GGTTTCGGGA TGTTGTCCCA CC                                               22
```

(2) INFORMATION FOR SEQ ID NO: 176:

(i) SEQUENCE CHARACTERISTICS:
        (A) LENGTH: 21 base pairs

```
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 176:

CGACTGAGGT CGACGTGGTG T                                              21

(2) INFORMATION FOR SEQ ID NO: 177:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 177:

GGTGTTTGAG CATTGAATAG TGGTTGC                                        27

(2) INFORMATION FOR SEQ ID NO: 178:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 178:

GTTGGGCAGC AGGCAGTAAC C                                              21

(2) INFORMATION FOR SEQ ID NO: 179:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 179:

CCGGCAACGG TTACGTGTTC                                                20

(2) INFORMATION FOR SEQ ID NO: 180:

(i) SEQUENCE CHARACTERISTICS:
        (A) LENGTH: 21 base pairs
        (B) TYPE: nucleic acid
        (C) STRANDEDNESS: single
        (D) TOPOLOGY: linear
```

```
    (ii) MOLECULE TYPE: cDNA (iii) HYPOTHETICAL: NO (iv) ANTI-SENSE: NO (xi) SEQUENCE DESCRIPTION: SEQ ID NO: 180:

TCGTTGGATG GCCTCGCACC T                                              21

(2) INFORMATION FOR SEQ ID NO: 181:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 181:

ACTTGGCGTG GGATGCGGGA A                                              21

(2) INFORMATION FOR SEQ ID NO: 182:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 182:

CCCTCAGGGA TTTTCTGGGT GTTG                                           24

(2) INFORMATION FOR SEQ ID NO: 183:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 183:

GGACTCGTCC AAGAGTGTTG TCC                                            23

(2) INFORMATION FOR SEQ ID NO: 184:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: cDNA
```

(iii) HYPOTHETICAL: NO (iv) ANTI-SENSE: NO (xi) SEQUENCE DESCRIPTION: SEQ ID NO: 184:

TCGGGCTTGG CCAGAGCTGT T                                        21

(2) INFORMATION FOR SEQ ID NO: 185:

(i) SEQUENCE CHARACTERISTICS:
       (A) LENGTH: 20 base pairs
       (B) TYPE: nucleic acid
       (C) STRANDEDNESS: single
       (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 185:

GGGTGCGCAA CAGCAAGCGA                                          20

(2) INFORMATION FOR SEQ ID NO: 186:

(i) SEQUENCE CHARACTERISTICS:
       (A) LENGTH: 19 base pairs
       (B) TYPE: nucleic acid
       (C) STRANDEDNESS: single
       (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 186:

GATGCGTTGC CCCTACGGG                                           19

(2) INFORMATION FOR SEQ ID NO: 187:

(i) SEQUENCE CHARACTERISTICS:
       (A) LENGTH: 24 base pairs
       (B) TYPE: nucleic acid
       (C) STRANDEDNESS: single
       (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 187:

CCCTACGGGT AGCGTGTTCT TTTG                                     24

(2) INFORMATION FOR SEQ ID NO: 188:

(i) SEQUENCE CHARACTERISTICS:
       (A) LENGTH: 23 base pairs
       (B) TYPE: nucleic acid
       (C) STRANDEDNESS: single
       (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 188:

CGGATCGATT GAGTGCTTGT CCC                                                      23

(2) INFORMATION FOR SEQ ID NO: 189:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 189:

TCTAAATGAA CGCACTGCCG ATG                                                      23

(2) INFORMATION FOR SEQ ID NO: 190:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 190:

TGAGGGAGCC CGTGCCTGTA                                                          20

(2) INFORMATION FOR SEQ ID NO: 191:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 191:

CATGTTGGGC TTGATCGGGT GC                                                       22

(2) INFORMATION FOR SEQ ID NO: 192:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 192:

```
CCTGGGTTTG ACATGCACAG                                                    20

(2) INFORMATION FOR SEQ ID NO: 193:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 193:

GCGTAGTAGC GTTTGCGTCG G                                                  21

(2) INFORMATION FOR SEQ ID NO: 194:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 194:

CGCAAGAAGC TTGCTCAAGC C                                                  21

(2) INFORMATION FOR SEQ ID NO: 195:

(i) SEQUENCE CHARACTERISTICS:
        (A) LENGTH: 470 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 195:

CCTAATGATA TTGATTCGCG TGAAGTGCTC ACACAGATTG TCTGATGAAA AGTAACGAG          60

CAGAAATACC TTTATAGGCT TGTAGCTCAG GTGGTTAGAG CGCACCCCTG ATAAGGGTGA        120

GGTCGGTGGT TCAAGTCCAC TCAGGCCTAC CACTTCTCGA AGTGGAAAAG GTACTGCACG        180

TGACTGTATG GGGCTATAGC TCAGCTGGGA GAGCGCCTGC CTTGCACGCA GGAGGTCAGC        240

GGTTCGATCC CGCTTAGCTC CACCATATAG TCCTGTATTT CAATACTTCA GAGTGTACTG        300

GCAACAGTAT GCTGCGAAGT ATTTTGCTCT TTAACAATCT GGAACAAGCT GAAAATTGAA        360

ACATGACAGC TGAAACTTAT CCCTCCGTAG AAGTATTGGG GTAAGGATTA ACCTGTCATA        420

GAGTCTCTCA AATGTAGCAG CACGAAAGTG GAAACACCTT CGGGTTGTGA                   470

(2) INFORMATION FOR SEQ ID NO: 196:

(i) SEQUENCE CHARACTERISTICS:
        (A) LENGTH: 453 base pairs
        (B) TYPE: nucleic acid
```

(C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 196:

CCTAATGATA TTGATTCGCG TGAAGTGCTC ACACAGATTG TTTGATAGAA ACGTAATGAG      60

CAAAAGCGCT ACCTGTTGAT GTAATGAGTC ACTGACTCAT GCTGATACGA ACCGATTAAG     120

ACAGTCAGTT TAATCGGATT TTCGTGTCCC CATCGTCTAG AGGCCTAGGA CACTGCCCTT     180

TCACGGCTGT AACAGGGGTT CGAATCCCCT TGGGGACGCC ATTCGATAAT GAGTGAAAGA     240

CATTATCACC GGTTCTTGGA ACCGAAAACA TCTTAAAGAT GACTCTTGCG AGTCGTGTTT     300

AAGATATTGC TCTTTAACAA TCTGGAACAA GCTGAAAATT GAAACATGAC AGCTGAAACT     360

TATCCCTCCG TAGAAGTATT GGGGTAAGGA TTAACCTGTC ATAGAGTCTC TCAAATGTAG     420

CAGCACGAAA GTGGAAACAC CTTCGGGTTG TGA                                 453

(2) INFORMATION FOR SEQ ID NO: 197:

(i) SEQUENCE CHARACTERISTICS:
        (A) LENGTH: 248 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 197:

TAAGGATAAG GAAGAAGCCT GAGAAGGTTT CTGACTAGGT TGGGCAAGCA TTTATATGTA      60

AGAGCAAGCA TTCTATTTCA TTTGTGTTGT TAAGAGTAGC GCGGTGAGGA CGAGACATAT     120

AGTTTGTGAT CAAGTATGTT ATTGTAAAGA AATAATCATG GTAACAAGTA TATTTCACGC     180

ATAATAATAG ACGTTTAAGA GTATTTGTCT TTTAGGTGAA GTGCTTGCAT GGATCTATAG     240

AAATTACA                                                             248

(2) INFORMATION FOR SEQ ID NO: 198:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 198:

GGAAAAGGTA CTGCACGTGA CTG                                             23

(2) INFORMATION FOR SEQ ID NO: 199:

(i) SEQUENCE CHARACTERISTICS:
        (A) LENGTH: 23 base pairs
        (B) TYPE: nucleic acid (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 199:

GACAGCTGAA ACTTATCCCT CCG                                          23

(2) INFORMATION FOR SEQ ID NO: 200:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 200:

GCTACCTGTT GATGTAATGA GTCAC                                        25

(2) INFORMATION FOR SEQ ID NO: 201:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 201:

GAGTAGCGCG GTGAGGACGA GA                                           22

(2) INFORMATION FOR SEQ ID NO: 202:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 202:

CTTTTATGTC AGATAAAGTA TGCAA                                        25

(2) INFORMATION FOR SEQ ID NO: 203:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: cDNA (iii) HYPOTHETICAL: NO -continued (iv) ANTI-SENSE: NO (xi) SEQUENCE DESCRIPTION: SEQ ID NO: 203:

CGTAAAAGGG TATGATTATT TG                                              22

(2) INFORMATION FOR SEQ ID NO: 204:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 204:

TCGAGAATTG GAAAGAGGTC                                                 20

(2) INFORMATION FOR SEQ ID NO: 205:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 205:

AAGAGGTCGG ATTTATCCG                                                  19

(2) INFORMATION FOR SEQ ID NO: 206:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 206:

TTCGACTGCA AATGCTCG                                                   18

(2) INFORMATION FOR SEQ ID NO: 207:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 207:

TCTTAAAGCC GCATTATGC                                            19

(2) INFORMATION FOR SEQ ID NO: 208:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 208:

CCTAATGATA TTGATTCGCG                                           20

(2) INFORMATION FOR SEQ ID NO: 209:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 209:

ATGACAGGTT AATCCTTACC CC                                        22

(2) INFORMATION FOR SEQ ID NO: 210:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 210:

GGTGTGGTCC TTGACTTATG GATAG                                     25

(2) INFORMATION FOR SEQ ID NO: 211:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 211:

TCGGGCCGCG TGTTCGTCAA A                                         21

(2) INFORMATION FOR SEQ ID NO: 212:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 212:

```
CGTTTTCATA AGCGATCGCA CGTT                                              24
```

(2) INFORMATION FOR SEQ ID NO: 213:

(i) SEQUENCE CHARACTERISTICS:
        (A) LENGTH: 235 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 213:

```
TAAGGATAAG GAAACCTGTG AATCTTTTTC CCTTCTTTTG TTCAGTTTTG AGAGGTTCAT        60
CTCTCAAAAC GTGTTCTTTG AAAACTAGAT AAGAAAAGTT AGTGTAAAAA GACGAAGAGA       120
AACCGTAGGT TTTTCTTCAA CCAAAACCGA GAATCAAACC GAGAAAGAAT CTTTCCGTTT       180
TCATAAGCGA TCGCACGTTT ATGAAAACAC AACAACACCT TCGTAAGAAG GATGA            235
```

(2) INFORMATION FOR SEQ ID NO: 214:

(i) SEQUENCE CHARACTERISTICS:
        (A) LENGTH: 475 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 214:

```
TAAGGATAAG GAAACCTGTG AATCTTTTTC CCTTCTTTTG TTCAGTTTTG AGAGGTCAAT        60
GACGCTCATA CTGAGTACCA GGTGACACGT TTTTGAGGTG TCTCTTCGTA TGAGGGGCCT       120
ATAGCTCAGC TGGTTAGAGC GCACGCCTGA TAAGCGTGAG GTCGGTGGTT CGAGTCCACT       180
TAGGCCCACT TTTTTGAATA AACCTTTCTT TTTTATATGT TAATAAGGGG CCTTAGCTCA       240
GCTGGGAGAG CGCCTGCTTT GCACGCAGGA GGTCAGCGGT TCGATCCCGC TAGGCTCCAC       300
CAAAGATAGT TTGTTCTTTG AAAACTAGAT AAGAAAAGTT AGTGTAAAAA GACGAAGAGG       360
AACCGTAGGT TTTTCTTCAA CCAAAACCGA GAATCAAACC GAGAAAGAAT CTTTCCGTTT       420
TCATAAGCGA TCGCACGTTT ATGAAAACAC AACAACACCT TCGTAAGAAG GATGA            475
```

(2) INFORMATION FOR SEQ ID NO: 215:

```
    (i) SEQUENCE CHARACTERISTICS:
        (A) LENGTH: 463 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 215:

TAAGGATAAG GAAACCTGTG AATCTTTTTC CCTTCTTTTG TTCAGTTTTG AGAGGTCAAT     60

GACGCTCATA CTGAGTACCA GGTGACACGT TTTTGAGGTG TCTCTTCGTA TGAGGGGCCT    120

ATAGCTCAGC TGGTTAGAGC GCACGCCTGA TAAGCGTGAG GTCGGTGGTT CGAGTCCACT    180

TAGGCCCACT TTTTTGAATA AACCTTTCTT TTTTATATGT TAATAAGGGG CCTTAGCTCA    240

GCTGGGAGAG CGCCTGCTTT GCACGCAGGA GGTCAGCGGT TCGATCCCGC TAGGCTCCAC    300

CAAAGATAGT TTGTTCTTTG AAAACTAGAT AAGAAAAGTT AGTGTAAAAA GACGAAGAGA    360

AACCGTAGGT TTTTCTTCAA CCAAAACCGA GAAAGAATCT TTCCGTTTTC ATAAGCGATC    420

GCACGTTTAT GAAAACACAA CAACACCTTC GTAAGAAGGA TGA                     463

(2) INFORMATION FOR SEQ ID NO: 216:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 216:

TGGCCGGTGC AAAGGGCTG                                                  19
```

DETECTION AND IDENTIFICATION OF PSEUDOMONAS SPECIES USING THE 16S-23S RRNA SPACER

The present application is divisional of application Ser. No. 09/448,894, filed Nov. 29, 1999 (now U.S. Pat. No. 6,312,903), which in turn is a divisional application of Ser. No. 08/765,332, filed Dec. 23, 1996 (now U.S. Pat. No. 6,025,132), which is a 371 U.S. national phase of PCT/EP95/02452, filed Jun. 23, 1995, the entire contents of each of which are incorporated herein by reference.

The present invention relates to nucleic acid probes derived from the spacer region between the 16S and 23S ribosomal ribonucleic acid (rRNA) genes, to be used for the specific detection of eubacterial organisms in, a biological sample by a hybridization procedure, as well as to nucleic acid primers to be used for the amplification of said spacer region of eubacterial organisms in a biological sample. The present invention also relates to new spacer region sequences from which said probes or primers may be derived.

Since the advent of the polymerase chain reaction and some other nucleic acid amplification techniques the impact of DNA-probe technology in the diagnosis of micro-organisms in biological samples of all sorts is increasing. Being often more specific and potentially more sensitive—if an adequate amplification and or detection system is used the DNA probe approach may eventually replace the conventional identification techniques.

The reliability of nucleic acid based tests essentially depends on the sensitivity and specificaty of the probes and/or primers used. Thus the corner stone of this type of assay is the identification of nucleic acid sequences which are unique to the group of organisms of interest.

Most of the nucleic acid based tests either described in literature and/or commercially available aim at the detection of just one particular organism in a biological sample, Since most biological samples usually may contain a great variety of clinically relevant micro-organisms, a multitude of separate assays have to be performed to detect all relevant organisms possibly present. This approach would be very expensive, laborious and time-consuming. Consequently, the number of tests actually performed in most routine diagnostic labs on a particular sample is restricted to the detection of just a few of the most relevant organisms. Therefore it would be extremely convenient to have access to a system which enables the fast, easy and simultaneous detection of a multitude of different organisms. The more organisms that can be screened for in the same assay, the more cost-effective the procedure would be.

As put forward in earlier published documents, the spacer region situated between the 16S rRNA and the 23S rRNA gene, also referred to as the internal transcribed spacer (ITS), is an advantageous target region for probe development for detection of pathogens of bacterial origin (International application WO 91/16454; Rossau et al., 1992; EP-A-0 395 292).

One of its most appreciated advantages, is that sequences unique to a great variety of bacterial taxa can be found in a very limited area of the bacterial genome. This characteristic allows for an advantageous design of "probe-panels" enabling the simultaneous detection of a set of organisms possibly present in a particular type of a biological sample. Moreover, being flanked by quasi-universally conserved nucleotide sequences—more particularly located in the 3'-part of the 16S rRNA gene and the 5'-part of the 23S rRNA gene respectively—almost all spacers can be simultaneously amplified with a limited set of amplification primers. Alternatively, specific primer sets can be derived from the spacer sequences themselves, thereby allowing species- or group-specific amplifications.

The 16S–23S rRNA spacer region is a relatively short (about 200 to 1000 base pairs) stretch of DNA present in one or multiple copies in the genome of almost all eubacterial organisms. If multiple copies are present in the genome of one bacterium these copies can either be identical (as is most probably the case in some *Neisseria* species) or may differ from each other (as is the case for *E. coli*). This difference can be limited to a few nucleotides but also deletions and insertions of considerable length may be present.

Uptil now, spacer probes are only described and made publicly available for a limited number of organisms many of which were disclosed in international application WO 91/16454. As described above, it would be very advantageous to be able to detect simultaneously a panel of pathogens: e.g. a panel of pathogens possibly present in the same type of biological sample, or a panel of pathogens possibly causing the same type of disease symptoms, which are difficult to differentiate clinically and/or biochemically, or a panel of organisms belonging to the same taxon. In order to make the different panels as complete as possible, additional probes or sets of probes located in the spacer region and enabling the identification of at least the following bacterial groups or species are required:

*Mycobacterium* species
*Listeria* species
*Chlamydia* species
*Acinetobacter* species
*Mycoplasma* species
*Streptococcus* species
*Staphylococcus* species
*Salmonella* species
*Brucella* species
*Yersinia* species
*Pseudomonas* species These additional spacer probes need to be meticulously designed such that they can be used simultaneously with at least one other probe, under the same hybridization and wash conditions, allowing the detection of a particular panel of organisms.

It is thus the aim of the present invention to select probes or sets of probes, which have as target the 16S–23S rRNA spacer region, and which allow the detection and identification of at least one, and preferably more than one, of the above mentioned micro-organisms. The probes or probe sets are selected in such a way that they can be used in combination with at least one other probe, preferably also originating from the 16S-23S rRNA spacer region, under the same hybridization and wash conditions, to allow possibly the simultaneous detection of several micro-organisms in a sample.

It is also an aim of the present invention to provide for a selection method for use in the selection of said spacer probes or probe sets.

It is also an aim of the present invention to provide a rapid and reliable hybridization method for detection and identification of at least one micro-organism in a sample, or for the simultaneous detection and identification of several micro-organisms in a sample.

It is more particularly an aim of the present invention to provide a hybridization method allowing simultaneous detection and identification of a set of micro-organisms, liable to be present in a particular type of sample.

It is more particularly an aim of the present invention to provide probes or sets of probes for the possible simultaneous detection of micro-organisms in a sample originating from respiratory tract.

It is another particular aim of the present invention to provide probes or sets of probes for the possible simultaneous detection of micro-organisms in a sample originating from cerebrospinal fluid.

It is still another particular aim of the present invention to provide probes or sets of probes for the possible simultaneous detection of micro-organisms in a sample originating from urogenital tract.

It is still another particular aim of the present invention to provide probes or sets of probes for the possible simultaneous detection of micro-organisms in a sample taken from the gastro-intestinal tract of a patient.

It is still another particular aim of the present invention to provide probes or sets of probes for the possible simultaneous detection of micro-organisms in a sample originating from food or environmental samples.

It is moreover an aim of the present invention to provide a method for detection and identification of a particular taxon in a sample, or a set of particular taxa, said taxon being either a complete genus, or a subgroup within a genus, a species or even subtypes within a species (subspecies, serovars, sequevars, biovars . . . ).

It is more particularly an aim of the present invention to provide probes or sets of probes for the detection of *Mycobacterium* species and subspecies, more particularly for the detection of *M. tuberculosis* complex strains. *Mycobacterium* strains from the MAIS-complex, *M. avium* and *M. paratuberculosis, M. intracellulare* and *M. intracellulare*-like strains, *M. scrofulaceum, M. kansasii, M. chelonae, M. gordonae, M. ulcerans, M. genavense, M. xenopi, M. simiae, M. fortuitum, M. malmoense, M. celatum* and *M. haemophilum*.

It is also an aim of the present invention to provide probes or sets of probes for the detection of *Mycoplasma* strains, more particularly of *M. pneumoniae* and *M. genitalium*.

It is also an aim of the present invention to provide probes or sets of probes for the detection of *Pseudomonal* strains, more particularly *P. aeruginosa*.

It is also an aim of the present invention to provide probes or sets of probes for detection of *Staphylococcus* species, more particularly *S. aureus* and *S. epidermidis*.

It is also an aim of the present invention to provide probes or sets of probes for the detection of *Acinetobacter* strains, more particularly *A. baumanii*.

It is also an aim of the present invention to provide probes or sets of probes for the detection of *Listeria* strains, more particularly *Listeria monocytogenes*.

It is also an aim of the present invention to provide probes or sets of probes for the detection of *Brucella* strains.

It is also an aim of the present invention to provide probes or sets of probes for the detection of *Salmonella* strains.

It is also an aim of the present invention to provide probes or sets of probes for the detection of *Chlamydia* strains, more particularly *C. trachomatis* and *C. psittaci*.

It is also an aim of the present invention to provide probes or sets of probes for the detection of *Streptococcus* strains.

It is also an aim of the present invention to provide probes or sets of probes for the detection of *Yersinia enterolitica* strains.

It is also an aim of the present invention to provide primers allowing specific amplification of the 16S–23S rRNA spacer region for certain organisms. More particularly, it is an aim of the present invention to provide primers for the specific amplification of the spacer region of *Mycobacterium, Chlamydia, Listeria, Brucella* and *Yersinia enterolitica* strains.

It is also an aim of the present invention to provide new sequences of 16S–23S rRNA spacer regions from which useful spacer probes or primes can be derived.

It is also an aim of the present invention to provide for kits for detection of at least one organism in a sample in which said probes and/or primers are used.

It is noted that for a few of the above-mentioned organisms spacer sequences have already been published in literature or in publicly accessable data-banks.

However, it should be made clear that the spacer region sequences disclosed in the current invention (FIGS. 1–103) are new and, in case they originate from the same species as those of which a spacer sequence was already described in the prior art, they differ to some extent from the already described sequences.

Moreover, it is the principal aim of the present invention to select, from the compilation of sequence data on spacer regions, specific probes and sets of probes enabling the detection and identification of a particular panel of organisms, be it the organisms belonging to a common taxon, or the organism possibly present in the same type of sample.

The selection procedure usually consists of a theoretical and an experimental part. First of all, the different spacer sequences need to be aligned to those of the 'closest neighbours' or to the spacer sequences of other micro-organisms liable to be present in the same sample. This requires of course the sequence determination of the spacer region, as described in the examples. From the alignment, regions of divergence can be defined, from which probes with desired hybridization characteristics are designed, according to guidelines known to the man skilled in the art and specified in more detail below, Secondly, the designed probes need to be tested experimentally and evaluated for their usefulness under specific hybridization conditions and/or in combination with other probes. Experimental tasting can be done according to any hybridization method known in the art, but a preferred assay for the simultaneous testing of different probes under the same conditions is the reverse hybridization assay. A specific format for reverse hybridization of different probes simultaneously used in the current invention is the LiPA (Line Probe Assay) as described below.

Upon experimental testing unexpected hybridization behaviour may show up when the probes are hybridized to the target nucleic acid, and specific probe adaptations may be required.

Moreover, specificity and sensitivity of the probes need to be tested with a large collection of straits, both belonging to the taxon to be detected and belonging to other ma. Due to genome heterogeneity in the spacer region, or the existence of multiple spacer regions with different sequences in the same organisms, it is quite often necessary to sequence spacer regions of additional strains, or to sequence additional spacer regions in the same strain, and redesign the probes according to the new sequence data in order to obtain a better sensitivity and/or specificity (see e.g. example 3). In some cases it may be necessary or preferable to use several probes for the same organism (see e.g. example 2 and 7). Also, upon sequencing the spacer region, some organisms may show unexpected (un)relatedness, which may lead to a revision of strain classification contrary to classical taxonomic criteria (see e.g. examples 2 and 7).

In conclusion, the experimental part of the probe selection procedure is indispensable and complementary to the theoretical part. Probe design, especially under the fixed conditions of reverse hybridization (the same conditions for each probe) is not straightforward and probes have to be evaluated meticulously before they can be used in a reverse hybridization format. Therefor, probes cannot always be simply derived on a theoretical basis from a known gene sequence.

For designing probes with desired characteristics the following useful guidelines may be followed.

Because the extent and specificity of hybridization reactions such as those described herein are affected by a number of factors, manipulation of one or more of those factors will determine the exact sensitivity and specificity of a particular probe, whether perfectly complementary to its target or not. The importance and effect of various assay conditions, explained further herein, are known to those skilled in the art.

First, the stability of the [probe:target] nucleic acid hybrid should be chosen to be compatible with the assay conditions. This may be accomplished by avoiding long A and T rich sequences, by terminating the hybrids with G:C base pairs, and by designing the probe with an appropriate Tm. The beginning and end points of the probe should be chosen so that the length and % GC result in a Tm about 2–10° C. higher than the temperature at which the final assay will be performed. The base composition of the probe is significant because G-C base pairs exhibit greater thermal stability as compared to A-T base pairs due to additional hydrogen bonding. Thus, hybridization involving complementary nucleic acids of higher G-C content will be stable at higher temperatures.

Conditions such as ionic strength and incubation temperature under which a probe will be used should also be taken into account in constructing a probe. It is known that hybridization will increase as the ionic strength of the reaction mixture increases, and that the thermal stability of the hybrids will increase with increasing ionic strength. On the other hand, chemical reagents, such as formamide, urea, DMSO and alcohols, which disrupt hydrogen bonds, will increase the stringency of hybridization. Destabilization of the hydrogen bonds by such reagents can greatly reduce the Tm. In general, optimal hybridization for synthetic oligonucleotide probes of about 10–50 bases in length occurs approximately 5° C. below the melting temperature for a given duplex. Incubation at temperatures below the optimum may allow mismatched base sequences to hybridize and can therefore result in reduced specificity.

It is desirable to have probes which hybridize only under conditions of high stringency. Under high stringency conditions only highly complementary nucleic acid hybrids will form; hybrids without a sufficient degree of complementarity will not form. Accordingly, the stringency of the assay conditions determines the amount of complementarity needed between two nucleic acid strands forming a hybrid. Stringency is chosen to maximize the difference in stability between the hybrid formed with the target and the nontarget nucleic acid. In some examples of the current invention, e.g. when highly related organisms need to be differentiated, it may be necessary to detect single base pair changes. In those cases, conditions of very high stringency are needed.

Second, probes should be positioned so as to minimize the stability of the [probe:nontarget] nucleic acid hybrid. This may be accomplished by minimizing the length of perfect complementarity to non-target organisms, avoiding CC rich regions of homology to non-target sequences, and by positioning the probe to span as many destabilizing mismatches as possible. Whether a probe sequence is useful to detect only a specific type of organism depends largely on the thermal stability difference between [probe:target] hybrids and [probe:nontarget] hybrids. In designing probes, the differences in these Tm values should be as large as possible (e.g. at least 2° C. and preferably 5° C.), The length of the caret nucleic acid sequence and, accordingly, the length of the probe sequence can also be important. In some cases, there may be several sequences from a particular region, varying in location and length, which will yield probes with the desired hybridization characteristics. In other cases, one sequence may be significantly better than another which differs merely by a single base. While it is possible for nucleic acids that are not perfectly complementary to hybridize, the longest stretch of perfectly complementary base sequence will normally primarily determine hybrid stability. While oligonucleotide probes of different lengths and base composition may be used, oligonucleotide probes preferred in this invention are between about 10 to 50 bases in length and are sufficiently homologous to the target nucleic acid.

Third, regions in the target DNA or RNA which are known to form strong internal structures inhibitory to hybridization are less preferred. Likewise, probes with extensive self-complementarity should be avoided. As explained above, hybridization is the association of two single strands of complementary nucleic acids to form a hydrogen bonded double strand. It is implicit that if one of the two strands is wholly or partially involved in a hybrid that it will be less able to participate in formation of a new hybrid. There can be intermolecular and intermolecular hybrids formed within the molecules of one type of probe if there is sufficient self complementarity. Such structures can be avoided through careful probe design. By designing a probe so that a substantial portion of the sequence of interest is single stranded, the rate and extent of hybridization may be greatly increased. Computer programs are available to search for this type of interaction. However, in certain instances, it may not be possible to avoid this type of interaction.

The probes of the present invention are designed for attaining optimal performance under the same hybridization conditions so that they can be used in sets for simultaneous hybridization; this highly increases the usability of these probes and results in a significant gain in time and labour. Evidently, when other hybridization conditions should be preferred, all probes should be adapted accordingly by adding or deleting a number of nucleotides at their extremities. It should be understood that these concomitant adaptations should give rise to essentially the same result, namely that the respective probes still hybridize specifically with the defined target. Such adaptations might also be necessary if the amplified material should be RNA in nature and not DNA as in the case for the NASBA system.

The hybridization conditions can be monitored relying upon several parameters, such as the nature and concentration of the components of the media, and the temperatures under which the hybrids are formed and washed.

The hybridization and wash temperature is limited in upper value depending on the sequence of the probe (its nucleic acid composition, kind and length). The maximum hybridization or wash temperature of the probes described to the present invention ranges from 40° C. to 60° C., more preferably from 45° C. to 55° C., in the specific hybridization and wash media as described in the Examples section. At higher temperatures duolexing (=formation of the hybrids) competes with the dissociation (or denaturation) of the hybrid formed between the probe and the target.

In a preferred hybridization medium of the invention, containing 3×SSC and 20% formamide, hybridization temperances can range from 45° C. to 55° C., with a preferred hybridization temperature of 50° C. A preferred wash medium contains 3×SSC and 20% formamide, and preferred wash temperatures are the same as the preferred hybridization temperatures, i.e. preferably between 45° C, and 55° C., and most preferably 50° C.

However, when modifications are introduced, be it either in the probes or in the media, the temperatures at which the probes can be used to obtain the required specity should be changed according to known relationships, such as those described in the following reference: Hames B and Higgins S (eds.). Nucleic acid hybridization. A practical approach, IRL Press, Oxford, U.K., 1985.

The selected nucleic acid probes derived from the 16S–23S rRNA spacer region and described by the present invention are listed in Table 1a (SEQ ID NO 1 to 64, 175 to 191, 193 to 201, and 210 to 212). As described in the examples section, some of these probes show a better sensitivity and/or specificity than others, and the better probes are therefore preferentially used in methods to detect the organism of interest in a biological sample. However, it is possible that for certain applications (e.g. epidemiology, substrata typing, . . . ) a set of probes including the less specific and/or less sensitive probes may be very informative (see e.g. example 7).

The following definitions serve to illustrate the terms and expressions used in the different embodiments of the present Invention as set out below.

The term "spacer" is an abbreviated term referring to the 16S–23S rRNA internal transcribed spacer region.

The term "probe" refers to single stranded sequence-specific oligonucleotides which have a sequence which is sufficiently complementary to hybridize to the target sequence to be detected.

The more specific term "spacer probe" refers to a probe as defined above having a sequence which is sufficiently complementary to hybridize to a target sequence which is located in the spacer region(s) of the organism (or group of organisms) to be detected.

Preferably said probes are 70%, 80%, 90%, or more than 95% homologous to the exact complement of the target sequence to be detected. These target sequences are either genomic DNA or precursor RNA, or amplified versions thereof.

Preferably, these probes are about 5 to 50 nucleotides long, more preferably from about 10 to 25 nucleotides. The nucleotides as used in the present invention may be ribonucleotides, deoxyribonucleotides and modified nucleotides such as inosine or nucleotides containing modified groups which do not essentially alter their hybridization characteristics. Moreover, it is obvious to the man skilled in the art that any of the below-specified probes can be used as such, or in their complementary form, or in their RNA form (wherein T is replaced by U).

The probes according to the invention can be formed by cloning of recombinant plasmids containing inserts including the corresponding nucleotide sequences, if need be by cleaving the latter out from the closed plasmids upon using the adequate nucleases and recovering them, e.g. by fractionation according to molecular weight. The probes according to the presets invention can also be synthesized chemically, for instance by the conventional phosphotriester method.

The term "complementary" nucleic acids as used herein means that the nucleic acid sequences can form a perfect base-paired double helix with each other.

The term "homologous" as used in the current application is synonymous for identical: this means that polynucleic acids which are said to be e.g. 80% homologous show 80% identical base pairs in the same position upon alignment of the sequences.

The term "polynucleic acid" corresponds to either double-stranded or single stranded cDNA or genomic DNA or RNA, containing at least 10, 20, 30, 40 or 50 contiguous nucleotides. A polynucleic acid which is smaller than 100 nucleotides in length is often also referred to as an oligonucleotide. Single stranded polynucleic acid sequences are always represented in the current invention from the 5' end to the 3' end.

The term "closest neighbour" means the taxon which is known or expected to be most closely related in terms of DNA homology and which has to be differentiated from the organism of interest.

The expression "desired hybridization characteristics" means that the probe only hybridizes to the DNA or RNA from organisms for which it was designed, and not to DNA or RNA from other organisms (closest neighbours or organisms liable to be present in the same sample). In practice, this means that the intensity of the hybridization signal is at least two, three, four, five, ten or more times stronger with the target DNA or RNA from the organisms for which the probes were designed, as compared to non-target sequences.

These desired hybridization characteristics correspond to what is called later in the text "specific hybridization".

The expression "taxon-specific hybridization" or "taxon-specific probe" means that the probe only hybridizes to the DNA or RNA from the taxon for which it was designed and not to DNA or RNA from other taxa.

The term taxon can refer to a complete genus or a sub-group within a genus, a species or even subtype within a species (subspecies, serovars, sequevars, biovars, . . . ).

The term "specific amplification" or "specific primers" refers to the fact that said primers only amplify the spacer region from these organisms for which they were designed, and not from other organisms.

The term "sensitivity" refers to the number of false negatives: i.e. if 1 of the 100 strains to be detected is missed out, the test shows a sensitivity of (100−1/100)%=99%.

The term "specificity" refers to the number of false positives; i.e. if on 100 strains detected, 2 seem to belong to organisms for which the test is not designed, the specificity of the test is (100−2/100)%=98%.

The probes selected as being "preferential" show a sensitivity and specificity of more than 80%, preferably more than 90% and most preferably more than 95%.

The term "primer" refers to a single stranded DNA oligonucleotide sequence capable of acting as a point or initiation for synthesis or a primer extension product which is complementary to the nucleic acid strand to be copied. The length and the sequence of the primer must be such that they allow to prime the synthesis of the extension products. Preferably the primer is about 5–50 nucleotides long. Specific length and sequence will depend on the complexity of the required DNA or RNA targets, as well as on the conditions of primer use such as temperature and ionic strength. The fact that amplification primers do not have to match exactly with the corresponding template sequence to warrant proper amplification is amply documented in the literature (Kwok et al., 1990).

The amplification method used can be either polymerase chain reaction (PCR; Saiki et al., 1988), ligase chain reaction (LCR; Landgren et al., 1988: Wu & Wallace, 1989; Barany, 1991), nucleic acid sequence-based amplification (NASBA;

Guatelli et al., 1990; Compton. 1991), transcription-based amplification system (TAS; Kwoh et al., 1989), strand displacement amplification (SDA; Duck, 1990; Walker et al., 1992) or amplification by means of Qβ replicate (Lizardi et al., 1988; Lomeii et al., 1989) or any other suitable method to amplify nucleic acid molecules known in the art.

The oligonucleotides used as primers or probes may also comprise nucleotide analogues such as phosphorothioares (Matsukura et al., 1987), alkylphosphorothioates (Miller et al., 1979) or peptide nucleic acids (Nielsen et al., 1991; Nielsen et al., 1993) or may contain intercalating agents (Asseline et al., 1984).

As most other variations or modifications introduced into the original DNA sequences of the invention these variations will necessitate adaptions with respect to the conditions under which the oligonucleotide should be used to obtain the required specificity and sensitivity. However the eventual results of hybridization will be essentially the same as those obtained with the unmodified oligonucleotides.

The introduction of these modifications may be advantageous in order to positively influence characteristics such as hybridization kinetics, reversibility of the hybrid-formation, biological stability of the oligonucleotide molecules, etc.

The term "solid support" can refer to any substrate to which an oligonucleotide probe can be coupled, provided that it retains its hybridization characteristics acid provided that the background level of hybridization remains low. Usually the solid substrate will be a microliter plate, a membrane (e.g. nylon or nitrocellulose) or a microsphere (bead). Prior to application to the membrane or fixation it may be convenient to modify the nucleic acid probe in order to facilitate fixation or improve the hybridization efficiency. Such modifications may encompass homopolymer tailing, coupling with different reactive groups such as aliphatic groups. $NH_2$ groups, SH groups, carboxylic groups, or coupling with biotin, haptens or proteins.

The term "labelled" refers to the use of labelled nucleic acids. Labelling may be carried out by the use of labelled nucleotides incorporated during the polymerase step of the amplification such as illustrated by Saiki et al. (1988) or Bej et al. (1990) or by the use of labelled primers, or by any other method known to the person skilled in the art. The nature of the label may be isotopic ($^{32}P$, $^{35}S$, etc.) or non-isotopic (biotin, digoxigenin, etc.).

The "sample" may be any biological material taken either directly from the infected human being (or animal), or after culturing (enrichment), or a sample taken from food or feed. Biological material may be e.g. expectoration of any kind, broncheolavages, blood, skin tissue, biopsies, lymphocyte blood culture material, colonies, etc. Said samples may be prepared or extracted wording to any of the techniques known in the art.

The "target" trial in these samples may be either genomic DNA or precursor RNA of the organism to be detected (=target organism), or amplified versions thereof as set out above. More specifically, the nucleic acid sequence of the target material is localized in the spacer region of the target organism(s).

Detection and identification of the target material can be performed by using one of the many electrophoresis methods, hybridization methods or sequencing methods described in literature and currently known by men skilled in the art. However, a very convenient and advantageous technique for the simultaneous detection of nucleic acids possibly present in biological samples is the Line Probe Assay technique. The Line Probe Assay (LiPA) is a reverse hybridization format (Saiki et al., 1989) using membrane strips onto which several oligonucleotide probes (including negative or positive control oligonucleotides) can be conveniently applied as parallel lines.

The LiPA technique, as described by Stuyver et al. (1993) and in international application WO 94/12670, provides a very rapid and user-friendly hybridization test. Results can be read within 4 h, after the start of the amplification. After amplification during which usually a non-isotopic label is incorporated in the amplified product, and alkaline denaturation, the amplified product is contacted with the probes on the membrane and the hybridization is carried out for about 1 to 1,5 h. Consequently, the hybrids formed are detected by an enzymatic procedure resulting in a visual purple-brown precipitate. The LiPA format is completely compatible with commercially available scanning devices, thus rendering automatic interpretation of the results possible. All those advantages make the LiPA format liable for use in a routine setting.

The LiPA format is not only an advantageous tool for identification and detection of pathogens at the species level but also at higher or lower taxonomical levels. For instance, probe-configurations on LiPA strips can be selected in such a manner that they can detect a complete genus (e.g. *Niesseria, Listera*, etc.) or an identify subgroups within a genus (e.g. subgroups in the *Mycobacterium avium-intracellulare-scrofulaceum* complex) or can in some cases even detect subtypes (subspecies, serovars, sequevars, biovars, etc. whatever is clinically relevant) within a species.

It should be stressed that the ability to simultaneously generate hydridization results with a number of probes is an outstanding benefit of the LiPA technology. In many cases the amount of information which can be obtained by a particular combination of probes greatly outnumbers the data obtained by using single probe assays. Therefor the selection of probes an the membrane strip is of utmost importance since an optimized set of probes will generate the maximum of information possible. This is more particularly exemplified further herein.

The fact that different probes can be combined on one strip also offers the possibility to conveniently cope with a lack of sensitivity due to sequence heterogenity in the target region of the group of organisms to be detected. Due to this heterogenity, two or more probes may be required to positively identify all organisms of the particular group. These probes can be applied to membrane strips at different locations and the result is interpreted as positive if at least one of these probes is positive. Alternatively these probes can be applied as a mixture at the same location, hereby reducing the number of lines on a strip. This reduction may be convenient in order to make the strip more concise or to be able to extend the total number of probes on one strip. Another alternative approach, in view of its practical benefits, is the synthesis of oligonucleotides harbouring the sequences of two (or more) different probes (degenerate probes) which then can be further processed and applied to the strip as one oligonucleotide molecule. This approach would considerably simplify the manufacturing procedures of the LiPA-strips. For example, probes with nucleotide sequences A and B are both required to detect all strains of taxon X. In the latter alternative a probe can be synthesized having the nucleotide sequence AB. This probe will have the combined characteristics of probes A and B.

By virtue of the above-mentioned properties the LiPA system can be considered as a preferential format for a hybridization method wherein several organisms need to be detected simultaneously in a sample. Moreover, as described in the examples section, the LiPA system is a preferred format for a selection method for the experimental evaluation and selection of theoretically designed probes.

However, it should be clear that any other hybridization assay, whereby different probes are used under the same hybridization and wash conditions can be used for the above-mentioned detection and/or selection methods. For example, it may be possible to immobilize the target nucleic acid to a solid support, and use mixtures of different probes, all, differently labeled, resulting in a different detection signal for each of the probes hybridized to the target.

As an example, the procedure to be followed for the detection of one or more organisms in a sample using the LiPA format is outlined below:

First, the nucleic acids of the organism(s) to be detected in the sample, is made available for amplification and/or hybridization.

Secondly, the nucleic acids, if present, are amplified with one or another target amplification system, as specified below. Usually, amplification is need to enhance the subsequent hybridization signal. However for some samples or some organisms amplification might not be necessary. This might also be the case if, for the detection of the hybrids formed, highly sensitive signal-amplification systems are used.

Thirdly, eventually after a denaturation step, the nucleic acids present in the sample or the resulting amplified product are contacted with LiPA strips onto which one or more DNA-probes, allowing the detection of the organisms of interest, are immobilized, and hybridization is allowed to proceed.

Finally, eventually after having performed a wash step, the hybrids are detected using a convenient and compatible detection system. From the hybridization signals or patterns observed the presence or absence of one or several organisms screened for in that particular biological sample can be deduced.

The amplification system used may be more or less universal, depending on the specific application needed.

By using universal primers located in the conserved flanking regions (16S and 23S gene) or the rRNA spacer, the spacer region or most if not all organisms or eubacterial origin will be amplified. The same result may be obtained by using a combination of different sets of primers with reduced universality (multiplex amplification, i.e. an amplification procedure in which two or more primer sets are used simultaneously in one and the same reaction mixture).

For some applications it may be appropriate to amplify not all organisms present in the sample but more specifically, beforehand defined taxa. This may be achieved using specific primers located either in less conserved parts of the flanking genes of the spacers (e.g. MYCP1–5 for amplification of the spacer region of mycobacteria) or located in the spacers themselves (e.g. LIS-P1-P7, BRU-P1–4, CHTR-P1–2 and YEC-P1–2 for specific amplification of the spacer regions) of *Listeria* species, *Brucella* species, *Chlamydia trachomatis*, and *Yersinia enterocolitica* respectively).

The present invention thus provides a method for detection and identification of at least one micro-organism, or for the simultaneous detection of several micro-organisms in a sample, comprising the steps of:

(i) if need be releasing, isolating and/or concentrating the polynucleic acids from the micro-organism(s) to be detected in the sample;

(ii) if need be amplifying the 16S–23S rRNA spacer region, or a part of it, from the micro-organism(s) to be detected, with at least one suitable primer pair;

(iii) hybridizing the polynucleic acids of step (i) or (ii) with a set of probes comprising at least two probes, under the same hybridization and wash conditions, with, said probes being selected from the sequences of table 1a or equivalents thereof and/or from taxon-specific probes derived from any of the spacer sequences represented in FIGS. 1–103, with said taxon-specific probe being selected such that it is capable of hybridizing under the same hybridization and wash conditions as at least one of the probes of table 1a;

(iv) detecting the hybrids formed in step (iii);

(v) identification of the micro-organism(s) present in the sample from the differential hybridization signals obtained in step (iv).

The probes as mentioned in table 1a are all selected in such a way that they show the desired hybridization characteristics at a hybridization and wash temperature of 50° C. in a preferred hybridization and wash medium of 3×SSC and 20% formamide.

The term "equivalents" of a probe, also called "variants" or "homologues" or "obvious derivatives", refers to probes differing in sequence from any of the probes specified in table 1 either by addition to or removal from any of their respective extremities of one or several nucleotides, or by changing one or more nucleotides within said sequences, or a combination of both, provided that said equivalents still hybridize with the same RNA or DNA target as the corresponding unmodified probe sequence. Said equivalents share at least 75% homology, preferably more than 80%, most preferably more than 85% homology with the corresponding unmodified probe sequence. It should be noted that, when using an equivalent of a probe, it may be necessary to modify the hybridization conditions to obtain the same specificity as the corresponding unmodified probe. As a consequence, since it is the aim of this invention to use a set of probes which work under the same hybridization and wash conditions, it will also be necessary to modify accordingly the sequence of the other probes, belonging to the same set as the original unmodified probe. These modifications can be done according to principles known in the art, e.g. such as those described in Hames B and Higgins S (Eds): Nucleic acid hybridization. Practical approach. IRL Press. Oxford, UK, 1985.

The invention also provides for a method to select taxon-specific probes from the spaces region sequence(s) of said taxon, said probes being selected such that they show their desired hybridization characteristics under unified hybridization and wash conditions.

The term "unified" conditions means that these conditions are the same for the different probes enabling the detection of different taxa.

Preferentially, the present invention provides for a method as described above wherein at least 2 micro-organisms are detected simultaneously.

In a preferred embodiment, the set of probes as described in step (iii) is comprising at least two probes being selected from the sequences of table 1a, or equivalents thereof.

In another embodiment, the set of probes as described in step (iii) is comprising at least one probe being selected from the sequences of table 1a, or equivalents thereof, and at least one taxon-specific probe derived from any of the spacer sequences as represented in FIGS. 1–103.

In still another embodiment, the set of probes as described in step (iii) is comprising at least two taxon-specific probes derived from any of the spacer sequences as represented in FIGS. 1–103.

The present invention also provides for a method as described above, wherein the probes as specified in step (iii)

are combined with at least one other probe, preferentially also from the 16S–23S rRNA spar region, enabling the simultaneous detection of different pathogenic bacteria liable to be present in the same sample.

The organisms of clinical relevance present in biological samples may vary considerably depending on the origin of die sample. The most common pathogenic bacteria which may be found in sputum samples, or in samples originating from the respiratory tract, are:

Moraxella catarrhalis
Streptococcus pneumomiae
Haemophilus influenzae
Pseudomonas aeruginosa
Mycoplasma pneumomiae
Acinetobacter species
Mycobacterium species
Staphylococcus aureus
Legionella pneumophila A LiPA-strip harbouring spacer-probes enabling the detection of most if not all of these organisms would be extremely benificial for reasons explained above.

Evidently, this also applies for other biological samples, as there are: cerebrospinal fluid, urogenital samples, gastrointestinal samples, blood, urine, food products, soil, etc. For example, a preferred panel for cerebrospinal fluid would contain probe combinations enabling the detection and differentiation of the following organisms:

Neisseria meningitidis
Streptococcus pneumoniae
Streptococcus agalactiae
Listeria monocytogenes
Mycobacterium tuberculosis For some of the above mentioned organisms, spacer probes were already designed in a previous patent application (WO 91/16454). In order to be able to detect most pathogens possibly present in a sample in a single test, the probes of the present invention may be combined with at least one of the probes of WO 91/16454, or their obvious derivatives as specified in WO 91/16454. For clarity, these probes are listed hereafter:

Neisseria gonorrheoae:
  NGI1: CGATGCGTCGTTATTCTACTTCGC
  NGI2: TTCGTTTACCTACCCGTTGACTAAG-TAAGCAAAC
Neisseria meningitidis:
  NMI1: GGTCAAGTGTGACGTCGCCCTG
  NMI2: GTTCTTGGTCAAGTGTGACGTC
  NMI3: GCGTTCGTTATAGCTATCTACTGTGC
  NMI4: TGCGTTCGATATTGCTATCTACTGTCA
  NMI5: TTTTGTTCTTGGTCAAGTGTGACGTCGC-CCTGAATGGATTCTGTTCCATT
  NMI6: TTTGCCTAACATTCCGTTGACTAGAA-CATCAGAC
Haemophilus ducrevi
  HDI1: TTATTATGCGCGAGCCATATTG
Branhamella catharralis
  BCI1: TTAAACATCTTACCAAAG
  BCI2: TTGATGTTTAAACTTGCTTGGTGGA
Bordetella pertussis
  BPI1: CCACACCCATCCTCTGGACAGGCTT
Haemophilus influenzae
  HII1: ACGCATCAAATTGACCGCACTT
  HII2: ACTTTGAAGTGAAAACTTAAAG Streptococcus agalactiae
  SAI1: AATCGAAAGGTTCAAATTGTT
  SAI2: GGAAACCTGCCATTTGCGTCTT
  SAI3: TCCACGATCTAGAATTTAGATTGTAGAA
  SAI4: TCTAGTTTTAAAGAAACTAGGTT
Streptococcus pneumoniae
  SPI1: GTGAGAGATCACCAAGTAATGCA
  SPI2: AGGAACTGCGCATTGGTCTT
  SPI3: GAGTTTATGACTGAAAGGTCAGAA The invention thus provides for a method as described above, wherein said sample is originating from the respiratory tract, and wherein the set of probes as defined in step (iii) comprises at least one probe chosen from the following spacer probes:

MYC-ICG-1: ACTGGATAGTGGTTGCGAGCATCTA (SEQ ID NO 1)
MYC-ICG-22: CTTCTGAATAGTGGTTGCGAG-CATCT (SEQ ID NO 2)
MTB-ICG-1: GGGTGCATGACAACAAAGTTGGCCA (SEQ ID NO 3)
MTB-ICG-2: GACTTGTTCCAGGTGTTGTCCCAC (SEQ ID NO 4)
MTB-ICG-3: CGGCTAGCGGTGGCGTGTTCT (SEQ ID NO 5)
MAI-ICG-1: CAACAGCAAATGATTGCCAGACA-CAC (SEQ ID NO 6)
MIL-ICG-11: GAGGGGTTCCCGTCTGTAGTG (SEQ ID NO 7)
MIL-ICG-22: TGAGGGGTTCTCGTCTGTAGTG (SEQ ID NO 8)
MAC-ICG-1: CACTCGGTCGATCCGTGTGGA (SEQ ID NO 9)
MAV-ICG-1: TCGGTCCGTCCGTGTGGAGTC (SEQ ID NO 10)
MAV-ICG-22: GTGGCCGGCGTTCATCGAAA (SEQ ID NO 11)
MIN-ICG-1: GCATAGTCCTTAGGGCTGATGCGTT (SEQ ID NO 12)
MIN-ICG-2: GCTGATGCGTTCGTCGAAATGTGTA (SEQ ID NO 13)
MIN-ICG-22: CTGATGCGTTCGTCGAAATGTGT (SEQ ID NO 14)
MEN-ICG-222: TGATGCGTTCGTCGAAATGTGT (SEQ ID NO 15)
MIN-ICG-2222: GGCTGATGCGTTCGTCGAAATGT-GTAA (SEQ ID NO 16)
MAL-ICG-1: ACTAGATAACGCGTAGTCCTTGT (SEQ ID NO 17)
MHEF-ICG-1: TGGACGAAAACCGGGTGCACAA (SEQ ID NO 18)
MAH-ICG-1: GTGTAATTTCTTTTTTAACTCTTGT-GTGTAAGTAAGTG (SEQ ID NO 19)
MCO-ICG-11: TGGCCGGCGTGTTCATCGAAA (SEQ ID NO 20)
MTH-ICG-11: GCACTTCAATTGGTGAAGTGC-GAGCC (SEQ ID NO 21)
MTH-ICG-2: GCGTGGTCTTCATGGCCGG (SEQ ID NO 22)
MEF-ICG-11: ACGCGTGGTCCTTCGTGG (SEQ ID NO 23)
MSC-ICG-1: TCGGCTCGTTCTGAGTGGTGTC (SEQ ID NO 24)

MKA-ICG-1: GATGCGTTTGCTACGGGTAGCGT (SEQ ID NO 25)

MKA-ICG-2: GATGCGTTGCCTACGGGTAGCGT (SEQ ID NO 26)

MKA-ICG-3: ATGCGTTGCCCTACGGGTAGCGT (SEQ ID NO 27)

MKA-ICG-4: CGGGCTCTGTTCGAGAGTTGTC (SEQ ID NO 28)

MKA-ICG-5: CCCTCAGGGATTTTCTGGGTGTTG (SEQ ID NO 182)

MKA-ICG-6: GGACTCGTCCAAGAGTGTTGTCC (SEQ ID NO 183)

MKA-ICG-7: TCGGGCTTGGCCAGAGCTGTT (SEQ ID NO 184)

MKA-ICG-8: GGGTGCGCAACAGCAAGCGA (SEQ ID NO 185)

MKA-ICG-9: GATGCGTTGCCCCTACGGG (SEQ ID NO 186)

MKA-ICG-10: CCCTACGGGTAGCGTGTTCTTTTG (SEQ ID NO 187)

MCH-ICG-1: GGTGTGGACTTTGACTTCTGAATAG (SEQ ID NO 29)

MCH-ICG-2: CGGCAAAACGTCGGACTGTCA (SEQ ID NO 30)

MCH-ICG-3: GGTGTGGTCCTTGACTTATGGATAG (SEQ ID NO 210)

MGO-ICG-1: AACACCCTCGGGTGCTGTCC (SEQ ID NO 31)

MCO-ICG-2: GTATGCGTTGTCGTTCGCGGC (SEQ ID NO 32)

MGO-ICG-5: CGTGAGGGGTCATCGTCTGTAG (SEQ ID NO 33)

MUL-ICG-1: GGTTTCGGGATGTTGTCCCACC (SEQ ID NO 175)

MGV-ICG-1: CGACTGAGGTCGACGTGGTGT (SEQ ID NO 176)

MGV-ICG-2: GGTGTTTGAGCATTGAATAGTGGTTGC (SEQ ID NO 177)

MGV-ICG-3: TCGGGCCGCGTGTTCGTCAAA (SEQ ID NO 211)

MXE-ICG-1: GTTGGGCAGCAGGCAGTAACC (SEQ ID NO 178)

MSI-ICG-1: CCGGCAACGGTTACGTGTTC (SEQ ID NO 179)

MFO-ICG-1: TCGTTGGATGGCCTCGCACCT (SEQ ID NO 180)

MFO-ICG-2: ACTTGGCGTGGGATGCGGGAA (SEQ ID NO 181)

MML-ICG-1: CGGATCCATTGAGTCCTTGTCCC (SEQ ID NO 188)

MML-ICG-2: TCTAAATGAACGCACTGCCGATGG (SEQ ID NO 189)

MCE-ICG-1: TGAGGGAGCCCGTGCCTGTA (SEQ ID NO 190)

MHP-ICG-1: CATGTTGGGCTTGATCGGGTGC (SEQ ID NO 191)

PA-ICG 1: TGGTGTGCTGCGTGATCCGAT (SEQ ID NO 34)

PA-ICG 2: TGAATGTTCGTGGATGAACATTGATT (SEQ ID NO 35)

PA-ICG 3: CACTGGTGATCATTCAACTCAAG (SEQ ID NO 36)

PA-ICG 4: TGAATGTTCGT(G/A)(G/A)ATGAACATTGATTTCTGGTC (SEQ ID NO 37)

PA-ICG 5: CTCTTTCACTGGTGATCATTCAAGTCAAG (SEQ ID NO 38)

MPN-ICG 1: ATCGGTGGTAAATTAAACCCAAATCCCTGT (SEQ ID NO 49)

MPN-ICG 2: CAGTTCTGAAAGAACATTTCCGCTTCTTTC (SEQ ID NO 50)

MGE-ICG 1: CACCCATTAATTTTTTCGGTGTTAAAACCC (SEQ ID NO 51)

Mycoplasma-ICG: CAAAACTGAAAACGACAATCTTTCTAGTTCC (SEQ ID NO 52)

STAU-ICG 1: TACCAAGCAAAACCGAGTGAATAAAGAGTT (SEQ ID NO 53)

STAU-ICG 2: CAGAAGATGCGGAATAACGTGAC (SEQ ID NO 54)

STAU-ICG 3: AACGAAGCCGTATGTGAGCATTTGAC (SEQ ID NO 55)

STAU-ICG 4: GAACGTAACTTCATGTTAACGTTTGACTTAT (SEQ ID NO 56)

ACI-ICG 1: GCTTAAGTGCACAGTGCTCTAAACTGA (SEQ ID NO 57)

ACI-ICG 2: CACGGTAATTAGTGTGATCTGACGAAG (SEQ ID NO 58)

and more preferably from the following spacer probes:

MYC-ICG-1: ACTGGATAGTGGTTGCGAGCATCTA (SEQ ID NO 1)

MYC-ICG-22: CTTCTGAATAGTGTTGCGAGCATCT (SEQ ID NO 2)

MTB-ICG-1: GGGTGCATGACAACAAAGTTGGCCA (SEQ ID NO 3)

MTB-ICG-2: GACTTGTTCCAGGTGTTGTCCCAC (SEQ ID NO 4)

MTB-ICG-3: CGGCTACCGGTGGCGTGTTCT (SEQ ID NO 5)

MAI-ICG-1: CAACAGCAAATGATTGCCAGACACAC (SEQ ID NO 6)

MIL-ICG-11: GAGGGGTTCCCGTCTGTAGTG (SEQ ID NO 7)

MIL-ICG-22: TGAGGGGTTCTCGTCTGTAGTG (SEQ ID NO 8)

MAC-ICG-1: CACTCGGTCGATCCGTGTGGA (SEQ ID NO 9)

MAV-ICG-1: TCGGTCCGTCCGTGTGGAGTC (SEQ ID NO 10)

MAV-ICG-22: GTGGCCGGCGTTCATCGAAA (SEQ ID NO 11)

MIN-ICG-1: GCATAGTCCTTAGGCCTGATGCGTT (SEQ ID NO 12)

MAL-ICG-1: ACTAGATGAACGCGTAGTCCTTGT (SEQ ID NO 17)

MCO-ICG-11: TGGCCGGCGTGTTCATCGAAA (SEQ ID NO 20)

MTH-ICG-11: GCACTTCAATTGGTGAAGTGCGAGCC (SEQ ID NO 21)

MTH-ICG-2: GCGTGCTCTTCATGGCCGG (SEQ ID NO 22)

MEF-ICG-11: ACGCGTGGTCCTTCGTGG (SEQ ID NO 23)

MSC-ICG-1: TCGGCTCGTTCTGAGTGGTGTC (SEQ ID NO 24)

MKA-ICG-3: ATGCGTTGCCCTACGGGTAGCGT (SEQ ID NO 27)

MKA-ICG-4: CGGGCTCTGTTCGAGAGTTGTC (SEQ ID NO 28)

MKA-ICG-5: CCCTCAGGGATTTTCTGGGTGTTG (SEQ ID NO 182)

MKA-ICG-6: GGACTCGTCCAAGAGTGTTGTCC (SEQ ID NO 183)

MKA-ICG-7: TCGGGCTTGGCCAGAGCTGTT (SEQ ID NO 184)

MKA-ICG-8: GGGTGCGCAACAGCAAGCGA (SEQ ID NO 185)

MKA-ICG-9: GATGCGTTGCCCCTACGGG (SEQ ID NO 186)

MKA-ICG-10: CCCTACGGGTAGCGTGTTCTTTTG (SEQ ID NO 187)

MCH-ICG-1: GGTGTGGACTTTGACTTCTGAATAG (SEQ ID NO 29)

MCH-ICG-2: CGGCAAAACGTCGGACTGTCA (SEQ ID NO 30)

MCH-ICG-3: GGTGTGGTCCTTGACTTATGGATAG (SEQ ID NO 210)

MGO-ICG-5: CGTGAGGGGTCATCGTCTGTAG (SEQ ID NO 33)

MUL-ICG-1: GGTTTCGGGATGTTGTCCCACC (SEQ ID NO 175)

MGV-ICG-1: CGACTGAGGTCGACGTGGTGT (SEQ ID NO 176)

MGV-ICG-2: GGTGTTTGAGCATTGAATAGTGGTTGC (SEQ ID NO 177)

MGV-ICG-3: TCGGGCCGCGTGTTCGTCAAA (SEQ ID NO 211)

MXE-ICG-1: GTTGGGCACCAGGCAGTAACC (SEQ ID NO 178)

MSI-ICG-1: CCGGCAACGGTTACGTGTTC (SEQ ID NO 179)

MFO-ICG-1: TCGTTGGATGGCCTCGCACCT (SEQ ID NO 180)

MFO-ICG-2: ACTTGGCGTGGGATGCGGGAA (SEQ ID NO 181)

MML-ICG-1: CGGATCGATTGAGTGCTTGTCCC (SEQ ID NO 188)

MML-ICG-2: TCTAAATGAACGCACTGCCGATGG (SEQ ID NO 189)

MCE-ICG-1: TGAGGGAGCCCGTGCCTGTA (SEQ ID NO 190)

MHP-ICG-1: CATGTTGGGCTTGATCGGGTGC (SEQ ID NO 191)

PA-ICG 1: TGGTGTGCTGCGTGATCCGAT (SEQ ID NO 34)

PA-ICG 4: TGAATGTTCGT(G/A)(G/A)ATGAACATTGATTTCTGGTC (SEQ ID NO 37)

PA-ICG 5: CTCTTTCACTGGTGATCATTCAAGTCAAG (SEQ ID NO 38)

MPN-ICG 1: ATCGGTGGTAAATTAAACCCAAATCCCTGT (SEQ ID NO 49)

MPN-ICG 2: CAGTTCTGAAAGAACATTTCCGCTTCTTTC (SEQ ID NO 50)

MGE-ICG 1: CACCCATTAATTTTTTCGGTGTTAAAACCC (SEQ ID NO 51)

Mycoplasma-ICG: CAAAACTGAAAACGACAATCTTTCTAGTTCC (SEQ ID NO 52)

STAU-ICG 1: TACCAAGCAAAACCGAGTGAATAAAGAGTT (SEQ ID NO 53)

STAU-ICG 2: CAGAAGATGCGGAATAACGTGAC (SEQ ID NO 54)

STAU-ICG 3: AACGAAGCCGTATGTGAGCATTTGAC (SEQ ID NO 55)

STAU-ICG 4: GAACGTAACTTCATGTTAACGTTTGACTTAT (SEQ ID NO 56)

ACI-ICG 1: GCTTAAGTGCACAGTGCTCTAAACTGA (SEQ ID NO 57)

ACI-ICG 2: CACGGTAATTAGTGTGATCTGACGAAG (SEQ ID NO 58)

or equivalents of said probes, and/or wherein the set of probes comprises at least one taxon-specific probe derived from the spacer region sequence corresponding to one of the micro-organisms to be detected in said sample, said spacer region sequence being chosen from any of the sequences as represented by SEQ ID NO 76 to 106, 157 to 174, 124, 125, 111 to 115, 139 to 144, or 126 to 130, and with said probes or equivalents being possibly used in combination with any probe detecting at least one of the following organisms: *Haemophilus influenzae, Streptococcus pneumoniae, Moraxella catarrhalis* or *Bordetella pertussis*.

The above mentioned probes of the invention are designed for the detection of *Mycobacterium* species (SEQ ID NO 1 to 33 and 175 to 191), of *Pseudomonas aeruginosa* (SEQ ID NO 34 to 38), of *Mycoplasma* species (SEQ ID NO 49 to 52), of *Staphylococcus aureus* (SEQ ID NO 53 to 56) and of *Acinetobacter baumanii* (SEQ ID NO 57 and 58).

Preferentially, at least two, three, four, five, six, seven, eight or more of said probes are used simultaneously.

The invention also relates to a method as described above, wherein said sample is a sample taken from the cerebrospinal fluid, and wherein the set of probes as described in step (iii) comprises at least one probe chosen from the following spacer probes:

MYC-ICG-1: ACTGGATAGTGGTTGCGAGCATCTA (SEQ ID NO 1)

MYC-ICG-22: CTTCTGAATAGTGGTTGCGAGCATCT (SEQ ID NO 2)

MTB-ICG-1: GGGTGCATGACAACAAAGTTGGCCA (SEQ ID NO 3)

MTB-ICG-2: GACTTGTTCCAGGTGTTGTCCCAC (SEQ ID 4)

MTB-ICG-3: CGGCTAGCGGTGGCGTGTTCT (SEQ ID NO 5)

LIS-ICG 1: CAAGTAACCGAGAATCATCTGAAAGTGAATC (SEQ ID NO 39)

LMO-ICG 1: TTTTCAACCTTTACTTCGTAGAAGTAAATTGGTTAAG (SEQ ID NO 40)

LMO-ICG 2: TGAGAGGTTAGTACTTCTCAGTATGTTTGTTC (SEQ ID NO 41)

LMO-ICG 3: AGGCACTATGCTTGAAGCATCGC (SEQ ID NO 42)

LISP-ICG 1: CGTTTTCATAAGCGATCGCACGTT (SEQ ID NO 212)

and preferably from the following spacer probes:

MYC-ICG-1: ACTGGATAGTGGTTGCGAGCATCTA (SEQ ID NO 1)

MYC-ICG-22: CTTCTGAATAGTGGTTGCGAGCATCT (SEQ ID NO 2)

MTB-ICG-1: GGGTGCATGACAACAAAGTTGGCCA (SEQ ID NO 3)

MTB-ICG-2: GACTTGTTCCAGGTGTTGTCCCAC (SEQ ID NO 4)

MTB-ICG-3: CGGCTAGCGGTGGCGTGTTCT (SEQ ID NO 5)

LIS-ICG 1: CAAGTAACCGAGAATCATCTGAAAGT-GAATC (SEQ ID NO 39)

LMO-ICG 3: AGGCACTATGCTTGAAGCATCGC (SEQ ID NO 42)

LISP-ICG 1: CGTTTTCATAAGCGATCGCACGTT (SEQ ID NO 212)

or equivalents of said probes, and/or wherein the set of probes comprises at least one taxon-specific probe derived from the spacer region sequence corresponding to one of the micro-organisms to be detected in said sample, said spacer region sequence being chosen from any of the sequences as represented by SEQ ID NO 116, 118–121, or 213–215, and with said probes or equivalents being possibly used in combination with any probe detecting at least one of the following organisms: *Neisseria meningitidis, Haemophilus influenzae* or *Streptococcus pneumoniae.*

The above mentioned probes of the invention are designed for the detection of *Mycobacterium* species, and more particularly *Mycobacterium tuberculosis* (SEQ ID NO 1 to 5), and of *Listeria* species; more particularly *Listeria monocytogenes* (SEQ ID NO 39 to 42).

Preferentially, at least two, three, four, five, six, seven, eight or more of said probes are used simultaneously.

The invention also relates to a method as described above, wherein said sample is a sample taken from the urogenital tract, and wherein the set of probes as described in step (iii) comprises at least one probe chosen from the following spacer probes:

CHTR-ICG 1: GGAAGAAGCCTGAGAAGGTTTCT-GAC (SEQ ID NO 45)

CHTR-ICG 2: GCATTTATATGTAAGACCAAGCAT-TCTATTTCA (SEQ ID NO 46)

CHTR-ICG 3: GAGTAGCGTGGTGAGGACGAGA (SEQ ID NO 47)

CHTR-ICG 4: GAGTAGCGCGGTGAGGACGAGA (SEQ ID NO 201)

CHPS-ICG 1: GGATAACTCTCTTAGGACG-GTTTGAC (SEQ ID NO 48)

MGE-ICG 1: CACCCATTAATTTTTTCGGTGT-TAAAACCC (SEQ ID NO 51)

Mycoplasma-ICG: CAAAACTOAAAACGA-CAATCTTTCTAGTTCC (SEQ ID NO 52)

or equivalents of said probes, and/or wherein the set of probes comprises at least one taxon-specific probe derived from the spacer region sequence corresponding to one of the micro-organisms to be detected in said sample, said spacer region sequence being chosen from any of the sequences as represented by SEQ ID NO 122, 123, 197, 124 or 125, with said probes or equivalents being possibly used in combination with any probe detecting at least one of the following organisms: *Neisseria gonorrhoeae, Haemophilus ducrevi* or *Streptococcus agalactiae.*

The above mentioned probes of the invention are designed for the detection of *Chlamydia* species (SEQ ID NO 45 to 48 and 201) and of *Mycoplasma* species (SEQ ID NO 51 and 52).

Preferentially, at least two, three, four, five, six or seven of said probes are used simultaneously.

The invention also relates to a method as described above, wherein said sample is a sample taken from food, and wherein the set of probes as defined in step (iii) comprises at least one probe chosen from the following spar probes:

LIS-ICG 1: CTTGTAACCGAGAATCATCTGAAAGT-GAATC (SEQ ID NO 39)

LMO-ICG 1: AAACAACCTTTACTTCGTAGAAG-TAAATTGGTTAAG (SEQ ID NO 40)

LMO-ICG 2: TGAGAGGTTAGTACTTCTCAGTAT-GTTTGTTC (SEQ ID NO 41)

LMO-ICG 3: AGGCACTATGCTTGAAGCATCGC (SEQ ID NO 42)

LIV-ICG 1: GITAGCATAAATAGGTAACTATTTATGA-CACAAGTAAC (SEQ ID NO 43)

LSE-ICG 1: AGTTAGCATAAGTAGTGTAACTATT-TATGACACAAG (SEQ ID NO 44)

LISP-ICG 1: CGTTTTCATAAGCGATCGCACGTT (SEQ ID NO 212)

STAU-ICG 1: TACCAAGCAAAACCGAGT-GAATAAAGAGTT (SEQ ID NO 53)

STAU-ICG 2: CAGAAGATGCGGAATAACGTGAC (SEQ ID NO 54)

STAU-ICG 3: AACGAAGCCGTATGTGAG-CATTTGAC (SEQ ID NO 55)

STAU-ICG 4: GAACGTAACTTCATGT-TAACGTTTGACTTAT (SEQ ID NO 56)

BRU-ICG 1: CGTGCCGCCTTCGTTTCTCTTT (SEQ ID NO 59)

BRU-ICG 2: TTCGCTTCGGGGTGGATCTGTG (SEQ ID NO 60)

BRU-ICG 3: GCGTAGTAGCGTTTGCGTCGG (SEQ ID NO 193)

BRU-ICG 4: CCCAAGAAGCTTGCTCAAGCC (SEQ ID NO 194)

SALM-ICG 1: CAAAACTGACTTACGAGT-CACGTTTGAG (SEQ ID NO 61)

SALM-ICG 2: GATGTATGCTTCGTTATTCCACGCC (SEQ ID NO 62)

STY-ICG 1: GGTCAAACCTCCAGGGACGCC (SEQ ID NO 63)

SED-ICG 1: GCGGTAATGTGTGAAAGCGTTGCC (SEQ ID NO 64)

YEC-ICG 1: GGAAAAGGTACTGCACGTGACTG (SEQ ID NO 198)

YEC-ICG 2: GACAGCTGAAACTTATCCCTCCG (SEQ ID NO 199)

YEC-ICG 3: GCTACCTGTTGATGTAATGAGTCAC (SEQ ID NO 200)

and preferably from the following spacer probes:

LIS-ICG 1: CAAGTAACCGAGAATCATCTGAAAGT-GAATC (SEQ ID NO 39)

LMO-ICG 3: AGGCACTATGCTTGAAGCATCGC (SEQ ID NO 42)

LISP-ICG 1: CGTTTTCATAAGCGATCGCACGTT (SEQ ID NO 212)

STAU-ICG 1: TACCAAGCAAAACCGAGT-GAATAAAGAGTT (SEQ ID NO 53)

STAU-ICG 2: CAGAAGATGCGGAATTTCGTGAC (SEQ ID NO 54)

STAU-ICG 3: AACGAAGCCGTATGTGAG-CATTTGAC (SEQ ID NO 55)

STAU-ICG 4: GAACGTAACTTCATGT-TAACGTTTGACTTAT (SEQ ID NO 56)

BRU-ICG 2: TTCGCTTCGGGGTGGATCTGTG (SEQ ID NO 60)

BRU-ICG 3: GCGTAGTAGCGTTTGCGTCGG (SEQ ID NO 193)

BRU-ICG 4: CGCAAGAAGCTTGCTCAAGCC (SEQ ID NO 194)

SALM-ICG 1: CAAAACTGACTTACGAGT-CACGTTTGAG (SEQ ID NO 61)

YEC-ICG 1: GGAAAAGGTACTGCCACGTGACTG (SEQ ID NO 198)

YEC-ICG 2: GACAGCTGAAACTTATCCCTCCG (SEQ ID NO 199)

YEC-ICG 3: GCTACCTGTTGATGTTATGAGTCAC (SEQ ID NO 200)

or equivalents of said probes,
and/or wherein the set of probes comprises at least one taxon-specific probe derived from the spacer region sequence corresponding to one of the micro-organisms to be detected in said sample, said spacer region sequence being chosen from any of the sequences as represented by SEQ ID NO 116, 118–121, 213–215, 139–144, 131, 132, 154, 133–138, 195 or 196,
with said probes or equivalents being possibly used in combination with any probe detecting strains of Campylobacter species.

The above mentioned probes of the invention are designed for the detection of Listeria species (SEQ ID NO 39 to 44), of Staphylococcus species (SEQ ID NO 53 to 56), of Brucella species (SEQ ID NO 59, 60, 193 and 194), of Salmonella species (SEQ ID NO 61 to 64) and of Yersinia enterocolitica (SEQ ID NO 198 to 200).

Preferentially, at least two, three, four, five, six, seven, eight or more of said probes are used simultaneously.

The invention also relates to a method as described above, wherein said sample is a sample taken from the gastrointestinal tract of a patient, and wherein the set of probes as defined in step (iii) comprises at least one probe chosen from the following spacer probes:

SALM-ICG 1: CAAAACTGACTTACGAGT-CACGTTTGAG (SEQ ID NO 61)

SALM-ICG 2: GATGTATGCTTCGTTATTCCACGCC (SEQ ID NO 62)

STY-ICG 1: GGTCAAACCTCCAGGGACGCC (SEQ ID NO 63)

SED-ICG 1: GCGCTAATGTCTGAAAGCGTTGCC (SEQ ID NO 64)

YEC-ICG 1: GGAAAAGGTACTGCACGTGACTG (SEQ ID NO 198)

YEC-ICG 2: GACAGCTGAAACTTATCCCTCCG (SEQ ID NO 199)

YEC-ICG 3: GCTACCTGTTGATGTAATGAGTCAC (SEQ ID NO 200)

and preferably from the following spacer probes:

SALM-ICG 1: CAAAACTGACTTACGAGT-CACGTTTGAG (SEQ ID NO 61)

YEC-ICG 1: GGAAAAGGTACTGCACGTGACTG (SEQ ID NO 198)

YEC-ICG 2: GACAGCTGAAACTTATCCCTCCG (SEQ ID NO 199)

YEC-ICG 3: GCTACCTGTTGATGTAATGAGTCAC (SEQ ID NO 200)

or equivalents of said probes,
and/or wherein the set of probes comprises at least one taxon-specific probe derived from the spacer region sequence corresponding to one of the micro-organisms to be detected in said sample, said spacer region sequence being chosen from any of the sequences as represented by SEQ ID NO 133–138 or 195–196,
with said probes or equivalent being possibly used in combination with any probe detecting Campylobacter species.

The above mentioned probes of the invention are designed to detect Salmonella species (SEQ ID NO 61 to 64) and Yersinia enterocolitica (SEQ ID NO 198 to 200).

Preferentially, at least two, three, four, five, six or seven of said probes are used simultaneously.

The invention also relates to the use of the selected probes or their equivalents for the detection of specific bacterial taxa, said taxa being either a complete genus, or a subgroup within a genus, a species, or even a subtype within a species.

The invention thus provides for a method as described above to detect and identify one or more strains of Mycobacterium species and subspecies in a sample, wherein step (iii) comprises hybridizing to at least one of the following probes:

MYC-ICG-1: ACTGGATAGTGGTTGCGAGCATCTA (SEQ ID NO 1)

MYC-ICG-22: CTTCTGAATAGTGGTTGCGAG-CATCT (SEQ ID NO 2)

MTB-ICG-1: GGGTGCATGACAACAAAGTTGGCCA (SEQ ID NO 3)

MTB-ICG-2: GACTTGTTCCAGGTGTTGTCCCAC (SEQ ID NO 4)

MTB-ICG-3: CGGCTAGCGGTGGCGTGTTCT (SEQ ID NO 5)

MAI-ICG-1: CAACAGCAAATGATTGCCAGACA-CAC (SEQ ID NO 6)

MIL-ICG-11: GAGGGGTTCCCGTCTGTAGTG (SEQ ID NO 7)

MIL-ICG-22: TGAGGGGTTCTCGTCTGTAGTG (SEQ ID NO 8)

MAC-ICG-1: CACTCGGTCGATCCGTGTGGA (SEQ ID NO 9)

MAV-ICG-1: TCGGTCCGTCCGTGTGGAGTC (SEQ ID NO 10)

MAV-ICG-22: GTGGCCGGCGTTCATCGAAA (SEQ ID NO 11)

KIN-ICG-1: GCATAGTCCTTAGGGCTGATGCGTT (SEQ ID NO 12)

MIN-ICG-2: GCTGATGCGTTCGTCGAAATGTGTA (SEQ ID NO 13)

MIN-ICG-22: CTGATGCGTTCGTCGAAATGTGT (SEQ ID NO 14)

MIN-ICG-22: TGATGCGTTCGTCGAAATGTGT (SEQ ID NO 15)

MIN-ICG-2222: GGCTGATGCGTTCGTCGAAATGT-GTAA (SEQ ID NO 16)

MAL-ICG-1: ACTAGATGAACGCGTAGTCCTTGT (SEQ ID NO 17)

MHEF-ICG-1: TGGACGAAAACCGGGTGCACAA (SEQ ID NO 18)

MAH-ICG-1: GTGTAATTTCTTTTTTAACTCTTGT-GTGTAAGTAAGTG (SEQ ID NO 19)

MCO-ICG-11: TGGCCGGCGTGTTCATCGAAA (SEQ ID NO 20)

MTH-ICG-11: GCACTTCAATTGGTGAAGTGC-GAGCC (SEQ ID NO 21)

MTH-ICG-2: GCGTGGTCTTCATGGCCGG (SEQ ID NO 22)

MEF-ICG-11: ACGCGTGGTCCTTCGTGG (SEQ ID NO 23)

MSC-ICG-1: TCGGCTCGTTCTGAGTGGTGTC (SEQ ID NO 24)

MKA-ICG-1: GATGCGTTTGCTACGGGTAGCGT (SEQ ID NO 25)

MKA-ICG-2: GATGCGTTGCCTACGGGTAGCGT (SEQ ID NO 26)

MKA-ICG-3: ATGCGTTGCCCTACGGGTAGCGT (SEQ ID NO 27)

MKA-ICG-4: CGGGCTCTGTTCGAGAGTTGTC (SEQ ID NO 28)

MKA-ICG-5: CCCTCAGGGATTTTCTGGGTGTTG (SEQ ID NO 182)

MKA-ICG-6: GGACTCGTCCAAGAGTGTTGTCC (SEQ ID NO 183)

MKA-ICG-7: TCGGGCTTGGCCAGAGCTGTT (SEQ ID NO 184)

MKA-ICG-8: GGGTGCGCAACAGCAAGCGA (SEQ ID NO 185)

MKA-ICG-9: GATGCGTTGCCCCTACGGG (SEQ ID NO 186)

MKA-ICG-10: CCCTACGGGTAGCGTGTTCTTTTG (SEQ ID NO 187)

MCH-ICG-1: GGTGTGGACTTTGACTTCTGAATAG (SEQ ID NO 29)

MCH-ICG-2: CGGCAAAACGTCGGACTGTCA (SEQ ID NO 30)

MGO-ICG-1: AACACCCTCGGGTGCTGTCC (SEQ ID NO 31)

MCO-ICG-2: GTATGCGTTGTCGTTCGCGGC (SEQ ID NO 32)

MGO-ICG-5: CGTGAGGGGTCATCGTCTGTAG (SEQ ID NO 33)

MUL-ICG-1: GGTTTCGGGATGTTGTCCCACC (SEQ ID NO 175)

MGV-ICG-1: CGACTGAGGTCGACGTGGTGT (SEQ ID NO 176)

MGV-ICG-2: GGTGTTTGAGCATTGAATAGTGGTTGC (SEQ ID NO 177)

MXE-ICG-1: GTTGGGCAGCAGGCAGTAACC (SEQ ID NO 178)

MSI-ICG-1: CCGGCAACGGTTACGTGTTC (SEQ ID NO 179)

MFO-ICG-1: TCGTTGGATGGCCTCGCACCT (SEQ ID NO 180)

MFO-ICG-2: ACTTGGCGTGGGATGCGGGAA (SEQ ID NO 181)

MML-ICG-1: CGGATCGATTGAGTGCTTGTCCC (SEQ ID NO 188)

MML-ICG-2: TCTAAATGAACGCACTGCCGATGG (SEQ ID NO 189)

MCE-ICG-1: TGAGGGAGCCCGTGCCTGTA (SEQ ID NO 190)

MHP-ICG-1: CATGTTGGGCTTGATCGGGTGC (SEQ ID NO 191)

and more preferably to at least one probe of the following restricted group of spacer probes:

MYC-ICG-1: ACTGGATAGTGGTTGCGAGCATCTA (SEQ ID NO 1)

MYC-ICG-22: CTTCTGAATAGTGGTTGCGAGCATCT (SEQ ID NO 2)

MTB-ICG-1: GGGTGCATGACAACAAAGTTGGCCA (SEQ ID NO 3)

MTB-ICG-2: GACTTGTTCCAGGTGTTGTCCCAC (SEQ ID NO 4)

MTB-ICG-3: CGGCTAGCGGTGGCGTGTTCT (SEQ ID NO 5)

MAI-ICG-1: CAACAGCAAATGATTGCCAGACACAC (SEQ ID NO 6)

MIL-ICG-11: GAGGGGTTCCCGTCTGTAGTG (SEQ ID NO 7)

MIL-ICG-22: TGAGGGGTCTCGTCTGTAGTG (SEQ ID NO 8)

MAC-ICG-1: CACTCGGTCGATCCGTGTGGA (SEQ ID NO 9)

MAV-ICG-1: TCGGTCCGTCCGTGTGGAGTC (SEQ ID NO 10)

MAV-ICG-22: GTGGCCGGCGTTCATCGAAA (SEQ ID NO 11)

MIN-ICG-1: GCATAGTCCTTAGGGCTGATGCGTT (SEQ ID NO 12)

MAL-ICG-1: ACtAGATGAACGCGTAGTCCITGT (SEQ ID NO 17)

MCO-ICG-11: TGGCCGGCGTGTTCATCGAAA (SEQ ID NO 20)

MTH-ICG-11: GCACTTCAATTGGTGAAGTGCGAGCC (SEQ ID NO 21)

MTH-ICG-2: GCGTGGTCTTCATGGCCGG (SEQ ID NO 22)

MEF-ICG-11: ACGCGTGGTCCTTCGTGG (SEQ ID NO 23)

MSC-ICG-1: TCGGCTCGTTCTGAGTGGTGTC (SEQ ID NO 24)

MKA-ICG-3: ATGCGTTGCCCTACGGGTAGCGT (SEQ ID NO 27)

MKA-ICG-4: CGGGCTCTGTTCGAGAGTTGTC (SEQ ID NO 28)

MKA-ICG-5: CCCTCAGGGATTTTCTGGGTGTTG (SEQ ID NO 182)

MKA-ICG-6: GGACTCGTCCAAGAGTGTTGTCC (SEQ ID NO 183)

MKA-ICG-7: TCGGGCTTGGCCAGAGCTGTT (SEQ ID NO 184)

MKA-ICG-8: GGGTGCGCAACAGCAAGCGA (SEQ ID NO 185)

MKA-ICG-9: GATGCGTTGCCCCTACGGG (SEQ ID NO 186)

MKA-ICG-10: CCCTACGGGTAGCGTGTTCTTTTG (SEQ ID NO 187)

MCH-ICG-1: GGTGGACTTTGACTTCTGAATAG (SEQ ID NO 29)

MCH-ICG-2: CGGCAAAACGTCGGACTGTCA (SEQ ID NO 30)

MCH-ICG-3: GGTGTGGTCCTTGACTTATGGATAG (SEQ ID NO 210)

MGO-ICG-5: CGTGAGGGGTCATCGTCTGTAG (SEQ ID NO 33)

MUL-ICG-1: GGTTTCGGGATGTTGTCCCACC (SEQ ID NO 175)

MGV-ICG-1: CGACTGAGGTCGACGTGGTGT (SEQ ID NO 176)

MGV-ICG-2: GGTGTTTGAGCATTGAATAGTGGTTGC (SEQ ID NO 177)

MGV-ICG-3: TCGGGCCGCGTGTTCGTCAAA (SEQ ID NO 211)

MXE-ICG-1: GTCGGGCAGCAGGCAGTAACC (SEQ ID NO 178)

MSI-ICG-1: CCGCCAACGGTTACGTGTTC (SEQ ID NO 179)

MFO-ICG-1: TCGTTGGATGGCCTCGCACCT (SEQ ID NO 180)

MFO-ICG-2: ACTTGGCGTGGGATGCGGGAA (SEQ ID NO 181)

MML-ICG-1: CGGATCGATTGAGTGCTTGTCCC (SEQ ID NO 188)

MML-ICG-2: TCTAAATGAACGCACTGCCGATGG (SEQ ID NO 189)

MCE-ICG-1: TGAGGGAGCCCGTGCCTGTA (SEQ ID NO 190)

MHP-ICG-1: CATGTTGGGCTTGATCGGGTGC (SEQ ID NO 191)

or to equivalents of said probes,
and/or to any probe derived from SEQ ID NO 76–110, or 157–174 provided said probe hybridizes specifically to a *Mycobacterium* species.

The sequences represented by SEQ ID NO 76–110 and 157–174 are new.

Preferentially, at least two, three, four, five, six, seven, eight or more of said probes are used simultaneously.

As described above, the preferred restricted set of probes are those probes which showed a sensitivity and specificity of more than 80%, preferably more than 90%, most preferably more than 95%, under the specific hybridization conditions as described in the examples section.

In one specific embodiment, the invention provides for a method as described above to detect and identify one or more *Mycobacterium tuberculosis* complex strains in a sample, wherein step (iii) comprises hybridizing to at least one of the following probes:

MTB-ICG-1: GGGTGCATGACAACAAAGTTGGCCA (SEQ ID NO 3)

MTB-ICG-2: GACTTGTTCCAGGTGTTGTCCCAC (SEQ ID NO 4)

MTB-ICG-3: CGGCTAGCGGTGGCGTGTTCT (SEQ ID NO 5)

or to equivalents of said probes,
and/or to any probe derived from SEQ ID NO 76 provided said probe hybridizes specifically to the *M. tuberculosis* complex. The *M. tuberculosis* complex comprises *M. tuberculosis, M. bovis, M. bovis BCG, M. africanum* and *M. microri* strains.

The sequence represented in SEQ ID NO 76 is new.

Preferentially, at least two, or three of said probes are used simultaneously.

In another specific embodiment, the invention provides for a method as described above to detect and identify one or more *Mycobacterium* strains from the MAIS-complex, wherein step (iii) comprises hybridizing to at least one of the following probes:

MAI-ICG-1: CAACACCAAATGATTGCCAGACA-CAC (SEQ ID NO 6)

MIL-ICG-11: GAGGGGTFCCCGTCTGTAGTG (SEQ ID NO 7)

MIL-ICG-22: TGAGGGGTTCTCGTCTGTAGTG (SEQ ID NO 8)

MAC-ICG-1: CACTCGGTCGATCCGTGTGGA (SEQ ID NO 9)

MAV-ICG-1: TCGGTCCGTCCGTGTGGAGTC (SEQ ID NO 10)

MAV-ICG-22: GTGGCCGGCGTTCATCGAAA (SEQ ID NO 11)

MIN-ICG-1: GCATAGTCCTTAGGGCTGATGCGTT (SEQ ID NO 12)

MIN-ICG-2: GCTGATGCGTTCGTCGAAATGTGTA (SEQ ID NO 13)

MIN-ICG-22: CTGATGCGTTCGTCGAAATGTGT (SEQ ID NO 14)

MIN-ICG-222: TGATGCGTTCGTCGAAATGTGT (SEQ ID NO 15)

MIN-ICG-2222: GGCTGATGCGTTCGTCGAAATGT-GTAA (SEQ ID NO 16)

MAL-ICG-1: ACTAGATGAACGCGTAGTCCTTGT (SEQ ID NO 17)

MHEF-ICG-1: TGGACGAAAACCGGGTGCACAA (SEQ ID NO 18)

MAH-ICG-1: GTGTAATTTCTTTTTTAACTCTTGT-GTGTAAGTAAGTG (SEQ ID NO 19)

MCO-ICG-11: TGGCCGGCGTGTTCATCGAAA (SEQ ID NO 20)

MTH-ICG-11: GCACTTCAATTGGTGAAGTGC-GAGCC (SEQ ID NO 21)

MTH-ICG-2: GCGTGGTCTTCATGGCCGG (SEQ ID NO 22)

MEF-ICG-11: ACGCGTGGTCCTTCGTGG (SEQ ID NO 23)

MSC-ICG-1: TCGGCTCGTTCTGAGTGGTGTC (SEQ ID NO 24)

or to equivalents of said probes,
and/or to any probe derived from SEQ ID NO 77–100 or 108–110, provided said probe hybridizes specifcally to strains from the MAIS complex. The MAIS complex as defined in this invention comprises all strains of *M. avium, M. intracellulare* and *M. scrorulaceum* and all strains closely related to the above mentioned species and not clearly belonging to another defined *Mycobacterium* species. The latter group of strains are defined in this invention as "MIC strains" (*M. intracellulare* complex).

Preferentially, at least two, three, four, five, six, seven, eight or more of said probes are used simultaneously.

In still another specific embodiment, the invention provides for a method as described above, to detect and identify one or more *M. avium* and *M. paratuberculosis* strains in a sample, wherein step (iii) comprises hybridizing to at least one of the following probes:

MAV-ICG-1: TCGGTCCGTCCGTGTGGAGTC (SEQ ID NO 10)

MAV-ICG-22: GTGGCCGGCGTTCATCGAAA (SEQ ID NO 11)

or to equivalents of said probes,
and/or to any probe derived from SEQ ID NO 77 and 78 provided said probe hybridizes specifically to *M. avium* or *M. paratuberculosis.*

The sequences as represented in SEQ ID NO 77 and 78 are new.

Preferentially, this embodiment uses both probes in combination.

In still another specific embodiment, the invention provides for a method as described above to detect and identify one or more *Mycobacterium intracellulare* strains and MIC-strains in a sample, wherein step (iii) comprises hybridizing to at least one of the following probes:

MAI-ICG-1: CAACAGCAAATGATTGCCAGACA-CAC (SEQ ID NO 6)

MIL-ICG-11: GAGGGGTTCCCGTCTGTAGTG (SEQ ID NO 7)

MIL-ICG-22: TGAGGGGTTCTCGTCTGTAGTG (SEQ ID NO 8)

MAC-ICG-1: CACTCGGTCGATCCGTGTGGA (SEQ ID NO 9)

MIN-ICG-1: GCATAGTCCTTAGGGCTGATGCGTT (SEQ ID NO 12)

MIN-ICG-2: GCTGATGCGTTCGTCGAAATGTGTA (SEQ ID NO 13)

MIN-ICG-22: CTGATGCGTTCGTCGAAATGTGT (SEQ ID NO 14)

MIN-ICG-222: TGATGCGTTCGTCGAAATGTGT (SEQ ID NO 15)

MIN-ICG-2222: GGCTGATGCGTTCGTCGAAATGT-GTAA (SEQ ID NO 16)

MAL-ICG-1: ACTAGATGAACGCGTAGTCCTTGT (SEQ ID NO 17)

MAEF-ICG-1: TGGACGAAAACCGGGTGCACAA (SEQ ID NO 18)

MAH-TCG-1: GTGTAATTTCTTTTTTAACTCTTGT-GTGTAAGTAAGTG (SEQ ID NO 19)

MCO-ICG-11: TGGCCGGCGTGTTCATCGAAA (SEQ ID NO 20)

MTH-ICG-11: GCACTTCAATTGGTGAAGTGC-GAGCC (SEQ ID NO 21)

MTH-ICG-2: GCGTGGTCTTCATGGCCGG (SEQ ID NO 22)

MEF-ICG-11: ACGCGTGGTCCTTCGTGG (SEQ ID NO 23)

or to equivalents of said probes, and/or to any probe derived from SEQ ID NO 79, 80, 81, 82, 83, 84, 85, 86, 87, 88, 89, 90, 91, 92, 93, 94, 95, 96, 97, 98 or 99 provided said probe hybridizes specifically to *M. intracellulare* strains and MIC-strains.

The sequences as represented in SEQ ID NO 79, 80, 81, 82, 83, 84, 85, 86, 87, 88, 89, 90, 91, 92, 93, 94, 95, 96, 97, 98 or 99 are new.

Preferentially, at least two, three, four, five, six, seven, eight or more of said probes are used simultaneously.

In still another specific embodiment, the invention provides for a method as described above, to detect and identify one or more *Mycobacterium intracellulare* strains in a sample, wherein step (iii) comprises hybridizing to at least the following probes:

MIN-ICG-1: GCATAGTCCTTAGGGCTGATGCGTT (SEQ ID NO 12)

or to equivalents of said probe, and/or to any probe derived from SEQ ID NO 89 provided said probe hybridizes specifically to *M. intracellulare* strains.

In still another specific embodiment, the invention provides for a method as described above, to detect and identify one or more *Mycobacterium scrofulaceum* strains in a sample, wherein step (iii) comprises hybridizing to the following probe:

MSC-ICG-1: TCGGCTCGTTCTGAGTGGTGTC (SEQ ID NO 24)

or to equivalents of said probes, and/or to any probe derived from SEQ ID NO 100 provided said probe hybridizes specifically to *M. scrofulaceum*.

The sequence as represented in SEQ ID NO 100 is new.

In still another specific embodiment the invention provides for a method as described above to detect and identify one or more *Mycobacterium kansasii* strains in a sample, wherein step (iii) comprises hybridizing to at least one of the following probes:

MKA-ICG-1: GATGCGTTTGCTACGGGTAGCGT (SEQ ID NO 25)

MKA-ICG-2: GATGCGTTGCCTACGGGTAGCGT (SEQ ID NO 26)

MKA-ICG-3: ATGCGTTGCCCTACGGGTAGCGT (SEQ ID NO 27)

MKA-ICG-4: CGGGCTCTGTTCGAGAGTTGTC (SEQ ID NO 28)

MKA-ICG-5: CCCTCAGGGATTTTCTGGGTGTTG (SEQ ID NO 182)

MKA-ICG-6: GGACTCGTCCAAGAGTGTTGTCC (SEQ ID NO 183)

MKA-ICG-7: TCGGGCTTGGCCAGAGCTGTT (SEQ ID NO 184)

MKA-ICG-8: GGGTGCGCAACAGCAAGCGA (SEQ ID NO 185)

MKA-ICG-9: GATGCGTTGCCCCTACGGG (SEQ ID NO 186)

MKA-ICG-10: CCCTACGGGTAGCGTGTTCTTTTG (SEQ ID NO 187)

and more preferably to:

MKA-ICG-3: ATGCGTTGCCCTACGGGTAGCGT (SEQ ID NO 27)

MKA-ICG-4: CGGGCTCTGTTCGAGAGTTGTC (SEQ ID NO 28)

MKA-ICG-5: CCCTCAGGGATTTTCTGGGTGTTG (SEQ ID NO 182)

MKA-ICG-6: GGACTCGTCCAAGAGTGTTGTCC (SEQ ID NO 183)

MKA-ICG-7: TCGGGCTTGGCCAGAGCTGTT (SEQ ID NO 184)

MKA-ICG-8: GGGTGCGCAACAGCAAGCGA (SEQ ID NO 185)

MKA-ICG-9: GATGCGTTGCCCCTACGGG (SEQ ID NO 186)

MKA-ICG-10: CCCTACGGGTAGCGTGTTCTTTTG (SEQ ID NO 187)

or to equivalents of said probes, and/or to any probe derived from SEQ ID NO 101, 167, 168 or 169 provided said probe hybridizes specifically to *M. kansasii*.

The sequences as represented in SEQ ID NO 101, 167, 168 and 169 are new.

Preferentially, at least two, three or four of said probes are used simultaneously.

In still another specific embodiment, the invention provides for a method as described above to detect and identify one or more *Mycobacterium chelonae* strains in a sample, wherein step (iii) comprises hybridizing to at least one of the following probes:

MCH-ICG-1: GGTGTGGACTTTGACTTCTGAATAG (SEQ ID NO 29)

MCH-ICG-2: CGGCAAAACGTCGGACTGTCA (SEQ ID NO 30)

MCH-ICG-3: GGTGTGGTCCTTGACTATGGATAG (SEQ ID NO 210)

or to equivalents of said probes, and/or to any probe derived from SEQ ID NO 102, 103 or 174 provided said probe hybridizes specifically to *M. chelonae*. According to another preferential embodiment, these three probes are used in combination.

The sequences as represented in SEQ ID NO 102, 103 and 174 are new.

In still another specific embodiment, the invention provides for a method as described above to detect and identify one or more *Mycobacterium gordonae* strains in a sample, wherein step (iii) comprises hybridizing to at least one of the following probes:

MGO-ICG-1: AACACCCTCGGGTGCTGTCC (SEQ ID NO 31)

MGO-ICG-2: GTATGCGTTGTCGTTCGCGGC (SEQ ID NO 32)

MGO-ICG-5: CGTGAGGGGTCATCGTCTGTAG (SEQ ID NO 33)

and more preferably to:

MGO-ICG-5: CGTGAGGGGTCATCGTCTGTAG (SEQ ID NO 33)

or to equivalents of said probes,
and/or to any probe derived from SEQ ID NO 104, 105 or 106 provided said probe hybridizes specifically to *M. gordonae.*

The sequences as represented in SEQ ID NO 104 to 106 are new.

Preferentially, at least two or three of said probes are used simultaneously.

In still another specific embodiment, the invention provides for a method as described above to detect and identify one or more *Mycobacterium ulcerans* strains or *Mycobacterium marinum* strains in a sample, wherein step (iii) comprises hybridizing to the following probe:

MUL-MG-1: GGTTTCGGGATGTTGTCCCACC (SEQ ID NO 175)

or to equivalents of said probe,
and/or to any probe derived from SEQ ID NO 157 provided said probe hybridizes specifically to *M. ulcerans* and *M. marinum.*

The sequence as represented in SEQ ID NO 157 is new.

In still another specific embodiment, the invention provides for a method as described above to detect and identify one or more *Mycobacterium genavense* strains in a sample, wherein step (iii) comprises hybridizing to at least one of the following probes:

MGV-ICG-1: CGACTGAGGTCGACGTGGTGT (SEQ ID NO 176)

MGV-ICG-2: GGTGTTTGAGCATTGAATAGTGGT-TGC (SEQ ID NO 177)

MGV-ICG-3: TCGGGCCGCGTGTTCGTCAAA (SEQ ID NO 211)

or to equivalents of said probes,
and/or to any probe derived from SEQ ID NO 158, 159, 160, 161 or 162 provided said probe hybridizes specifically to *M. genavense.*

The sequences as represented in SEQ ID NO 158 to 162 are new.

As described in the examples, *M. genavense* includes *M. genavense* strains sensu strictu and a group of closely related snags called *M. simiae*-like. The former group of strains can be detected specifically with probe MGV-ICG-1 while the latter group hybridizes specifically with probe MGV-ICG-3. Probe MGV-ICG-2 detects both groups.

In still another specific embodiment, the invention provides for a method as described above to detect and identify one or more *Mycobacterium xenopi* strains in a sample, wherein step (iii) comprises hybridizing to the following probe:

MXE-ICG-1: GTTGGGCAGCAGGCAGTAACC (SEQ ID NO 178)

or to equivalents of said probe,
and/or to any probe derived from SEQ ID NO 163 provided said probe hybridizes specifically to *M. xenopi.*

The sequence as represented in SEQ ID NO 163 is new.

In still another specific embodiment, the invention provides for a method as described above to detect and identify one or more *Mycobacterim simiae* strains in a sample, wherein step (iii) comprises hybridizing to the following probe:

MSI-ICG-1: CCGGCAACGGTTACGTGTTC (SEQ ID NO 179)

or to equivalents of said probe,
and/or to any probe derived from SEQ ID NO 164 or 165 provided said probe hybridizes specifically to *M. simiae.*

The sequence as represented in SEQ ID NO 164 or 165 is new.

In still another specific embodiment, the invention provides for a method as described above to detect and identify one or more *Mycobacterium fortuitum* strains in a sample. wherein step (iii) comprises hybridizing to at least one of the the following probes:

MFO-ICG-1: TCGTTGGATGGCCTCGCACCT (SEQ ID NO 180)

MPO-ICG-2: ACTTGGCGTGGGATGCGGGAA (SEQ ID NO 181)

or to equivalents of said probes or to any probe derived from SEQ ID NO 166 provided said probe hybridizes specifically to *M. fortuitum.*

The sequence as represented in SEQ ID NO 166 is new.

In still another specific embodiment, the invention provides for a method as described above to detect and identify one or more *Mycobacterium celatum* strains in a sample, wherein step (iii) comprises hybridizing to the following probe:

MCE-ICG-1: TGAGGGAGCCCGTGCCTGTA (SEQ ID NO 190)

or to equivalents of said probe,
and/or to any probe derived from SEQ ID NO 170 provided said probe hybridizes specifically to *M. celatum.*

The sequence as represented in SEQ ID NO 170 is new.

In still another specific embodiment, the invention provides for a method as described above to detect and identify one or more *Mycobacterium haemophilum* strains in a sample, wherein step (iii) comprises hybridizing to the following probe:

MHP-ICG-1: CATGTTGGGCTTGATCGGGTGC (SEQ ID NO 191)

or to equivalents of said probe,
and/or to any probe derived from SEQ ID NO 171, 172 or 173 provided said probe hybridizes specifically to *M. haemophilum.*

The sequences as represented in SEQ ID NO 171 to 173 are new.

In still another specific embodiment, the invention provides for a method as described above to detect and identify one or more *Mycobacterium malmoense* strains in a sample, wherein step (iii) comprises hybridizing to at least one of the following probes:

MML-ICG-1: CGGATCGATTGAGTGCTTGTCCC (SEQ ID NO 188)

MML-ICG-2: TCTAAATGAACGCACTGCCGATGG (SEQ ID NO 189)

or to equivalents of said probes,
and/or to any probe derived from SEQ ID NO 107 provided said probe hybridizes specifically to *M. malmoense.*

The sequence as represented in SEQ ID NO 107 is new.

In still another specific embodiment, the invention provides for a method as described above to detect and identify one or more *Mycobacterium* strains in a sample, wherein step (iii) comprises hybridizing to at least are of the following probes:

MYC-ICG-1: ACTGGATAGTGGTTGCGAGCATCTA (SEQ ID NO 1)

MYC-ICG-22: CTTCTGAATAGTGGTTGCGAGCATCT (SEQ ID NO 2)

or to equivalents of said probes.

According to a preferred embodiment, both probes are used in combination.

The invention also provides for a method as described above to detect and identify one or more *Mycoplasma* strains in a sample, wherein step (iii) comprises hybridizing to at least one of the following probes:

MPN-ICG 1: ATCGGTGGTAAATTAAACCCAAATCCCTGT (SEQ ID NO 49)

MPN-ICG 2: CAGTTCTGAAAGAACATTTCCGCTTCTTTC (SEQ ID NO 50)

MGE-ICG 1: CACCCATTAATTTTTTCGGTGTTAAAACCC (SEQ ID NO 51)

*Mycoplasma*-ICG: CAAAACTGAAAACGACAATCTTTCTAGTTCC (SEQ ID NO 52)

or to equivalents of said probes, and/or to any probe derived from SEQ ID NO 124 or 125 provided said probe hybridizes specifically with *Mycoplasma* species.

Preferentially, at least two, three or four of said probes are used simultaneously.

More particularly, the invention provides for a method as described above to detect and identify one or more *Mycoplasma pneumoniae* strains in a sample, wherein step (iii) comprises hybridizing to at least one of the following probes:

MPN-ICG 1: ATCGGTGGTAAATTAAACCCAAATCCCTGT (SEQ ID NO 49)

MPN-ICG 2: CAGTTCTGAAAGAACATTTCCGCTTCTTTC (SEQ ID NO 50)

or to equivalents of said probes, and/or to any probe derived from SEQ ID NO 125 provided said probe hybridizes specifically to *Mycoplasma pneumoniae*. According to a preferred embodiment, both these probes are used in combination.

The sequence as represented in SEQ ID NO 125 is new.

In another particular embodiment, the invention provides for a method as described above to detect and identify one or more *Mycoplasma genitalium* strains in a sample, wherein step (iii) comprises hybridizing to the following probe:

MGE-ICG 1: CACCCATTAATTTTTTCGGTGTTAAAACCC (SEQ ID NO 51)

or to equivalents of said probes, and/or to any probe derived from SEQ ID NO 124 provided said probe hybridizes specifically to *Mycoplasma genitalium*.

The sequence as represented in SEQ ID NO 124 is new.

The invention also provides for a method as described above to detect and identify one or more *Pseudomonas* strains in a sample, wherein step (iii) comprises hybridizing to at least one of the following probes:

PA-ICG 1: TGGTGTGCTGCGTGATCCGAT (SEQ ID NO 34)

PA-ICG 2: TGAATGTTCGTGGATGAACATTGATT (SEQ ID NO 35)

PA-ICG 3: CACTGGTGATCATTCAAGTCAAG (SEQ ID NO 36)

PA-ICG 4: TGAATGTTCGT(G/A)(G/A)ATGAACATTGATTTCTGGTC (SEQ ID NO 37)

PA-ICG 5: CTCTTTCACTGGTGATCATTCAAGTCAAG (SEQ ID NO 38)

or to equivalent of said probes, and/or to any probe derived from SEQ ID NO 111, 112, 113, 114 or 115 provided said probe hybridizes specifically to *Pseudomonas* strains.

The sequences as represented in SEQ ID NO 111 to 115 are new.

Preferentially, at least two, three or four of said probes are used simultaneously.

More particularly, the invention provides for a method as described above to detect and identify one or more *Pseudomonas aeruginosa* strains in a sample, wherein step (iii) comprises hybridizing to at least one of the following probes:

PA-ICG 1: TGGTGTGCTGCGTGATCCGAT (SEQ ID NO 34)

PA-ICG 2: TGAATGTTCGTGGATGAACATTGATT (SEQ ID NO 35)

PA-ICG 3: CACTGGTGATCATTCAAGTCAAG (SEQ ID NO 36)

PA-ICG 4: TGAATGTTCGT(G/A)(G/A)ATGAACATTGATTTCTGGTC (SEQ ID NO 37)

PA-ICG 5: CTCTTFCACTGGTGATCATTCAAGTCAAG (SEQ ID NO 38)

and most preferably to at least one of the following probes:

PA-ICG 1: TGGTGTGCTGCGTGATCCGAT (SEQ ID NO 34)

PA-ICG 4: TGAATGTTCGT(G/A)(G/A)ATGAACATTGATTTCTGGTC (SEQ ID NO 37)

PA-ICG 5: CTCTTTCACTGGTGATCATTCAAGTCAAG (SEQ ID NO 38)

or to equivalents of said probes, and/or to any probe derived from SEQ ID NO 111 provided said probe hybridizes specifically to *Pseudomonas aeruginosa*.

The sequence as represented in SEQ ID NO 111 is new.

Preferentially, at least two, three, four or five of said probes are used simultaneously.

The invention also provides for a method as described above to detect and identify one or more *Staphylococcus* species in a sample, wherein step (iii) comprises hybridizing to at least one of the following probes:

STAU-ICG 1: TACCAAGCAAAACCGAGTGAATAAAGAGTT (SEQ ID NO 53)

STAU-ICG 2: CAGAAGATGCGGAATAACGTGAC (SEQ ID NO 54)

STAU-ICG 3: AACGAAGCCGTATGTGAGCATTTGAC (SEQ ID NO 55)

STAU-ICG 4: GAACGTAACTTCATGTTAACGTTTGACTTAT (SEQ ID NO 56)

or to equivalents of said probes, and/or to any probe derived from SEQ ID NO 139, 140, 141, 142, 143 or 144 provided said probe hybridizes specifically to *Staphylococcus* species.

The sequences as represented in SEQ ID NO 139 to 144 are new.

Preferentially, at least two, three or four of said probes are used simultaneously.

More particularly, the invention provides for a method as described above to detect and identify one or more *Staphy-

*lococcus aureus* strains in a sample, wherein step (iii) comprises hybridizing to at least one, and preferably both of the following probes:

STAU-ICG 3: AACGAAGCCGTATGTGAG-CATTTGAC (SEQ ID NO 55)

STAU-ICG 4: GAACGTAACTCATGT-TAACGTTTGACTTAT (SEQ ID NO 56)

or to equivalents of said probes, and/or to any probe derived from SEQ ID NO 139, 140, 141, 142 or 143 provided said probe hybridizes specifically to *Staphylococcus aureus*. According to a preferred embodiment, both these probes are used in combination.

In another specific embodiment the invention provides for a method as described above to detect and identify one or more *Staphylococcus epidermidis* strains in a sample, wherein step (iii) comprises hybridizing to any probe derived from SEQ ID NO 144 as long as this probe can be caused to hybridize specifically to *Staphylococcus epidermidis*.

The invention also provides for a method as described above to detect and identify one or more Acinerobacter strains in a sample, wherein step (iii) comprises hybridizing to at least one of the following probes:

ACI-ICG 1: GCTTAAGTGCACAGT-GCTCTAAACTGA (SEQ ID NO 57)

ACI-ICG 2: CACGGTAATTAGTGTGATCTGAC-GAAG (SEQ ID NO 58)

or to equivalents of said probes, and/or to any probe derived from SEQ ID NO 126, 127, 128, 129 or 130 provided said probe hybridizes specifically to *Acinetobacter* spp. According to a preferred embodiment, both these probes are used in combination.

The sequences as represented in SEQ ID NO 126 to 130 are new.

More particularly, the invention provides for a method as described above to detect and identify one or more *Acinetobacter baumanii* strains in a sample, wherein step (iii) comprises hybridizing to at least one of the following probes:

ACI-ICG 1: GCTTAAGTGCACAGT-GCTCTAAACTGA (SEQ ID NO 57)

ACI-ICG 2: CACGGTAATTAGTGTGATCTGAC-GAAG (SEQ ID NO 58)

or to equivalents of said probes, and/or to any probe derived from SEQ ID NO 126 provided said probe hybridizes specifically to *Acinetobacter baumanii*. According to a preferred embodiment, both these probes are used in combination.

The invention also provides for a method as described above, to detect and identify one or more *Listeria* strains in a sample, wherein step (iii) comprises hybridizing to at least one of the following probes:

LIS-MG 1: CTTTGTAACCGAGAATCATCTGAAAGT-GAATC (SEQ ID NO 39)

LMO-ICG 1: AAACAACCTTTACTTCGTAGAAG-TAAATTGGTTAAG (SEQ ID NO 40)

LMO-ICG 2: TGAGAGGTTAGTACTTCTCAGTAT-GTTTGTTC (SEQ ID NO 41)

LMO-ICG 3: AGGCACTATGCTTGAAGCATCGC (SEQ ID NO 42)

LIV-ICG 1: GTTAGCATAAATAGGTAACTATTTAT-GACACAAGTAAC (SEQ ID NO 43)

LSE-ICG 1: AGTTAGCATAAGTAGTGTAACTATT-TATGACACAAG

LISP-ICG 1: CGTTTTCATAAGCGATCGCACGTT (SEQ ID NO 212)

and most preferably to at least one of the following probes:

LIS-ICG 1: CAAGTAACCGAGAATCATCTGAAAGT-GAATC (SEQ ID NO 39)

LMO-ICG 3: AGGCACTATGCTTGAAGCATCGC (SEQ ID NO 42)

LISP-ICG 1: CGTTTTCATAAGCGATCGCACGTT (SEQ ID NO 212)

or to equivalents of said probes, and/or to any probe derived from SEQ ID NO 116, 118, 119, 120, 121, 213, 214 or 215 provided said probe hybridizes specifically to *Listeria* species.

As described in the examples section, *Listeria* species encompass *Listeria* species sensu strictu, and a group of closely related organisms referred to as "*Listeria*-Like organisms". The latter group can be specifically recognized by probe LISP-ICG 1.

The sequences as represented in SEQ ID NO 116, 118 to 121 and 213 to 215 are new.

Preferentially, at least two, three, four, five or six of said probes are used simultaneously.

More particularly, the invention provides for a method as described above, to detect and identity one or more *Listeria monocytogenes* strains in a sample, wherein step (iii) comprises hybridizing to at least one of the following probes:

LMO-ICG 1: AAACAACCTTTACTTCGTAGAAG-TAAATTGGTTAAG (SEQ ID NO 40)

LMO-ICG 2: TGAGAGGTTAGTACTCTCAGTAT-GTTTGTTC (SEQ ID NO 41)

LMO-ICG 3: AGGCACTATGCTTGAAGCATCGC (SEQ ID NO 42)

and most preferably to the following probe:

LMO-ICG 3: AGGCACTATGCTTGAAGCATCGC (SEQ ID NO 42)

or to equivalents of said probes, and/or to any probe derived from SEQ ID NO 120 provided said probe hybridizes specifically to *Listeria monocytogenes*.

Preferentially, at least two, or three of said probes are used simultaneously.

The invention also provides for a method as described above to detect and identify one or more *Brucella*, strains in a sample, wherein step (iii) comprises hybridizing to at least one of the following probes:

BRU-ICG 1: CGTGCCGCCTTCGTTTCTCTTT (SEQ ID NO 59)

BRU-ICG 2: TTCGCTTCGGGGTGGATCTGTG (SEQ ID NO 60)

BRU-ICG 3: GCGTAGTAGCGTTTGCGTCGG (SEQ ID NO 193)

BRU-ICG 4: CGCAAGAAGCTTGCTCAAGCC (SEQ ID NO 194)

and most preferably to at least one of the following probes:

BRU-ICG 2: TTCGCTTCGGGGTGGATCTGTG (SEQ ID NO 60)

BRU-ICG 3: GCGTAGTAGCGTTTGCGTCGG (SEQ ID NO 193)

BRU-ICG 4: CGCAAGAAGCTTGCTCAAGCC (SEQ ID NO 194)

or to equivalents of said probes, and/or to any probe derived from SEQ ID NO 131, 132 or 154 provided said probe hybridizes specifically to *Brucella* strains.

The sequences as represented in SEQ ID NO 131, 132 and 154 are stew.

The invention also provides for a method as described above to detect and identity one or more *Salmonella* strains in a sample, wherein step (iii) comprises hybridizing to at least one of the following probes:

SALM-ICG 1: CAAAACTGACTTACGAGT-CACGTTTGAG (SEQ ID NO 61)

SALM-ICG 2: GATGTATGCTTCGTTATTCCACGCC (SEQ ID NO 62)

STY-ICG 1: GGTCAAACCTCCAGGGACGCC (SEQ ID NO 63)

SED-ICG 1: GCGGTAATGTGTGAAAGCGTTGCC (SEQ ID NO 64)

and most preferably to the following probe:

SALM-ICG 1: CAAAACTGACTTACGAGT-CACGTTTGAG (SEQ ID NO 61)

or to equivalents of said probes, and/or to any probe derived from SEQ ID NO 133, 134, 135, 136, 137 or 138 provided said probe hybridizes specifically to *Salmonella* strains.

The sequences as represented in SEQ ID NO 133 to 138 are new.

Preferentially, at least two, three, or four of said probes are used simultaneously.

The invention also relates to a method as described above to detect and identify one or more *Chlamydia* strains in a sample, wherein step (iii) comprises hybridizing to at least one of the following probes:

CHTR-ICG 1: GGAAGAAGCCTGAGAAGGTTTCT-GAC (SEQ ID NO 45)

CHTR-ICG 2: GCATTTATATGTAAGAGCAAGCAT-TCTATTTCA (SEQ ID NO 46)

CHTR-ICG 3: GAGTAGCGTGGTGAGGACGAGA (SEQ ID NO 47)

CHTR-ICG 4: GAGTAGCGCGGTGAGGACGAGA (SEQ ID NO 201)

CHPS-ICG 1: GGATAACTGTCTTAGGACG-GTTTGAC (SEQ ID NO 48)

or to equivalents of said probes, and/or to any probe derived from SEQ ID NO 122, 123 or 197 provided that said probe hybridizes specifically to *Chlamydia* strains.

Preferentially, at least two, three, four or five of said probes are used simultaneously.

More particularly, the invention relates to a method as described above to detect and identify one or more *Chlamydia trachomatis* strains in a sample, wherein step (iii) comprises hybridizing to at least one of the following probes:

CHTR-ICG 1: GGAAGAAGCCTGAGAAGGTTTCT-GAC (SEQ ID NO 45)

CHTR-ICG 2: GCATTTATATGTAAGAGCAAGCAT-TCTATTTCA (SEQ ID NO 46)

CHTR-ICG 3: GAGTAGCGTGGTGAGGACGAGA (SEQ ID NO 47)

CHTR-ICG 4: GAGTAGCGCGGTGAGCACGAGA (SEQ ID NO 201)

or to equivalents of said probes, and/or to any probe derived from SEQ ID NO 123 or 197 provided said probe hybridizes specifically to *Chlamydia trachomatis*.

The sequences as represented in SEQ ID NO 123 and 197 are new,

Preferentially, at least two, three or four of said probes are used simultaneously.

In another particular embodiment, the invention provides for a method as described above to detect and identify one or more *Chlamydia psittaci* strains in a sample, wherein step (iii) comprises hybridizing to at least the following probe:

CHPS-ICG 1: GGATAACTGTCTTAGGACG-GTTTGAC (SEQ ID NO 48)

or to equivalents of said probe, and/or to any probe derived from SEQ ID NO 122 provided said probe hybridizes specifically to *Chlamydia psittaci*.

The sequence of SEQ ID NO 122 is new,

The invention also provides for a method as described above, to detect one or more *Streptococcus* strains in a sample, wherein step (iii) comprises hybridizing to any probe derived from SEQ ID NO 145, 146, 147, 148, 149, 150, 151, 152 or 153 provided said probe hybridizes specifically to *Streptococcus* strains, or equivalents of these probes.

The sequences as represented in SEQ ID NO 145, 146, 147, 148, 149, 150, 151, 152 or 153 are new.

The invention also provides for a method as described above, to detect one or more *Yersinia enterocolitica* strains in a sample, wherein step (iii) comprises hybridizing to at least one of the following probes:

YEC-ICG 1: GGAAAAGGTACTGCACGTGACTG (SEQ ID NO 198)

YEC-ICG 2: GACAGCTGAAACTTATCCCTCCG (SEQ ID NO 199)

YEC-ICG 3: GCTACCTGTTGATGTAATGAGTCAC (SEQ ID NO 200)

or to equivalents of said probes, and/or to any probe derived from SEQ ID NO 195 or 196, provided said probe hybridize specifically to *Yersinia enterocolitica*.

The sequences as represented in SEQ ID NO 195 and 196 are new.

In some cases it may be advantageous to amplify not all organisms present in a sample, but only more specific taxa, which are considered to be relevant. In these cases the invention provides for primers allowing the specific amplification of the spacer region for only those beforehand defined taxa.

The invention thus provides for a method as described above to detect and identify specifically *Chlamydia trachomatis* is a sample, wherein step (ii) comprises amplification of the 16S–23S rRNA spacer region or a part of it, using at least one of the following primers:

CHTR-P1: AAGGTTTCTGACTAGGTTGGGC (SEQ ID NO 69)

CHTR-P2: GGTGAAGTGCTTGCATGGATCT (SEQ ID NO 70)

or equivalents of these primers, said equivalents differing in sequences from the above mentioned primers by changing one or more nucleotides, provided that said equivalents still amplify specifically the spacer region or part of it from *Chlamydia trachomatis*.

Preferably both primers are used.

The invention also provides for a method as described above to detect and identify specifically *Listeria* species in a sample, wherein step (ii) comprises amplification of the 16S–23S rRNA spacer region or a part of it, using at least one of the following primers:

LIS-P1: ACCTGTGAGTTTTCGTTCTTCTC (SEQ ID NO 71)

LIS-P2: CTATTTGTTCAGTTTTGAGAGGTT (SEQ ID NO 72)

LIS-P3: ATTTTCCGTATCAGCGATGATAC (SEQ ID NO 73)

LIS-P4: ACGAAGTAAAGGTTGTTTTPCT (SEQ ID NO 74)

LIS-P5: GAGAGGTTACTCTCTTTTATGTCAG (SEQ ID NO 75)

LIS-P6: CTTTTATGTCAGATAAAGTATGCAA (SEQ ID NO 202)

LIS-P7: CGTAAAAGGGTATGATTATTTG (SEQ ID NO 203)

or equivalents of these primers, said equivalents differing in sequence from the above mentioned primers by changing one or more nucleotides, provided that said equivalents still amplify specifically the spacer region or part of it from *Listeria* species.

The invention also relates to a method as described above to detect and identify specifically *Mycobacterium* species in a sample, wherein step (ii) comprises amplification of the 16S–23S rRNA spacer region or a part of it, using at least one of the following primers:

MYC-P1: TCCCTTGTGGCCTGTGTG (SEQ ID NO 65)

MYC-P2: TCCTTCATCGGCTCTCGA (SEQ ID NO 66)

MYC-P3: GATGCCAAGGCATCCACC (SEQ ID NO 67)

MYC-P4: CCTCCCACGTCCTTCATCG (SEQ ID NO 68)

MYC-P5: CCTGGGTTTGACATGCACAG (SEQ ID NO 192)

or equivalents of these primers, said equivalents differing in sequence from the above mentioned primers by changing one or more nucleotides, provided that said equivalents still amplify specifically the spar region or part of it from *Mycobacterium* species.

The invention also provides for a method as described above to detect and identify specifically *Brucella* species in a sample, wherein step (ii) comprises amplification of the 16S–23S rRNA spacer region or part of it, using at least one of the following primers:

BRU-P1: TCGAGAATTGGAAAGACGTC (SEQ ID NO 204)

BRU-P2: AAGAGGTCGGATTTATCCG (SEQ ID NO 205)

BRU-P3: TTCGACTCCAAATGCTCG (SEQ ID NO 206)

BRU-P4: TCTTAAAGCCGCATTATGC (SEQ ID NO 207)

or equivalents of these primers, said equivalents differing in sequence from the above-mentioned primers by changing one or more nucleotides, provided that said equivalents still amplify specifically the spacer region of part of it from *Brucella* species.

The invention also provides for a method as described above to detect and identify specifically *Yersinia enterocolitica* species in a sample, wherein step (ii) comprises amplification of the 16S–23S rRNA spacer region or part of it, using at least one of the following primers:

YEC-P1: CCTAATGATATTGATTCGCG (SEQ ID NO 208)

YEC-P2: ATGACAGGTTAATCCTTACCCC (SEQ ID NO 209)

or equivalents of these primers, said equivalents differing in sequence from the above-mentioned primers by changing one or more nucleotides, provided that said equivalents still amplify specifically the spacer region of part of it from *Yersinia enterocolitica* species.

The invention also provides for a composition comprising at least one of the probes and/or primers as defined above.

Said composition may comprise any carrier, support, label or diluent known in the art for probes or primers, more particularly any of the labels or supports detailed in the definitions section.

The invention relates more particularly to isolated probes and primers as defined above, more particularly any of the probes as specified in Table 1a or any of the primers as specified in Table 1b.

According to another embodiment, the present invention relates also to new spacer region sequences as defined above and as set out in FIGS. 1–103 (SEQ ID NO 76 to 154, SEQ ID NO 157 to 174, SEQ ID NO 195 to 197 and SEQ ID NO 213 to 215).

In another embodiment the invention provides for a reverse hybridization method comprising any of the probes as defined above, wherein said probes are immobilized on a known location on a solid support, more preferably on a membrane strip.

In yet another embodiment the invention provides for a kit for the detection and identification of at least one micro-organism, or the simultaneous detection and identification of several micro-organisms in a sample, comprising the following components:

(i) when appropriate, at least one suitable primer pair to allow amplification of the intercistronic 16S–23S rRNA spacer region, or a part of it;

(ii) at least one of the probes as defined above;

(iii) a buffer, or components necessary to produce the buffer, enabling a hybridization reaction between said probes and the polynucleic acids present in the sample, or the amplified products thereof;

(iv) a solution, or components necessary to produce the solution, enabling washing of the hybrids formed under the appropriate wash conditions;

(v) when appropriate, a means for detecting the hybrids resulting from the preceding hybridization.

BRIEF DESCRIPTION OF THE DRAWINGS

FIG. 1: represents the DNA sequence of the 16S–23S rRNA spacer region from *Mycobacterium tuberculosis* strain H37RV ATCC 27294 (SEQ ID NO 76)

FIG. 2: represents the DNA sequence of the 16S–23S rRNA spacer region from *Mycobacterium avium* ATCC 151.769 (ITG 4991) (SEQ ID NO 77)

FIG. 3: represents the DNA sequence of the 16S–23S rRNA spacer region from *Mycobacterium paratuberculosis* strains 316F and 2E (SEQ ID NO 78)

FIG. 4: represents the DNA sequence of the 16S–23S rRNA spacer region from *Mycobacterium* strain ITG 5513 (SEQ ID NO 79)

FIG. 5: represents the DNA sequence of the 16S–23S rRNA spacer region from *Mycobacterium* strain ITG 8695 (SEQ ID NO 80)

FIG. 6: represents the DNA sequence of the 16S–23S rRNA spacer region from *Mycobacterium* strain ITG 8708 (SEQ ID NO 81)

FIG. 7: represents the DNA sequence of the 16S–23S rRNA spacer region from *Mycobacterium* strain ITG 8715 (SEQ ID NO 82)

FIG. 8: represents the DNA sequence of the 16S–23S rRNA spacer region from *Mycobacterium* strain ITG 8054 (SEQ ID NO 83)

FIG. 9: represents the DNA sequence of the 16S–23S rRNA spacer region from *Mycobacterium* strain ITG 8/37 (SEQ ID NO 84)

FIG. 10: represents the DNA sequence of the 16S–23S rRNA spacer region from *Mycobacterium* strain ITG 8743 (SEQ ID NO 85)

FIG. 11: represents the DNA sequence of the 16S–23S rRNA spacer region from *Mycobacterium* strain ITG 8745 (SEQ ID NO 86)

FIG. 12: represents the DNA sequence of the 16S–23S rRNA spacer region from *Mycobacterium* strain ITG 8748 (SEQ ID NO 87)

FIG. 13: represents the DNA sequence of the 16S–23S rRNA spacer region from *Mycobacterium* strain ITG 8752 (SEQ ID NO 88)

FIG. 14: represents the DNA sequence of the 16S–23S rRNA spacer region from *Mycobacterium intracellulare* serovar ITG 5915 (SEQ ID NO 89)

FIG. 15: represents the DNA sequence of the 16S–23S rRNA spacer region from *Mycobacterium lufu* ITC 4755 (SEQ ID NO 90)

FIG. 16: represents the DNA sequence of the 16S–23S rRNA spacer region from *Mycobacterium* strain ITG 5922 (SEQ ID NO 91)

FIG. 17: represents the DNA sequence of the 16S–23S rRNA spacer region from *Mycobacterium* strain ITG 1329 (SEQ ID NO 92)

FIG. 18: represents the DNA sequence of the 16S–23S rRNA spacer region from *Mycobacterium* strain ITG 1812 (SEQ ID NO 93)

FIG. 19: represents the DNA sequence of the 16S–23S rRNA spacer region from *Mycobacterium* strain ITG 5280 (SEQ ID NO 94)

FIG. 20: represents the DNA sequence of the 16S–23S rRNA spacer region from *Mycobacterium* strain ITG 5620 (SEQ ID NO 95)

FIG. 21: represents the DNA sequence of the 16S–23S rRNA spacer region from *Mycobacterium* strain ITG 5165 (SEQ ID NO 96)

FIG. 22: represents the DNA sequence of the 16S–23S rRNA spacer region from *Mycobacterium* ITG 7395 (SEQ ID NO 97)

FIG. 23: represents the DNA sequence of the 16S–23S rRNA spacer region from *Mycobacterium* ITG 8738 (SEQ ID NO 98)

FIG. 24: represents the DNA sequence of the 16S–23S rRNA spacer region from *Mycobacterium* ITG 926 (SEQ ID NO 99)

FIG. 25: represents the DNA sequence of the 16S–23S spacer region from *Mycobacterium scrofulaceum* ITG 4988 (SEQ ID NO 100)

FIG. 26: represents the DNA sequence of the 16S–23S spacer region from *Mycobacterium kansasii* ATCC 22478 (=ITG 4987) (SEQ ID NO 101)

FIG. 27: represents the DNA sequence of the 16S–23S spacer region from *Mycobacterium chelonae abcessus* ITG 4975 (SEQ ID NO 102)

FIG. 28: represents the DNA sequence of the 16S–23S spacer region from *Mycobacterium chelonae chelonae* ITG 9855 (SEQ ID NO 103)

FIG. 29: represents the DNA sequence of the 16S–23S spacer region from *Mycobacterium gordonae* ITG 7703 (SEQ ID NO 104)

FIG. 30: represents the DNA sequence of the 16S–23S spacer region from *Mycobacterium gordonae* ITG 7836 (SEQ ID NO 105)

FIG. 31: represents the DNA sequence of the 16S–23S spacer region from *Mycobacterium gordonae* ITG 8059 (SEQ ID NO 106)

FIG. 32: represents the DNA sequence of the 16S–23S spacer region from *Mycobacterium malmoense* ITG 4842 and ITG 4832 (SEQ ID NO 107)

FIG. 33: represents the DNA sequence of the 16S–23S spacer region from *Mycobacterium* strain 8757 (SEQ ID NO 108)

FIG. 34: represents the DNA sequence of the 16S–23S spacer region from *Mycobacterium* ITG 8723 (SEQ ID NO 109)

FIG. 35: represents the DNA sequence of the 16S–23S spacer region from *Mycobacterium* ITG 8724 (SEQ ID NO 110)

FIG. 36: represents the DNA sequence of the 16S–23S spacer region from *Pseudomonas aeruginosa* UZG 5669 (SEQ ID NO 111)

FIG. 37: represents the DNA sequence of the 16S–23S spacer region from *Pseudomonas pseudoalcaligenes* LMG 1225 (SEQ ID NO 111)

FIG. 38: represents the DNA sequence of the 16S–23S spacer region from *Pseudomonas stutzeri* LMG 2333 (SEQ ID NO 113)

FIG. 39: represents the DNA sequence of the 16S–23S spacer region from *Pseudomonas alcaligenes* LMG 1224 (SEQ ID NO 114)

FIG. 40: represents the DNA sequence of the 16S–23S spacer region from *Pseudomonas putida* LMG 2232 (SEQ ID NO 115)

FIG. 41: represents the DNA sequence of the small 16S–23S spacer region from *Listeria ivanovii* CIP 782 (SEQ ID NO 116)

FIG. 42: represents the DNA sequence of the small 16S–23S spacer region from *Listeria monocytogenes* (SEQ ID NO 117)

FIG. 43: represents the DNA sequence of the small 16S–23S spacer region from *Listeria seeligeri* serovar 4A nr. 4268 (SEQ ID NO 118)

FIG. 44: represents the partial DNA sequence of the large 16S–23S spacer region from partial sequence of the long spacer region of *Listeria ivanovii* CIP 7842 (SEQ ID NO 119)

FIG. 45: represents the DNA sequence of the large 16S–23S spacer region from *Listeria monocytogenes* IHE serovar 4B (SEQ ID NO 120)

FIG. 46: represents the DNA sequence of the large 16S–23S spacer region from *Listeria seeligeri* serovar 4A nr. 4268 (SEQ ID NO 121)

FIG. 47: represents the DNA sequence of the 16S–23S spacer region from *Chlamydia psittaci* 6BC (SEQ ID NO 122)

FIG. 48: represents the DNA sequence of the 16S–23S spacer region from *Chlamydia trachomatis* (SEQ ID NO 123)

FIG. 49: represents the DNA sequence of the 16S–23S spacer region from *Mycoplasma gentalium* (U. Gobel) (SEQ ID NO 124)

FIG. 50: represents the DNA sequence of the 16S–23S spacer region from *Mycoplasma pneumoniae* ATCC 29432 (SEQ ID NO 125)

FIG. 51: represents the DNA sequence of the 16S–23S spacer region from *Acinetobacter baumanii* LMG 1041 (SEQ ID NO 126)

FIG. 52: represents the DNA sequence of the 16S–23S spacer region from *Acinetobacter calcoaceticus* LMG 1046 (SEQ ID NO 127)

FIG. 53: represents the DNA sequence of the 16S–23S spacer region from *Acinetobacter haemolyticus* LMG 996 (SEQ ID NO 128)

FIG. 54: represents the DNA sequence of the 16S–23S spacer region from *Acinetobacter johnsonii* LMG 999 (SEQ ID N4O 129)

FIG. 55: represents the DNA sequence of the 16S–23S spacer region from *Acinetobacter junii* LMG 998 (SEQ ID NO 130)

FIG. 56: represents the DNA sequence of the 16S–23S spacer region from *Brucella melitensis* NIDO Biovar 1 (SEQ ID NO 131)

FIG. 57: represents the DNA sequence of the 16S–23S spacer region from *Brucella suis* NIDO Biovar 1 (SEQ ID NO 132)

FIG. 58: represents the DNA sequence of one of the 16S–23S spacer region from *Salmonella dublin* (SEQ ID NO 133)

FIG. 59: represents the DNA sequence of one of the 16S–23S spacer region from *Salmonella dublin* (SEQ ID NO 134)

FIG. 60: represents the DNA sequence of one of the 16S–23S spacer region from *Salmonella enteritidis* (SEQ ID NO 135)

FIG. 61: represents the DNA sequence of one of the 16S–23S spacer region from *Salmonella enteritidis* (SEQ ID NO 136)

FIG. 62: represents the DNA sequence of one of the 16S–123 spacer region from *Salmonella typhimurium* (SEQ ID NO 137)

FIG. 63: represents the DNA sequence of one of the 16S–23S spacer region from *Salmonella typhimurium* (SEQ ID NO 138)

FIG. 64: represents the DNA sequence of one of the 16S–23S spacer region from *Staphylococcus aureus* strain UZG 5M8 (SEQ ID NO 139)

FIG. 65: represents the DNA sequence of one of the 16S–23S spacer region from *Staphylococcus aureus* strain UZG 6289 (SEQ ID NO 140)

FIG. 66: represents the DNA sequence of one of the 16S–23S spacer region from *Staphylococcus aureus* strain UZG 6289 (SEQ ID NO 141)

FIG. 67: represents the DNA sequence of one of the 16S–23S spacer region from *Staphylococcus aureus* strain UZG 6289 (SEQ ID NO 142)

FIG. 68: represents the DNA sequence of one of the 16S–23S spacer region from *Staphylococcus aureus* strain UZG 6289 (SEQ ID NO 143)

FIG. 69: represents the DNA sequence of one of the 16S–23S spacer region from *Staphylococcus epidermidis* strain UZG CNS41 (SEQ ID NO 144)

FIG. 70: represents the DNA sequence of the 16S–23S spacer region from *Streptococcus mitis* UZG 2465 (SEQ ID NO 145)

FIG. 71: represents the DNA sequence of the 16S–23S spacer region from *Streptococcus pyogenes* UZG 3671 (SEQ ID NO 146)

FIG. 72: represents the DNA sequence of the 16S–23S spacer region from *Streptococcus sanguis* UZG 1042 (SEQ ID NO 14,)

FIG. 73: represents the DNA sequence of the 16S–23S spacer region from *Staphylococcus saprophyticus* UZG CNS46 (SEQ ID NO 148).

FIG. 74: represents the DNA sequence of the 16S–23S spacer region from *Streptococcus* species UZG 536 (84) (SEQ ID NO 14l9)

FIG. 75: represents the DNA sequence of the 16S–23S spacer region from *Streptococcus* species UZG 4341 (SEQ ID NO 150)

FIG. 76: represents the DNA sequence of the 16S–23S spacer region from *Streptococcus* species UZG 457 (44B) (SEQ ID NO 151)

FIG. 77: represents the DNA sequence of the 16S–23S spacer region from *Streptococcus* species UZG 97A (SEQ ID NO 152)

FIG. 78: represents the DNA sequence of the 16S–23S spacer region from *Streptococcus* species UZG 483 (76) (SEQ ID NO 153)

FIG. 79: represents the DNA sequence of the 16S–23S spacer region from *Brucella abortus* NIDO Tulya biovar 3 (SEQ ID NO t54)

FIG. 80 represent the DNA sequence of the 16S–3S spacer region from *Mycobacterium ulcerans* ITG 1837 and *Mycobacterium marinum* ITG 7732 (SEQ ID NO 157)

FIG. 81: represents the DNA sequence of the 16S–23S spacer region from *Mycobacterium genavense* ITG 8777 (SEQ ID NO 158)

FIG. 82: represents the DNA sequence of the 16S–23S spacer region from *Mycobacterium genavense* ITG 92–742 (SEQ ID NO 159)

FIG. 83: represents the DNA sequence of the 16S–23S spacer region from *Mycobacterium genavense* ITG 9500 (SEQ ID NO 160)

FIG. 84: represents the DNA sequence of the 16S–23S spacer region from *Mycobacterium simiae*-like ITG 7379 (SEQ ID NO 161)

FIG. 85: represents the DNA sequence of the 16S–23S spacer region from *Mycobacterium simiae*-like ITG 9745 (SEQ ID NO 162)

FIG. 86: represents the DNA sequence of the 16S–23S spacer region from *Mycobacterium xenopi* ITG 4986 (SEQ ID NO 163)

FIG. 87: represents the DNA sequence of the 16S–23S spacer region from *Mycobacterium simiae* A ITG 4485 (SEQ ID NO 164)

FIG. 88: represents the DNA sequence of the 16S–23S spacer region from *Mycobacterium simiae* B ITG 4484 (SEQ ID NO 165)

FIG. 89: represents the DNA sequence of the 16S–23S spacer region from *Mycobacterium fortuitum* ITG 4304 (SEQ ID NO 166)

FIG. 90: represents the DNA sequence of the 16S–23S spacer region from *Mycobacterium kansasii* ITG 6323 (SEQ ID NO 167)

FIG. 91: represents the DNA sequence of the 16S–23S spacer region from *Mycobacterium kansasii* ITG 8698 (SEQ ID NO 168)

FIG. 92: represents the DNA sequence of the 16S–23S spacer region from *Mycobacterium kansasii* ITG 8973 (SEQ ID NO 169)

FIG. 93: represents the DNA sequence of the 16S–23S spacer region from *Mycobacterium celatum* ITG 94-123 (SEQ ID NO 170)

FIG. 94: represents the DNA sequence of the 16S–23S spacer region from *Mycobacterium haemophilum* ITG 776 (SEQ ID NO 171)

FIG. 95: represents the DNA sequence of the 16S–23S spacer region from *Mycobacterium haemophilum* ITG 778 (SEQ ID NO 172)

FIG. 96: represents the DNA sequence of the 16S–23S spacer region from *Mycobacterium haemophilum* ITG 3071 (SEQ ID NO 173)

FIG. 97: represents the DNA sequence of the 16S–23S spacer region from *Mycobacterium chelonae* ITG 94-330 and ITG 94-379 (SEQ ID NO 174)

FIG. 98: represents the DNA sequence of a L6S–23S spacer region from *Yersinia enterocalitica* strain P95 (SEQ ID NO 195)

FIG. 99: represents the DNA sequence of a 16S–23S spacer region from *Yersinia enterocolitica* strain P95 (SEQ ID NO 196)

FIG. 100: represents the DNA sequence of a 16S–23S spacer region from *Chlamydia trachomatis* SSDZ 94 M 1961 (SEQ ID NO 197)

FIG. 101: represents the DNA sequence of a 16S–23S spacer region from *Listeria*-like isolate MB 405 (SEQ ID NO 213)

FIG. 102: represents the DNA sequence of a 16S–23S spacer region from *Listeria*-like isolate MB 405 (SEQ ID NO 214)

FIG. 103: represents the DNA sequence of a 16S–23S spacer region from *Listeria*-like isolate MB 405 (SEQ ID NO 215)

TABLE LEGENDS

Table 1a: List of all new probes originating from the 16S–23S rRNA spacer region.

Table 1b: List of possible primers to be used for taxon-specific amplification of the spacer region or part of it.

Table 2: Hybridization results for *Pseudomonas*

Table 3: Different probe patterns obtained for mycobacterial strain-types

Table 4: Mycobacteria strains tested in LiPA

Table 5: Hybridization results for *Listeria* (Probes LMO1, 2, LSE1, LIV1, LIS1)

Table 6: Hybridization results for *Listeria* (Probes LMO3, LIS1)

Table 7: Hybridization results for *Chlamydia*

Table 8: New mycobacterial probes and hybridization results

Table 9: Hybridization results for *Brucella*

Table 10: Hybridization results for *Staphylococcus*

TABLE 1A

| PROBE | SEQUENCE | SEQ ID NO |
|---|---|---|
| MYC-ICG-1 | ACTGGATAGTGGTTGCGAGCATCTA | 1 |
| MYC-ICG-22 | CTTCTGAATAGTGGTTGCGAGCATCT | 2 |
| MTB-ICG-1 | GGGTGCATGACAACAAAGTTGGCCA | 3 |
| MTB-ICG-2 | GACTTGTTCCAGGTGTTGTCCCAC | 4 |
| MTB-ICG-3 | CGGCTAGCGGTGGCGTGTTCT | 5 |
| MAI-ICG-1 | CAACAGCAAATGATTGCCAGACACAC | 6 |
| MIL-ICG-11 | GAGGGGTTCCCGTCTGTAGTG | 7 |
| MIL-ICG-22 | TGAGGGGTTCTCGTCTGTAGTG | 8 |
| MAC-ICG-1 | CACTCGGTCGATCCGTGTGGA | 9 |
| MAV-ICG-1 | TCGGTCCGTCCGTGTGGAGTC | 10 |
| MAV-ICG-22 | GTGGCCGGCGTTCATCGAAA | 11 |
| MIN-ICG-1 | GCATAGTCCTTAGGGCTGATGCGTT | 12 |
| MIN-ICG-2 | GCTGATGCGTTCGTCGAAATGTGTA | 13 |
| MIN-ICG-22 | CTGATGCGTTCGTCGAAATGTGT | 14 |
| MIN-ICG-222 | TGATGCGTTCGTCGAAATGTGT | 15 |
| MIN-ICG-2222 | GGCTGATGCGTTCGTCGAAATGTGTAA | 16 |
| MAL-ICG-1 | ACTAGATGAACGCGTAGTCCTTGT | 17 |
| MHEF-ICG-1 | TGGACGAAAACCGGGTGCACAA | 18 |
| MAH-ICG-1 | GTGTAATTTCTTTTTTAACTCTTGTGTGTAAGTAAGTG | 19 |
| MCO-ICG-11 | TGGCCGGCGTGTTCATCGAAA | 20 |
| MTH-ICG-11 | GCACTTCAATTGGTGAAGTGCGAGCC | 21 |
| MTH-ICG-2 | GCGTGGTCTTCATGGCCGG | 22 |
| MEF-ICC-11 | ACGCGTGGTCCTTCGTGG | 23 |
| MSC-ICG-1 | TCGGCTCGTTCTGAGTGGTGTC | 24 |
| MKA-ICG-1 | GATGCGTTTGCTACGGGTAGCGT | 25 |
| MKA-ICG-2 | GATGCGTTGCCTACGGGTAGCGT | 26 |
| MKA-ICG-3 | ATGCGTTGCCCTACGGGTAGCGT | 27 |
| MKA-ICG-4 | CGGGCTCTGAGAGTTGTC | 28 |
| MCH-ICG-1 | GGTGTGGACTTTGACTTCTGAATAG | 29 |
| MCH-ICG-2 | CGGCAAAACGTCGGACTGTCA | 30 |
| MCH-ICG-3 | GGTGTGGTCCTTGACTTATGGATAG | 210 |
| MGO-ICG-1 | AACACCCTCGGGTGCTGTCC | 31 |
| MGO-ICG-2 | GTATGCGTTGTCGTTCGCGGC | 32 |
| MGO-ICG-5 | CGTGAGGGGTCATCGTCTGTAG | 33 |
| MUL-ICG-1 | GGTTTCGGGATGTTGTCCCACC | 175 |
| MGV-ICG-1 | CGACTGAGGTCGACGTGGTGT | 176 |
| MGV-ICG-2 | GGTGTTTGAGCATTGAATAGTGGTTGC | 177 |
| MGV-ICG-3 | TCGGGCCGCGTGTTCGTCAAA | 211 |
| MXE-ICG-1 | GTTGGGCAGCAGGCAGTAACC | 178 |
| MSI-ICG-1 | CCGGCAACGGTTACGTGTTC | 179 |
| MFO-ICG-1 | TCGTTGGATGGCCTCGCACCT | 180 |
| MFO-ICG-2 | ACTTGGCGTGGGATGCGGGAA | 181 |
| MKA-ICG-5 | CCCTCAGGGATTTTCTGGGTGTTG | 182 |
| MKA-ICG-6 | GGACTCGTCCAAGAGTGTTGTCC | 183 |

TABLE 1A-continued

| PROBE | SEQUENCE | SEQ ID NO |
|---|---|---|
| MKA-ICG-7 | TCGGGCTTGGCCAGAGCTGTT | 184 |
| MKA-ICG-8 | GGGTGCGCAACAGCAAGCGA | 185 |
| MKA-ICG-9 | GATGCGTTGCCCCTACGGG | 186 |
| MKA-ICG-10 | CCCTACGGGTAGCGTGTTCTTTTG | 187 |
| MML-ICG-1 | CGGATCGATTGAGTGCTTGTCCC | 188 |
| MML-ICG-2 | TCTAAATGAACGCACTGCCGATGG | 189 |
| MCE-ICG-1 | TGAGGGAGCCCGTGCCTGTA | 190 |
| MHP-ICG-1 | CATGTTGGGCTTGATCGGGTGC | 191 |
| PA-ICG 1 | TGGTGTGCTGCGTGATCCGAT | 34 |
| PA-ICG 2 | TGAATGTTCGTGGATGAACATTGATT | 35 |
| PA-ICG 3 | CACTGGTGATCATTCAAGTCAAG | 36 |
| PA-ICG 4 | TGAATGTTCGT(G/A)(G/A)ATGAACATTGATTTCTGGTC | 37 |
| PA-ICG 5 | CTCTTTCACTGGTGATCATTCAAGTCAAG | 38 |
| LIS-ICG 1 | CAAGTAACCGAGAATCATCTGAAAGTGAATC | 39 |
| LMO-ICG 1 | AAACAACCTTTACTTCGTAGAAGTAAATTGGTTAAG | 40 |
| LMO-ICG 2 | TGAGAGGTTAGTACTTCTCAGTATGTTTGTTC | 41 |
| LMO-ICG 3 | AGGCACTATGCTTGAAGCATCGC | 42 |
| LIV-ICG 1 | GTTAGCATAAATAGGTAACTATTTATGACACAAGTAAC | 43 |
| LSE-ICG 1 | AGTTAGCATAAGTAGTGTAACTATTTATGACACAAG | 44 |
| LISP-ICG 1 | CGTTTTCATAAGCGATCGCACGTT | 212 |
| CHTR-ICG 1 | GGAAGAAGCCTGAGAAGGTTTCTGAC | 45 |
| CHTR-ICG 2 | CGATTTATATGTAAGAGCAAGCATTCTATTTCA | 46 |
| CHTR-ICG 3 | GAGTAGCGTGGTGAGGACGACA | 47 |
| CHPS-ICG 1 | GGATAACTGTCTTAGGACGGTTTGAC | 48 |
| MPN-ICG 1 | ATCGGTGGTAAATTAAACCCAAATCCCTGT | 49 |
| MPN-ICG 2 | CAGTTCTGAAAGAACATTTCCGCTTCTTTC | 50 |
| MGE-ICG 1 | CACCCATTAATTTTTTCGGTGTTAAAACCC | 51 |
| Mycoplasma-ICG | CAAAACTGAAAACGACAATCTTTCTAGTTCC | 52 |
| STAU-ICG 1 | TACCAAGCAAAACCGAGTGAATAAAGAGTT | 53 |
| STAU-ICG 2 | CAGAAGATGCGGAATAACGTGAC | 54 |
| STAU-ICG 3 | AACGAAGCCGTATGTGAGCATTTGAC | 55 |
| STAU-ICG 4 | GAACGTAACTTCATGTTAACGTTTGACTTAT | 56 |
| ACI-ICG 1 | GCTTAAGTGCACAGTGCTCTAAACTGA | 57 |
| ACI-ICG 2 | CACGGTAATTAGTGTGATCTGACGAAG | 58 |
| BRU-ICG 1 | CGTGCCGCCTTCGFTTTCTTT | 59 |
| BRU-ICG 2 | TTCGCTTCGGGGTGGATCTGTG | 60 |
| BRU-ICG 3 | GCGTAGTAGCGTTTGCGTCGG | 193 |
| BRU-ICG 4 | CGCAAGAAGCTTGCTCAAGCC | 194 |
| SALM-ICG 1 | CAAAACTGACTTACGAGTCACGTTTGAG | 61 |
| SALM-ICG 2 | GATGTATGCTTCGTTATTCCACGCC | 62 |
| STY-ICG 1 | GGTCAAACCTCCAGGGACGCC | 63 |
| SED-ICG 1 | GCGGTAATGTGTGAAAGCGTTGCC | 64 |
| YEC-ICG 1 | GGAAAAGGTACTGCACGTGACTG | 198 |
| YEC-ICG 2 | GACAGCTCAAACTTATCCCTCCG | 199 |
| YEC-ICG 3 | GCTACCTGTTGATGTAATGAGTCAC | 200 |
| CHTR-ICG 4 | GAGTAGCGCGGTGAGGACGAGA | 201 |

TABLE 1b

| PRIMERS | SEQUENCE | SEQ ID NO |
|---|---|---|
| MYC-P1 | TCCCTTGTGGCCTGTGTG | 65 |
| MYC-P2 | TCCTTCATCGGCTCTCGA | 66 |
| MYC-P3 | GATGCCAAGGCATCCACC | 67 |
| MYC-P4 | CCTCCCACGTCCTTCATCG | 68 |
| MYC-P5 | CCTGGGTTTGACATGCACAG | 192 |
| CHTR-P1 | AAGGTTTCTGACTAGGTTGGGC | 69 |
| CHTR-P2 | GGTGAAGTGCTTGCATGGATCT | 70 |
| LIS-P1 | ACCTGTGAGTTTTCGTTCTTCTC | 71 |
| LIS-P2 | CTATTTGTTCAGTTTTGAGAGGTT | 72 |
| LIS-P3 | ATTTTCCGTATCAGCGATGATAC | 73 |
| LIS-P4 | ACGAAGTAAAGGTTGTTTTTCT | 74 |
| LIS-P5 | GAGAGGTTACTCTCTTTTATGTCAG | 75 |
| LIS-P6 | CTTTTATGTCAGATAAAGTATGCAA | 202 |
| LIS-P7 | CGTAAAAGGGTATGATTATTTG | 203 |
| BRU-P1 | TCGAGAATTGGAAAGAGGTC | 204 |
| BRU-P2 | AAGAGGTCGGATTTATCCG | 205 |
| BRU-P3 | TTCGACTGCAAATGCTCG | 206 |
| BRU-P4 | TCTTAAAGCCGCATTATGC | 207 |
| YEC-P1 | CCTAATGATATTGATTCGCG | 208 |
| YEC-P2 | ATGACAGGTTAATCCTTACCCC | 209 |

EXAMPLE 1

Pseudomonas aeruginosa

*Pseudomonas aeruginosa* is a significant human pathogen, usually in the context of serious underlying disease. It is also a major cause of nosocomial infections, which are characteristically prone to resistance to antimicrobial agents. This gram-negative, non-fermentative rod can be responsible for different clinical manifestations, like wound infections, bacteremia, respiratory and urinary tract infections, and is also a major cause of morbidity and mortality in patients with cystic fibrosis.

*Pseudomonas* species are currently differentiated based on growth characteristics and several biochemical features implying a time schedule of 24 h to 72 h to get a correct identification of the pathogen.

Already the development of monoclonal or polyclonal antibodies significantly improved the identification of *Pseudomonas* species. Recently however it has been shown that it is possible to detect organisms directly in clinical samples on a very sensitive and specific way using DNA probes with or without a prior amplification of the target DNA.

DNA probes to study *Pseudomonas aeruginosa* are already described and are mainly used for epidemiological typing (Ogle et al., 1987: Samadpour et al., 1988: McIntosh et al., 1992). However, none of these probes have been derived from the 16S–23S spacer.

The 16S–23S rRNA gene spacer region and a part of the 23S rRNA gene was amplified with conserved primers (upper primer: TGGGGTGAAGTCGTAACAAGGTA SEQ ID NO 155: lower primer: CCTTTCCCTCACGG-TACTGGT SEQ ID NO 156) using the polymerase chain reaction for the following species:

Pseudomonas aeruginosa 5669

Pseudomonas alcaligenes LMG 1224$^T$

Pseudomonas fluorescens LMG 5167

Pseudomonas putida LMG 2232

Pseudomonas stuzeri LMG 23337

Pseudomonas pseudoalcaligenes LMG 1225$^T$

To facilitate cloning of the obtained amplicons a NotI recognition site was added to the lower primer. After purification and digestion of the fragment with NotI, the amplicon was cloned in a EcoRV/NotI digested pBluescript SK⁻ plasmid vector.

Sequencing of the 16S–23S rRNA gene spacer region was performed according the dideoxy-chain terminating chemistry either using double stranded plasmid DNA combined with primers located in the plasmid vector or directly on the PCR products after purification combined with internal PCR primers.

FIGS. 36 to 40 represent the nucleotide sequence of the 16S–23S rRNA gene spacer regions from the different *Pseudomonas* species described above. For *P. flourescens* only partial sequence information was obtained.

From the nucleic acid sequence of the spacer from *P. aeruginosa* strain 5669 five oligonucleotide-probes were chosen and chemically synthesized. The sequences of the oligonucleotides are the following:

PA1=PA-ICG 1: TCCTGTGCTGCGTGATCCGATA

PA2=PA-ICG 3: TGAATCTTCGTGGATGAACAT-TGATT

PA3=PA-ICG 3: CACTGGTGATCATTCAAGTCAAG

Specificity and sensitivity testing of the oligonucleotide-probes was carried out using a reverse hybridization assay. Genomic DNA of the different bacteria tested was amplified using biotinylated primers (idem primers as for cloning procedure, see above). The obtained amplicon, spanning the 16S–23S rRNA gene spacer region, was denatured and hybridized to a membrane-strip onto which the different oligonucleotide probes were immobilized in a line-wise fashion (LiPA). Hybridization was carried out in a mixture of 3×SSC (1×SSC=0.15 M NaCl, 0.015 M sodium citrate, pH 7.0) and 20% formamide (FA) at a temperature of 50° C. for one hour. Washing was done in the same mixture at the same temperature for 15 min.

Hybrids were detected using a streptavidine conjugate coupled to alkaline phosphatase and the probes were visualized through a precipitation reaction using NBT (nitrobluetetrazoltium) and BCIP (bromo-chloro-indolylphosphate).

The hybridization results obtained with probes PA1, PA2 and PA3 are given in table 4 and show that probes PA1 and PA3 were 100% specific for *Pseudomonas aerguinosa* and hybridized to all the strains tested. The hybridization signal with probe PA3 at 50° C. was not optimal, so the oligonucleotide-probe was improved by adding some additional nucleotides to the specific probe. This newly designed probe is PA5.

PA5=PA-CG 5: CTCTTTCACTGGTGATCATTCAAGT-CAAG

Hybridization experiments with probe PA5 proved that this probe also shows a 100% specificity and 100% sensitivity for *P. aeruginosa*.

Oligonucleotide probe PA2 hybridized only to 5 out of 17 *P. aeruginosa* strains tested. Direct sequencing of the 16S–23S rRNA gene spacer region of the strains which did not hybridize to these probes, showed some heterogeneity between different strains. Two mismatches were seen in comparison to the fast developed PA2 probe. To overcome this heterogeneity between different strains in the region of probe PA2 a new probe PA4 was designed. This probe is degenerated at the position of the mismatches and some additional nucleotides were added to improve the hybridization signal at 50° C.

PA4=PA-KG 4: TGAATGTTCGT(G/A)(G/A)ATGAACATTGATTTCTGGTC

A 100% specificity and 100% sensitivity was obtained with this degenerated probe as is shown by the hybridization results.

TABLE 2

Hybridization results for Pseudomonas

| taxa tested | PA1 | PA2 | PA3 | PA4 | PA5 |
| --- | --- | --- | --- | --- | --- |
| Pseudomonas aeruginosa | 17/17 | 5/17 | 17/17 | 17/17 | 17/17 |
| Pseudomonas alcaligenes | 0/1 | 0/1 | 0/1 | 0/1 | 0/1 |
| Pseudomonas fluorescens | 0/1 | 0/1 | 0/1 | 0/1 | 0/1 |
| Pseudomonas purida | 0/1 | 0/1 | 0/1 | 0/1 | 0/1 |
| Pseudomonas pseudoalcaligenes | 0/1 | 0/1 | 0/1 | 0/1 | 0/1 |
| Pseudomonas stutzeri | 0/1 | 0/1 | 0/1 | 0/1 | 0/1 |
| Pseudomonas cepacia | 0/1 | 0/1 | 0/1 | ND | ND |
| Neisseria gonorrhoeae | 0/1 | 0/1 | 0/1 | ND | ND |
| Escherichia coli | 0/1 | 0/1 | 0/1 | ND | ND |
| Bordetella pertussis | 0/1 | 0/1 | 0/1 | ND | ND |
| Bordetella parapertussis | 0/1 | 0/1 | 0/1 | ND | ND |
| Borderella bronchiseptica | 0/1 | 0/1 | 0/1 | ND | ND |
| Mycobacterium tuberculosis | 0/1 | 0/1 | 0/1 | ND | ND |
| Mycobacerium avium | 0/1 | 0/1 | 0/1 | ND | ND |
| Moraxella catarrhalis | 0/4 | 0/4 | 0/4 | ND | ND |
| Haemophilus influenzae | 0/2 | 0/2 | 0/2 | ND | ND |
| Streptococcus pneumoniae | 0/3 | 0/3 | 0/3 | ND | ND |
| Acinetobacter calcoaceticus | 0/1 | 0/1 | 0/1 | ND | ND |
| Staphylococcus aureus | 0/2 | 0/2 | 0/2 | ND | ND |

(n/m: number of strains positive/number of strains tested)
(ND: not done)

EXAMPLE 2

Mycobacterium

A variety of mycobacterial species may be involved in serious human infectious disease. Notorious examples are *Mycobacterium tuberculosis* and *Mycobacterium leprae*. Recently other species such as *M. avium*, *M. intracellulare* and *M. kansaii* have been more frequently encountered as human pathogens especially in immunocompromised hosts.

Consequently, laboratory diagnosis of mycobacterial infections should not be restricted to the *M. tuberculosis* complex but should ideally include most other clinically relevant mycobacterial species.

The identification and differentiation of pathogenic mycobacteria at the species level by conventional laboratory techniques is, in general, difficult and time-consuming.

To overcome these problems DNA-techniques were implemented. The techniques described extended from straightforward DNA-probing to automated sequence analysis. Several approaches have been recently reported (Jonas et al., 1993: Frothingham and Wilson, 1993; Tomioka et al., 1993; Saito et at., 1989; Vaneechoutte et al., 1993; Telenti et al., 1993; Böddinghaus et al., 1990).

However, these methods all have their particular disadvantages, and most of them still rely on culture. Moreover, and most importantly, none of these techniques allows for a simultaneous detection of the different clinically relevant mycobacterial species in a single test run. Besides, the differentiation of particular groups within the *Mycobacterium avium-intracellulare* complex is problematic and often even impossible.

To overcome the above-mentioned disadvantages, a LiPA-test was developed which allows for the simultaneous and reliable detection and differentiation of a number of *Mycobacterium* species and groups. The sets of probes used to achieve these goals were all derived from the 16S–23S rRNA spacer region. The methods used are analogous to those mentioned in example 1.

The 16S–23S rRNA spacer region, and part of the 16S and 23S rRNA flanking genes, was amplified by PCR with primers conserved for the genus *Mycobacterium*. At least one of the following primers located in the 16S gene were used as upper primers:

MYC-P1: TCCCTTGTGGCCTGTGTG (SEQ ID NO 65)
MYC-P5: CCTGGGTTTGACATGCACAG (SEQ ID NO 192)

At least one of the following primers, located in the 23S gene, were used as lower primers for the amplification:

MYC-P2: TCCTTCATCGGCTCTCGA (SEQ ID NO 66)
MYC-P3: GATGCCAAGGCATCCACC (SEQ ID NO 67)
MYC-P4: CCTCCCACGTCCTTCATCG (SEQ ID NO 68)

All the above mentioned primers amplified the spacer region of all *Mycobacterium* strains tested, except primer MYC-P2 which was not functional for *M. chelonae*. In order to enhance the sensitivity of the detection, a nested PCR was sometimes carried out, using P5 and P4 as outer primers and P1 and P3 as inner primers.

In order to be able to design and select the probes and probe combinations which fit our purpose, the 16S–23S rRNA spacer region of a number or mycobacterial strains was sequenced. The obtained sequences were compared to each other and to those already known from literature (e.g. Frothingham et al., 1993, 1994; Kempsell et al., 1992; Suzuki et al., 1988; EP-A-0395292; Van der Giessen et al., 1994;) or from publicly accessible data banks. The corresponding sequences are represented in FIGS. 1 to 35 (SEQ ID NO 76 to SEQ ID NO 110).

The probes derived from these data were all adjusted in such a way that the desired hybridization-behaviour was obtabaed using unified hybridization and wash conditions (i.e. 3×SSC, 20% deionized formamide, 50° C.). The set of adjusted probes used for hybridization to different mycobacterial strains is represented in table 1a. SEQ ID NO 1–33. Please note that the probe nomenclature used in this example is an abbreviated version of the one used in table 1a: i.e. the letters "ICG" have always been omitted. According to the specific hybridization pattern obtained, the strains tested could be assigned to one of the following species or species groups: *M. tuberculosis* complex, *M. avium, M. intracellulare* or *M. intracellulare* complex, *M. kansasii, M. chelonae* and *M. gordonae*. The strains tested which belong to each group are summarized in Table 4. All strains were obtained from the Institute of Tropical Medecine, Antwerp, Belgium. The different probe-patterns obtained for each group are illustrated in Table 3, and are discussed in more detail hereafter.

*M. tuberculosis* Complex

The *M. tuberculosis* complex harbours all strains belonging to *M. tuberculosis, M. bovis, M. africanum* and *M. micron*. The probes Mtb1, Mtb2 and Mtb3 hybridize with DNA originating from all *M. tuberculosis* complex strains tested. None of the other strains tested hybridized with these probes at the conditions used.

In addition, *M. tuberculosis* complex strains, as is the case with all other mycobacterial strains tested, hybridize with either the mvci or the mvc22 probe or both. The latter two probes are designed as general *Mycobacterium* probes, either alone or in combination with each other.

*M. avium/M. paratuberculosis*

All *M. avium* and *M. paratuberculosis* strains studied reveal an identical hybridization pattern with the set of probes, For this type of organisms positive hybridization signals are obtained with the probes myc1/myc22, mai1, mil11, mav1, mah1 and mav22. The lacer two probes hybridize exclusively with *M. avium* and *M. paratuberculosis* strains, and can thus be used as species-specific probes. Since the 16S–23S spacer sequences of *M. avium* isolates and *M. paratuberculosis* isolates are identical or nearly identical these two taxa cannot be discriminated from each other. This finding supports 16S rRNA sequencing data which indicate that *M. avium* and *M. paratuberculosis* should in fact be considered as belonging to one geno-species (Rogal et al., 1990). *M. avium* ssp. avium and *M. avium* ssp. paratuberculosis.

*M. intracellulare* and *M. intracellulare* complex (MIC)

MIC strains are genotypically highly related organisms, which, according to sequence data of the 16S–23S rRNA spacer region, belong to a distinct cluster which is separate from other *Mycobacterium* species. *M. avium* and *M. scrofulaceum* are their closest relatives. Almost all strains tested which are generally referred to as *M. avium* complex (MAC) strains (the former MAIS-complex) can be found in the MIC group. Thus, the MIC group defined in the current invention encompasses the MAC-type strains described by Frothingham and Wilson (1993) with the exception of MAC-G which appears to be *M. scrofulaceum*. Also *M. intracellulare* strains sensu micro (*M. intracellulare* s.s.) are part of this cluster.

Because this MIC group contains a quite large group of strains with, among them, subgroups showing different hybridization characteristics to the set of probes, a further subdivision into MIC-types was envisaged.

Type MIC 1 harbours *M. intracellulare* s.s., together with some other MAC-strains. All MIC 1 type isolates, without exception, hybridize to the following Probes: myc1/myc22, mai1 and mac1. The following probes can be used to make further subdivisions within the MIC 1 group: mil11, min1, min2 to 2222, mil22 and mhef1.

*M. intracellulare* sensu stricto strains (type MIC 1.1.a) can be distinguished from other subtypes in this group by virtue of probe mini which is positive only for this group of strains. All strains of type MIC 1.1.a strains are positive when tested with the *M. intracellulare* probe of the Gen-Probe Rapid Diagnostic system for MAC. Type MIC 1.1.b and MIC 1.2 harbour strains which are highly related to *M. intracellulare*. They can be differentiated by using probes mil11 and mil22 (see Table 3). Further subdivision within these groups was not attempted although this could be achieved by using the probes:

min2, min22, min222 and min2222. Further subdivision might be of value for epidemiological reasons.

Only two of our collection or strains tested grouo as MIC 2 strains. One of these strains is a "*Mycobacrerium lufu*" strain (ITG 4755). The spesific probe pattern generated by these strains is characterized by a positive hybridization signal with the following probes: myc1/myc22, mai1, mil22, mah1 and mal1. Variable hybridization results are obtained with probes min2222, mac1and mhef1. Tne other probes are negative. It is not unlikely that MIC 2 would eventually prove to be a heterogeneous group when more strains of this type are being identified. The variable probes may help in a further differentiation, if this would become relevant.

Type MIC 3 groups a fairly high number of MAC-strains which are rather remotely related to *M. intracellulare* s.s. strains and most other MAC-strains. This cluster should be regarded as distinct from *M. avium* and *M. intracellulare* on genotypical grounds. All MIC 3 subtypes hybridize to probes myc1/myc22, mai1, mil22 and mco1. A positive signal with the latter probe (mco1) is characteristic for MIC 3 strains. Variable hybridization results are obtained with the following probes: mac1, mhef1 and mah1. MIC 3 can be further subdivided into four subtypes by using three probes: mth11, mth2 and mef11. Probe mth2 is specific for type MIC 3.1 which encompasses a group of highly related MAC-strains isolated from immuno-compromised human beings. Most MIC 3 strains are located in the MIC 3.1 subtype. Eventually species status may be assigned to this group of strains, as might also be the case for other groups of MAC strains, yet unnamed, in subtypes MIC 3.4, MIC 3.3 and MIC 3.2 only two, one and one strain are found respectively in our collection of strains tested.

Type MIC 4 is a collection of "MAIS" strains (including *M. malmoense*) which are remotely related to *M. intracellulare*. The only probe of the above-described set which hybridizes to MIC 4, apart from the general myc1/myc22 probes, is the mai1 probe. This probe shows a broad specificity, hybridizing also with *M. avium*, *M. intracellulare* and other MIC strains and *M. scrofulaceum*.

M. scrofulaceum

All *M. scrofulaceum* strains tested reveal an identical hybrdization pattern with the set of probes. A positive signal with probe mscI is unique to *M. scrofulaceum* strains. The only other probes with a positive signal for this species are evidently myc1/myc22 and also mai1.

M. kansasii

Probes mka3 and mka4 are specific for *M. kansasii*; i.e. a distinct positive signal is obtained on the LiPA strip when amplified DNA from the *M. kansasii* strains is used in the hybridization whilst with all other organisms tested the signal is absent. Although the sequences of probes mka1 and mka2 are not absolutely complementary to the target sequence (3 and 1 mismatches, respectively), these probes also proved to be useful since they hybridized exclusively to *M. kansasii* DNA and not to any other mycobacterial DNA tested under the conditions used (50° C., 3×SSC. 20% formamide). This illustrates that probes not necessarily have to match perfectly to the target to be useful, and that modifications in sequence and length may be allowed up to a certain degree.

M. chelonae

The species *M. chelonae* encompasses *M. chelonae* ssp. chelonae and *M. chelonae* ssp. abscessus strains. The spacer region was sequenced for one strain of each subspecies and small differences were noticed (SEQ ID NO 103 and SEQ ID NO 102). Probes mch1 and mch2 hybridize to both strains. All other probes are negative for these 2 strains except for myc1/myc22.

Upon testing of probes mch1 and mch2 with 2 additional *M. chelonae* strains not mentioned in table 4, i.e. *M. chelonae* 94-379 and *M. chelonae* 94-330, both obtained from the Institute of Tropical Medecine in Antwerp, Belgium. It appeared that they did not hybridize to probe mch1. This was confirmed by sequencing the spacer region of these two strains (SEQ ID NO 184). Cluster analysis of the spacer region with other mycobacteria revealed that *M. chelonae* strains can be subdivided in two groups. A third probe mch3 was designed to specifically detect this second group of strains, to which 94-379 and 94-410 belong.

This illustrates that the use of DNA probes derived from the 16S–23S rRNA spacer region can be helpful in differentiating different groups of strains, which belong to the same species according to the classical identification methods, and possibly can be used to detect and describe new species within the mycobacteria. In this case mch2 detects all *M. chelonae* strains, whereas mch1 and mch3 differentiate between different subgroups.

M. gordonae

The five *M. gordonae* strains tested all hybridize to probe mgo5. Positive hybridization signals are also obtained with probes myc1/myc22, and some *M. gordonae* strains also hybridize to probes mgo1 and mgo2.

other mycobacterial species

Strains belonging to other mycobacterial species than those mentioned above only hybridize to the general probes myc1/myc2. This indicates that these strains most probably belong to the genus *Mycobacterium*, but do not belong to one of the species or groups which can be specifically identified by using one or more of the other probes described.

In conclusion we can state that, according to the particular combinations of probes of the invention used, DNA probe tests at different levels can be provided.

When all probes are used in one and the same LiPA-test, differentiation at the species level as well as subtyping of certain groups of mycobacteria can be achieved. However, the probe-assembly on one strip could be restricted to those probes which are species-specific: in that case identification is performed at the species level. A further reduction of the number of probes on the strip might lead to the specific detection of only one or just a few species. Obviously, LiPA strips can be designed which solely attempt to subtype strains, e.g., those belonging to the *M. intracellulare* complex (MSC). Depending on the particular needs of the laboratoria performing diagnosis and/or typing of mycobacteria, all these different applications might be of value, However, it is clear that by using a combination of probes in a LiPA-format the amount of information obtained as to the identity of the organisms present in the clinical sample, is considerably increased as compared to DNA probe tests using only a single probe. For some groups, or at least for further subdivision of some groups, a single probe uniquely hybridizing to this (sub)group could not be designed. In that ease only probe-patterns are able to provide the information needed. For these applications the LiPA is an advantageous format.

TABLE 3

Different probe patterns obtained for mycobacterial (sub)species

| Mycobacterium | myc1 myc22 | mtb1 mtb2 mtb3 | mal1 | mll11 | mav1 mav22 | mln1 | mln222 | mln22 | mln2 | mln2222 | mll22 | mac1 |
|---|---|---|---|---|---|---|---|---|---|---|---|---|
| M. tuberculosis | + | + | − | − | − | − | − | − | − | − | − | − |
| M. bovis | | | | | | | | | | | | |
| M. avium | + | − | + | + | + | − | − | − | − | − | − | − |
| M. paratuberculosis | | | | | | | | | | | | |
| MIC 1.1.a | + | − | + | + | − | + | + | + | + | + | − | + |
| MIC 1.1.b | + | − | + | + | − | − | ± | ± | ± | ± | − | + |
| MIC 1.2 | + | − | + | − | − | − | ± | ± | ± | + | + | + |
| MIC 2 | + | − | + | − | − | − | − | − | − | ± | + | ± |
| MIC 3.4 | + | − | + | − | − | − | − | − | − | − | + | ± |
| MIC 3.3 | + | − | + | − | − | − | − | − | − | − | + | + |
| MIC 3.1 | + | − | + | − | − | − | − | − | − | − | + | + |
| MIC 3.2 | + | − | + | − | − | − | − | − | − | − | + | + |
| MIC 4 | + | − | + | − | − | − | − | − | − | − | − | − |
| M. scrofulaceum | + | − | + | − | − | − | − | − | − | − | − | − |
| M. kansasii | + | − | − | − | − | − | − | − | − | + | − | − |
| M. chelonae | + | − | − | − | − | − | − | − | − | − | − | − |
| M. gordonae | + | − | − | − | − | − | − | − | − | − | − | − |
| Mycobacterium sp. | + | − | − | − | − | − | − | − | − | − | − | − |

| Mycobacterium | mco1 | mth11 | mth2 | mef11 | mhef1 | mah1 | mal1 | msc1 | mka1,2,3,4 | mch 1,2,3 | mgo1,2 | mgo5 |
|---|---|---|---|---|---|---|---|---|---|---|---|---|
| M. tuberculosis | − | − | − | − | − | − | − | − | − | − | − | − |
| M. bovis | | | | | | | | | | | | |
| M. avium | − | − | − | − | − | + | − | − | − | − | − | − |
| M. paratuberculosis | | | | | | | | | | | | |
| MIC 1.1.a | − | − | − | − | − | − | − | − | − | − | − | − |
| MIC 1.1.b | − | − | − | − | − | − | − | − | − | − | − | − |
| MIC 1.2 | − | − | − | − | ± | − | − | − | − | − | − | − |
| MIC 2 | − | − | − | − | ± | + | + | − | − | − | − | − |
| MIC 3.4 | + | − | − | + | + | ± | − | − | − | − | − | − |
| MIC 3.3 | + | + | − | + | + | + | − | − | − | − | − | − |
| MIC 3.1 | + | + | + | − | ± | ± | − | − | − | − | − | − |
| MIC 3.2 | + | − | − | − | + | + | w | − | − | − | − | − |
| MIC 4 | − | − | − | − | − | − | − | − | − | − | − | − |
| M. scrofulaceum | − | − | − | − | − | − | − | + | − | − | − | − |
| M. kansasii | − | − | − | − | − | − | − | − | + | − | − | − |
| M. chelonae | − | − | − | − | − | − | − | − | − | ± | − | − |
| M. gordonae | − | − | − | − | − | − | − | − | − | − | ± | + |
| Mycobacterium sp. | − | − | − | − | − | − | − | − | − | − | − | − | w: weak/v: very weak/ ±: + or −, variable according to the strain tested

TABLE 4

Mycobacteria strains tested in LiPA

| species/group | strain numbers from Institute of Tropical Medecine Antwerp (except those between parenthesis) |
|---|---|
| M. tuberculosis complex | 7602, 8004, 8017, 8647, 8872, 9081, 9129, 9173, 9517, (ATCC 27294), 8324, 8428 |
| M. avium/ M.paratuberculosis | 1101, 1983, 2070, 2074, 4176, 4189, 4191, 4193, 4197, 4204, 4386, 4991, 5872, 5874, 5884, 5887, 5893, 5894, 5897, 5903, 5904, 5905, 5927, 5983, 8180, 8750, (ATCC 25291), M. naratub: (316F), (2E) |
| M. intracellulare (MIC 1.1.a) | 4199, 4208, 5701, 5880, 5906, 5908, 5909, 5913, 5915, 5917, 5918, 5920 5921, 5924, 5925, 5929, 8713, 8717, 8718, 8720, 8721, 8722, 8732, 8740, 8741, 8742, 8744, 8747, 8749 |
| MIC 1.1.b | 8694, 8745, 8754 8708 5513, 8743 8054, 8190 |
| MIC 1.2 | 8710, 8711, 8712, 8714, 8715, 8716, 8725, 8729, 8733, 8737, 8746, 8751, 8752 5919 8695 8748 |
| MIC 2 | 5922 4755 (M. lufu) |
| MIC 3.4 | 1815 8707 |

TABLE 4-continued

Mycobacteria strains tested in LiPA

| species/group | strain numbers from Institute of Tropical Medecine Antwerp (except those between parenthesis) |
|---|---|
| MIC 3.3 | 5620 |
| MIC 3.1 | 925, 926, 1329, 1788, 1794, 1812, 1818, 2069, 2073, 2076, 4541, 4543, 5074, 5280, 5789, 7395, 8739, 8753 8738 |
| MIC 3.2 | 5765 |
| M. scrofulacecum | 4979, 4988, 5907, 8706, 8726, 8727, 8735, (MB022), (MB023), (MB024) |
| M. kansasii | 4987, (ATCC 22478) |
| M. chelonae | 4975, 9855 |
| M. gardonae | 7703, 7704, 7836, 7838, 8059 |
| MIC 4 | 8723, 8724 8757 4842 (M. malmoense) |
| other mycobacterial species | 7732 (M. marinum), 94–123 (M. celarum), 778 (M. haemophilum), 8777 (M. genavense), 4484 (M. siniae), 4986 (M. xenopi), 4304 (M. fortuinum), 1837 (M. ulcerans) |

EXAMPLE 3

Listeria

Listeria species are a group of Gram-positive rods widely spread in nature. Within this group it seems that only L. monocytogenes is pathogenic to humans and animals. L. monocytogenes is the causative agent of listeriosis, giving rise to meningitis, abortions, encephalitis and septicemia. Immunocompromised individuals, newborn infants and pregnant women are high risk groups for this foodborn disease. Most cases have been caused by the consumption of food of animal origin, particularly soft cheeses. Therefore, the presence of L. monocytogenes should be excluded from food. For safety measurements, in some countries, the absence of all Listeria species is required in food products.

The classical identification method for L. monocytogenes in dairy products involves an enrichment culture for 48 h and subsequently colony forming on selective agar medium, for 48 h followed by a whole set of biochemical and morphological assays (Farber, and Peterkin, 1991). This procedure could be very much simplified by the use of gene probes.

Several DNA probes are already described for the identification of L. monocytogenes. Some probes are derived from genes responsible for the pathogenicity of the organism, for instance the listeriolysin O gene (Dana et al., 1993) or the invasion-associated-protein (iap) (Robert et al., 1992).

A commercially available identification system, based on a specific 16S rRNA probe, was introduced by GenProbe (Herman and De Ridder, 1993; Ninet et al., 1992).

These specific probes are used as confirmation assays on colonies obtained after enrichmnent and plating on selective agar medium.

Recently several publications reported on the use of the polymerase chain reaction to amplify the target region for the DNA probes, which can shorten the time of the assay without interfering with the specificity and the sensitivity of the assay. Different primer sets are described that can specifically amplify L. monocytogenes DNA, These primer sets were derived from the listeriolysin O gene (Golstein Thomas et al., 1991), and the iap gene (Jaton et al., 1992).

We used the 16S–23S rRNA gene spacer region as the target for the development of a genus-specific probe for Listgria and a probe specific for Listeria monocytogenes.

Using conserved primers derived from the 3' end of the 16S rRNA and the 5' end of the 23S rRNA (sequences are given in example 1) the spacer region was amplified using the polymerise chain reaction and subsequently cloned in a suitable plasmid vector following the same procedures as in example 3.

Two amplicons differing in length (800 bp and 1100 bp) were obtained. Both PCR fragments were cloned for the following Listeria species:

Listeria monocytogenes, serovar 4b. IHE (Instituut voor Hygiëne en Epidemiologie, Belgium)

Listeria ivanovii CIP 78.42 (Collection Nationale de Cultures de Microorganisms de l'Institut Pasteur, France)

Listeria seeligeri serovar 4a. nr. 42.68 (Bacteriologisches Institut, Südd, Versuchs- and Forschungsanstalt für Milchwirtschaft Weihenstephan, Germany)

The sequence of the spacer region between the 16S and 23S rRNA gene was determined using the cloned material originating from the 800 bp PCR fragment and this was done for the three described Listeria species. FIGS. 41 to 43 show the sequences of the different short spacer regions obtained. The sequence of this short spacer region of L. monocytogenes was also retrieved from the EMBL databank (LMRGSPCR).

Based on this sequence information, following oligonucleotides for species-specific detection were chosen and chemically synthesized:

LMO-ICG-1: AAACAACCTTTACTTCGTAGAAG-TAAATTGGTTAAG

LMO-ICG-2: TGAGAGGTTAGTACTTCTCAGTAT-GTTTGTTC

LSE-ICG-1: AGTTAGCATAAGTAGTGTAACTATT-TATGACACAAG

LIV-ICG-1: GTTAGCATAAATAGGTAACTATTTAT-GACACMGTAAC

Also, a genus specific probe for Listeria was designed:

LIS-ICG-1: CAAGTAACCGAGAATCATCTGAAAGT-GAATC

The oligonucleotide-probes were immobilized on a membrane strip and following reverse hybridization with biotinylated PCR fragments, the hybrids were visualized using a precipitation reaction. The hybridization results of different Listeria species are summarized in table 5.

TABLE 5

| Species | n | LIS1 | LMO1 | LMO2 | LSE1 | LIV1 |
|---|---|---|---|---|---|---|
| L. monocytogenes | 1 | + | + | + | − | − |
| L. seeligeri | 2 | + | + | ± | + | ± |
| L. ivanovii | 3 | + | ± | − | ± | + |
| L. welshimeri | 3 | + | + | ± | − | − |
| L. innocua | 2 | + | + | + | − | − |

These hybridization results show that probe LIS1 can detect all described *Listeria* species, but also that the species-specific probes cross-hybridize to each other. Hence, from this short spacer region probes with sufficient specificity could not be found.

For *Listeria monocytogenes* the 16S–23S rRNA gene spacer was also determined originating from the 1100 bp fragment. FIG. 45 shows the sequence obtained for this species. This sequence information was also obtained for *L. seeligeri* (see FIG. 46) and partial sequence information of the large spacer region was obtained for *L. ivanovii* (see FIG. 44).

Based on sequence alignment with *L. seeligeri* following oligonucleotide-probe was chosen to specifically detect *L. monocytogenes*.

LMO-ICG-3: AGGCACTATGCTTGAAGCATCGC

Initial hybridization results (not shown) indicated that no cross-hybridization with other *Listeria* species was seen with this *L. monocytogenes* probe LMO3, and that all *Listeria* strains used hybridized to the general probe LIS1.

The oligonucleotide-probes, LIS1 for detection of all *Listeria* species and LMO3 for specific detection of *L. monocytogenes*, were immobilized on a membrane strip and hybridized to labeled amplicons, containing the 16S–23S rRNA spacer region, derived from different organisms. The hybridization results are shown in the following table.

An excellent specificity and sensitivity were obtained for probes LMO3 and LIS1 respectively at the species and genus level.

TABLE 6

| Taxa tested | n | LISI | LMO3 |
|---|---|---|---|
| Listeria monocytogenes | 44 | + | + |
| Listeria ivanovii | 10 | + | − |
| Listeria seeligeri | 11 | + | − |
| Listeria welshimeri | 16 | + | − |
| Listeria innocua | 23 | + | − |
| Listeria murravi | 3 | + | − |
| Listeria gravi | 2 | + | − |
| Brochotrix thermosphacta | 1 | − | − |
| Brochorrix campestris | 1 | − | − |
| Bacillus cereus | 3 | − | − |
| Bacillus brevis | 2 | − | − |
| Bacillus coagulans | 1 | − | − |
| Bacillus pumilis | 1 | − | − |
| Bacillus macerans | 1 | − | − |
| Bacillus lentus | 1 | − | − |
| Bacillus firmus | 2 | − | − |
| Bacillus subtilis | 2 | − | − |
| Bacillus megantum | 1 | − | − |
| Enterococcus faecalis | 1 | − | − |
| Enterococcus faecium | 1 | − | − |
| Enterococcus durans | 1 | − | − |
| Lactococcus lactis | 3 | − | − |
| Lactococcus casei | 1 | − | − |
| Escherichia coli | 1 | − | − |
| Harnia halvei | 1 | − | − |
| Agrobacterium tumefaciens | 2 | − | − |
| Mycoplasma dimorpha | 1 | − | − |
| Clostridium tyrobutyricum | 1 | − | − |

TABLE 6-continued

| Taxa tested | n | LISI | LMO3 |
|---|---|---|---|
| Clostridium perfringens | 1 | − | − |
| Clostridium sporogenes | 1 | − | − |
| Clostridium acetobutyricum | 1 | − | − |
| Brucella abortus | 1 | − | − |
| Brucella suis | 1 | − | − |
| Brucella melitensis | 1 | − | − |
| Staphylococcus aureus | 1 | − | − |
| Salmonella typhimurium | 1 | − | − |
| Salmonella enteritidis | 1 | − | − |
| Yersinta enterocolitica | 1 | − | − | n: number of strains tested

These two probes can be used for the detection of *Listeria* species and *Listeria monocytogenes* directly on food samples or after enrichment of the samples in liquid broth. In both cases amplification problems can occur with the conserved primerset due to the enormous background flora in these samples.

To circumvent this problem, we designed several sets of primers derived from the 16S–23S rRNA spacer regions of *Listeria* species.

Primers LIS-P1 and LIS-P2 are upper primers, whereas LIS-P3 and LIS-P4 are lower primers. These primerset amplify the smaller 16S–23S rRNA spacer region as well as the larger spacer of *Listeria* species (except *L. gravi* and *L. murravi*). If needed these primers can be used in a nested PCR assay where LIS-P1/LIS-P4 are the outer primers and LIS-P2/LIS-P3 are the inner primers.

For the specific detection of *Listeria monocytogene*; probe LMO-ICG-3 was designed and derived from the large 16S–23S rRNA spacer region. In order to specifically amplify only this large spacer region for an improved detection of this pathogen directly in samples a set of primers was derived from the part of sequence information from the large 16S–23S rRNA spacer region that is not present in the smaller rRNA spacer. For this aim, primers LIS-P5 and LIS-P6 are used as the upper primers and LIS-P7 is used as the lower primer.

LIS-P1: ACCTGTGAGTTTTCGTTCTTCTC 71
LIS-P2: CTATTTGTTCAGTTTTGAGAGGTT 72
LIS-P3: ATTTTCCGTATCAGCGATGATAC 73
LIS-P4: ACGAAGTAAAGGTTGTTTTTCT 74
LIS-P5: GAGAGGTTACTCTCTTTTATGTGAG 75
LIS-P6: CTTTTATGTCAGATAAAGTATGCAA 202
LIS-P7: CGTAAAAGGGTATGATTATTTG 203

During the evaluation of the probes for *Listeria* spp. an organism was isolated from cheese that resembled *Listeria* according to the classical determination methods. This isolate (MB 405) showed the following characteristics (similar to Liberia spp.): Gram positive growth on Oxford and Tryptic Soy Agar, catalase positive. The only difference with the *Listeria* spp. was the motility, which was negative.

Using the conserved primers as described in example 1 in order to amplify the 16S–23S rRNA spacer region of this isolate MB 405, the same amplicon pattern was obtained with this strain as with *Listeria* spp. Hybridization of the amplicon showed that there was no signal obtained with any of the probes for *Listeria* spp.

Sequencing of the 16S rRNA of isolate MB 405 and subsequent comparison with *Listeria* spp. and relatives showed that the organism was more closely related to *Listeria* spp. than to any other species descried in the literature until now. Taxonomial studies will show if this isolate does or does not belong to the genus *Listeria*. This isolate, and subsequently isolated organisms from the same type, are referred to in this application as *Listeria* like organisms.

Isolate MB 405 seemed to contain at least 3 different 16S–23S rRNA spacer regions which were cloned and sequenced. Following alignment with *Listeria* spp. an oligonucleotide-probe was chosen to specifically detect *Listeria*-like strains:

LISP-ICG-1: CGTTTTCATAAGCGATCCCACGTT

Reverse hybridization reactions of this probe with the 16S–23S rRNA spacer regions of *Listeria* spp. showed that there was no cross-hybridization.

EXAMPLE 4

*Chlamydia trachomatis*

*Chlamydia trachomatis* is a small obligate intracellular gram-negative bacterium, which has 15 serovars (A–K, Ba, L1, L2, and L3) distinguished by the major outer membrane protein (MOMP) and contains a cryptic plasmid required for intracellular growth. The A–K and Ba serovars constitute the trachoma biovar, while the L1, L2, and L3 serovars constitute the LGV biavar.

Serovars A, B, Ba, and C are commonly associated with trachoma, the leading cause of preventable blindness worldwide. The D–K serovars are found mainly in sexually transmitted infections and are the major cause of cervicitis and pelvic inflammatory disease in women, and urethritis and epididymitis in men. Serovars L1, L2 and L3 are involved in lymphogranuloma venereum, a rare sexually transmitted disease.

Cell culture is regarded as the benchmark method for laboratory diagnosis, although specimen viability is difficult to maintain during transport and laboratory techniques are time-consuming and technically demanding. Therefore, a number of more rapid test kits were developed, such as an enzyme-linked immunosorbent assay, and direct fluorescent-antibody straining. However, none of these immunoassays have been shown to have high levels of sensitivity or specificity.

A nonisotopic DNA probe assay (Gen-Probe PACE: Woods et al., 1990) that detects chlamydial rRNA is commercially available. Rec:ntly, the polymerase chain reaction (PCR) method has been used for detection of *Chlamydia* infections. Detection was targeted at either the cryptic plasmid (Locffelholz et al., 1992), or the omp1 gene, which encodes for the major outer membrane protein (Taylor-Robinson et al., 1992). Compared with other techniques, PCR has higher sensitivity and specificity (Ossewaarde et al., 1992). None of these assays make use of DNA probes derived from the 16S–23S rRNA gene spacer region.

For a *Chlamydia trachomatis* L2 and a *Chlamydia psittaci* 6BC strain, a part of the ribosomal RNA cistron, containing the 16S–23S rRNA spacer region was amplified using conserved primers (see example 1) and subsequently cloned in a plasmid vector. The 16S–23S rRNA spacer region was sequenced using the dideozychain terminating chemistry.

The sequence of the spacer region of both *Chlamydia* species is shown in FIGS. 47 to 48.

Based on this sequence information, following oligonucleotide-probes were chemically synthesized:

CHTR-ICG-1: GGAAGAAGCCTGAGAAGGTTTCT-GAC

CHTR-ICG-2: GCATTTATATGTAAGAGCAAGCAT-TCTATTTCA

CHTR-ICG-3: GAGTAGCGTGGfGAGGACGAGA

CHPS-ICG-1: GGATAACTGTCTTAGGACG-GTTTGAC

The oligonucleotide-probes were immobilized in a line-wise fashion on a membrane strip and subsequently used in a reverse hybridization assay with biotinylated PCR products, containing the 16S–23S rRNA spacer region, as target.

Hybridizations were done in a solution of 3×SSC and 20% formamide (FA) at a temperature of 50° C.

The hybridization results with the different probes are shown in the following table.

TABLE 7

| Strains tested | CHTR1 | CHTR2 | CHTR3 | CHPS1 |
| --- | --- | --- | --- | --- |
| *Chlamydia trachomatis* L2 | + | + | + | − |
| *Chlamydia psittaci* 6BC | − | − | − | + |
| *Chlamydia psittaci* CP | − | − | − | + |
| *Chlamydia psittaci* TT | − | − | − | + |
| *Haemophilus ducreyi* CIP 542 | − | − | − | − |
| *Haemophilus influenzae* NCTC 8143 | − | − | − | − |
| *Neisseria gonorrhoeae* NCTC 8375 | − | − | − | − |
| *Moraxella catarrhalis* LMG 5128 | − | − | − | − |
| *Escherichia coil* B | − | − | − | − |
| *Streptococcus pneumoniae* S92-2102 | − | − | − | − |

As shown in the table at a hybridization temperature of 50° C. the probes CHTR1, CHTR2 and CHTR3 are specific for *Chlamydia trachomatis* and probe CHPS1 is specific for *Chlamydia psittaci*.

Several clinical isolates, obtained from the SSDZ, Delft, Netherlands, identified as *Chlamydia trachomatis* using conventional methods were tested in a reverse hybridization assay with the different oligonucleotide-probes. All *Chlamydia trachomatis* specific probes gave a positive hybridization signal and none of the isolates reacted with the *Chlamydia psittaci* probe. For some clinical isolates the CHTR2 probe reacted significantly weaker than CHTR1 or CHTR3. The spacer region of one of these isolates (94 M 1961) was sequenced (SEQ ID NO 197) and the sequence revealed one mismatch with the spacer sequence of strain L2. An additional probe (CHTR4) was derived from this new spacer sequence:

CHTR-ICG-4: GAGTAGCGCGGTGAGGACGAGA (SEQ ID NO 201)

This probe gives a stronger hybridization signal than CHTR2 with some clinical isolates from *Chlamydia trachomatis*. It can be used alone, or in combination with the CHTR2 probe (e.g. both probes applied in one LiPA-line).

In order to develop very sensitive assays for the detection of *Chlamydia trachomatis* directly in clinical specimens a specific primerset was derived from the 16S–23S rRNA spacer region, CHTR-P1 (upper primer) and CHTR-P2 (lower primer); amplifying specifically the spacer region of *Chlamydia* species.

CHTR-P1: AAGGTTTCTGACTAGGTTGGGC 69

CHTR-P2: GGTGAAGTGCTTGCATGGATCT 70

EXAMPLE 6

*Mycoplasma pneumoniae* and *Mycoplasma genitalium*

Mycoplasmas are a group of the smallest prokaryotes known that are able to grow in cell-free media, lack a cell wall, and have very small genomes with a low G+C content. More than 100 different species have been isolated from humans, animals, plants, and insects.

In humans, mycoplasmas have been recognized either as pathogenic organisms or as commensals. The best known pathogen is *Mycoplasma pneumoniae*, the causative agent of primary atypical pneumonia, especially in children and young adults. The diagnosis of *M. pneumoniae* has been based on the direct isolation by the culture method or on the detection of specific antibodies against *M. pneumoniae* in the patient's serum.

Another pathogen, first isolated from urethral specimens from patients with nongonococcal urethritis, has been described as *Mycoglasma genitalium*. This mycoplasma has several properties in common with *M. pneumoniae*. Born species are pathogenic, and both possess the capability to adhere to erythrocytes, various tissue cells, glass, and plastic surfaces. Furthermore, *M. genitalium* and *M. pneumaniae* share antigens, giving rise to extensive cross-reactions in serological tests. The observation that *M. genitalium* could also be found in respiratory tract specimens from patients with pneumonia and isolated from a mixture with *M. pneumoniae* has raised questions to the possible pathogenicity of *M. genitalium*.

Since cultivation of both species is time-consuming and serology lacks specificity, more rapid and more specific assays were developed to identify these mycoplasmas. The use of hybridization assays with DNA probes was described for these species, but despite good specificities these tests do not allow the detection of low levels of *M. pneumoniae* or *M. genitalium*. So more recently, DNA hybridization techniques were developed using the polymerase chain reaction, pneumoniae-specific PCR assays have been reported using the P1 adhesin gene (Buck et al., 1992) and the 16S rRNA gene (Kuppeveld et al., 1992). Specific PCR assays for *M. genitalium*, were described using sequences from the adhesin gene and the 16S rRNA gene.

The spacer sequences of clinical isolates of *M. pneumoniae* and *M. genitalium* (obtained from U. Göbel, University of Freiburg, Germany) were determined. They are shown in FIGS. 49 to 50. The sequences show some differences to those from other strains of the same species deposited in the EMBL databank (MPMAC and MGG37 respectively). Based on this information four probes were derived: one general *Mycoplasma* probe, two *M. pneumoniae* specific, and one *M. genitalium* specific probe:

Mycoplasma-ICG: CAAAACTGAAAACGA-CAATCTTTCTAGTTCC

MPN-ICG-1: ATCGGTGGTAAATTAAACCCAAATC-CCTGT

MPN-ICG-2: CAGTTCTGAAAGAACATTTCCGCT-TCTTTC

MGE-ICG-1: CACCCATTAATTTTTTCGGTGT-TAAAACCC

The probes were applied to LiPA strips and hybridized under standard conditions (3×SSC, 20% formamide at 50° C.) to amplified spacer material from four *M. pneumoniae* strains, one *M. genitalium* strain and twenty-two non-*Mycoplasma* species strains. The general probe hybridized only to the five *Mycoplasma* strains tested, while the specific probes hybridized only to strains of the species for which they were designed.

EXAMPLE 7

Other Mycobacterial Species

With the steady improvement of laboratory techniques the information on the systematics and clinical significance of the so called "potentially pathogenic environmental mycobacteria" increased rapidly. With the emergence of newly recognized diseases, additional syndromes associated with different mycobacterial species have emerged and have assumed major importance.

In order to extend the LiPA test for the simultaneous detection of different mycobacterial species as described in example 2, a new set of DNA probes was designed to specifically identify the following species: *Mycobacterium ulcerans, Mycobacterium genavense, Mycobacterium xenopi, Mycobacterium simiae, Mycobacterium fortuitum, Mycobacterium malmoense, Mycobacterium celatum* and *Mycobacterium haemophilum*.

These probes were derived from the 16S–23S rRNA spacer region sequence. For the above mentioned species this information was obtained through direct sequencing of FCR products or after cloning of the PCR-amplified spacer region. The sequences obtained are represented in FIGS. 80 to 97, and in FIG. 38 for *M. malmoense*.

The sequences of the spacer region of the above-mentioned mycobacterial species were compared and aligned to those already described in example 2 or in publicly available sources. From the regions of divergence, species-specific DNA probes were designed. The probes were selected and designed in such a way that the desired hybridization behaviour (i.e. species-specific hybridization) was obtained under the same conditions as those specified for the other mycobacterial probes mentioned in example 2, i.e. 3×SSC, 20% deionized formamide, 50° C. This allows simultaneous detection of at least two, and possibly all, of the mycobacterial species described in the current invention.

The following oligonucleotide probes were designed from the spacer region sequence of respectively *M. ulcerans, M. genavense, M. xenopi, M. simiae, M. fortuitum, M. malmoense, M. celatum* and *M. haemophilum:*

MUL-ICG-1: GGTTTCGGGATGTTGTCCCACC

MGV-ICG-1: CGACTGAGGTCGACGTGGTGT

MGV-ICG-2: GGTGTTTGAGCATTGAATAGTGGT-TGC

MXE-ICG-1: GTTGGGCAGCAGGCAGTAACC

MSI-ICG-1: GCCGGCAACGGTTACGTGTC

MFO-ICG-1: TCGTTGGATGGCCTCGCACCT

MFO-ICG-2: ACTTGGCGTGGGATGCGGGAA

MML-ICG-1: CGGATCGATTGAGTGCTTGTCCC

MML-ICG-2: TCTAAATGAACGCACTGCCGATGG

MCE-ICG-1: TGAGGGAGCCCGTGCCTGTA

MHP-ICG-1: CATGTCGGGCTTGATCGGGTGC

The probes were immobilized on a LiPA strip and hybridized with amplified biocinylated material derived from a set of representative mycobacterial species as described in example 2. Amplification of the spar region was carried out by PCR using a primer set as described in example 2. The different strains used for specificity testing are shown in table 8 together with the hybridization results obtained. The strains were obtained from the collection of the Institute for Tropical Medicine, Antwerp, Belgium.

The probes tested (MSI-ICG1, MXE-ICG-1, MFO-ICG-1, MFO-ICG-2, MML-ICG-1, MML-ICG-2, MCE-ICG-1 and MHP-ICG-1) specifically detected, *M. simiae, M. xenopi, M. fortuitum, M. maimoense, M. celatum* and *M. haemophilum* respectively and showed no cross-hybridization with the other mycobacterial species tested. Thus, these probes allow a specific detection of mycobacterial species which were not further identifiable using the set of DNA probes described in example 2. *M. malmoense* was classified in example 2 as a "MIC 4"-type, while the other species mentioned above were only hybridizing to the general probes MYC1/MYC22 for the genus *Mycobacterium*, and were thus classified in example 2 as "other mycobacterial species".

All tested *M. genavense* isolates reacted with MGV-ICG1 and MGV-ICG2, and not with MSI-ICG1 designed for *M. simiae*, closely related to *M. genavense*. A group of "intermediate" organisms, situated in between *M. simiae* and *M. genavense*, were received from the Tropical Institute of Medecine, Antwerp, where they were classified as "*M. simiae*-like" (strains 4358, 4824, 4833, 4844, 4849, 4857, 4859, 7375, 7379, 7730, 9745, 94-1228). These strains reacted only with probe MGV-ICG2 and not with probe MSI-ICG1 which specifically detects *M. simiae* strains sensu stricto. Sequencing of the 16S–23S rRNA spacer region of two of these "*M. simiae*-like" isolates (strains 7379 and 9745) (see SEQ ID NO 161 and 162) confirmed that they were more closely related *M. genavense* than to *M. simiae*. A new probe MGV-ICG3 was designed to specifically detect this group of organisms, which possibly belong to a new species.

MGV-ICG 3: TCGGGCCGCGTGTTCGTCAAA

This illustrates again that the use of DNA probes derived from the 16S–23S spacer region can be helpful in differentiating different groups of strains, which are also found indeterminate by classical taxonomic criteria. Tne use of these DNA probes may possibly lead to the description of new (sub)species within mycobacteria. In this case, the MGV-1 probe would react only with *M. genavense* strains sensu stricto. MGV-3 probe would react only with the intermediate "*M. simiae*-like" strains, and MGV-2 probe would detect both types of strains.

The probe MUL-ICG-1 reacted with all *M. ulcerans* strains tested, but also showed cross-hybridization with *M. marinum* strain ITC 7732. Sequencing of the spacer region of this *M. marinum* strain indeed revealed an identical sequence to that of *M. ulcerans* strain 1837 (see FIG. 80). Further differentiation between *M. marinum* and *M. ulcerans* can be done using a probe from the 16S-rRNA gene of *M. ulcerans*, part of which is co-amplified with the spacer region when primers MYC P1–P5 are used for amplification. A species-specific 16S rRNA probe for *M. ulcerans*, which can work under the same hybridization conditions as the spacer probes for mycobacterium species differentiation, is for example:

TGGCCGGTGCAAAGGGCTG (SEQ ID NO 216)

The above paragraph shows that, although it is preferable to use probes derived from the spacer region, it is also possible, and sometimes necessary, to combine the spacer probes with probes derived from other gene sequences, e.g. the 16S rRNA gene. Here again, these additional probes are selected such that they show the desired hybridization characteristics under the same hybridization and wash conditions as the spacer probes.

For *M. kansasii*, additional strains to the ones mentioned in example 2 have been tested with probes MKA-ICG-1, 2, 3 and 4 described in example 2. Since none of these probes was entirely satisfactory, additional probes were designed for *M. kansasii* detection. Therefor, the spacer region of some of the additional *M. kansasii* strains ITG 6328, 8698 and 8973 was sequenced (see FIGS. 90 to 92). These strains were also obtained from the Institute of Tropical Medecine in Antwerp, Belgium. Apparently, *M. kansasii* strains constitute a quite heterogeneous group, with remarkable differences in the spacer sequence between different strains. Additional probes MKA-ICG-5, 6, 7, 8, 9 and 10 were designed, all hybridizing again under the same conditions as those earlier described, i.e. 3×SSC, 20% deionized formamide, 50° C. The probes were tested with a collection of test strains obtained from the Institute of Tropical Medicine, Antwerp, Belgium, and results are shown in table 8.

None of the *M. kansasii* probes hybridizes with a species other than *M. kansasii*, as far as tested. However, due to the heterogeneous character of this species, none of the *M. kansasii* probes hybridizes with all *M. kansasii* strains. The different *M. kansasii* probes recognize different strains of *M. kansasii*. This differential hybridization may be of clinical significance. On the other hand, if detection of all *M. kansasii* strains is desirable, a combination of different *M. kansasii* probes can be envisaged.

TABLE 8 additional mycobacterial probes

| species/type | strain | MUL ICG-1 | MGV ICG- 1 | 2 | 3 | MXE ICG-1 | MFO ICG-1 | ICG-2 | MSI ICG-1 | MML ICG-2 | MCE ICG-1 | MHP ICG-1 |
|---|---|---|---|---|---|---|---|---|---|---|---|---|
| *M. tuberculosis* | 8004 | − | − | − | | − | − | − | − | − | − | − |
| *M. avium* | 5887 | − | − | − | | − | − | − | − | − | − | − |
| *M. intracellulare* | 5915 | − | − | − | | − | − | − | − | | | |
| | 5913 | | | | | | | | | | − | − |
| MIC 3.1 strain | 1812 | − | − | − | | − | − | − | | | | |
| MIC-4 strain | 8724 | | | | | | | | | − | | |
| *M. scrophulaceum* | 4979 | − | − | − | | − | − | − | − | − | − | − |
| *M. kansaii* | 4987 | − | − | − | | − | − | − | − | − | − | − |
| | 2795 | | | | | | | | | | | |
| | 6238 | − | − | − | | − | − | − | − | − | − | − |
| | 6362 | | | | | | | | | | | |
| | 8698 | − | − | − | | − | − | − | − | − | − | − |
| | 8973 | − | − | − | | − | − | − | − | − | − | − |
| | 8974 | | | | | | | | | | | |
| | 8971 | | | | | | | | | | | |

TABLE 8-continued additional mycobacterial probes

| species/type | strain | | | | | | | | | |
|---|---|---|---|---|---|---|---|---|---|---|
| M. ulcerans | 1837 | + | – | – | – | – | – | – | – | – |
|  | 3129 | + | – | – | – | – | – | – | – | – |
|  | 5114 | + | – | – | – | – | – | – |  |  |
|  | 5115 | + | – | – | – | – | – | – |  |  |
| M. marinum | 7732 | + | – | – | – | – | – | – | – | – |
| M. matmoense | 4832 | – | – | – | – | – | – | + |  |  |
|  | 4842 | – |  |  |  |  |  | + |  |  |
| M. gordonae | 7703 | – | – | – | – | – | – | – | – | – |
| M. chelonae | 4975 | – | – | – | – | – | – |  |  |  |
|  | 9855 | – | – | – | – | – | – |  |  |  |
|  | 94–330 | – | – | – | – | – | – |  |  |  |
|  | 94–379 | – | – | – | – | – | – |  |  |  |
| M. gordonae | 94–123 | – | – | – | – | – | – | – | + | – |
| M. haemophilum | 778 | – |  |  |  |  |  |  | – | + |
|  | 3071 |  |  |  |  |  |  |  | – | + |
| M. genavense | 8777 | – | + | + | – | – | – | – |  |  |
| and M. simiae-like | 9745 | – | – | + | + | – | – | – |  |  |
|  | 92–742 | – | + | + | – | – | – | – |  |  |
|  | 7379 | – | – | + | + | – | – | – |  |  |
|  | 9500 | – | + | + | – | – | – | – |  |  |
| M. simiae | 4484 | – | – | – | – | – | + |  |  |  |
|  | 4485 | – | – | – | – | – | + |  |  |  |
| M. xenopl | 4986 | – | – | – | + | – | – |  |  |  |
| M. fortuitum | 4304 | – | – | – | – | + | – |  |  |  |

| species/type | strain | MKA ICG-3 | MKA ICG-4 | MKA ICG-5 | MKA ICG-6 | MKA ICG-7 | MKA ICG-8 | MKA ICG-9 | MKA-ICG-10 |
|---|---|---|---|---|---|---|---|---|---|
| M. tuberculosis | 8004 | – | – | – | – | – | – | – | – |
| M. avium | 5887 | – | – | – | – | – | – | – | – |
| M. intracellulare | 5915 | – | – | – | – |  |  |  |  |
|  | 5913 |  |  |  |  | – | – | – | – |
| MIC 3.1 strain | 1812 | – | – |  |  |  |  |  |  |
| MIC-4 strain | 8724 | – | – | – | – |  |  |  |  |
| M. scrophulaceum | 4979 | – | – | – | – | – | – | – | – |
| M. kansasii | 4987 | + | + | – | – | – | – | – | + |
|  | 2795 | + | + | – | – | – | – | – | + |
|  | 6238 | + | – | + | – | – | + | + | + |
|  | 6362 | + | – | + | – | – | + | + | + |
|  | 8698 | – | – | – | – | + | – | + | w |
|  | 8973 | – | – | – | + | – | + | – | – |
|  | 8974 | – | – | – | + | – | + | – | – |
|  | 8971 | – | – | – | + | – | + | – | – |
| M. ulcerans | 1837 |  |  | – | – | – | – | – | – |
|  | 3129 |  |  | – | – | – | – | – | – |
|  | 5114 |  |  | – | – |  |  |  |  |
|  | 5115 |  |  | – | – |  |  |  |  |
| M. marinum | 7732 | – | – | – | – | – | – | – | – |
| M. matmoense | 4832 | – | – | – | – |  |  |  |  |
|  | 4842 |  |  |  |  |  |  |  |  |
| M. gordonae | 7703 | – | – | – | – | – | – | – | – |
| M. chelonae | 4975 |  |  |  |  |  |  |  |  |
|  | 9855 |  |  |  |  |  |  |  |  |
|  | 94–330 |  |  |  |  |  |  |  |  |
|  | 94–379 |  |  |  |  |  |  |  |  |
| M. celatum | 94–123 |  |  |  |  | – | – | – | – |
| M. haemophilum | 778 |  |  |  |  | – | – | – | – |
|  | 3071 |  |  |  |  | – | – | – | – |
| M. genavense | 8777 |  |  |  |  |  |  |  |  |
| and M. simiae-like | 9745 |  |  |  |  |  |  |  |  |
|  | 92–742 |  |  |  |  |  |  |  |  |
|  | 7379 |  |  |  |  |  |  |  |  |
|  | 9500 |  |  |  |  |  |  |  |  |
| M. simiae | 4484 |  |  |  |  |  |  |  |  |
|  | 4485 |  |  |  |  |  |  |  |  |
| M. xenopl | 4986 |  | – | – |  |  |  |  |  |
| M. fortuitum | 4304 |  |  |  |  |  |  |  |  |

– = negative reaction, + = positive reaction, w = weak reaction, ± = variable reaction, blanc = non tested

EXAMPLE 8

Brucella

Brucellosis is a very widespread and economically important zoonosis which also affects humans.

For the identification of Brucella spp., mainly bacteriological and immunological detection techniques are being used. These tests are time-consuming and often give false-positive results. Quick and reliable identification methods are being developed, mainly based on DNA amplification and hybridization.

Specific detection of *Brucella* spp. based on the amplification of a 43 kDa outer membrane protein (Fekete A. et al., 1990) or of a part of the 16S rRNA gene (Herman and De Ridder, 1992) were already described.

In order to develop specific DNA probes and primers for the detection of *Brucella* spp. we analyzed the 16S–23S rRNA gene spacer region. Using conserved primers (sequences are given in example 1) the spacer region was amplified and subsequently cloned into the Bluescript SK+ vector following the same procedures as in example 1.

The obtained amplicon of about 1400 bp in length was cloned for the following *Brucella* species:

*Brucella abortus* NIDO Tulya biovar 3 (SEQ ID NO 154)

*Brucella melitensis* NIDO biovar 1 (SEQ ID NO 131)

*Brucella suis* NIDO biovar 1 (SEQ ID NO 132)

HindIII digestion of the constructs, followed by subcloning of the obtained fragments (n=3) facilitated the sequencing of the spacer region for the three described *Brucella* spp., FIGS. 56, 57 and 79 represent the sequences of the spacer regions obtained for the above-mentioned strains of respectively *Brucella melitensis, Brucella suis* and *Brucella abortus*. Due to the high homology of these spacer region sequences between different *Brucella* species, no species-specific DNA probes were deduced from this sequence information, and only genus-specific probes were designed.

For this purpose, the following probes were chemically synthesized:

BRU-ICG 1: CGTGCCGCCTTCGTTTCTCTTT

BRU-ICG 2: TTCGCTTCGGGGTGGATCTGTG

BRU-ICG 3: GCGTAGTAGCGTTTGCGTCGG

BRU-ICG 4: CGCAAGAAGCTTGCTCAAGCC

The oligoaucteotides were immobilized on a membrane strip and following reverse hybridization with biotinylated PCR fragments, the hybrids were visualized using a precipitation reaction. The hybridization results of the immobilized probes with different *Brucella* spp. and related organisms are represented in the table 9.

These hybridization results show that probes BRU-ICG 2, BRU-ICG 3 and BRU-ICG 4 are specific for *Brucella* spp, and can be used in a reverse hybridization assay for detection of these pathogens. Probe BRU-ICG 1 cross-hybridizes with *Ochrobactrum antropi* and *Rhizobium loti* strains, which are two taxonomically highly related organisms, but which are not expected to be present in the same sample material as used for *Brucella* detection.

As described in previous examples (e.g. 3 and 4) also for *Brucella* specific primers were chosen from the 16S–23S rRNA spacer region, in order to specifically amplify the spacer region from ruclla strains.

BRU-P1 and BRU-P2 are used as upper primers, while BRU-P3 and BRU-P4 are used as lower primers. When used in a nested PCR assay the combination BRU-P1/BRU-4 is the outer primerset whereas the combination BRU-P2/BRU-P3 is the inner primerset.

BRU-P1: TCGAGAATTGGAAAGAGGTC 204

BRU-P2: AAGAGGTCGGATTTATCCG 205

BRU-P3: TTCGACPGCAAATGCTCG 206

BRU-P4: TCTTAAAGCCGCATTATGC 207

TABLE 9

| TAXA TESTED | n | BRU-ICG 1 | BRU-ICG 2 | BRU-ICG 3 | BRU-ICG 4 |
|---|---|---|---|---|---|
| *Brucella abortus* | 6 | + | + | + | + |
| *Brucella suis* | 3 | + | + | + | + |
| *Brucella melirensis* | 4 | + | + | + | + |
| *Brucella ovis* | 2 | + | + | + | + |
| *Brucella canis* | 2 | + | + | + | + |
| *Brucella neotomae* | 1 | + | + | + | + |
| *Phyllobacterium rubiacearium* | 1 | – | – | NT | NT |
| *Ochrobactrum anthropi* | 8 | + | – | – | – |
| *Agrobacterium tumefaciens* | 2 | – | – | NT | NT |
| *Agrobacterium rhizogenes* | 1 | – | – | NT | NT |
| *Mycoplana dimorpha* | 1 | – | – | NT | NT |
| *Rhizobium lori* | 1 | + | – | – | – |
| *Rhizobium melilori* | 1 | – | – | NT | NT |
| *Rhizobium leguminosarum* | 1 | – | – | NT | NT |
| *Bradyrhizobium japonicum* | 1 | – | – | NT | NT |
| *Brochothrix thermosphacta* | 1 | – | – | NT | NT |
| *Brochothrix campestris* | 1 | – | – | NT | NT |
| *Bacillus cereus* | 3 | – | – | NT | NT |
| *Bacillus brevis* | 2 | – | – | NT | NT |
| *Bacillus coalgulans* | 1 | – | – | NT | NT |
| *Bacillus pumilis* | 1 | – | – | NT | NT |
| *Bacillus macerans* | 1 | – | – | NT | NT |
| *Bacillus lentus* | 1 | – | – | NT | NT |
| *Bacillus firmus* | 2 | – | – | NT | NT |
| *Bacillus subtilis* | 2 | – | – | NT | NT |
| *Bacillus megantum* | 1 | – | – | NT | NT |
| *Enterococcus faecalis* | 1 | – | – | NT | NT |
| *Enterococcus faecium* | 1 | – | – | NT | NT |
| *Enterococcus durans* | 1 | – | – | NT | NT |
| *Lactobacillus lactis* | 3 | – | – | NT | NT |
| *Lactobacillus casei* | 1 | – | – | NT | NT |
| *Lauconostoc lactis* | 1 | – | – | NT | NT |
| *Escherichia coli* | 1 | – | – | NT | NT |
| *Hafnia halvei* | 1 | – | – | NT | NT |
| *Clostridium tyroburvricum* | 1 | – | – | NT | NT |
| *Clostridium perfringens* | 1 | – | – | NT | NT |
| *Clostridium sporogenes* | 1 | – | – | NT | NT |
| *Clostridium acetobutvricum* | 1 | – | – | NT | NT |
| *Staphylococus aureus* | 1 | – | – | NT | NT |
| *Salmonella enteritidis* | 1 | – | – | NT | NT |
| *Yersinia enterocolitica* | 1 | – | – | NT | NT |
| *Listeria monocytogenes* | 1 | – | – | NT | NT |
| *Listeria ivanovii* | 1 | – | – | NT | NT |
| *Listeria seeligeri* | 1 | – | – | NT | NT |
| *Listeria welshimeri* | 1 | – | – | NT | NT |
| *Listeria innocua* | 1 | – | – | NT | NT |
| *Listeria murravi* | 1 | – | – | NT | NT |
| *Listeria gravi* | 1 | – | – | NT | NT |

NT = Not tested
n = number of strains tested

EXAMPLE 9

*Staphylococcus aureus*

*Staphylococcus aureus* is the staphylococcal species most commonly associated with human and animal infections. *Staphylococcus aureus* strains have been identified as important etiologic agents in both community-acquired and nosocomial infections. Recently nosocomial infection with methicillin-resistant *S. aureus* (MRSA) appear to be increasingly prevalent in many countries. The strains belonging to this species are also causative agents of food spoilage and poisoning.

In order to discriminate in a fast and specific way *S. aureus* strains from other staphylococci, the use of molecular techniques based on DNA probes and/or PCR were already described in the literature. Examples of target genes used for the development of these DNA based assays are the 16S rRNA gene (De Buyser et al., 1992: Geha et al., 1994). the mecA gene (Ubukata et al., 1992; Shimaoka et al., 1994) and the nuc gene (Brakstad et al., 1992; Chesneau et al., 1993).

nor probe STAU-ICG 4 detects all *S. aureus* strains tested, but when both probes are used simultaneously in a LiPA assay, all *S. aureus* strains tested hybridize with one of these probes or with both.

TABLE 10

| Strains tested | n | STAU-ICG 1 | STAU-ICG 2 | STAU-ICG 3 | STAU-ICG 4 |
|---|---|---|---|---|---|
| *Staphylococcus aureus* | 13 | + | + | + | + |
| *Staphylococcus aureus* | 10 | + | + | − | + |
| *Staphylococcus aureus* | 3 | + | + | w | + |
| *staphylococcus aureus* | 1 | + | + | + | − |
| *Staphylococcus epidermidis* | 11 | + | − | − | − |
| *Staphylococcus saprophyticus* | 1 | + | − | − | − |
| *Staphylococcus haemolyticus* | 1 | + | − | − | − |
| *Staphylococcus capitis* | 1 | + | − | − | − |
| *Staphylococcus lugdinensis* | 1 | + | + | − | − |
| *Staphylococcus hominis* | 1 | + | − | − | − |
| *Bordetella pertussis* | 1 | + | − | − | − |
| *Bordetella parapertussis* | 1 | − | − | − | − |
| *Bordetella bronchiseptica* | 1 | − | − | − | − |
| *Mycobacterium tuberculosis* | 1 | − | − | − | − |
| *Mycobacterium avium* | 1 | − | − | − | − |
| *Moraxella catarrhalis* | 4 | − | − | − | − |
| *Haemophilus influenzae* | 2 | − | − | − | − |
| *Streptococcus pneumoniae* | 3 | − | − | − | − |
| *Pseudomonas cepacia* | 1 | − | − | − | − |
| *Pseudomonas aeruginosa* | 3 | − | − | − | − |
| *Acinetobacter calcoaceticus* | 1 | − | − | − | − |

As a target for the development of specific DNA probes we chose the 16S–23S rRNA gene spacer region. Amplification using conserved primers derived from the 16S and the 23S rRNA genes (sequences, see example 1) showed that the pattern obtained was not similar in all *S. aureus* strains tested. A lot of variation was seen in either the number of fragments obtained and in the size of these different fragments.

One spacer region from strain UZG 5728 and four spacer regions (differing in length) from strain UZG 6289 were cloned into Bluescript SK+ vector and subsequently sequenced. The sequences are represented in FIG. 64 to FIG. 68 (SEQ ID NO 139 to SEQ ID NO 143). For the development of specific DNA probes these different spacer regions were compared to each other and to the spacer region derived from *Staphylococcus epidermidis* strain UZG CNS41 (SEQ ID NO 144).

The following probes were chemically synthesized:

STAU-ICG 1: TACCAAGCAAAACCGAGT-GAATAAAGAGTT

STAU-ICG 2: CAGAAGATGCGGAATAACGTGAC

STAU-ICG 3: AACGAAGCCGTATGTGAG-CATTTGAC

STAU-ICG 4: GAACGTAACTTCATGT-TAACGTTTGACTTAT

The oligonucleotides were immobilized on a membrane strip and following reverse hybridization with biotinylated PCR fragments, the hybrids were visualized using a colorimetric precipitation reaction.

The hybridization result of the immobilized probes with different *Staphylococcus* spp. and non-staphylococcal organisms are presented in Table 10.

These hybridization results show that only probes STAU-ICG 3 and STAU-ICG 4 are specific for *Staphylococcus aureus* strains. Probe STAU-ICG 1 react with all *Staphylococcus* spp. tested and probe STAU-ICG 2 cross-hybridizes with the *S. lugdinensis* strain. Neither probe STAU-ICG 3

REFERENCES

Asseline U, Delarue M, Lancelot G. Toulme F, Thuong N (1984) Nucleic acid-binding molecules with high affinity and base sequence specificity: intercalating agents covalendy linked to oligodeoxynucleotides. Proc. Natl. Acad. Sci. USA 81(11):3297–301.

Barany F (1991). Genetic disease detection and DNA amplification using cloned thermostable ligase. Proc Natl Acad Sci USA 88: 189–193.

Bej A, Mahbubani M, Miller R, Di Cesare J, Haff L, Atlas R (1990) Mutiplex PCR amplification and immobilized rapture probes for detection of bacterial pathogens and indicators in water. Mol Cell Probes 4;353–365.

Böddinghaus B, Rogall T, Flohr T, Blöcker H, Böuger E (1990). Detection and identification of Mycabacteria by amplification of rRNA. Journal of Clinical Microbiology, 28:1751–1759.

Brakstad, O. G., K. Aasbakk, and J. A. Maeland. 1992. Detection of *Staphylococcus aureus* by polymerase chain reaction amplification of the nuc gene. J. Clin. Microbiol, 30:1654–1660.

Bubert A, Köhler S, Goebel W (1992). The homologous and heterologous regions within the lap gene allow genus- and species-specific identification of *Listeria* spp. by polymerise chain reaction. Applied and Environmental Microbiology, 58: 2625–2632.

Buck G, O'Hara L, Summersgill J (1992). Rapid, sensitive detection of *Mycoplasma pneumoniae* in simulated clinical specimens by DNA amplification. Journal of Clinical Microbiology, 30: 3280–3283.

Bukh J, Purcell R, Miller R (1993). At least 12 genotypes . . . PNAS 90,8234–8238.

Chesneau, O., J. Allignec and N. El Solh. 1993. Thermonuclease gene as a target nucleotide sequence for specific recognition of *Staphylococcus aureus*. Mol. Cell. Probes. 1:301–310.

Chomczynski P, Saccbi N (1987) Single step method of RNA isolation by acid guanidinium thiocyanate-phenol-chloroform extraction. Anal Biochem 162:156–159.

Compton J (1991). Nucleic acid sequence-based amplification. Nature, 350: 91–92.

Dana A, Moore M, Wentz B, Lune J (1993). Identification and enumeration of *Listeria monocytogenes* by nonradioactive DNA probe colony hybridization. Applid and Environmental Microbiology, 59: 144–449.

De Buyser, M., A. Moran, S. Aubert, F. Dilasser and N. El Solh. 1992. Evaluation of a ribosomal RNA gene probe for the identification of species and subspecies within the genus *Staphylococcus*. J. Gen. Microbiol. 138:889–899.

Duck P (1990). Probe amplifier system based an chimeric cycling oligoancleotides. Biotechniques 9, 142–147.

Farber J, Peterkin P (1991). *Listeria monocytogenes*, a food-borne pathogen. Microbiological Reviews, 55: 476–511.

Fekete, A., J. A. Bantle, S. M. Balling and M. R. Sanborn. 1990. Preliminary development of a diagnostic test for *Brucella* using polymerise chain reaction. J. Appl. Bacterial. 69:216–227.

Frothingham R, Wilson K (1993). Sequence-based differentiation of strains in the *Mycobacterium avium* complex, Journal of Bacteriology, 175.

Frothingham R, Wilson K (1994). Molecular phylogeny of the *Mycobacterium avium* complex demonstrates clinically meaningful divisions. J Infect Diseases, 169: 305–312.

Geha, D. J., J. R. Uhl, C. A. Gustaferro, and D. H. Persing. 1994. Multiplex PCR for identification of methicillin-resistant staphylococci in the clinical laboratory. J. Clin. Micobiol. 32:1768–1772.

Goisteyn Thomas E, King R, Burebak J, Gannon V (1991). Sensitive and specific detection of *Listeria monocytogenes* in milk and ground beef with the polymerise chain reaction. Applied and Environmental Microbiology, 57: 2576–2580.

Guatelii J, Whitfield K, Kwoh D, Barringer K, Richman D, Gengeras T (1990) Isothermal, in vitro amplification of nucleic acids by a multienzyme reaction modeled after retroviral replication. Proc Natl Acad Sci USA 87: 1874–1878.

Herman L, De Ridder H (1993). Evaluation of a DNA-probe assay for the identification of *Listeria monocyrogenes*. Milchwissenschaft, 48: 126–128.

Herman, L. and H. De Ridder. 1992. Identification of *Brucella* spp. by using the polymerise chain reaction. Appl. Env. Microbial. 58:2099–2101.

Jacobs K, Rudersdorf R, Neill S, Dougherty J, Brown E, Fritsch E (1988) The thermal stability of oligonucleotide duplexes is sequence independent in tetraalkylammonium salt solutions: application to identifying recombinant DNA clones. Nucl Acids Res 16:4637–4650.

Jaton K, Sahli R, Bille J (1992). Development of polymerise chain reaction assays for detection of *Listeria monocytogenes* in clinical cerebrospinal fluid samples. Journal of Clinical Microbiology, 30: 1931–1936.

Jonas V, Aldan M, Curry J, Kamisango K, Knott C, Lankford R, Wolfe J, Moore D (1993). Detection and identification of *Mycobacterium tuberculosis* directly from sputum sediments by amplification of rRNA. Journal of Clinical Microbiology, 31: 2410–2416.

Kempsell K et al. (1992). The nucleotide sequence of the promoter, 16S rRNA and spacer region of the ribosomal RNA operon of *Mycobacterium tuberculosis* and comparison with *M. leprae* precursor rRNA. Journal of Gen Mierobiol 138: 1717–1727.

Kwoh D, Davis G, Whitfield K, Chappelle H, Dimichele L, Gingeras T (1989). Transcription-based amplification system and detection of amplified human immunodeficiency virus type 1 with a bead-based sandwich hybridization format. Proc Natl Acad Sci USA, 86: 1173–1177.

Kwak S, Kellogg D, McKinney N, Spasic D, Goda L, Levenson C, Sinisky J, (1990). Effects of primer-template mismatches on the polymerase chain reaction: Human immunodeficiency views type 1 model studies. Nucl. Acids Res., 18: 999.

Landgren U, Kaiser R, Sanders J, Hood L (1988). A ligase-mediated gene detection technique. Science 241:1077–1080.

Lizardi P, Guerra C, Lomeli H, Tussie-Luna I, Kramer F (1988) Exponential amplification of recombinant RNA hybridization probes. Bio/technology 6:1197–1202.

Loeffelholz M, Lewinski C, Silver S, Purohit A, Herman S, Buonagurio D, Dragon E (1992). Detection of *Chlamydia trachomatis* in endocervical specimens by polymerase chain reaction. Journal of Clinical Microbiology, 30: 2847–2851.

Lomeli H, Tyagi S, Printchard C, Lisardi P, Kramer F (1989) Quantitative assays based on the use of replicatable hybridization probes. Clin Chem 35: 1826–1831.

Maniatis T, Fritsch E, Sambrook J (1982) Molecular cloning: a laboratory manual. Cold Spring Harbor Laboratory Press, Cold Spring Harbor, N.Y.

Matsukura M, Shinozuka K, Zon G, Mitsuya H, Reitz M, Cohen J, Broder S (1987) Phosphorothioate analogs of oligodeoxynucleotides: inhibitors of replication and cytopathic effects of human immunodeficiency virus. Proc. Natl. Acad. Sci. USA 84(21):7706–10.

McIntosh I, Govan J, Brock D (1992), Detection of *Pseudomonas aeruginosa* in sputum from cystic fibrosis patients by the polymerase chain reaction. Molecular and Cellular Probes, 6: 299–304.

Miller P, Yano J, Yano E, Carroll C, Jayaram K, Ts'o P (1979) Nonionic nucleic acid analogues. Synthesis and characterization of dideoxyriboncleoside methylphosphonates. Biochemistry 18(23):5134–3.

Nielsen P, Egholm M, Berg R, Buchardt O (1991) Sequence-selective recognintion of DNA by strand displacent with a thymine-substituted polyamide. Science 254(5037):1497–500.

Nielsen P, Egholm M, Berg R, Buchardt O (1993) Sequence specific inhibition of DNA restriction enzyme cleavage by PNA. Nucleic-Acids-Res. 21(2):197–200.

Ninet B, Bannerman E., Bille J (199). Assessment of the accuprobe *Listeria monocytogenes* culture identification reagent kit for rapid colony confermation and its application in various enrichment broths. Applied and Environmental Microbiology, 58: 4055–4059.

Ogle J, Janda J, Woods D, Vasil M (1987). Characterization and use of a DNA probe as an epidemiological marker for *Pseudomonas aeruginosa*. The Journal of Infectious Diseases, 155: 119.

Ossewaarde J, Rieffe M, Rozenburg-Arska M, Ossenkoppele P, Nawrocki R, Van Loon A (1992). Development and clinical evaluation of a polymerase chain reaction test for detection of *Chlamydia trachomatis*. Journal of Clinical Microbiology, 30: 2122–2128.

Rogall T. Wolters J, Flohr T. Böuger E (1990). Towards a phylogeny and definiion of species at the molecular level within the genus *Mycobacterium*. Int. J. Syst. Bacteriol. 40: 323–330.

Rossau R, Michielsen A, Jannes G, Duhamel M, Kersten K, Van Heuverswyn H. DNA probes for Bordetella species and a colorimetric reverse hybridization assay for the detection of *Bordetella pertussis*. Mol. Cell. Probes 6: 281–289, 1992

Saiki R, Gelfand D, Stoffel S, Scharf S, Higuchi R, Horn G, Mullis K, Erlich H (1988). Primer-directed enzymatic amplification of DNA with a thermostable DNA polymerase. Science 239: 487–491.

Saiki R, Walsh P, Levenson C, Erlich H (1989) Genetic analysis of amplified DNA with immobilized sequence-specific oligonucleotide probes (1989) Proc Natl Acad Sci USA 86:6230–6234.

Saito H, Tomioka H, Sam K, Hiromichi T, Tsukamura M, Kuze F, Asano K (1989). Identification and partial characterization of *Mycobacterium avium* and *Mycobacterium intracellulare* by using DNA probes. Journal of Clinical Microbiology, 27: 994–997.

Samadpour M, Moseley S, Lory S (1988). Biotinylated DNA probes for exotoxin A and pilin genes in the differentiation of *Pseudomonas aeruginasa* strains. Journal of Clinical Microbiology, 26: 2319–2323.

Sano T, Smith C, Cantor C (1992) Immuno-PCR very sensitive antigen detection by means of specific antibody-DNA conjugates. Science 258:120–122.

Shizuoka, M., M. Yoh, A. Segawa, Y. Takarada, K. Yamamoto and T. Honda. 1994. Development of enzyme-labeled oligonucleotide probe for detection of mecA gene in methiciliin-resistant *Staphylococcus aureus*. J. Clin. Microbiol. 32:1866–1869.

Stuyver L, Rossau R, Wyseur A, Duhamel M, Vanderborght B, Van Heuverswyn H, Maertens G (1993) Typing of hepatitis C virus (HCV) isolates and characterization of new (sub)types using a Line Probe Assay. J Gen Virology, 74: 1093–1102.

Suzuki Y et al. (1988). Complete nucleotide sequence of the 16S rRNA gene of *Mycobacterium bovis* BCG. J Bacterial, 170: 2886–2889.

Taylor-Robinson D, Gilroy C, Thomas B, Keat A (1992). Detection of *Chlamydia trachomatis* DNA in joints of reactive arthritis patients by polymerase chain reaction. Lancet 340: 81–82.

Telenti A, Marchesi F, Bala M, Bally F, Bouger E, Bodmer T (1993). Rapid identification of Mycobacteria to the species level by polymerise chain reaction and restriction enzyme analysis. Journal of Clinic Microbiology, 31: 175–178.

Tomioka H. Saito H, Sato K, Tasaka H, Dawson (1993). Idendfcation of *Mycobacterium avium* complex strains belonging to serovars 21–28 by three commercial DNA probe tests. Tubercle and Lung Disease, 74: 91–95.

Ubukata, K., S. Nakegami, A. Nitta, A. Yamane, S. Kawakami, M. Suguria and M. Konno. 1992. Rapid detection of the mecA gene in metlaicillin-resistant staphylococci by enzymatic detection of polymerise chain reaction product. J. Clin. Microbiol. 30:1728–1733.

Van der Giessen, J et al (1994). Comparison of the 23S rRNA genes and the spacer region between the 16S and 23S rRNA genes of the closely related *M. avium* and *M. paratuberculosis* and the fast-growing *M. phlei*. Microbiology, 140: 1103–1108.

Vaneechoutte M, De Beenhouwer H, Claeys G, Verschraegen G, De Rouck A, Paepe N, Elaichouni A, Portaels F (1993). Identification of *Mycobacterium* species by using amplified ribosomal DNA restriction analysis. Journal of Clinical Microbiology, 31: 2061–2065.

Van Kuppeveld F, Van Der Logt J, Angulo A, Van Zoest M, Quint W, Niesters H, Galama J, Melchers W (1992). Genus- and species-specific identification of mycoplasmas by 16S rRNA amplification. Applied and Environmental Microbiology, 58: 2606–2615.

Walker G, Little M, Nadeau J, Shank D (1992). Isothermal in vitro amplification of DNA by a restriction enzyme/DNA polymerise system. Proc Nat Acad Sci USA 89:392–396.

Woods G, Young A, Scott J, Blair T, Johnson A (1990). Evaluation of a nonisotopic probe for detection of *Chlamydia trachomatis* in endacervical specimens. Journal of Clinical Microbiology, 28: 370–372.

Wu D, Wallace B (1989). The ligation amplification reaction (LAR)—amplification of specific DNA sequences using sequential rounds of template-dependent ligation. Genomics 4:560–569.

What is claimed is:

1. An isolated nucleic acid sequence comprising a 16S–23S rRNA spacer sequence selected from the group consisting of: SEQ ID NO:111, SEQ ID NO: 112, SEQ ID NO: 113, SEQ ID NO: 114, SEQ ID NO: 115, a sequence complementary to any of the above-recited sequences; and a sequence recited above which contains a U in place of T.

2. An isolated nucleic acid sequence consisting of a 16S–23S rRNA spacer sequence selected from the group consisting of: SEQ ID NO:111, SEQ ID NO: 112, SEQ ID NO: 113, SEQ ID NO: 114, SEQ ID NO: 115, a sequence complementary to any of the above-recited sequences; and a sequence recited above which contains a U in place of T.

3. Method for the detection and identification of one *Pseudomonas* species, or for the simultaneous detection of several *Pseudomonas* species in a sample, comprising the steps of:

(i) optionally releasing, isolating and/or concentrating the polynucleic acids to be detected in the sample;

(ii) optionally amplifying the 16S–23S rRNA spacer region, or a part thereof, with at least one primer pair;

(iii) detecting the presence of a nucleic acid according to claim 2;

(iv) identifying the *Pseudomonas* species present in said sample from the nucleic acid(s) detected in said sample.

4. Method according to claim 3, wherein said detecting comprises sequence analysis of said nucleic acid(s).

5. Method according to claim 3 wherein said detecting comprises specifically hybridizing at least one probe to said nucleic acid.

6. Method according to claim 3 for the detection and identification of *Pseudomonas aeruginosa* wherein said nucleic acid of step (iii) is a sequence consisting of SEQ ID NO 111.

7. Method according to claim 3 for the detection and identification of *Pseudomonas pseudoalcaligenes* wherein said nucleic acid of step (iii) is a sequence consisting of SEQ ID NO 112.

8. Method according to claim 3 for the detection and identification of *Pseudomonas stutzeri* wherein said nucleic acid of step (iii) is a sequence consisting of SEQ ID NO 113.

9. Method according to claim 3 for the detection and identification of *Pseudomonas alcaligenes* wherein said nucleic acid of step (iii) is sequence consisting of SEQ ID NO 114.

10. Method according to claim 3 for the detection and identification of *Pseudomonas putida* wherein said nucleic acid of step (iii) is sequence consisting of SEQ ID NO 115.

11. Method for the detection and identification of one *Pseudomonas* species, or for the simultaneous detection of several *Pseudomonas* species in a sample, comprising the steps of:
  (i) optionally releasing, isolating and/or concentrating the polynucleic acids to be detected in the sample;
  (ii) optionally amplifying the 16S–23S rRNA spacer region, or a part thereof, with at least one primer pair;
  (iii) detecting the presence of a nucleic acid sequence selected from the group consisting of: SEQ ID NO:111, SEQ ID NO:111 containing a U in place of T, a sequence complementary to SEQ ID NO:111, a sequence complementary to SEQ ID NO:111 containing a U in place of T, SEQ ID NO:112, SEQ ID NO:112 containing a U in place of T, a sequence complementary to SEQ ID NO:112, a sequence complementary to SEQ ID NO:112 containing a U in place of T, SEQ ID NO:113, SEQ ID NO:113 containing a U in place of T, a sequence complementary to SEQ ID NO:113, a sequence complementary to SEQ ID NO:113 containing a U in place of T, SEQ ID NO:114, SEQ ID NO:114 containing a U in place of T, a sequence complementary to SEQ ID NO:114, a sequence complementary to SEQ ID NO:114 containing a U in place of T, SEQ ID NO:115, SEQ ID NO:115 containing a U in place of T, a sequence complementary to SEQ ID NO:115, and a sequence complementary to SEQ ID NO:115 containing a U in place of T; and
  (iv) identifying the *Pseudomonas* species present in said sample from the nucleic acid(s) detected in said sample.

12. Method according to claim 11 wherein said detecting comprises sequence analysis of said nucleic acid sequence.

13. Method according to claim 11 for the detection and identification of *Pseudomonas aeruginosa* wherein said nucleic acid sequence is a sequence selected from the group consisting of: SEQ ID NO:111, a sequence complementary to SEQ ID NO:111, SEQ ID NO:111 which contains a U in place of T; and a sequence complementary to SEQ ID NO:111 which contains a U in place of T.

14. Method according to claim 11 for the detection and identification of *Pseudomonas pseudoalcaligenes* wherein said nucleic acid sequence is a sequence selected from the group consisting of SEQ ID NO:112, a sequence complementary to SEQ ID NO:112, SEQ ID NO:112 which contains a U in place of T; and a sequence complementary to SEQ ID NO:112 which contains a U in place of T.

15. Method according to claim 11 for the detection and identification of *Pseudomonas stutzeri* wherein said nucleic acid sequence is a sequence selected from the group consisting of: SEQ ID NO:113, a sequence complementary to SEQ ID NO: 113, SEQ ID NO: 113 which contains a U in place of T; and a sequence complementary to SEQ ID NO:113 which contains a U in place of T.

16. Method according to claim 11 for the detection and identification of *Pseudomonas alcaligenes* wherein said nucleic acid sequence is a sequence selected from the group consisting of: SEQ ID NO:114, a sequence complementary to SEQ ID NO:114, SEQ ID NO:114 which contains a U in place of T; and a sequence complementary to SEQ ID NO:114 which contains a U in place of T.

17. Method according to claim 11 for the detection and identification of *Pseudomonas putida* wherein said nucleic acid sequence is a sequence selected from the group consisting of: SEQ ID NO:115, a sequence complementary to SEQ ID NO:115, SEQ ID NO:115 which contains a U in place of T; and a sequence complementary to SEQ ID NO: 115 which contains a U in place of T.

18. An isolated nucleic acid sequence comprising a 16S–23S rRNA spacer sequence selected from the group consisting of: SEQ ID NO: 112, SEQ ID NO: 113, SEQ ID NO: 114, a sequence complementary to any of the above-recited sequences; and a sequence recited above which contains a U in place of T.

19. An isolated nucleic acid sequence selected from the group consisting of SEQ ID NO:111, SEQ ID NO:115, a sequence complementary to SEQ ID NO:111 or SEQ ID NO:115, and a sequence recited above which contains a U in place of T.

* * * * *